(12) United States Patent
Kuehnert et al.

(10) Patent No.: US 7,300,939 B2
(45) Date of Patent: Nov. 27, 2007

(54) SUBSTITUTED 1-PROPIOLYLPIPERAZINE COMPOUNDS, THEIR PREPARATION AND USE

(75) Inventors: Sven Kuehnert, Dueren (DE); Stefan Oberboersch, Aachen (DE); Michael Haurand, Aachen (DE); Ruth Jostock, Stolberg (DE); Klaus Schiene, Duesseldorf (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/649,156

(22) Filed: Jan. 4, 2007

(65) Prior Publication Data
US 2007/0112011 A1 May 17, 2007

Related U.S. Application Data

(63) Continuation of application No. PCT/EP05/07248, filed on Jul. 5, 2005.

(51) Int. Cl.
*C07D 417/04* (2006.01)
*A61K 31/496* (2006.01)

(52) U.S. Cl. .............................. 514/253.06; 514/253.1; 514/254.02; 514/254.03; 544/363; 544/364; 544/367; 544/369

(58) Field of Classification Search ................ 544/363, 544/364, 367, 369; 514/253.06, 253.1, 254.02, 514/254.03
See application file for complete search history.

(56) References Cited

FOREIGN PATENT DOCUMENTS

| EP | 0 552 418 A1 | 7/1993 |
|---|---|---|
| WO | WO 01/32690 A1 | 5/2001 |
| WO | WO 2003/093236 A1 | 11/2003 |
| WO | WO 2004/029044 A1 | 4/2004 |

OTHER PUBLICATIONS

PCT/IPEA/409 (International Preliminary Report On Patentability) with English translation (Eleven (11) Pages).
Susana Morales-Alcelay et al., "AMPA Glutamate Receptors and Neuropathic Pain" Mini Reviews in Medicinal Chemistry, Bentham Science Publishers Hilversum, NL, vol. 3, No. 7, Nov. 2003, pp. 757-763.
Michael Williams et al., "Emerging Molecular Approaches to Pain Therapy" Journal of Medicinal Chemistry, vol. 42, No. 9, 1999, pp. 1481-1500, XP-002344884.
Camille G. Wermuth, "Molecular Variations Based on Isosteric Replacements" The Practice of Medicinal Chemistry, 1996, pp. 203-237, XP-002190259.
G.L. Regnier et al., "Triphenylpropylpiperazine Derivatives as new Potent Analgetic Substances", Journal of Medicinal Chemistry, vol. 15, No. 3, 1972, pp. 295-301.
Jon L. Collins et al., "N-(2-Benzoylphenyl)-L-tyrosine PPARγ Agonists. 2. Structure-Activity Relationship and Optimization of the Phenyl Alkyl Ether Moiety", Journal of Medicinal Chemistry, vol. 41, No. 25, 1998, pp. 5037-5054.
Theodora W. Greene et al. "Protective Groups in Organic Synthesis" 3rd Edition, Table of Contents, 1999, Wiley, New York.
Philip J. Kocieński "Protecting Groups" 3rd Edition, Table of Contents, 2005, Georg Thieme Verlag, Stuttgart.
Alfonso R. Gennaro, "Remington's Pharmaceutical Sciences", 17th Edition, Table of Contents, Mack Publishing Company, Easton, PA, 1985.
David Dubuisson et al. "The Formalin Test: A Quantitative Study of the Analgesic Effects of Morphine, Meperidine, and Brain Stem Stimulation in Rats and Cats", Pain, 4, 1977, pp. 161-174, Elsevier/North-Holland Biomedical Press.
International Search Report dated Sep. 27, 2005 (Three (3) pages).
German Search Report dated Oct. 22, 2004 with an English translation of the pertinent portions (Eight (8) pages).

*Primary Examiner*—Fiona T Powers
(74) *Attorney, Agent, or Firm*—Crowell & Moring LLP

(57) ABSTRACT

Substituted 1-propiolylpiperazine compounds corresponding to formula I

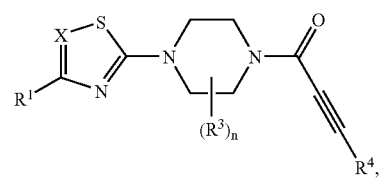

in which X denotes N or C—$R^2$, and n is an integer from 0 to 8, a method for producing such substituted 1-propiolylpiperazine compounds, pharmaceutical compositions containing such substituted 1-propiolylpiperazine compounds, and the use of such substituted 1-propiolylpiperazine compounds for modulating mGluR5 receptor activity or for treating or inhibiting pain and various other conditions, especially conditions at least partly mediated by the mGluR5 receptor.

46 Claims, No Drawings

SUBSTITUTED 1-PROPIOLYLPIPERAZINE COMPOUNDS, THEIR PREPARATION AND USE

CROSS REFERENCE TO RELATED APPLICATIONS

This application is a continuation of international patent application No. PCT/EP2005/007248, filed Jul. 5, 2005 designating the United States of America and published in German on Jan. 12, 2006 as WO 2006002981, the entire disclosure of which is incorporated herein by reference. Priority is claimed based on Federal Republic of Germany patent application no. DE 10 2004 032 567.7, filed Jul. 5, 2004.

BACKGROUND OF THE INVENTION

The present invention relates to substituted 1-propiolylpiperazines, to processes the preparation thereof, to medicinal drugs comprising said compounds, and to the use of said compounds in the preparation of medicinal drugs.

Pain is one of the basic symptoms found in the clinical field. There is a worldwide need effective pain therapies. The urgent need attaining patient-friendly, target-orientated treatment of chronic and non-chronic states of pain, by which is to be understood the successful and satisfactory treatment of pain in the patient, is also documented by the large number of scientific papers which have recently been published in the field of applied analgesics and basic research on nociception.

Conventional opioids, such as, example, morphine, are active in the therapy of severe to very severe pain, but often lead to undesirable concomitant symptoms, such as, example, respiratory depression, vomiting, sedation, constipation or development of immunity. Furthermore, they are often not sufficiently effective on neuropathic pain, from which tumor patients suffer in particular.

SUMMARY OF THE INVENTION

An object of the present invention is therefore to provide novel compounds which are particularly well-suited as pharmaceutically active compounds in medicinal drugs, preferably in medicinal drugs the treatment of pain.

It has now been found, surprisingly, that the substituted 1-propiolylpiperazines corresponding to formula I given below are suitable mGluR5 receptor regulation and therefore can be employed in particular as pharmaceutically active compounds in medicinal drugs inhibition and/or treatment of disorders or diseases associated with these receptors or processes.

Thus the present invention relates to substituted 1-propiolylpiperazines corresponding to formula I,

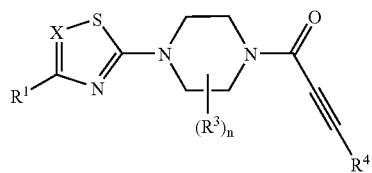

I in which
X denotes N or C—$R^2$,
$R^1$ and $R^2$ each independently denote a hydrogen, a halogen radical, or a nitro group, a cyano group, an amino group, a hydroxyl group, a thiol group, a carboxyl group, a formyl group, an —NH—C(=O)—H group, an —NH—$R^5$ group, an —$NR^6R^7$ group, a —C(=O)—$R^8$ group, a —C(=O)—O—$R^9$ group, an —O—C(=O)—$R^{10}$ group, an —NH—C(=O)—$R^{11}$ group, an —$NR^{12}$—C(=O)—$R^{13}$ group, a —C(=O)—$NH_2$ group, a —C(=O)—NH—$R^{14}$ group, a —C(=O)—$NR^{15}R^{16}$ group, an —O—$R^{17}$ group, an —S—$R^{18}$ group, an —S(=O)—$R^{19}$ group, an —S(=O)$_2$—$R^{20}$ group, an —NH—C(=O)—NH—$R^{21}$ group, an —NH—C(=S)—NH—$R^{22}$ group, an —NH—S(=O)$_2$—$R^{23}$ group, an —$NR^{24}$—S(=O)$_2$—$R^{25}$ group, or a linear or branched, saturated or unsaturated, unsubstituted or at least monosubstituted aliphatic radical optionally containing at least one hetero atom as link, an unsubstituted or at least monosubstituted, unsaturated or saturated cycloaliphatic radical optionally containing at least one hetero atom as ring member, which cycloaliphatic radical can be bonded via a linear or branched, unsubstituted or at least monosubstituted alkylene group, alkenylene group, or alkynylene group optionally containing at least one hetero atom as link and/or optionally condensed with an unsubstituted or at least monosubstituted monocyclic or polycyclic ring system, or an unsubstituted or at least monosubstituted aryl or heteroaryl radical, which can be bonded via a linear or branched, unsubstituted or at least monosubstituted alkylene group, alkenylene group, or alkynylene group optionally containing at least one hetero atom as link and/or optionally condensed with an unsubstituted or at least monosubstituted monocyclic or polycyclic ring system, $R^3$ denotes a halogen radical, or a nitro group, a cyano group, an amino group, a hydroxyl group, a thiol group, a carboxyl group, a formyl group, an —NH—C(=O)—H group, an oxo group (=O), an —NH—$R^5$ group, an —$NR^6R^7$ group, a —C(=O)—$R^8$ group, a —C(=O)—O—$R^9$ group, an —O—C(=O)—$R^{10}$ group, an —NH—C(=O)—$R^{11}$ group, an —$NR^{12}$—C(=O)—$R^{13}$ group, a —C(=O)—$NH_2$ group, a —C(=O)—NH—$R^{14}$ group, a —C(=O)—$NR^{15}R^{16}$ group, an —O—$R^{17}$ group, an —S—$R^{18}$ group, an —S(=O)—$R^{19}$ group, an —S(=O)$_2$—$R^{20}$ group, an —NH—C(=O)—NH—$R^{21}$ group, an —NH—C(=S)—NH—$R^{22}$ group, an —NH—S(=O)$_2$—$R^{23}$ group, an —$NR^{24}$—S(=O)$_2$—$R^{25}$ group, or a linear or branched, saturated or unsaturated, unsubstituted or at least monosubstituted aliphatic radical optionally containing at least one hetero atom as link, or an unsubstituted or at least monosubstituted, unsaturated or saturated cycloaliphatic radical optionally containing at least one hetero atom as ring member, which cycloaliphatic radical can be bonded via a linear or branched, unsubstituted or at least monosubstituted alkylene group, alkenylene group, or alkynylene group optionally containing at least one hetero atom as link and/or optionally condensed with an unsubstituted or at least monosubstituted monocyclic or polycyclic ring system, or an unsubstituted or at least monosubstituted aryl or heteroaryl radical, which can be bonded via a linear or branched, unsubstituted or at least monosubstituted alkylene group, alkenylene group, or alkynylene group optionally containing at least one hetero atom as link and/or optionally condensed with an unsubstituted or at least monosubstituted monocyclic or polycyclic ring system, $R^4$ denotes a hydrogen, a fluorine atom, a chlorine atom, a bromine atom, a nitro group, a cyano group, an amino group, a hydroxyl group, a thiol group, a carboxyl group, a formyl group, an —NH—C(=O)—H group, an —NH—$R^5$ group, an —$NR^6R^7$ group, a —C(=O)—$R^8$ group, a —C(=O)—O—R$^9$ group, an —O—C(=O)—R$^{10}$ group, an —NH—C(=O)—R$^{11}$ group, an —NR$^{12}$—C(=O)—R$^{13}$ group, a —C(=O)—NH$_2$ group, a —C(=O)—NH—R$^{14}$ group, a —C(=O)—NR$^{15}$R$^{16}$ group, an —O—R$^{17}$ group, an —S—R$^{18}$ group, an —S(=O)—R$^{19}$ group, an —S(=O)$_2$—R$^{20}$ group, an —NH—C(=O)—NH—R$^{21}$ group, an —NH—C(=S)—NH—R$^{22}$ group, an —NH—S(=O)$_2$—R$^{23}$ group, an —NR$^{24}$—S(=O)$_2$—$^{25}$ group, or a linear or branched, saturated or unsaturated, unsubstituted or at least monosubstituted aliphatic radical optionally containing at least one hetero atom as link, or an unsubstituted or at least monosubstituted, unsaturated or saturated cycloaliphatic radical optionally containing at least one hetero atom as ring member, which cycloaliphatic radical can be bonded via a linear or branched, unsubstituted or at least monosubstituted alkylene group, alkenylene group, or alkynylene group optionally containing at least one hetero atom as link and/or optionally condensed with an unsubstituted or at least monosubstituted monocyclic or polycyclic ring system, or an unsubstituted or at least monosubstituted aryl or heteroaryl radical, which can be bonded via a linear or branched, unsubstituted or at least monosubstituted alkylene group, alkenylene group, or alkynylene group optionally containing at least one hetero atom as link and/or optionally condensed with an unsubstituted or at least monosubstituted monocyclic or polycyclic ring system, R$^5$ to R$^{25}$ independently denote a linear or branched, saturated or unsaturated, unsubstituted or at least monosubstituted aliphatic radical optionally comprising at least one heteroatom as link, an unsubstituted or at least monosubstituted, unsaturated or saturated cycloaliphatic radical optionally containing at least one hetero atom as ring member, which cycloaliphatic radical can be bonded via a linear or branched, unsubstituted or at least monosubstituted alkylene group, alkenylene group, or alkynylene group optionally containing at least one hetero atom as link and/or optionally condensed with an unsubstituted or at least monosubstituted monocyclic or polycyclic ring system, or an unsubstituted or at least monosubstituted aryl or heteroaryl radical, which can be bonded via a linear or branched, unsubstituted or at least monosubstituted alkylene group, alkenylene group, or alkynylene group optionally containing at least one hetero atom as link, n is equal to 0, 1, 2, 3, 4, 5, 6, 7, or 8, in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

If one or more of the substituents R$^1$ to R$^{25}$ denote a saturated or unsaturated aliphatic radical, ie an alkyl radical, alkenyl radical or alkynyl radical, which is monosubstituted or polysubstituted, this can be preferably substituted by 1, 2, 3, 4, or 5 substituents independently selected from the group consisting of F, Cl, Br, —NO$_2$, —CN, —OH, —SH, and —NH$_2$. Alkenyl radicals have at least one and preferably 1, 2, 3, or 4 C—C double bonds and alkynyl radicals have at least one and preferably 1, 2, 3, or 4 C—C triple bonds.

Examples of suitable alkyl, alkenyl, and alkynyl radicals, which can be monosubstituted or polysubstituted, are methyl, ethyl, n-propyl, isopropyl, n-butyl, isobutyl, sec-butyl, tert-butyl, n-pentyl, 2-pentyl, 3-pentyl, isopentyl, neopentyl, n-hexyl, 2-hexyl, 3-hexyl, n-heptyl, n-octyl, n-nonyl, n-decyl, —C(H)(C$_2$H$_5$)$_2$, —C(H)(n—C$_3$H$_7$)$_2$, —CH$_2$—CH$_2$—C(H)(CH$_3$)—(CH$_2$)$_3$—CH$_3$, vinyl, ethynyl, 1-propenyl, 2-propenyl, 1-propynyl, 2-propynyl, 1butenyl, 2-butenyl, 3-butenyl, 1-butynyl, 2-butynyl, 3-butynyl, 1-pentenyl, 2-pentenyl, 3-pentenyl, 4-pentenyl, 1-pentynyl, 2-pentynyl, 3-pentynyl, 4-pentynyl, hexenyl, hexynyl, —CH=CH—CH=CH—CH$_3$, and —CH$_2$—CH$_2$—CH=CH$_2$.

Examples of suitable substituted alkyl and alkenyl radicals are trifluoromethyl, difluoromethyl, monofluoromethyl, —(CH$_2$)—OH, —(CH$_2$)—NH$_2$, —(CH$_2$)—CN, —(CH$_2$)—(CF$_3$), —(CH$_2$)—(CHF$_2$), —(CH$_2$)—(CH$_2$F), —(CH$_2$)—(CH$_2$)—OH, —(CH$_2$)—(CH$_2$)—NH$_2$, —(CH$_2$)—(CH$_2$)—CN, —(CF$_2$)—(CF$_3$), —(CH$_2$)—(CH$_2$)—(CF$_3$), —CH=CH—(CH$_2$)—OH, —CH=CH—(CH$_2$)—NH$_2$, —CH=CH—CN, and —(CH$_2$)—(CH$_2$)—(CH$_2$)—OH.

If one or more of the substituents R$^1$ to R$^{25}$ denote a saturated or unsaturated aliphatic radical, ie an alkyl radical, alkenyl radical or alkynyl radical, containing one or more, preferably 1, 2 or 3, hetero atom(s) as link(s), these hetero atoms can be independently selected preferably from the group consisting of oxygen, sulfur, and nitrogen (NH).

Preferably, these hetero atoms are located in a non-terminal position of the respective radical. Mention may be made, example, of radicals such as —(CH$_2$)—(CH$_2$)—O—(CH$_3$), —(CH$_2$)—(CH$_2$)—S—(CH$_3$), —(CH$_2$)—S—(CH$_2$)—(CH$_2$)—S—(CH$_3$), —(CH$_2$)—O—(CH$_2$)—(CH$_2$)—O—(CH$_3$), —(CH$_2$)—O—(CH$_3$), or —(CH$_2$)—S—(CH$_3$).

If one or more of the substituents R$^1$ to R$^{25}$ denote a cycloaliphatic radical or contain a cycloaliphatic radical, which is monosubstituted or polysubstituted, this can be preferably substituted by 1, 2, 3, 4, or 5 substituents independently selected from the group consisting of F, Cl, Br, I, —CN, —CF$_3$, —OH, —NH$_2$, —O—CF$_3$, —SH, —O—(C$_{1-5}$ alkyl), —(CH$_2$)—O—(C$_{1-5}$ alkyl), —S—(C$_{1-5}$ alkyl), —(C$_{1-5}$ alkyl), —C$_{2-5}$ alkenyl, —C$_{2-5}$ alkynyl, —C≡C—Si(CH$_3$)$_3$, —C≡C—Si(C$_2$H$_5$)$_3$, —C(=O)—O—(C$_{1-5}$ alkyl), —C(=O)—CF$_3$, —S(=O)$_2$—(C$_{1-5}$ alkyl), —S(=O)—(C$_{1-5}$ alkyl), —S(=O)$_2$ phenyl, oxo (=O), thioxo (=S), —N(C$_{1-5}$ alkyl)$_2$, —N(H)(C$_{1-5}$ alkyl), —NO$_2$, —S—CF$_3$, —C(=O)—OH, —NH—S(=O)$_2$—(C$_{1-5}$ alkyl), —NH—C(=O)—(C$_{1-5}$ alkyl), —C(=O)—H, —C(=O)—(C$_{1-5}$ alkyl), —C(=O)—NH$_2$, —C(=O)—N(C$_{1-5}$ alkyl)$_2$, —C(=O)—N(H)(C$_{1-5}$ alkyl), and phenyl, wherein the aforementioned (C$_{1-5}$ alkyl) radicals can in each case be linear or branched and the phenyl radicals can in each case be unsubstituted or substituted by 1, 2, 3, 4, or 5 and preferably by 1, 2, 3, or 4 substituents independently selected from the group consisting of F, Cl, Br, I, —CN, —CF$_3$, —OH, —NH$_2$, —O—CF$_3$, —SH, —O—(C$_{1-5}$ alkyl), —(CH$_2$)—O—(C$_{1-5}$ alkyl), —S—(C$_{1-5}$ alkyl), —(C$_{1-5}$ alkyl), —C$_{2-5}$ alkenyl, —C$_{2-5}$ alkynyl, —C≡C—Si(CH$_3$)$_3$, —C≡C—Si(C$_2$H$_5$)$_3$, —C(=O)—O—(C$_{1-5}$ alkyl), and —C(=O)—CF$_3$.

More preferably, the substituents can be independently selected from the group consisting of F, Cl, Br, I, —CN, methyl, ethyl, n-propyl, isopropyl, n-butyl, sec-butyl, isobutyl, tert-butyl, vinyl, allyl, ethynyl, propynyl, —C≡C—Si(CH$_3$)$_3$, —C≡C—Si(C$_2$H$_5$)$_3$, —OH, oxo, thioxo, —O—CH$_3$, —O—C$_2$H$_5$, —O—C$_3$H$_7$, —(CH$_2$)—O—CH$_3$, —(CH$_2$)—O—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —S—CH$_3$, —S—C$_2$H$_5$, —S(=O)—CH$_3$, —S(=O)$_2$—CH$_3$, —S(=O)—C$_2$H$_5$, —S(=O)$_2$—

$C_2H_5$, —NH—S(=O)$_2$—CH$_3$, —C(=O)—OH, —C(=O)—H; —C(=O)—CH$_3$, —C(=O)—C$_2$H$_5$, —C(=O)—N(CH$_3$)$_2$, —C(=O)—NH—CH$_3$, —C(=O)—NH$_2$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$, and phenyl, wherein the phenyl radical can be substituted by 1, 2, 3, 4, or 5 and preferably 1, 2, or 3 substituents independently selected from the group consisting of F, Cl, Br, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, sec-butyl, isobutyl, tert-butyl, vinyl, allyl, ethynyl, propynyl, —C≡C—Si(CH$_3$)$_3$, —C≡C—Si(C$_2$H$_5$)$_3$, —C(=O)—O—(C$_{1-5}$ alkyl), and —C(=O)—CF$_3$.

If the cycloaliphatic radicals contain one or more hetero atoms as ring members, these can preferably contain 1, 2, 3, 4, or 5 and more preferably 1, 2, or 3 hetero atom(s) as ring member(s), which can be independently selected from the group consisting of nitrogen, oxygen, and sulfur.

Examples of suitable cycloaliphatic radicals, which can be monosubstituted or polysubstituted, are cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl, morpholinyl, pyrrolidinyl, tetrahydrothiophenyl, tetrahydropyranyl, thiomorpholinyl, dioxolanyl, azepanyl, diazepanyl, and dithiolanyl.

If one or more of the substituents $R^1$ to $R^{25}$ denote an aryl or heteroaryl radical or contain an aryl or heteroaryl radical, which is monosubstituted or polysubstituted, they can preferably be substituted by optionally 1, 2, 3, 4, or 5 substituents independently selected from the group consisting of halogen, —CN, —NO$_2$, —OH, —SH, —NH$_2$, —C(=O)—OH, —(C$_{1-5}$ alkyl), —(CH$_2$)—O—(C$_{1-5}$ alkyl), —C$_{2-5}$ alkenyl, —C$_{2-5}$ alkynyl, —C≡C—Si(CH$_3$)$_3$, —C≡C—Si(C$_2$H$_5$)$_3$, —S—(C$_{1-5}$ alkyl), —O—(C$_{1-5}$ alkyl), —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$ phenyl, —S(=O)$_2$—(C$_{1-5}$ alkyl), —S(=O)—(C$_{1-5}$ alkyl), —NH—(C$_{1-5}$ alkyl), N(C$_{1-5}$Alkyl)$_2$, —C(=O)—O—(C$_{1-5}$ alkyl), —C(=O)—H; —C(=O)—(C$_{1-5}$ alkyl), —CH$_2$—O—C(=O) phenyl, —O—C(=O)—phenyl, —NH—S(=O)$_2$—(C$_{1-5}$ alkyl), —NH—C(=O)—(C$_{1-5}$ alkyl), —C(=O)—NH$_2$, —C(=O)—NH—(C$_{1-5}$ alkyl), —C(=O)—N(C$_{1-5}$ alkyl)$_2$, pyrazolyl, phenyl, furyl (furanyl), thiazolyl, thiadiazolyl, thiophenyl (thienyl), phenoxy, benzyl, and phenethyl, wherein the cyclic substituents or the cyclic radicals of these substituents can themselves be substituted by 1, 2, 3, 4, or 5 and preferably by 1, 2, 3, or 4 substituents independently selected from the group consisting of F, Cl, Br, I, —CN, —NO$_2$, —OH, —SH, —NH$_2$, —C(=O)—OH, —(C$_{1-5}$ alkyl), —(CH$_2$)—O—(C$_{1-5}$ alkyl), —C$_{2-5}$ alkenyl, —C$_{2-5}$ alkynyl, —C≡C—Si(CH$_3$)$_3$, —C≡C—Si(C$_2$H$_5$)$_3$, —S—(C$_{1-5}$ alkyl), —O—(C$_{1-5}$ alkyl), —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, and —S—CH$_2$F.

More preferably, the substituents can be independently selected from the group consisting of F, Cl, Br, I, —CN, —NO$_2$, —OH, —SH, methyl, ethyl, n-propyl, isopropyl, n-butyl, isobutyl, sec—butyl, tert—butyl, n—pentyl, neopentyl, vinyl, allyl, ethynyl, propynyl, —C≡C—Si(CH$_3$)$_3$, —C≡C—Si(C$_2$H$_5$)$_3$, —OH, —SH, —CH$_2$—O—CH$_3$, —C(=O)—OH, —CH$_2$—O—C$_2$H$_5$, —NH$_2$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$ phenyl, pyrazolyl, phenyl, —N(CH$_3$)$_2$, —N(C$_2$H$_5$)$_2$, —NH—CH$_3$, —NH—C$_2$H$_5$, —CH$_2$—O—C(↑O) phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)—phenyl, —C(=O)—NH$_2$, —C(=O)—NH—CH$_3$, —C(=O)—N(CH$_3$)$_2$, phenyl, furyl (furanyl), thiadiazolyl, thiophenyl (thienyl), phenoxy, and benzyl, wherein each of the cyclic substituents or the cyclic radicals of these substituents can themselves be substituted by 1, 2, 3, 4, or 5 and preferably by 1, 2, 3, or 4 substituents independently selected from the group consisting of F, Cl, Br, I, —CN, —NO$_2$, —OH, —SH, —NH$_2$, —C(=O)—OH, methyl, ethyl, n-propyl, isopropyl, n-butyl, isobutyl, sec-butyl, tert-butyl, n-pentyl, neopentyl, vinyl, allyl, ethynyl, propynyl, —C≡C—Si(CH$_3$)$_3$, —C≡C—Si(C$_2$H$_5$)$_3$, —CH$_2$—O—CH$_3$, —CH$_2$—O—C$_2$H$_5$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)3, —CF3, —CHF2, —CH2F, —O—CF3, —O—CHF2, —O—CH2F, —C(=O)—CF3, —S—CF3, —S—CHF2, and —S—CH$_2$F. Examples of suitable aryl radicals include phenyl, 1-naphthyl, 2-naphthyl, and anthracenyl.

If one or more of the substituents $R^1$ to $R^{25}$ denote a heteroaryl radical or contain a heteroaryl radical, their hetero atom(s) can be independently selected from preferably the group consisting of oxygen, sulfur, and nitrogen. Preferably, a heteroaryl radical can optionally contain 1, 2, 3, 4, or 5 and more preferably 1, 2, or 3 hetero atoms.

Examples of suitable heteroaryl radicals are pyrrolyl, indolyl, furyl (furanyl), benzo[b]furanyl, thienyl (thiophenyl), benzo[b]thienyl, pyrazolyl, imidazolyl, thiazolyl, dithiazolyl, thiadiazolyl, triazolyl, oxazolyl, oxadiazolyl, isoxazolyl, pyridinyl, pyridazinyl, pyrimidinyl, pyrazinyl, pyranyl, indazolyl, purinyl, indolizinyl, quinolinyl, isoquinolinyl, and quinazolinyl.

For the purposes of the present invention, a monocyclic or polycyclic ring system is to be understood as meaning monocyclic or polycyclic hydrocarbon groups which can be saturated, unsaturated, or aromatic and can optionally contain one or more hetero atoms as ring members. Such a monocyclic or polycyclic ring system can, example, be condensed (anellated) with a cycloaliphatic radical, an aryl radical, or a heteroaryl radical. If a polycyclic ring system is present, the various rings can independently show a different degree of saturation, that is to say, be saturated, unsaturated, or aromatic. The hetero atoms of each ring can be independently and preferably selected from the group consisting of oxygen, nitrogen, and sulfur. Preferably, a ring contains 0, 1, 2, 3, 4, or 5 and more preferably 0, 1, 2, or 3 hetero atoms. Preferably, the respective rings of the monocyclic or polycyclic ring system are four-membered, five-membered, or six-membered.

If one or more of the substituents $R^1$ to $R^{25}$ have a monocyclic or polycyclic ring system, which is monosubstituted or polysubstituted, this can preferably be substituted by optionally 1, 2, 3, 4, or 5 substituents, which can be independently selected from the group consisting of halogen, —CN, —NO$_2$, —OH, —SH, —NH$_2$, oxo, thioxo (=S), —C(=O)—OH, (C$_{1-5}$ alkyl), —C$_{2-5}$ alkenyl, —(C$_{2-5}$ alkynyl), —C≡C—Si(CH$_3$)$_3$, —C≡C—Si(C$_2$H$_5$)$_3$, —(CH$_2$)—O—(C$_{1-5}$ alkyl), —S—(C$_{1-5}$ alkyl), —O—(C$_{1-5}$ alkyl), —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$ phenyl, —S(=O)$_2$—(C$_{1-5}$ alkyl), —S(=O)—(C$_{1-5}$ alkyl), —NH—(C$_{1-5}$ alkyl), N(C$_{1-5}$Alkyl)(C$_{1-5}$ alkyl), —C(=O)—O—(C$_{1-5}$ alkyl), —C(=O)—H, —C(=O)—(C$_{1-5}$ alkyl), —CH$_2$—O—C(=O) phenyl, —O—C(=O)—phenyl, —NH—S(=O)$_2$—(C$_{1-5}$ alkyl), —NH—C(=O)—(C$_{1-5}$ alkyl), —C(=O)—NH$_2$, —C(=O)—NH—(C$_{1-5}$ alkyl), —C(=O)—N(C$_{1-5}$ alkyl)$_2$, pyrazolyl, phenyl, furyl (furanyl), thiadiazolyl, thiophenyl (thienyl), phenoxy, and benzyl, wherein each of the cyclic substituents or the cyclic radicals of these substituents can themselves be substituted by 1, 2, 3, 4, or 5 and preferably by 1, 2, 3, or 4 substituents independently selected from the group consisting of F, Cl, Br, I, —CN, —CF$_3$, —OH, —NH$_2$, —O—CF$_3$, —SH, —O—(C$_{1-5}$ alkyl), —(CH$_2$)—O—(C$_{1-5}$ alkyl), —S—(C$_{1-5}$ alkyl), —(C$_{1-5}$ alkyl), —C$_{2-5}$ alkenyl, —C$_{2-5}$ alkynyl, —C≡C—Si(CH$_3$)$_3$, —C≡C—Si(C$_2$H$_5$)$_3$, —C(=O)—O—(C$_{1-5}$ alkyl), and —C(=O)—CF$_3$.

More preferably, the substituents can be independently selected from the group consisting of F, Cl, Br, I, —CN, —NO$_2$, —OH, —SH, methyl, ethyl, n-propyl, isopropyl, n-butyl, isobutyl, sec-butyl, tert-butyl, n-pentyl, neopentyl, vinyl, allyl, ethynyl, propynyl, —C≡C—Si(CH$_3$)$_3$, —C≡C—Si(C$_2$H$_5$)$_3$, —OH, —SH, —C≡C—Si(CH$_3$)$_3$, oxo, —C(=O)—OH, —C≡C—Si(C$_2$H$_5$)$_3$, —CH$_2$—O—CH$_3$, —CH$_2$—O—C$_2$H$_5$, —NH$_2$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —O—CH$_3$, —O—C$_2$H$_5$, —O—C$_3$H$_7$, —O—C(CH$_3$)$_3$, —CF$_3$, —CHF$_2$, —CH$_2$F, —O—CF$_3$, —O—CHF$_2$, —O—CH$_2$F, —C(=O)—CF$_3$, —S—CF$_3$, —S—CHF$_2$, —S—CH$_2$F, —S(=O)$_2$ phenyl, pyrazolyl, phenyl, —N(CH$_3$)$_2$, —N(C$_2$H$_5$)$_2$, —NH—CH$_3$, —NH—C$_2$H$_5$, —CH$_2$—O—C(=O) phenyl, —NH—S(=O)$_2$—CH$_3$, —C(=O)—O—CH$_3$, —C(=O)—O—C$_2$H$_5$, —C(=O)—O—C(CH$_3$)$_3$, —C(=O)—H, —C(=O)—CH$_3$, —C(=O)—C$_2$H$_5$, —NH—C(=O)—CH$_3$, —NH—C(=O)—C$_2$H$_5$, —O—C(=O)—phenyl, —C(=O)—NH$_2$, —C(=O)—NH—CH$_3$, —C(=O)—N(CH$_3$)$_2$, phenyl, furyl (furanyl), thiadiazolyl, thiophenyl (thienyl), phenoxy, and benzyl, wherein the cyclic substituents or the cyclic radicals of these substituents can themselves be substituted by 1, 2, 3, 4, or 5 and preferably by 1, 2, 3, or 4 substituents independently selected from the group consisting of F, Cl, Br, I, —CN, —CF$_3$, —OH, —NH$_2$, —O—CF$_3$, —SH, —O—CH$_3$, —O—C$_2$H$_5$, —O—C$_3$H$_7$, methyl, ethyl, n-propyl, isopropyl, n-butyl, sec-butyl, isobutyl, tert-butyl, vinyl, allyl, ethynyl, propynyl, —C≡C—Si(CH$_3$)$_3$, —C≡C—Si(C$_2$H$_5$)$_3$, —C(=O)—O—(C$_{1-5}$ alkyl), and —C(=O)—CF$_3$.

If one of the aforementioned substituents R$^1$ to R$^{25}$ exhibits a linear or branched alkylene group, alkenylene group, or alkynylene group, which is monosubstituted or polysubstituted, this can optionally preferably contain 1, 2, 3, 4, or 5 and more preferably 1, 2, or 3 substituents, which are independently and preferably selected from the group consisting of F, Cl, Br, —OH, and unsubstituted phenyl.

If an alkylene group, alkenylene group, or alkynylene group contains one or more, preferably 1, 2, or 3 hetero atoms as link(s), this can preferably be selected from the group consisting of oxygen, sulfur, and nitrogen (NH).

Mention may be made, example, of alkylene, alkenylene, or alkynylene groups, such as —(CH$_2$)—, —(CH$_2$)$_2$—, —C(H)(CH$_3$)—, —(CH$_2$)$_3$—, —(CH$_2$)$_4$—, —(CH$_2$)$_5$—, —C(H)(CH$_2$ phenyl)—, —C(H)—(phenyl), —C(H)(C(H)(CH$_3$)$_2$)—, —C(C$_2$H$_5$)(H)—, —(CH$_2$)—O—, —(CH$_2$)$_2$—O—, —(CH$_2$)$_3$—O—, —(CH$_2$)$_4$—O—, —O—(CH$_2$)—, —O—(CH$_2$)$_2$—, —O—(CH$_2$)$_3$—, —O—(CH$_2$)$_4$—, —C(C$_2$H$_5$)(H)—O—, —O—C(C$_2$H$_5$)(H)—, —CH$_2$—O—CH$_2$—, —CH$_2$—S—CH$_2$—, —C(CH$_3$)$_2$—, —C(H)(CH$_3$)—, —CH=CH—, and —C≡C—.

Preference is given to 1-propriolylpiperazines corresponding to formula I referred to above, in which:

X denotes N or C—R$^2$,

R$^1$ denotes a hydrogen, or a halogen radical, or a nitro group, or a cyano group, an amino group, a hydroxyl group, a thiol group, or a carboxyl group, or a formyl group, an —NH—C(=O)—H group, an —NH—R$^5$ group, an —NR$^6$R$^7$ group, or a —C(=O)—R$^8$ group, or a —C(=O)—O—R$^9$ group, an —O—C(=O)—R$^{10}$ group, an —NH—C(=O)—R$^{11}$ group, or an —NR$^{12}$—C(=O)—R$^{13}$ group, or a —C(=O)—NH$_2$ group, a —C(=O)—NH—R$^{14}$ group, a —C(=O)—NR$^{15}$R$^{16}$ group, or an —O—R$^{17}$ group, or an —S—R$^{18}$ group, an —S(=O)—R$^{19}$ group, an —S(=O)$_2$—R$^{20}$ group, an —NH—C(=O)—NH—R$^{21}$ group, an —NH—C(=S)—NH—R$^{22}$ group, or an —NH—S(=O)$_2$—R$^{23}$ group, or an —NR$^{24}$—S(=O)$_2$—R$^{25}$ group, a linear or branched, saturated or unsaturated, unsubstituted or at least monosubstituted aliphatic C$_{1-8}$ radical optionally containing 1, 2, or 3 hetero atoms independently selected from the group consisting of oxygen, sulfur, and nitrogen, as link(s), an unsubstituted or at least monosubstituted, unsaturated or saturated three-membered, four-membered, five-membered, six-membered, seven-membered, eight-membered, or nine-membered cycloaliphatic radical optionally containing at least one hetero atom as ring member, which cycloaliphatic radical can be bonded via a linear or branched, unsubstituted or at least monosubstituted C$_{1-5}$ alkylene group, C$_{2-5}$ alkenylene group, or C$_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl or heteroaryl radical, which can be bonded via a linear or branched, unsubstituted or at least monosubstituted C$_{1-5}$ alkylene group, C$_{2-5}$ alkenylene group, or C$_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, R$^2$ denotes a hydrogen, or a halogen radical, or a nitro group, or a cyano group, an amino group, a hydroxyl group, a thiol group, or a carboxyl group, or a formyl group, an —NH—C(=O)—H group, an —NH—R$^5$ group, an —NR$^6$R$^7$ group, or a —C(=O)—R$^8$ group, or a —C(=O)—O—R$^9$ group, an —O—C(=O)—R$^{10}$ group, an —NH—C(=O)—R$^{11}$ group, or an —NR$^{12}$—C(=O)—R$^{13}$ group, or a —C(=O)—NH$_2$ group, a —C(=O)—NH—R$^{14}$ group, a —C(=O)—NR$^{15}$R$^{16}$ group, or an —O—R$^{17}$ group, or an —S—R$^{18}$ group, an —S(=O)—R$^{19}$ group, an —S(=O)$_2$—R$^{20}$ group, an —NH—C(=O)—NH—R$^{21}$ group, an —NH—C(=S)—NH—R$^{22}$ group, or an —NH—S(=O)$_2$—R$^{23}$ group, or an —NR$^{24}$—S(=O)$_2$—R$^{25}$ group, a linear or branched, saturated or unsaturated, unsubstituted or at least monosubstituted aliphatic C$_{1-8}$ radical optionally containing 1, 2, or 3 hetero atoms independently selected from the group consisting of oxygen, sulfur, and nitrogen, as link(s), an unsubstituted or at least monosubstituted, unsaturated or saturated three-membered, four-membered, five-membered, six-membered, seven-membered, eight-membered, or nine-membered cycloaliphatic radical optionally containing at least one hetero atom as ring member, which cycloaliphatic radical can be bonded via a linear or branched, unsubstituted or at least monosubstituted $C_{1-5}$ alkylene group, $C_{2-5}$ alkenylene group, or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl or heteroaryl radical, which can be bonded via a linear or branched, unsubstituted or at least monosubstituted $C_{1-5}$ alkylene group, $C_{2-5}$ alkenylene group, or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polyclic ring system, $R^3$ denotes a halogen radical, or a nitro group, or a cyano group, an amino group, a hydroxyl group, a thiol group, or a carboxyl group, or a formyl group, an —NH—C(=O)—H group, an oxo group (=O), an —NH—$R^5$ group, an —NR$^6$R$^7$ group, or a —C(=O)—R$^8$ group, or a —C(=O)—O—R$^9$ group, an —O—C(=O)—R$^{10}$ group, an —NH—C(=O)—R$^{11}$ group, or —NR$^{12}$—C(=O)—R$^{13}$ group, a —C(=O)—NH$_2$ group, a —C(=O)—NH—R$^{14}$ group, or a —C(=O)—NR$^{15}$R$^{16}$ group, or an —O—R$^{17}$ group, or an —S—R$^{18}$ group, an —S(=O)—R$^{19}$ group, or an —S(=O)$_2$—R$^{20}$ group, an —NH—C(=)—NH—R$^{21}$ group, an —NH—C(=S)—NH—R$^{22}$ group, or an —NH—S(=O)$_2$—R$^{23}$ group, or an —NR$^{24}$—S(=O)$_2$—R$^{25}$ group, a linear or branched, saturated or unsaturated, unsubstituted or at least monosubstituted aliphatic $C_{1-8}$ radical optionally containing 1, 2, or 3 hetero atoms independently selected from the group consisting of oxygen, sulfur, and nitrogen, as link(s), an unsubstituted or at least monosubstituted, unsaturated or saturated three-membered, four-membered, five-membered, six-membered, seven-membered, eight-membered, or nine-membered cycloaliphatic radical optionally containing at least one hetero atom as ring member, which cycloaliphatic radical can be bonded via a linear or branched, unsubstituted or at least monosubstituted $C_{1-5}$ alkylene group, $C_{2-5}$ alkenylene group, or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl or heteroaryl radical, which can be bonded via a linear or branched, unsubstituted or at least monosubstituted $C_{1-5}$ alkylene group, $C_{2-5}$ alkenylene group, or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, $R^4$ denotes a hydrogen, a linear or branched, saturated or unsaturated, unsubstituted or at least monosubstituted aliphatic $C_{1-8}$ radical, an unsubstituted or at least monosubstituted, unsaturated or saturated three-membered, four-membered, five-membered, six-membered, seven-membered, eight-membered, or nine-membered cycloaliphatic radical optionally containing at least one hetero atom as ring member, which cycloaliphatic radical can be bonded via a linear or branched, unsubstituted or at least monosubstituted $C_{1-5}$ alkylene group, $C_{2-5}$ alkenylene group, or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl or heteroaryl radical, which can be bonded via a linear or branched, unsubstituted or at least monosubstituted $C_{1-5}$ alkylene group, $C_{2-5}$ alkenylene group, or $C_{2-5}$ alkynylene group optionally containing 1, 2, or 3 hetero atoms independently selected from the group consisting of oxygen, sulfur, and nitrogen, as link(s) and/or optionally condensed with an unsubstituted or at least monosubstituted monocyclic or polycyclic ring system, $R^5$ to $R^{25}$ each independently denote a linear or branched, saturated or unsaturated, unsubstituted or at least monosubstituted aliphatic $C_{1-8}$ radical, an unsubstituted or at least monosubstituted, unsaturated or saturated three-membered, four-membered, five-membered, six-membered, seven-membered, eight-membered, or nine-membered cycloaliphatic radical optionally containing at least one hetero atom as ring member, which cycloaliphatic radical can be bonded via a linear or branched, unsubstituted or at least monosubstituted $C_{1-5}$ alkylene group, $C_{2-5}$ alkenylene group, or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl or heteroaryl radical, which can be bonded via a linear or branched, unsubstituted or at least monosubstituted $C_{1-5}$ alkylene group, $C_{2-5}$ alkenylene group, or $C_{2-5}$ alkynylene group optionally containing 1, 2, or 3 hetero atoms independently selected from the group consisting of oxygen, sulfur, and nitrogen, as link(s) and/or optionally condensed with an unsubstituted or at least monosubstituted monocyclic or polycyclic ring system, and n is equal to 0, 1, 2, 3, 4, 5, 6, 7, or 8, in each case optionally in the form of pure stereoisomers thereof particularly enantiomers or diastereoisomers, the racemates thereof or in the form of a mixture of stereoisomers, particularly the enantiomers and/or diastereoisomers, in an arbitrary mixture ratio, or in each case in the form of appropriate salts thereof, or in each case in the form of appropriate solvates thereof.

Preference is also given to substituted 1-propiolylpiperazines of the aforementioned general formula I, in which X denotes N or C—$R^2$, n is equal to 0, 1, 2, 3, 4, 5, 6, 7, or 8, $R^1$ and $R^2$ each independently denote a hydrogen, a halogen radical, or a nitro group, or a cyano group, an amino group, a hydroxyl group, a thiol group, or a carboxyl group, or a formyl group, an —NH—C(=O)—H group, an —NH—$R^5$ group, an —NR$^6$R$^7$ group, or a —C(=O)—R$^8$ group, or a —C(=O)—O—R$^9$ group, an —O—C(=O)—R$^{10}$ group, an —NH—C(=O)—R$^{11}$ group, or an —NR$^{12}$—C(=O)—R$^{13}$ group, or a —C(=O)—NH$_2$ group, a —C(=O)—NH—R$^{14}$ group, a —C(=O)—NR$^{15}$R$^{16}$ group, or an —O—R$^{17}$ group, or an —S—R$^{18}$ group, an —S(=O)—R$^{19}$ group, an —S(=O)$_2$—R$^{20}$ group, an —NH—C(=O)—NH—R$^{21}$ group, an —NH—C(=S)—NH—R$^{22}$ group, or an —NH—S(=O)$_2$—R$^{23}$ group, or an —NR$^{24}$—S(=O)$_2$—R$^{25}$ group, a linear or branched, saturated or unsaturated, unsubstituted or at least monosubstituted aliphatic C$_{1-8}$ radical optionally containing 1, 2, or 3 hetero atoms independently selected from the group consisting of oxygen, sulfur, and nitrogen, as link(s), an unsubstituted or at least monosubstituted, unsaturated or saturated three-membered, four-membered, five-membered, six-membered, seven-membered, eight-membered, or nine-membered cycloaliphatic radical which optionally contains at least one hetero atom as ring member and which can be bonded via a linear or branched, unsubstituted or at least monosubstituted C$_{1-5}$ alkylene group, C$_{2-5}$ alkenylene group, or C$_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl or heteroaryl radical, which can be bonded via a linear or branched, unsubstituted or at least monosubstituted C$_{1-5}$ alkylene group, C$_{2-5}$ alkenylene group, or C$_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, R$^3$ denotes a halogen radical, or a nitro group, or a cyano group, an amino group, a hydroxyl group, a thiol group, or a carboxyl group, or a formyl group, an —NH—C(=O)—H group, an oxo group (=O), an —NH—R$^5$ group, an —NR$^6$R$^7$ group, or a —C(=O)—R$^8$ group, or a —C(=O)—O—R$^9$ group, an —O—C(=O)—R$^{10}$ group, an —NH—C(=O)—R$^{11}$ group, or —NR$^{12}$—C(=O)—R$^{13}$ group, a —C(=O)—NH$_2$ group, a —C(=O)—NH—R$^{14}$ group, or a —C(=O)—NR$^{15}$R$^{16}$ group, or an —O—R$^{17}$ group, an —S—R$^{18}$ group, an —S(=O)—R$^{19}$ group, or an —S(=O)$_2$—R$^{20}$ group, an —NH—C(=O)—NH—R$^{21}$ group, an —NH—C(=S)—NH—R$^{22}$ group, or an —NH—S(=O)$_2$—R$^{23}$ group, or an —NR$^{24}$—S(=O)$_2$—R$^{25}$ group, a linear or branched, saturated or unsaturated, unsubstituted or at least monosubstituted aliphatic C$_{1-8}$ radical optionally containing 1, 2, or 3 hetero atoms independently selected from the group consisting of oxygen, sulfur, and nitrogen, as link(s), an unsubstituted or at least monosubstituted, unsaturated or saturated three-membered, four-membered, five-membered, six-membered, seven-membered, eight-membered, or nine-membered cycloaliphatic radical which optionally contains at least one hetero atom as ring member and which can be bonded via a linear or branched, unsubstituted or at least monosubstituted C$_{1-5}$ alkylene group, C$_{2-5}$ alkenylene group, or C$_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl or heteroaryl radical, which can be bonded via a linear or branched, unsubstituted or at least monosubstituted C$_{1-5}$ alkylene group, C$_{2-5}$ alkenylene group, or C$_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system R$^4$ denotes a hydrogen, a —C(=O)—NH$_2$ group, a —C(=O)—NH—R$^{14}$ group, a —C(=O)—NR$^{15}$R$^{16}$ group, a linear or branched, saturated or unsaturated, unsubstituted or at least monosubstituted aliphatic C$_1$ radical, an unsubstituted or at least monosubstituted, unsaturated or saturated three—membered, four-membered, five-membered, six-membered, seven-membered, eight-membered, or nine-membered cycloaliphatic radical which optionally contains at least one hetero atom as ring member and which can be bonded via a linear or branched, unsubstituted or at least monosubstituted C$_{1-5}$ alkylene group, C$_{2-5}$ alkenylene group, or C$_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl or heteroaryl radical, which can be bonded via a linear or branched, unsubstituted or at least monosubstituted C$_{1-5}$ alkylene group, C$_{2-5}$ alkenylene group, or C$_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, and R$^5$ to R$^{25}$ each independently denote a linear or branched, saturated or unsaturated, unsubstituted or at least monosubstituted aliphatic C$_{1-8}$ radical, an unsubstituted or at least monosubstituted, unsaturated or saturated three-membered, four-membered, five-membered, six-membered, seven-membered, eight-membered, or nine-membered cycloaliphatic radical which optionally contains at least one hetero atom as ring member and which can be bonded via a linear or branched, unsubstituted or at least monosubstituted C$_{1-5}$ alkylene group, C$_{2-5}$ alkenylene group, or C$_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl or heteroaryl radical, which can be bonded via a linear or branched, unsubstituted or at least monosubstituted C$_{1-5}$ alkylene group, C$_{2-5}$ alkenylene group, or C$_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system;

wherein the aforementioned cycloaliphatic radicals can optionally contain 1, 2, 3, 4, or 5 hetero atom(s) as ring member(s), which can be independently selected from the group consisting of nitrogen, oxygen, and sulfur, and the rings of the aforementioned monocyclic or bicyclic ring systems are each four-membered, five-membered, or six-membered and each has optionally 0, 1, 2, 3, 4, or 5 hetero atom(s) as ring member(s), which are independently selected from the group consisting of oxygen, nitrogen, and sulfur;

and the aforementioned heteroaryl radicals can optionally have 1, 2, 3, 4, or 5 hetero atom(s) as ring member(s), which can be independently selected from the group consisting of oxygen, sulfur, and nitrogen;

in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

Preference is also given to substituted 1-propiolylpiperazines of the above general formula I, in which $R^1$ denotes a hydrogen, a halogen radical selected from the group consisting of F, Cl, Br, and I, a nitro group, a $CF_3$ group, a cyano group, an amino group, a hydroxyl group, a thiol group, a carboxyl group, an —NH—$R^5$ group, an —NR$^6$R$^7$ group, a —C(=O)—R$^8$ group, a —C(=O)—O—R$^9$ group, an —O—C(=O)—R$^{10}$ group, a —C(=O)—NH$_2$ group, a —C(=O)—NH—R$^{14}$ group, a —C(=O)—NR$^{15}$R$^{16}$ group, an —O—R$^{17}$ group, an —S—R$^{18}$ group, an —S(=O)—R$^{19}$ group, an —S(=O)$_2$—R$^{20}$ group, a linear or branched $C_{1-8}$ alkyl radical, a linear or branched $C_{2-8}$ alkenyl radical, a linear or branched $C_{2-8}$ alkynyl radical, an unsubstituted or at least monosubstituted unsaturated or three-membered, four-membered, five-membered, six-membered, or seven-membered saturated cycloaliphatic radical optionally containing 1, 2, or 3 hetero atoms independently selected from the group consisting of oxygen, sulfur, and nitrogen, as link(s), which can be bonded via a linear or branched, unsubstituted or at least monosubstituted $C_{1-5}$ alkylene group, $C_{2-5}$ alkenylene group or $C_{2-5}$ alkynylene group or an unsubstituted or at least monosubstituted five-membered to fourteen-membered aryl or heteroaryl radical, which can be bonded via a linear or branched, unsubstituted or at least monosubstituted $C_{1-5}$ alkylene group, $C_{2-5}$ alkenylene group or $C_{2-5}$ alkynylene group, and in each case the remaining radicals X, n, $R^2$, $R^3$, $R^4$, and $R^5$ to $R^{25}$ have the meanings stated above, in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

More preferably $R^1$ denotes a hydrogen, or a halogen radical selected from the group consisting of F, Cl, and Br, or a $CF_3$ group, a nitro group, a cyano group, an amino group, or a hydroxyl group, or a thiol group, a carboxyl group, an —NH—$R^5$ group, or an —NR$^6$R$^7$ group, or a —C(=O)—R$^8$ group, a —C(=O)—O—R$^9$ group, an —O—C(=O)—R$^{10}$ group, or a —C(=O)—NH—R$^{14}$ group, or a —C(=O)—NR$^{15}$R$^{16}$ group, an —O—R$^{17}$ group, an —S—R$^{18}$ group, or an —S(=O)—R$^{19}$ group, or an —S(=O)$_2$—R$^{20}$ group, a linear or branched $C_{1-4}$ alkyl radical, a linear or branched $C_{2-4}$ alkenyl radical, a linear or branched $C_{2-4}$ alkynyl radical, or a radical selected from the group consisting of cyclopropyl group, cyclobutyl group, cyclopentyl group, cyclohexyl group, pyrrolidinyl group, tetrahydrofuranyl group, tetrahydrothiophenyl group piperidinyl group, tetrahydropyranyl group, piperazinyl group, morpholinyl group, thiomorpholinyl group, dioxolanyl group, azepanyl group, diazepanyl group, imidazolidinyl group, phenyl, naphthyl group, anthracenyl group, pyrrolyl group, indolyl group, furanyl group, benzo[b]furanyl group, thiophenyl group, benzo[b]thiophenyl group, pyrazolyl group, imidazolyl group, thiazolyl group, dithiazolyl group, thiadiazolyl group, triazolyl group, oxazolyl group, oxadiazolyl group, isoxazolyl group, pyridinyl group, pyridazinyl group, pyrimidinyl group, pyrazinyl group, pyranyl group, indazolyl group, purinyl group, indolizinyl group, quinolinyl radical, isoquinolinyl radical, and quinazolinyl radical, each of which can be bonded via a $C_{1-3}$ alkylene group, $C_{2-5}$ alkenylene group or $C_{2-3}$ alkynylene group and/or is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —NH—S(=O)$_2$—CH$_3$, —C(=O)—OH, —C(=O)—CH$_3$, —C(=O)—C$_2$H$_5$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, and —C(=O)—O—C$_2$H$_5$.

Most preferably R1 denotes a hydrogen, or a halogen radical selected from the group consisting of F, Cl, and Br, or a $CF_3$ group, or a nitro group, a cyano group, an amino group, or a dimethylamino group, or a diethylamino group, a monomethylamino group, a monoethylamino group, or a hydroxyl group, or a thiol group, a carboxyl group, a —C(=O)—O—CH$_3$ group, or a —C(=O)—O—C$_2$H$_5$ group, or a —C(=O)—NH—R$^{14}$ group, a —C(=O)—NR$^{15}$R$^{16}$ group, an —O—R$^{17}$ group, or an —S—R$^{18}$ group, or an —S(=O)—R$^{19}$ group, an —S(=O)$_2$—R$^{20}$ group, an alkyl radical selected from the group consisting of methyl, ethyl, n-propyl, isopropyl, n-butyl, sec-butyl, isobutyl, and tert-butyl, or an alkenyl radical selected from the group consisting of vinyl, 1-propenyl, 2-propenyl, 1-butenyl, 2-butenyl, and 3-butenyl, or an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH$_3$, —O—C$_2$H$_5$, and —O—C$_3$H$_7$.

Preference is also given to substituted 1-propiolylpiperazines of the above general formula I in which $R^2$ denotes a hydrogen, a halogen radical selected from the group consisting of F, Cl, Br, and I, a nitro group, a $CF_3$ group, a cyano group, an amino group, a hydroxyl group, a thiol group, a carboxyl group, an —NH—$R^5$ group, an —NR$^6$R$^7$ group, a —C(=O)—R$^8$ group, a —C(=O)—O—R$^9$ group, an —O—C(=O)—R$^{10}$ group, a —C(=O)—NH$_2$ group, a —C(=O)—NH—R$^{14}$ group, a —C(=O)—NR$^{15}$R$^{16}$ group, an —O—R$^{17}$ group, an —S—R$^{18}$ group, an —S(=O)—R$^{19}$ group, an —S(=O)$_2$—R$^{20}$ group, a linear or branched $C_{1-8}$ alkyl radical, a linear or branched $C_{2-8}$ alkenyl radical, a linear or branched $C_{2-8}$ alkynyl radical, or an unsubstituted or at least monosubstituted unsaturated or saturated three-membered, four-membered, five-membered, six-membered, or seven-membered cycloaliphatic radical optionally containing 1, 2, or 3 hetero atoms independently selected from the group consisting of oxygen, sulfur, and nitrogen, as ring member(s), which can be bonded via a linear or branched, unsubstituted or at least monosubstituted $C_{1-5}$ alkylene group, $C_{2-5}$ alkenylene group or $C_{2-5}$ alkynylene group or denotes an unsubstituted or at least monosubstituted five-membered to fourteen-membered aryl or heteroaryl radical, which can be bonded via a linear or branched, unsubstituted or at least monosubstituted $C_{1-5}$ alkylene group, $C_{2-5}$ alkenylene group or $C_{2-5}$ alkynylene group, and in each case the remaining radicals X, n, $R^1$, $R^3$, $R^4$, and $R^5$ to $R^{25}$ have the meanings stated above, in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

More preferably $R^2$ denotes a hydrogen, or a halogen radical selected from the group consisting of F, Cl, and Br, or a $CF_3$ group, a nitro group, a cyano group, an amino group, or a hydroxyl group, or a thiol group, a carboxyl group, an —NH—$R^5$ group, or an —NR$^6$R$^7$ group, or a —C(=O)—R$^8$ group, a —C(=O)—O—R$^9$ group, an —O—C(=O)—R$^{10}$ group, or a —C(=O)—NH—R$^{14}$ group, or a —C(=O)—NR$^{15}$R$^{16}$ group, an —S(=O)—R$^{19}$ group, an —S(=O)$_2$—R$^{20}$ group, or an —O—R$^{17}$ group, or an —S—R$^{18}$ group, a linear or branched $C_{1-4}$ alkyl radical, or a linear or branched $C_{2-4}$ alkenyl radical, or a linear or branched $C_{2-4}$ alkynyl radical, or a radical selected from the group consisting of a cyclopropyl group, a cyclobutyl group, a cyclopentyl group, a cyclohexyl group, a pyrrolidinyl group, a tetrahydrofuranyl group, a tetrahydrothiophenyl group piperidinyl group, a tetrahydropyranyl group, a piperazinyl group, a morpholinyl group, a thiomorpholinyl group, a dioxolanyl group, an azepanyl group, a diazepanyl group, an imidazolidinyl group, a phenyl, a naphthyl group, an anthracenyl group, a pyrrolyl group, an indolyl group, a furanyl group, a benzo[b]furanyl group, a thiophenyl group, a benzo[b]thiophenyl group, a pyrazolyl group, an imidazolyl group, a thiazolyl group, a dithiazolyl group, a thiadiazolyl group, a triazolyl group, an oxazolyl group, an oxadiazolyl group, an isoxazolyl group, a pyridinyl group, a pyridazinyl group, a pyrimidinyl group, a pyrazinyl group, a pyranyl group, an indazolyl group, a purinyl group, an indolizinyl group, a quinolinyl radical, an isoquinolinyl radical, and a quinazolinyl radical, each of which can be bonded via a $C_{1-3}$ alkylene group, $C_{2-3}$ alkenylene group or $C_{2-3}$ alkynylene group and/or is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —NH—S(=O)$_2$—CH$_3$, —C(=O)—OH, —C(=O)—CH$_3$, —C(=O)—C$_2$H$_5$, —C(=O)—N(CH$_3$)$_2$, —C(=O)—N H—CH$_3$, —NH—C(=O)—CH$_3$, —NH—C(=O)—C$_2$H$_5$, —C(=O)—O—CH$_3$, and —C(=O)—O—C$_2$H$_5$.

Most preferably $R^2$ denotes a hydrogen, or a halogen radical selected from the group consisting of F, Cl, and Br, or a $CF_3$ group, or a nitro group, a cyano group, an amino group, or a dimethylamino group, or a diethylamino group, a monomethylamino group, a monoethylamino group, or a hydroxyl group, or a thiol group, a carboxyl group, a —C(=O)—O—CH$_3$ group, or a —C(=O)—O—C$_2$H$_5$ group, or a —C(=O)—NH—R$^{14}$ group, a —C(=O)—NR$^{15}$R$^{16}$ group, an —O—R$^{17}$ group, or an —S—R$^{18}$ group, or an —S(=O)—R$^{19}$ group, an —S(=O)$_2$—R$^{20}$ group, an alkyl radical selected from the group consisting of methyl, ethyl, n-propyl, isopropyl, n-butyl, sec-butyl, isobutyl, and tert-butyl, or an alkenyl radical selected from the group consisting of vinyl, 1-propenyl, 2-propenyl, 1-butenyl, 2-butenyl, and 3-butenyl, or an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH$_3$, —O—C$_2$H$_5$, and —O—C$_3$H$_7$.

Preference is also given to substituted 1-propiolylpiperazines of the above general formula I, in which $R^3$ denotes a halogen radical selected from the group consisting of F, Cl, and Br, a nitro group, a cyano group, an amino group, a hydroxyl group, a thiol group, a carboxyl group, an oxo group (O), or a linear or branched $C_{1-4}$ alkyl radical, or a radical selected from the group consisting of a cyclopropyl group, a cyclobutyl group, a cyclopentyl group, a cyclohexyl group, a pyrrolidinyl group, a tetrahydrofuranyl group, a tetrahydrothiophenyl group piperidinyl group, a tetrahydropyranyl group, a piperazinyl group, a morpholinyl group, a thiomorpholinyl group, a dioxolanyl group, an azepanyl group, a diazepanyl group, an imidazolidinyl group, a phenyl, a naphthyl group, an anthracenyl group, a pyrrolyl group, an indolyl group, a furanyl group, a benzo[b]furanyl group, a thiophenyl group, a benzo[b]thiophenyl group, a pyrazolyl group, an imidazolyl group, a thiazolyl group, a dithiazolyl group, a thiadiazolyl group, a triazolyl group, an oxazolyl group, an oxadiazolyl group, an isoxazolyl group, a pyridinyl group, a pyridazinyl group, a pyrimidinyl group, a pyrazinyl group, a pyranyl group, an indazolyl group, a purinyl group, an indolizinyl group, a quinolinyl radical, an isoquinolinyl radical, and a quinazolinyl radical, which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH$_3$, —O—C$_2$H$_5$, and —O—C$_3$H$_7$, and each of the remaining radicals X, n, $R^1$, $R^2$, $R^4$, and $R^5$ to $R^{25}$ has the meanings stated above, in each case optionally in the form of a pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

More preferably $R^3$ denotes an oxo group (=O), an alkyl radical selected from the group consisting of methyl, ethyl, n-propyl, isopropyl, n-butyl, sec-butyl, isobutyl, and tert-butyl or denotes a phenyl radical, which is unsubstituted or substituted by 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH$_3$, —O—C$_2$H$_5$, and —O—C$_3$H$_7$.

The person skilled in the art will appreciate that in any one case it is possible to select 1, 2, 3, 4, 5, 6, 7, or 8 radicals R$^3$, which can be the same or at least some can be different.

Particular preference is given to the aforementioned radicals R$^3$ when they are bonded to the piperazinyl radical of the aforementioned general formula I in the following manner so as to give the following formulas Ib to Ii:

in each case optionally in the form of a pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

Preference is also given to substituted 1-propiolylpiperazines of the above general formula I, in which R$^4$ denotes a hydrogen, or a —C(=O)—NH$_2$ group, a —C(=O)—NH—R$^{14}$ group, or a —C(=O)—NR$^{15}$R$^{16}$ group, a linear or branched, unsubstituted or at least monosubstituted C$_{1-8}$ alkyl radical, or a linear or branched, unsubstituted or at least monosubstituted C$_{2-8}$ alkenyl radical, or a linear or branched, unsubstituted or at least monosubstituted C$_{2-8}$ alkynyl radical, or an unsubstituted or at least monosubstituted unsaturated or saturated four-membered, five-membered, six-membered, or seven-membered cycloaliphatic radical, which can be condensed with an unsaturated, saturated or aromatic, unsubstituted or at least monosubstituted monocyclic or bicyclic ring system, while each of the rings can contain 1, 2, or 3 hetero atoms, which can be independently selected from the group consisting of oxygen, nitrogen, and sulfur and ?? and each of the rings of the monocyclic or bicyclic ring system is four-membered, five-membered, or six-membered, or an unsubstituted or at least monosubstituted five-membered, or six-membered aryl or heteroaryl radical, which can be condensed with a saturated, unsaturated or aromatic, unsubstituted or at least monosubstituted monocyclic or bicyclic ring system, while the heteroaryl radical and optionally one or both rings of the monocyclic or bicyclic ring system each have 1, 2, or 3 hetero atoms, which can be independently selected from the group consisting of oxygen, nitrogen, and sulfur and each of the rings of the monocyclic or bicyclic ring system is four-membered, five-membered, or six-membered, and in each case the remaining radicals X, n, $R^1$, $R^2$, $R^3$, and $R^5$ to $R^{25}$ have the meanings stated above, in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

More preferably R4 denotes a hydrogen, or a —C(=O)—NH$_2$ group, a —C(=O)—NH—$R^{14}$ group, or a —C(=O)—$NR^{15}R^{16}$ group, an alkyl radical selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, n-heptyl, and n-octyl, or a radical selected from the group consisting of cyclopropyl, cyclobutyl, cyclopentyl, cyclohexyl, cycloheptyl, cyclopentenyl, cyclohexenyl, pyrrolidinyl, tetrahydrofuranyl, tetrahydrothiophenyl, piperidinyl, tetrahydropyranyl, piperazinyl, morpholinyl, thiomorpholinyl, dioxolanyl, azepanyl, diazepanyl, imidazolidinyl, phenyl, naphthyl, anthracenyl, furanyl, thiophenyl, pyrazolyl, pyrazinyl, pyrimidinyl, pyridinyl, pyrrolyl, oxazolyl, isoxazolyl, thiazolyl, dithiazolyl, oxadiazolyl, triazolyl, imidazolyl, indolyl, benzo[b]thiophenyl, benzo[b]furanyl, quinolinyl, isoquinolinyl, and quinazolyl, each of which can be optionally substituted by 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, vinyl, allyl, ethynyl, propinyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CHF$_2$, —CH$_2$F, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$, and phenyl.

Most preferably R4 denotes a hydrogen, or a —C(=O)—NH$_2$ group, a —C(=O)—NH—$R^{14}$ group, or a —C(=O)—$NR^{15}R^{16}$ group, an alkyl radical selected from the group consisting of methyl, ethyl, n-propyl, isopropyl, n-butyl, sec-butyl, isobutyl, tert-butyl, n-pentyl, sec-pentyl, neopentyl, n-hexyl, n-heptyl, and n-octyl, or a radical selected from the group consisting of cyclopropyl, cyclobutyl, cyclopentyl, cyclohexyl, cycloheptyl, cyclopentenyl, cyclohexenyl, phenyl, pyrid-2-yl, pyrid-3-yl, pyrid-4-yl, pyrrol-2-yl, pyrrol-3-yl, thiophen-2-yl, thiophen-3-yl, 4-methylthiophen-2-yl, 3-methylthiophen-2-yl, 5-methylthiophen-2-yl, furan-2-yl, furan-3-yl, imidazol-2-yl, imidazol-4-yl, thiazol-2-yl, thiazol-4-yl, thiazol-5-yl, oxazol-2-yl, oxazol-4-yl, oxazol-5-yl, (1,2,4)-thiadiazol-5-yl, (1,2,4)-oxadiazol-5-yl, naphth-1-yl, naphth-2-yl, anthracen-1-yl, anthracen-2-yl, anthracen-9-yl, indol-2-yl, indol-3-yl, and indol-4-yl, indol-5-yl, indol-6-yl, indol-7-yl, 1-methylindol-2-yl, 1-methylindol-3-yl, 1-methylindol-4-yl, 1-methylindol-5-yl, 1-methylindol-6-yl, 1-methylindol-7-yl, quinolin-3-yl, quinolin-4-yl, quinolin-2-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-hydroxyphenyl, 3-hydroxyphenyl, 4-hydroxyphenyl, 2-aminophenyl, 3-aminophenyl, 4-aminophenyl, 2-dimethylaminophenyl, 3-dimethylaminophenyl, 4-dimethylaminophenyl, and 2-methylaminophenyl, 3-methylaminophenyl, 4-methylaminophenyl, 2-acetylphenyl, 3-acetylphenyl, 4-acetylphenyl, 2-methylsulfinylphenyl, 3-methylsulfinylphenyl, 4-methylsulfinylphenyl, 2-methylsulfonylphenyl, 3-methylsulfonylphenyl, 4-methylsulfonylphenyl, 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-trifluoromethylphenyl, 3-trifluoromethylphenyl, 4-trifluoromethylphenyl, 2-difluoromethylphenyl, 3-difluoromethylphenyl, 4-difluoromethylphenyl, 2-fluoromethylphenyl, 3-fluoromethylphenyl, 4-fluoromethylphenyl, 2-nitrophenyl, 3-nitrophenyl, 4-nitrophenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-tert-butylphenyl, 3-tert-butylphenyl, 4-tert-butylphenyl, 2-carboxyphenyl, 3-carboxyphenyl, 4-carboxyphenyl, 2-vinylphenyl, 3-vinylphenyl, 4-vinylphenyl, 2-ethynylphenyl, 3-ethynylphenyl, 4-ethynylphenyl, 2-allylphenyl, 3-allylphenyl, 4-allylphenyl, 2-trimethylsilanylethynylphenyl, 3-trimethylsilanylethynylphenyl, 4-trimethylsilanylethynylphenyl, 2-formylphenyl, 3-formylphenyl, 4-formylphenyl, 2-acetaminophenyl, 3-acetaminophenyl, 4-acetaminophenyl, 2-dimethylaminocarbonylphenyl, 3-dimethylaminocarbonylphenyl, 4-dimethylaminocarbonylphenyl, 2-methoxymethylphenyl, 3-methoxymethylphenyl, 4-methoxymethylphenyl, 2-ethoxymethylphenyl, 3-ethoxymethylphenyl, 4-ethoxymethylphenyl, 2-aminocarbonylphenyl, 3-aminocarbonylphenyl, 4-aminocarbonylphenyl, 2-methylaminocarbonylphenyl, 3-methylaminocarbonylphenyl, 4-methylaminocarbonylphenyl, 2-carboxymethylesterphenyl, 3-carboxymethylesterphenyl, 4-carboxymethylesterphenyl, 2-carboxyethylesterphenyl, 3-carboxyethylesterphenyl, 4-carboxyethylesterphenyl, 2-carboxy-tert-butylesterphenyl, 3-carboxy-tert-butylesterphenyl, 4-carboxy-tert-butylesterphenyl, 2-methylmercaptophenyl, 3-methylmercaptophenyl, 4-methylmercaptophenyl, 2-ethylmercaptophenyl, 3-ethylmercaptophenyl, 4-ethylmercaptophenyl, 2-biphenyl, 3-biphenyl, 4-biphenyl, 2-bromophenyl, 3-bromophenyl, 4-bromophenyl, 2-iodophenyl, 3-iodophenyl, 4-iodophenyl, 2-trifluoromethoxyphenyl, 3-trifluoromethoxyphenyl, 4-trifluoromethoxyphenyl, 2-fluoro-3-trifluoromethylphenyl, 2-fluoro-4-methylphenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, 2-chloro-4-nitrophenyl, 2-chloro-4-methylphenyl, 2-chloro-5-trifluoromethylphenyl, 2-chloro-5-methoxyphenyl, 2-bromo-5-trifluoromethylphenyl, 2-bromo-5-methoxyphenyl, (2,4)-dibromophenyl, (2,4)-dimethylphenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-methoxy-5-nitrophenyl, and 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, (2,6)-dichlorophenyl, 3-chloro-2-fluorophenyl, 3-chloro-5-methylphenyl, (3,4)-dichlorophenyl, (3,4)-dimethylphenyl, 3-methyl-4-methoxyphenyl, 4-chloro-3-nitrophenyl, (3,4)-dimethoxyphenyl, 4-fluoro-3-trifluoromethylphenyl, 3-fluoro-4-trifluoromethylphenyl, (3,4)-difluorophenyl, 3-cyano-4-fluorophenyl, 3-cyano-4-methylphenyl, 3-cyano-4-methoxyphenyl, 3-bromo-4-fluorophenyl, 3-bromo-4-methylphenyl, 3-bromo-4-methoxyphenyl, 4-chloro-2-fluorophenyl, 4-chloro-3-trifluoromethyl, 4-bromo-3-methylphenyl, 4-bromo-5-methylphenyl, 3-chloro-4-fluorophenyl, 4-fluoro-3-nitrophenyl, 4-bromo-3-nitrophenyl, (3,4)-dibromophenyl, 4-chloro-3-methylphenyl, 4-bromo-3-methylphenyl, 4-fluoro-3-methylphenyl, 3-fluoro-4-methylphenyl, 3-fluoro-5-methylphenyl, 2-fluoro-3-methylphenyl, and 4-methyl-3-nitrophenyl, (3,5)-dimethoxyphenyl, (3,5)-dimethylphenyl, (3,5)-bis-trifluoromethylphenyl, (3,5)-difluorophenyl, (3,5)-dinitrophenyl, (3,5)-dichlorophenyl, 3-fluoro-5-trifluoromethylphenyl, 5-fluoro-3-trifluoromethylphenyl, (3,5)-dibromophenyl, 5-chloro4-fluorophenyl, 5-chloro4-fluorophenyl, 5-bromo4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methyl, (2,4,5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (3,4,5)-trimethoxyphenyl, (2,3,4,5)-tetrafluorophenyl, 4-methoxy-(2,3,6)-trimethylphenyl, 4-methoxy-(2,3,6)-trimethylphenyl, 4-chloro-2,5-dimethylphenyl, 2-chloro-6-fluoro-3-methylphenyl, 6-chloro-2-fluoro-3-methyl, (2,4,6)-trimethylphenyl, (2,3,4,5,6)-pentafluorophenyl, 3-methylpyrid-2-yl, 4-methylpyrid-2-yl, 5-methylpyrid-2-yl, 6-methylpyrid-2-yl, 2-methylpyrid-3-yl, 4-methylpyrid-3-yl, 5-methylpyrid-3-yl, 6-methylpyrid-3-yl, 2-methylpyrid-4-yl, 3-methylpyrid-4-yl, 3-fluoropyrid-2-yl, 4-fluoropyrid-2-yl, 5-fluoropyrid-2-yl, 6-fluoropyrid-2-yl, 3-chloropyrid-2-yl, 4-chloropyrid-2-yl, 5-chloropyrid-2-yl, 6-chloropyrid-2-yl, 3-trifluoromethylpyrid-2-yl, 4-trifluoromethylpyrid-2-yl, 5-trifluoromethylpyrid-2-yl, 6-trifluoromethylpyrid-2-yl, 3-methoxypyrid-2-yl, 4-methoxypyrid-2-yl, 5-methoxypyrid-2-yl, 6-methoxypyrid-2-yl, 4-methylthiazol-2-yl, 5-methylthiazol-2-yl, 4-trifluoromethylthiazol-2-yl, 5-trifluoromethylthiazol-2-yl, 4-chlorothiazol-2-yl, 5-chlorothiazol-2-yl, 4-bromothiazol-2-yl, 5-bromothiazol-2-yl, 4-fluorothiazol-2-yl, 5-fluorothiazol-2-yl, 4-cyanothiazol-2-yl, 5-cyanothiazol-2-yl, 4-methoxythiazol-2-yl, 5-methoxythiazol-2-yl, and 4-methyloxazol-2-yl, 5-methyloxazol-2-yl, 4-trifluoromethyloxazol-2-yl, 5-trifluoromethyloxazol-2-yl, 4-chloroxazol-2-yl, 5-chloroxazol-2-yl, 4-bromoxazol-2-yl, 5-bromoxazol-2-yl, 4-fluoroxazol-2-yl, 5-fluoroxazol-2-yl, 4-cyano-oxazol-2-yl, 5-cyano-oxazol-2-yl, 4-methoxyoxazol-2-yl, 5-methoxyoxazol-2-yl, 2-methyl-(1,2,4)-thiadiazol-5-yl, 2-trifluoromethyl-(1,2,4)-thiadiazol-5-yl, 2-chloro-(1,2,4)-thiadiazol-5-yl, 2-fluoro-(1,2,4)-thiadiazol-5-yl, 2-methoxy-(1,2,4)-thiadiazol-5-yl, 2-cyano-(1,2,4)-thiadiazol-5-yl, 2-methyl-(1,2,4)-oxadiazol-5-yl, 2-trifluoromethyl-(1,2,4)-oxadiazol-5-yl, 2-chloro-(1,2,4)-oxadiazol-5-yl, 2-fluoro-(1,2,4)-oxadiazol-5-yl, 2-methoxy-(1,2,4)-oxadiazol-5-yl and 2-cyano-(1,2,4)-oxadiazol-5-yl.

Preference is also given to substituted 1-propiolylpiperazines of the above general formula I in which n is equal to 0, 1, 2, 3, or 4, more preferably to 0, 1, or 2, and most preferably to 0, and each of the remaining radicals X, $R^1$, $R^2$, $R^3$, $R^4$, and $R^5$ to $R^{25}$ has the meaning stated above, in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

The person skilled in the art will appreciate that the general formula Ia is obtained when n is equal to 0:

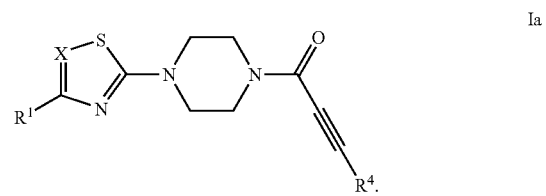

Furthermore, substituted 1-propiolylpiperazines of the above general formula I are preferred, in which $R^5$ to $R^{25}$ each independently denote a linear or branched, unsubstituted or at least monosubstituted $C_{1-8}$ alkyl radical, a linear or branched, unsubstituted or at least monosubstituted $C_{2-8}$ alkenyl radical, a linear or branched, unsubstituted or at least monosubstituted $C_{2-8}$ alkynyl radical, an unsubstituted or at least monosubstituted, unsaturated or saturated three-membered, four-membered, five-membered, six-membered, seven-membered, eight-membered, or nine-membered cycloaliphatic radical optionally containing at least one hetero atom as ring member, which cycloaliphatic radical can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), or an unsubstituted or at least monosubstituted five-membered to fourteen-membered aryl or heteroaryl radical, which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and each of the remaining radicals X, n, $R^1$, $R^2$, $R^3$ and $R^4$ has the meaning stated above, in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

More preferably $R^5$ to $R^{25}$ each independently denote an alkyl radical selected from the group consisting of methyl, ethyl, n-propyl, isopropyl, n-butyl, sec-butyl, isobutyl, and tert-butyl, or an alkenyl radical selected from the group consisting of vinyl, 1-propenyl, 2-propenyl, 1-butenyl, 2-butenyl, and 3-butenyl, or an alkynyl radical selected from the group consisting of ethynyl, 1-propynyl, 2-propynyl, 1-butynyl, 2-butynyl, and 3-butynyl, or a radical selected from the group consisting of cyclopropyl group, cyclobutyl group, cyclopentyl group, cyclohexyl group, pyrrolidinyl group, tetrahydrofuranyl group, tetrahydrothiophenyl group piperidinyl group, tetrahydropyranyl group, piperazinyl group, morpholinyl group, thiomorpholinyl group, dioxolanyl group, azepanyl group, diazepanyl group, imidazolidinyl group, phenyl, naphthyl group, anthracenyl group, pyrrolyl group, indolyl group, furanyl group, benzo[b]furanyl group, thiophenyl group, benzo[b]thiophenyl group, pyrazolyl group, imidazolyl group, thiazolyl group, dithiazolyl group, thiadiazolyl group, triazolyl group, oxazolyl group, oxadiazolyl group, isoxazolyl group, pyridinyl group, pyridazinyl group, pyrimidinyl group, pyrazinyl group, pyranyl group, indazolyl group, purinyl group, indolizinyl group, quinolinyl group, isoquinolinyl group, and quinazolinyl group, and the respective cyclic radical can be bonded via a $C_{1-3}$ alkylene group, a $C_{2-3}$ alkenylene group or a $C_{2-3}$ alkynylene group optionally exhibiting 1 or 2 hetero atoms selected from the group consisting of oxygen, sulfur, and nitrogen, as link(s), and/or is unsubstituted or substituted by 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, —O—$C_3H_7$, —$NH_2$, —$N(CH_3)_2$, —$N(C_2H_5)_2$, —NH—$CH_3$, —NH—$C_2H_5$, —$NO_2$, —$CF_3$, —O—$CF_3$, —S—$CF_3$, —SH, —NH—S($=$O)$_2$—$CH_3$, —C($=$O)—OH, —C($=$O)—$CH_3$, —C($=$O)—$C_2H_5$, —C($=$O)—$N(CH_3)_2$, —C($=$O)—N H—$CH_3$, —NH—C($=$O)—$CH_3$, —NH—C($=$O)—$C_2H_5$, —C($=$O)—O—$CH_3$, and —C($=$O)—O—$C_2H_5$.

Furthermore, substituted 1-propiolylpiperazines of the above general formula I are preferred in which X denotes C—$R^2$; and each of the remaining radicals n and $R^1$ to $R^{25}$ has the meanings stated above, in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

Preference is also given to substituted 1-propiolylpiperazines of the above general formula I in which $R^1$ denotes a hydrogen, a halogen radical selected from the group consisting of F, Cl, Br, and I, or a nitro group, a $CF_3$ group, or a cyano group, an amino group, a hydroxyl group, or a thiol group, or a carboxyl group, an —NH—$R^5$ group, an —$NR^6R^7$ group, or a —C($=$O)—$R^8$ group, or a —C($=$O)—O—$R^9$ group, an —O—C($=$O)—$R^{10}$ group, a —C($=$O)—$NH_2$ group, or a —C($=$O)—NH—$R^{14}$ group, or a —C($=$O)—$NR^{15}R^{16}$ group, an —O—$R^{17}$ group, an —S—$R^{18}$ group, or a linear or branched $C_{1-8}$ alkyl radical, or a linear or branched $C_{2-8}$ alkenyl radical or a linear or branched $C_{2-8}$ alkynyl radical, an unsubstituted or at least monosubstituted unsaturated or saturated three-membered, four-membered, five-membered, six-membered, or seven-membered cycloaliphatic radical which optionally contains 1, 2, or 3 hetero atoms independently selected from the group consisting of oxygen, sulfur, and nitrogen, as ring member(s), and which can be bonded via a linear or branched, unsubstituted or at least monosubstituted $C_{1-5}$ alkylene group, $C_{2-5}$ alkenylene group or $C_{2-5}$ alkynylene group or an unsubstituted or at least monosubstituted five-membered to fourteen-membered aryl or heteroaryl radical, which can be bonded via a linear or branched, unsubstituted or at least monosubstituted $C_{1-5}$ alkylene group, $C_{2-5}$ alkenylene group or $C_{2-5}$ alkynylene group, and each of the remaining radicals X, n, $R^2$, $R^3$, $R^4$, and $R^5$ to $R^{25}$ has the meanings stated above, in each case optionally in the form of one of the pure stereoisomers thereof, particularly enantiomers or diastereoisomers thereof, the racemates thereof or in the form of a mixture of stereoisomers thereof, particularly the enantiomers and/or diastereoisomers thereof, in an arbitrary mixture ratio, or in each case in the form of appropriate salts thereof, or in each case in the form of appropriate solvates thereof.

Preferably $R^1$ denotes a hydrogen, or a halogen radical selected from the group consisting of F, Cl, and Br, or a $CF_3$ group, a nitro group, a cyano group, an amino group, or a hydroxyl group, or a thiol group, a carboxyl group, an —NH—$R^5$ group, or an —$NR^6R^7$ group, or a —C($=$O)—$R^8$ group, a —C($=$O)—O—$R^9$ group, an —O—C($=$O)—$R^{10}$ group, or an —O—$R^{17}$ group, or an —S—$R^{18}$ group, a linear or branched $C_{1-4}$ alkyl radical, or a linear or branched $C_{2-4}$ alkenyl radical, or a linear or branched $C_{2-4}$ alkynyl radical, or a radical selected from the group consisting of cyclopropyl group, cyclobutyl group, cyclopentyl group, cyclohexyl group, pyrrolidinyl group, tetrahydrofuranyl group, tetrahydrothiophenyl group piperidinyl group, tetrahydropyranyl group, piperazinyl group, morpholinyl group, thiomorpholinyl group, dioxolanyl group, azepanyl group, diazepanyl group, imidazolidinyl group, phenyl, naphthyl group, anthracenyl group, pyrrolyl group, indolyl group, furanyl group, benzo[b]furanyl group, thiophenyl group, benzo[b]thiophenyl group, pyrazolyl group, imidazolyl group, thiazolyl group, dithiazolyl group, thiadiazolyl group, triazolyl group, oxazolyl group, oxadiazolyl group, isoxazolyl group, pyridinyl group, pyridazinyl group, pyrimidinyl group, pyrazinyl group, pyranyl group, indazolyl group, purinyl group, indolizinyl group, quinolinyl radical, isoquinolinyl radical, and quinazolinyl radical, each of which can be bonded via a $C_{1-3}$ alkylene group, $C_{2-3}$ alkenylene group or $C_{2-3}$ alkynylene group and/or is unsubstituted or substituted by 1, 2, or 3 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, —O—$C_3H_7$, —$NH_2$, —$N(CH_3)_2$, —$N(C_2H_5)_2$, —NH—$CH_3$, —NH—$C_2H_5$, —$NO_2$, —$CF_3$, —O—$CF_3$, —S—$CF_3$, —SH, —NH—S($=$O)$_2$—$CH_3$, —C($=$O)—OH, —C($=$O)—$CH_3$, —C($=$O)—$C_2H_5$, —C($=$O)—$N(CH_3)_2$, —C($=$O)—NH—$CH_3$, —NH—C($=$O)—$CH_3$, —NH—C($=$O)—$C_2H_5$, —C($=$O)—O—$CH_3$, and —C($=$O)—O—$C_2H_5$.

More preferably $R^1$ denotes a hydrogen, or a halogen radical selected from the group consisting of F, Cl, and Br, or a $CF_3$ group, or a nitro group, a cyano group, an amino group, or a dimethylamino group, or a diethylamino group, a monomethylamino group, a monoethylamino group, or a hydroxyl group, or a thiol group, a carboxyl group, a —C($=$O)—O—$CH_3$ group, or a —C($=$O)—O—$C_2H_5$ group, an alkyl radical selected from the group consisting of methyl, ethyl, n-propyl, isopropyl, n-butyl, sec-butyl, isobutyl, and tert-butyl, an alkenyl radical selected from the group consisting of vinyl, 1-propenyl, 2-propenyl, 1-butenyl, 2-butenyl, and 3-butenyl, an alkynyl radical selected from the group consisting of ethynyl, 1-propynyl, 2-propynyl, 1-butynyl, 2-butynyl, and 3-butynyl or an unsubstituted radical selected from the group consisting of ??? or (1,3)- dioxolan-2-yl, phenyl, benzyl, phenethyl, 2-pyridyl, 3-pyridyl, 4-pyridyl, 2-thienyl, 3-thienyl, 2-furyl, and 3-furyl.

Preference is also given to substituted 1-propiolylpiperazines of the above general formula I in which $R^2$ denotes a hydrogen, or a halogen radical selected from the group consisting of F, Cl, Br, and I, or a nitro group, or a $CF_3$ group, a cyano group, an amino group, or a hydroxyl group, or a thiol group, a carboxyl group, an —NH—$R^6$ group, or an —NR$^6$R$^7$ group, or a —C(=O)—$R^8$ group, a —C(=O)—O—$R^9$ group, an —O—C(=O)—$R^{10}$ group, or a —C(=O)—NH$_2$ group, or a —C(=O)—NH—$R^{14}$ group, a —C(=O)—NR$^{15}$R$^{16}$ group, an —O—$R^{17}$ group, or an —S—$R^{18}$ group, a linear or branched $C_{1-4}$ alkyl radical, a linear or branched $C_{2-8}$ alkenyl radical or a linear or branched $C_{2-8}$ alkynyl radical, an unsubstituted or at least monosubstituted unsaturated or saturated three-membered, four-membered, five-membered, six-membered, or seven-membered cycloaliphatic radical which optionally contains 1, 2, or 3 hetero atoms independently selected from the group consisting of oxygen, sulfur, and nitrogen, as ring member(s), and which can be bonded via a linear or branched, unsubstituted or at least monosubstituted $C_{1-5}$ alkylene group, $C_{2-5}$ alkenylene group or $C_{2-5}$ alkynylene group or an unsubstituted or at least monosubstituted five-membered to fourteen-membered aryl or heteroaryl radical, which can be bonded via a linear or branched, unsubstituted or at least monosubstituted $C_{1-5}$ alkylene group, $C_{2-5}$ alkenylene group or $C_{1-5}$ alkynylene group, and each of the remaining radicals X, n, $R^1$, $R^3$, $R^4$, and $R^5$ to $R^{25}$ has the meanings stated above, in each case optionally in the form of one of the pure stereoisomers thereof, particularly enantiomers or diastereoisomers thereof, the racemates thereof or in the form of a mixture of stereoisomers thereof, particularly the enantiomers and/or diastereoisomers thereof, in an arbitrary mixture ratio, or in each case in the form of appropriate salts thereof, or in each case in the form of appropriate solvates thereof.

Preferably $R^2$ denotes a hydrogen, or a halogen radical selected from the group consisting of F, Cl, and Br, or a $CF_3$ group, a nitro group, a cyano group, an amino group, or a hydroxyl group, or a thiol group, a carboxyl group, an —NH—$R^6$ group, or an —NR$^6$R$^7$ group, or a —C(=O)—$R^8$ group, a —C(=O)—O—$R^9$ group, an —O—C(=O)—$R^{10}$ group, or an —O—$R^{17}$ group, or an —S—$R^{18}$ group, a linear or branched $C_{1-4}$ alkyl radical, or a linear or branched $C_{2-4}$ alkenyl radical, or a linear or branched $C_{2-4}$ alkynyl radical, or a radical selected from the group consisting of cyclopropyl group, cyclobutyl group, cyclopentyl group, cyclohexyl group, pyrrolidinyl group, tetrahydrofuranyl group, tetrahydrothiophenyl group piperidinyl group, tetrahydropyranyl group, piperazinyl group, morpholinyl group, thiomorpholinyl group, dioxolanyl group, azepanyl group, diazepanyl group, imidazolidinyl group, phenyl, naphthyl group, anthracenyl group, pyrrolyl group, indolyl group, furanyl group, benzo[b]furanyl group, thiophenyl group, benzo[b]thiophenyl group, pyrazolyl group, imidazolyl group, thiazolyl group, dithiazolyl group, thiadiazolyl group, triazolyl group, oxazolyl group, oxadiazolyl group, isoxazolyl group, pyridinyl group, pyridazinyl group, pyrimidinyl group, pyrazinyl group, pyranyl group, indazolyl group, purinyl group, indolizinyl group, quinolinyl radical, isoquinolinyl radical, and quinazolinyl radical, each of which can be bonded via a $C_{1-3}$ alkylene group, $C_{2-5}$ alkenylene group or $C_{2-3}$ alkynylene group and/or is unsubstituted or substituted by 1, 2, or 3 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, —O—$C_3H_7$, —NH$_2$, —N(CH$_3$)$_2$, —N(C$_2$H$_5$)$_2$, —NH—CH$_3$, —NH—C$_2$H$_5$, —NO$_2$, —CF$_3$, —O—CF$_3$, —S—CF$_3$, —SH, —NH—S(=O)$_2$—CH$_3$, —C(=O)—OH, —C(=O)—CH$_3$, —C(=O)—C$_2$H$_5$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, and —C(=O)—O—C$_2$H$_5$.

More preferably $R^2$ denotes a hydrogen, or a halogen radical selected from the group consisting of F, Cl, and Br, or a $CF_3$ group, or a nitro group, a cyano group, an amino group, or a dimethylamino group, or a diethylamino group, a monomethylamino group, a monoethylamino group, or a hydroxyl group, or a thiol group, a carboxyl group, a —C(=O)—O—CH$_3$ group, or a —C(=O)—O—C$_2$H$_5$ group, an alkyl radical selected from the group consisting of methyl, ethyl, n-propyl, isopropyl, n-butyl, sec-butyl, isobutyl, and tert-butyl, an alkenyl radical selected from the group consisting of vinyl, 1-propenyl, 2-propenyl, 1-butenyl, 2-butenyl, and 3-butenyl, an alkynyl radical selected from the group consisting of ethynyl, 1-propynyl, 2-propynyl, 1-butynyl, 2-butynyl, and 3-butynyl or an unsubstituted radical selected from the group consisting of or (1,3)-dioxolan-2-yl, phenyl, benzyl, phenethyl, 2-pyridyl, 3-pyridyl, 4-pyridyl, 2-thienyl, 3-thienyl, 2-furyl, and 3-furyl.

Preference is also given to substituted 1-propiolylpiperazines of the above general formula I in which $R^3$ denotes a halogen radical selected from the group consisting of F, Cl, and Br, or a nitro group, a cyano group, or an amino group, a hydroxyl group, a thiol group, or a carboxyl group, or an oxo group (=O) or a linear or branched $C_{1-4}$ alkyl radical, and each of the remaining radicals X, n, $R^1$, $R^2$, $R^4$, and $R^5$ to $R^{25}$ has the meaning stated above, in each case optionally in the form of one of the pure stereoisomers thereof, particularly enantiomers or diastereoisomers thereof, the racemates thereof or in the form of a mixture of stereoisomers thereof, particularly the enantiomers and/or diastereoisomers thereof, in an arbitrary mixture ratio, or in each case in the form of appropriate salts thereof, or in each case in the form of appropriate solvates thereof.

Preferably $R^3$ an oxo group (=O) or an alkyl radical selected from the group consisting of methyl, ethyl, n-propyl, isopropyl, n-butyl, sec-butyl, isobutyl, and tert-butyl.

Preference is also given to substituted 1-propiolylpiperazines of the above general formula I, in which $R^4$ denotes an unsubstituted or at least monosubstituted unsaturated or saturated four-membered, five-membered, six-membered, or seven-membered cycloaliphatic radical, which can be condensed with an unsaturated, saturated or aromatic, unsubstituted or at least monosubstituted monocyclic or bicyclic ring system, while each of the rings can contain 1, 2, or 3 hetero atoms, which can be independently selected from the group consisting of oxygen, nitrogen, and sulfur and each of the rings of the monocyclic or bicyclic ring system is four-membered, five-membered, or six-membered, or an unsubstituted or at least monosubstituted five-membered, or six-membered aryl or heteroaryl radical, which can be condensed with an unsaturated or aromatic, unsubstituted or at least monosubstituted monocyclic or bicyclic ring system, and the heteroaryl radical and optionally the ring of the monocyclic ring system has, in each case, 1, 2, or 3 hetero atoms, which can be independently selected from the group consisting of oxygen, nitrogen, and sulfur, and each of the rings of the monocyclic or bicyclic ring system is four-membered, five-membered, or six-membered, and each of the remaining radicals X, n, $R^1$, $R^2$, $R^3$, and $R^5$ to $R^{25}$ has the meanings stated above, in each case optionally in the form of one of the pure stereoisomers thereof, particularly enantiomers or diastereoisomers thereof, the racemates thereof or in the form of a mixture of stereoisomers thereof, particularly the enantiomers and/or diastereoisomers thereof, in an arbitrary mixture ratio, or in each case in the form of appropriate salts thereof, or in each case in the form of appropriate solvates thereof.

Preferably $R^4$ denotes a radical selected from the group consisting of cyclopropyl, cyclobutyl, cyclopentyl, cyclohexyl, pyrrolidinyl, tetrahydrofuranyl, tetrahydrothiophenyl, piperidinyl, tetrahydropyranyl, piperazinyl, morpholinyl, thiomorpholinyl, dioxolanyl, azepanyl, diazepanyl, imidazolidinyl, phenyl, naphthyl, anthracenyl, furanyl, thiophenyl, pyrazolyl, pyrazinyl, pyrimidinyl, pyridinyl, pyrrolyl, oxazolyl, isoxazolyl, thiazolyl, dithiazolyl, and oxadiazolyl, triazolyl, imidazolyl, indolyl, benzo[b]thiophenyl, benzo[b]furanyl, quinolinyl, isoquinolinyl, and quinazolyl, which can be substituted by 1, 2, or 3 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, —O—$C_3H_7$, —$NH_2$, —$N(CH_3)_2$, —$N(C_2H_5)_2$, —NH—$CH_3$, —NH—$C_2H_5$, —$NO_2$, —$CF_3$, —O—$CF_3$, —S—$CF_3$, —SH, —NH—S(=O)$_2$—$CH_3$, —C(=O)—OH, —C(=O)—$CH_3$, —C(=O)—$C_2H_5$, —C(=O)—$N(CH_3)_2$, —C(=O)—NH—$CH_3$, —NH—C(=O)—$CH_3$, —NH—C(=O)—$C_2H_5$, —C(=O)—O—$CH_3$, and —C(=O)—O—$C_2H_5$.

More preferably $R^4$ denotes a radical selected from the group consisting of phenyl, pyrid-2-yl, pyrid-3-yl, pyrid-4-yl, pyrrol-2-yl, pyrrol-3-yl, thiophen-2-yl, thiophen-3-yl, furan-2-yl, furan-3-yl, imidazol-2-yl, imidazol-4-yl, thiazol-2-yl, thiazol-4-yl, thiazol-5-yl, oxazol-2-yl, oxazol-4-yl, oxazol-5-yl, 1,2,4-thiadiazol-5-yl, 1,2,4-oxadiazol-5-yl, naphth-1-yl, naphth-2-yl, anthracen-1-yl, anthracen-2-yl, anthracen-9-yl, indol-2-yl, indol-3-yl, indol-4-yl, indol-5-yl, indol-6-yl, indol-7-yl, quinolin-3-yl, quinolin-4-yl, quinolin-2-yl, isoquinolin-1-yl, isoquinolin-3-yl, isoquinolin-4-yl, 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-hydroxyphenyl, 3-hydroxyphenyl, 4-hydroxyphenyl, 2-aminophenyl, 3-aminophenyl, 4-aminophenyl, 2-acetylphenyl, 3-acetylphenyl, 4-acetylphenyl, 2,4-dimethylphenyl, 2,4,6-trimethylphenyl, 3,5-dimethylphenyl, 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2,4-difluorophenyl, 2-trifluoromethylphenyl, 3-trifluoromethylphenyl, 4-trifluoromethylphenyl, 2-nitrophenyl, and 3-nitrophenyl, 4-nitrophenyl, 3-methylpyrid-2-yl, 4-methylpyrid-2-yl, 5-methylpyrid-2-yl, 6-methylpyrid-2-yl, 2-methylpyrid-3-yl, 4-methylpyrid-3-yl, 5-methylpyrid-3-yl, 6-methylpyrid-3-yl, 2-methylpyrid-4-yl, 3-methylpyrid-4-yl, 3-fluoropyrid-2-yl, 4-fluoropyrid-2-yl, 5-fluoropyrid-2-yl, 6-fluoropyrid-2-yl, 3-chloropyrid-2-yl, 4-chloropyrid-2-yl, 5-chloropyrid-2-yl, 6-chloropyrid-2-yl, 3-trifluoromethylpyrid-2-yl, 4-trifluoromethylpyrid-2-yl, 5-trifluoromethylpyrid-2-yl, 6-trifluoromethylpyrid-2-yl, 3-methoxypyrid-2-yl, 4-methoxypyrid-2-yl, 5-methoxypyrid-2-yl, 6-methoxypyrid-2-yl, 4-methylthiazol-2-yl, 5-methylthiazol-2-yl, 4-trifluoromethylthiazol-2-yl, 5-trifluoromethylthiazol-2-yl, 4-chlorothiazol-2-yl, 5-chlorothiazol-2-yl, 4-bromothiazol-2-yl, 5-bromothiazol-2-yl, 4-fluorothiazol-2-yl, 5-fluorothiazol-2-yl, 4-cyanothiazol-2-yl, 5-cyanothiazol-2-yl, 4-methoxythiazol-2-yl, 5-methoxythiazol-2-yl, 4-methyloxazol-2-yl, 5-methyloxazol-2-yl, 4-trifluoromethyloxazol-2-yl, 5-trifluoromethyloxazol-2-yl, 4-chloroxazol-2-yl, 5-chloroxazol-2-yl, 4-bromoxazol-2-yl, 5-bromoxazol-2-yl, 4-fluoroxazol-2-yl, 5-fluoroxazol-2-yl, 4-cyano-oxazol-2-yl, 5-cyano-oxazol-2-yl, 4-methoxyoxazol-2-yl, 5-methoxyoxazol-2-yl, 2-methyl-(1,2,4)-thiadiazol-5-yl, 2-trifluoromethyl-(1,2,4)-thiadiazol-5-yl, 2-chloro-(1,2,4)-thiadiazol-5-yl, 2-fluoro-(1,2,4)-thiadiazol-5-yl, 2-methoxy-(1,2,4)-thiadiazol-5-yl, 2-cyano-(1,2,4)-thiadiazol-5-yl, 2-methyl-(1,2,4)-oxadiazol-5-yl, 2-trifluoromethyl-(1,2,4 )-oxadiazol-5-yl, 2-chloro-(1,2,4)-oxadiazol-5-yl, or 2-fluoro-(1,2,4)-oxadiazol-5-yl, 2-methoxy-(1,2,4)-oxadiazol-5-yl, and 2-cyano-(1,2,4)-oxadiazol-5-yl.

Preference is also given to substituted 1-propiolylpiperazines of the above general formula I in which n is equal to 0, 1, or 2, and more preferably equal to 0, and in each case the remaining radicals X, $R^1$, $R^2$, $R^3$, $R^4$, and $R^5$ to $R^{25}$ have the meanings stated above, in each case optionally in the form of one of the pure stereoisomers thereof, particularly enantiomers or diastereoisomers thereof, the racemates thereof or in the form of a mixture of stereoisomers thereof, particularly the enantiomers and/or diastereoisomers thereof, in an arbitrary mixture ratio, or in each case in the form of appropriate salts thereof, or in each case in the form of appropriate solvates thereof.

Furthermore, substituted 1-propiolylpiperazines of the above general formula I are preferred, in which $R^5$ to $R^{25}$ each independently denote a linear or branched, unsubstituted or at least monosubstituted $C_{1-8}$ alkyl radical, or a linear or branched, unsubstituted or at least monosubstituted $C_{2-8}$ alkenyl radical, or a linear or branched, unsubstituted or at least monosubstituted $C_{2-8}$ alkynyl radical, or an unsubstituted or at least monosubstituted, unsaturated or saturated three-membered, four-membered, five-membered, six-membered, seven-membered, eight-membered, or nine-membered cycloaliphatic radical which optionally contains at least one hetero atom as ring member, and which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), or an unsubstituted or at least monosubstituted five-membered to fourteen-membered aryl or heteroaryl radical, which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and each of the remaining radicals X, n, $R^1$, $R^2$, $R^3$ and $R^4$ has the meaning stated above, in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

Preferably $R^5$ to $R^{25}$ each independently denote an alkyl radical selected from the group consisting of methyl, ethyl, n-propyl, isopropyl, n-butyl, sec-butyl, isobutyl, and tert-butyl, or an alkenyl radical selected from the group consisting of vinyl, 1-propenyl, 2-propenyl, 1-butenyl, 2-butenyl, and 3-butenyl, or an alkynyl radical selected from the group consisting of ethynyl, 1-propynyl, 2-propynyl, 1-butynyl, 2-butynyl, and 3-butynyl, or a radical selected from the group consisting of a cyclopropyl group, a cyclobutyl group, a cyclopentyl group, a cyclohexyl group, a pyrrolidinyl group, tetrahydrofuranyl group, a tetrahydrothiophenyl group piperidinyl group, a tetrahydropyranyl group, a piperazinyl group, a morpholinyl group, a thiomorpholinyl group, a dioxolanyl group, a azepanyl group, a diazepanyl group, a imidazolidinyl group, a phenyl, a naphthyl group, a anthracenyl group, a pyrrolyl group, a indolyl group, a furanyl group, a benzo[b]furanyl group, a thiophenyl group, a benzo[b]thiophenyl group, a pyrazolyl group, a imidazolyl group, a thiazolyl group, a dithiazolyl group, a thiadiazolyl group, a triazolyl group, a oxazolyl group, a oxadiazolyl group, a isoxazolyl group, a pyridinyl group, a pyridazinyl group, a pyrimidinyl group, a pyrazinyl group, a pyranyl group, a indazolyl group, a purinyl group, a indolizinyl group, a quinolinyl radical, a isoquinolinyl radical, and a quinazolinyl radical, while the respective cyclic radicals can be bonded via a $C_{1-3}$ alkylene group, $C_{2-3}$ alkenylene group or $C_{2-3}$ alkynylene group optionally containing 1 or 2 hetero atoms selected from the group consisting of oxygen, sulfur, and nitrogen, as link(s), and/or can be unsubstituted or substituted by 1, 2, or 3 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, —O—$C_3H_7$, —$NH_2$, —$N(CH_3)_2$, —$N(C_2H_5)_2$, —NH—$CH_3$, —NH—$C_2H_5$, —$NO_2$, —$CF_3$, —O—$CF_3$, —S—$CF_3$, —SH, —NH—S(=O)$_2$—$CH_3$, —C(=O)—OH, —C(=O)—$CH_3$, —C(=O)—$C_2H_5$, —C(=O)—$N(CH_3)_2$, —C(=O)—NH—$CH_3$, —NH—C(=O)—$CH_3$, —NH—C(=O)—$C_2H_5$, —C(=O)—O—$CH_3$, and —C(=O)—O—$C_2H_5$.

Special preference is given to substituted 1-propiolylpiperazines corresponding to formula I, In which n is equal to 0, 1, 2, 3, or 4, X denotes N or C—$R^2$, $R^1$ denotes a hydrogen, or a halogen radical selected from the group consisting of F, Cl, and Br, or a $CF_3$ group, or a nitro group, a cyano group, an amino group, or a dimethylamino group, or a diethylamino group, a hydroxyl group, a thiol group, or a carboxyl group, or a —C(=O)—O—$CH_3$ group, a —C(=O)—O—$C_2H_5$ group, a —C(=O)—NH-$R^{14}$ group, or a —C(=O)—$NR^{15}R^{16}$ group, or an —O—$R^{17}$ group, an —S—$R^{18}$ group, an —S(=O)—$R^{19}$ group, or an —S(=O)$_2$—$R^{20}$ group, an alkyl radical selected from the group consisting of methyl, ethyl, n-propyl, isopropyl, n-butyl, sec-butyl, isobutyl, and tert-butyl, or an alkenyl radical selected from the group consisting of vinyl, 1-propenyl, 2-propenyl, 1-butenyl, 2-butenyl, and 3-butenyl, denotes an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, and —O—$C_3H_7$;

$R^2$ denotes a hydrogen, or a halogen radical selected from the group consisting of F, Cl, and Br, or a $CF_3$ group, or a nitro group, a cyano group, an amino group, or a dimethylamino group, or a diethylamino group, a hydroxyl group, a thiol group, or a carboxyl group, or a —C(=O)—O—$CH_3$ group, a —C(=O)—O—$C_2H_5$ group, a —C(=O)—NH-$R^{14}$ group, or a —C(=O)—$NR^{15}R^{16}$ group, or an —O—$R^{17}$ group, an —S—$R^{18}$ group, an —S(=O)—$R^{19}$ group, or an —S(=O)$_2$—$R^{20}$ group, an alkyl radical selected from the group consisting of methyl, ethyl, n-propyl, isopropyl, n-butyl, sec-butyl, isobutyl, and tert-butyl, an alkenyl radical selected from the group consisting of vinyl, 1-propenyl, 2-propenyl, 1-butenyl, 2-butenyl, and 3-butenyl, an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, and —O—$C_3H_7$, $R^3$ denotes an oxo group, an alkyl radical selected from the group consisting of methyl, ethyl, n-propyl, isopropyl, n-butyl, sec-butyl, isobutyl, and tert-butyl or a phenyl radical, which is unsubstituted or substituted by 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, and —O—$C_3H_7$, $R^4$ denotes a hydrogen, or a —C(=O)—$NH_2$ group, a —C(=O)—NH—$R^{14}$ group, or a —C(=O)—$NR^{15}R^{16}$ group, an alkyl radical selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, n-heptyl, and n-octyl, or a radical selected from the group consisting of cyclopropyl, cyclobutyl, cyclopentyl, cyclohexyl, cycloheptyl, cyclopentenyl, cyclohexenyl, pyrrolidinyl, tetrahydrofuranyl, tetrahydrothiophenyl, piperidinyl, tetrahydropyranyl, piperazinyl, morpholinyl, thiomorpholinyl, dioxolanyl, azepanyl, diazepanyl, imidazolidinyl, phenyl, naphthyl, anthracenyl, furanyl, thiophenyl, pyrazolyl, pyrazinyl, pyrimidinyl, pyridinyl, pyrrolyl, oxazolyl, isoxazolyl, thiazolyl, dithiazolyl, oxadiazolyl, triazolyl, imidazolyl, indolyl, benzo[b]thiophenyl, benzo[b]furanyl, quinolinyl, isoquinolinyl, and quinazolyl, each of which is optionally substituted with 1, 2, 3, 4, or 5 substituents independently selected from the group consisting of F, Cl, Br, I, —CN, methyl, ethyl, n-propyl, and isopropyl, n-butyl, sec-butyl, isobutyl, tert-butyl, vinyl, allyl, ethynyl, propinyl, —C≡C—Si($CH_3$)$_3$, —C≡C—Si($C_2H_5$)$_3$, —$CH_2$—O—$CH_3$, —$CH_2$—O—$C_2H_5$, —OH, —O—$CH_3$, —O—$C_2H_5$, —O—$C_3H_7$, —S—$CH_3$, —S—$C_2H_5$, —S(=O)—$CH_3$, —S(=O)$_2$—$CH_3$, —S(=O)—$C_2H_5$, —S(=O)$_2$—$C_2H_5$, —N$H_2$, —$N(CH_3)_2$, —$N(C_2H_5)_2$, —NH—$CH_3$, —NH—$C_2H_5$, —$NO_2$, —$CF_3$, —$CH_2F$, —$CHF_2$, —O—$CF_3$, —S—$CF_3$, —SH, —NH—S(=O)$_2$—$CH_3$, —C(=O)—OH, —C(=O)—H; —C(=O)—$CH_3$, —C(=O)—$C_2H_5$, —C(=O)—$NH_2$, —C(=O)—$N(CH_3)_2$, —C(=O)—NH—$CH_3$, —NH—C(=O)—$CH_3$, —NH—C(=O)—$C_2H_5$, —C(=O)—O—$CH_3$, —C(=O)—O—$C_2H_5$, —C(=O)—O—C($CH_3$)$_3$, and phenyl; and $R^{14}$, $R^{15}$, $R^{16}$, $R^{17}$, $R^{18}$, $R^{19}$ and $R^{20}$ each independently denote an alkyl radical selected from the group consisting of methyl, ethyl, n-propyl, isopropyl, n-butyl, sec-butyl, isobutyl, and tert-butyl;

in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

Very special preference is given to substituted 1-propiolylpiperazines corresponding to formula I:

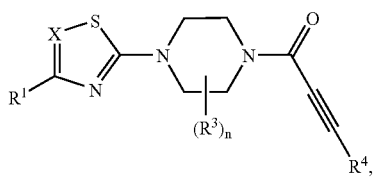

in which
n is 0,
X denotes N or C—$R^2$,
$R^1$ denotes a hydrogen, or a halogen radical selected from the group consisting of F, Cl, and Br, or a $CF_3$ group, or a nitro group, a cyano group, an amino group, or a dimethylamino group, or a diethylamino group, a hydroxyl group, a thiol group, or a carboxyl group, or a —C(=O)—O—$CH_3$ group, a —C(=O)—O—$C_2H_5$ group, an alkyl radical selected from the group consisting of methyl, ethyl, n-propyl, isopropyl, n-butyl, sec-butyl, isobutyl, and tert-butyl, or an alkenyl radical selected from the group consisting of vinyl, 1-propenyl, 2-propenyl, 1-butenyl, 2-butenyl, and 3-butenyl, or an alkynyl radical selected from the group consisting of ethynyl, 1-propynyl, 2-propynyl, 1-butynyl, 2-butynyl, and 3-butynyl or an unsubstituted radical selected from the group consisting of or (1,3)-dioxolan-2-yl, phenyl, benzyl, phenethyl, 2-pyridyl, 3-pyridyl, 4-pyridyl, 2-thienyl, 3-thienyl, 2-furyl, and 3-furyl;

$R^2$ denotes a hydrogen, or a halogen radical selected from the group consisting of F, Cl, and Br, or a $CF_3$ group, or a nitro group, a cyano group, an amino group, or a dimethylamino group, or a diethylamino group, a hydroxyl group, a thiol group, or a carboxyl group, or a —C(=O)—O—$CH_3$ group, a —C(=O)—O—$C_2H_5$ group, an alkyl radical selected from the group consisting of methyl, ethyl, n-propyl, isopropyl, n-butyl, sec-butyl, isobutyl, and tert-butyl, or an alkenyl radical selected from the group consisting of vinyl, 1-propenyl, 2-propenyl, 1-butenyl, 2-butenyl, and 3-butenyl, or an alkynyl radical selected from the group consisting of ethynyl, 1-propynyl, 2-propynyl, 1-butynyl, 2-butynyl, and 3-butynyl or an unsubstituted radical selected from the group consisting of or (1,3)-dioxolan-2-yl, phenyl, benzyl, phenethyl, 2-pyridyl, 3-pyridyl, 4-pyridyl, 2-thienyl, 3-thienyl, 2-furyl, and 3-furyl, and $R^4$ denotes a radical selected from the group consisting of phenyl, pyrid-2-yl, pyrid-3-yl, pyrid-4-yl, pyrrol-2-yl, pyrrol-3-yl, thiophen-2-yl, thiophen-3-yl, furan-2-yl, furan-3-yl, imidazol-2-yl, imidazol-4-yl, thiazol-2-yl, thiazol-4-yl, thiazol-5-yl, oxazol-2-yl, oxazol-4-yl, oxazol-5-yl, 1,2,4-thiadiazol-5-yl, 1,2,4-oxadiazol-5-yl, naphth-1-yl, naphth-2-yl, anthracen-1-yl, anthracen-2-yl, anthracen-9-yl, indol-2-yl, indol-3-yl, indol-4-yl, indol-5-yl, indol-6-yl, indol-7-yl, quinolin-3-yl, quinolin-4-yl, quinolin-2-yl, isoquinolin-1-yl, isoquinolin-3-yl, isoquinolin-4-yl, 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-hydroxyphenyl, 3-hydroxyphenyl, and 4-hydroxyphenyl, 2-aminophenyl, 3-aminophenyl, 4-aminophenyl, 2-acetylphenyl, 3-acetylphenyl, 4-acetylphenyl, 2,4-dimethylphenyl, 2,4,6-trimethylphenyl, 3,5-dimethylphenyl, 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2,4-difluorophenyl, 2-trifluoromethylphenyl, 3-trifluoromethylphenyl, 4-trifluoromethylphenyl, 2-nitrophenyl, 3-nitrophenyl, 4-nitrophenyl, 3-methylpyrid-2-yl, 4-methylpyrid-2-yl, 5-methylpyrid-2-yl, 6-methylpyrid-2-yl, 2-methylpyrid-3-yl, 4-methylpyrid-3-yl, 5-methylpyrid-3-yl, 6-methylpyrid-3-yl, 2-methylpyrid-4-yl, 3-methylpyrid-4-yl, 3-fluoropyrid-2-yl, 4-fluoropyrid-2-yl, 5-fluoropyrid-2-yl, 6-fluoropyrid-2-yl, 3-chloropyrid-2-yl, 4-chloropyrid-2-yl, 5-chloropyrid-2-yl, 6-chloropyrid-2-yl, 3-trifluoromethylpyrid-2-yl, 4-trifluoromethylpyrid-2-yl, 5-trifluoromethylpyrid-2-yl, 6-trifluoromethylpyrid-2-yl, 3-methoxypyrid-2-yl, 4-methoxypyrid-2-yl, 5-methoxypyrid-2-yl, 6-methoxypyrid-2-yl, 4-methylthiazol-2-yl, 5-methylthiazol-2-yl, 4-trifluoromethylthiazol-2-yl, 5-trifluoromethylthiazol-2-yl, 4-chlorothiazol-2-yl, 5-chlorothiazol-2-yl, 4-bromothiazol-2-yl, 5-bromothiazol-2-yl, 4-fluorothiazol-2-yl, 5-fluorothiazol-2-yl, 4-cyanothiazol-2-yl, 5-cyanothiazol-2-yl, 4-methoxythiazol-2-yl, 5-methoxythiazol-2-yl, and 4-methyloxazol-2-yl, 5-methyloxazol-2-yl, 4-trifluoromethyloxazol-2-yl, 5-trifluoromethyloxazol-2-yl, 4-chloroxazol-2-yl, 5-chloroxazol-2-yl, 4-bromoxazol-2-yl, 5-bromoxazol-2-yl, 4-fluoroxazol-2-yl, 5-fluoroxazol-2-yl, 4-cyano-oxazol-2-yl, 5-cyano-oxazol-2-yl, 4-methoxyoxazol-2-yl, 5-methoxyoxazol-2-yl, 2-methyl-(1,2,4)-thiadiazol-5-yl, 2-trifluoromethyl-(1,2,4)-thiadiazol-5-yl, 2-chloro-(1,2,4)-thiadiazol-5-yl, 2-fluoro-(1,2,4)-thiadiazol-5-yl, 2-methoxy-(1,2,4)-thiadiazol-5-yl, 2-cyano-(1,2,4)-thiadiazol-5-yl, 2-methyl-(1,2,4)-oxadiazol-5-yl, 2-trifluoromethyl-(1,2,4)-oxadiazol-5-yl, 2-chloro-(1,2,4)-oxadiazol-5-yl, 2-fluoro-(1,2,4)-oxadiazol-5-yl, 2-methoxy-(1,2,4)-oxadiazol-5-yl, and 2-cyano-(1,2,4)-oxadiazol-5-yl, in each case optionally in the form of one of the pure stereoisomers thereof, particularly enantiomers or diastereoisomers thereof, the racemates thereof or in the form of a mixture of stereoisomers thereof, particularly the enantiomers and/or diastereoisomers thereof, in an arbitrary mixture ratio, or in each case in the form of appropriate salts thereof, or in each case in the form of appropriate solvates thereof.

Likewise, special preference is given to substituted 1-propiolylpiperazines corresponding to formula I,

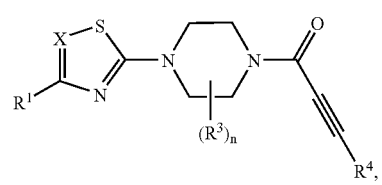

in which n is equal to 0, 1, 2, 3, or 4;

X denotes N or C—$R^2$;

$R^1$ denotes a hydrogen, or a halogen radical selected from the group consisting of F, Cl, and Br, or a $CF_3$ group, or a nitro group, a cyano group, an amino group, or a dimethylamino group, or a diethylamino group, a hydroxyl group, a thiol group, or a carboxyl group, or a —C(=O)—O—$CH_3$ group, a —C(=O)—O—$C_2H_5$ group, a —C(=O)—NH—$R^{14}$ group, or a —C(=O)—$NR^{15}R^{16}$ group, or an —O—$R^{17}$ group, an —S—$R^{18}$ group, an —S(=O)—$R^{19}$ group, or an —S(=O)$_2$—$R^{20}$ group, an alkyl radical selected from the group consisting of methyl, ethyl, n-propyl, isopropyl, n-butyl, sec-butyl, isobutyl, and tert-butyl, an alkenyl radical selected from the group consisting of vinyl, 1-propenyl, 2-propenyl, 1-butenyl, 2-butenyl, and 3-butenyl, an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, and —O—$C_3H_7$;

$R^2$ denotes a hydrogen, or a halogen radical selected from the group consisting of F, Cl, and Br, or a $CF_3$ group, or a nitro group, a cyano group, an amino group, or a dimethylamino group, or a diethylamino group, a hydroxyl group, a thiol group, or a carboxyl group, or a —C(=O)—O—$CH_3$ group, a —C(=O)—O—$C_2H_5$ group, a —C(=O)—NH—$R^4$ group, or a —C(=O)—$NR^{15}R^{16}$ group, or an —O—$R^{17}$ group, an —S—$R^{18}$ group, an —S(=O)—$R^{19}$ group, or an —S(=O)$_2$—$R^{20}$ group, an alkyl radical selected from the group consisting of methyl, ethyl, n-propyl, isopropyl, n-butyl, sec-butyl, isobutyl, and tert-butyl, an alkenyl radical selected from the group consisting of vinyl, 1-propenyl, 2-propenyl, 1-butenyl, 2-butenyl, and 3-butenyl, an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, and —O—$C_3H_7$;

$R^3$ denotes an oxo group, an alkyl radical selected from the group consisting of methyl, ethyl, n-propyl, isopropyl, n-butyl, sec-butyl, isobutyl, and tert-butyl or a phenyl radical, which is unsubstituted or substituted by 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, and —O—$C_3H_7$, and $R^4$ denotes a hydrogen, or a —C(=O)—$NH_2$ group, a —C(=O)—NH—$R^{14}$ group, or a —C(=O)—$NR^{15}R^{16}$ group, an alkyl radical selected from the group consisting of methyl, ethyl, n-propyl, isopropyl, n-butyl, sec-butyl, isobutyl, tert-butyl, n-pentyl, sec-pentyl, neopentyl, n-hexyl, n-heptyl, and n-octyl, or a radical selected from the group consisting of cyclopropyl, cyclobutyl, cyclopentyl, cyclohexyl, cycloheptyl, cyclopentenyl, cyclohexenyl, phenyl, pyrid-2-yl, pyrid-3-yl, pyrid-4-yl, pyrrol-2-yl, pyrrol-3-yl, thiophen-2-yl, thiophen-3-yl, 4-methylthiophen-2-yl, 3-methylthiophen-2-yl, 5-methylthiophen-2-yl, furan-2-yl, furan-3-yl, imidazol-2-yl, imidazol-4-yl, thiazol-2-yl, thiazol-4-yl, thiazol-5-yl, oxazol-2-yl, oxazol-4-yl, oxazol-5-yl, (1,2,4)-thiadiazol-5-yl, (1,2,4)-oxadiazol-5-yl, naphth-1-yl, naphth-2-yl, anthracen-1-yl, anthracen-2-yl, anthracen-9-yl, indol-2-yl, indol-3-yl, indol-4-yl, indol-5-yl, indol-6-yl, indol-7-yl, and 1-methylindol-2-yl, 1-methylindol-3-yl, 1-methylindol-4-yl, 1-methylindol-5-yl, 1-methylindol-6-yl, 1-methylindol-7-yl, quinolin-3-yl, quinolin-4-yl, quinolin-2-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-hydroxyphenyl, 3-hydroxyphenyl, 4-hydroxyphenyl, 2-aminophenyl, 3-aminophenyl, 4-aminophenyl, 2-dimethylaminophenyl, 3-dimethylaminophenyl, 4-dimethylaminophenyl, 2-methylaminophenyl, 3-methylaminophenyl, 4-methylaminophenyl, 2-acetylphenyl, and 3-acetylphenyl, 4-acetylphenyl, 2-methylsulfinylphenyl, 3-methylsulfinylphenyl, 4-methylsulfinylphenyl, 2-methylsulfonylphenyl, 3-methylsulfonylphenyl, 4-methylsulfonylphenyl, 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-trifluoromethylphenyl, 3-trifluoromethylphenyl, 4-trifluoromethylphenyl, 2-difluoromethylphenyl, 3-difluoromethylphenyl, 4-difluoromethylphenyl, 2-fluoromethylphenyl, 3-fluoromethylphenyl, 4-fluoromethylphenyl, 2-nitrophenyl, 3-nitrophenyl, 4-nitrophenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-tert-butylphenyl, 3-tert-butylphenyl, 4-tert-butylphenyl, 2-carboxyphenyl, 3-carboxyphenyl, 4-carboxyphenyl, 2-vinylphenyl, 3-vinylphenyl, 4-vinylphenyl, 2-ethynylphenyl, 3-ethynylphenyl, 4-ethynylphenyl, 2-allylphenyl, and 3-allylphenyl, 4-allylphenyl, 2-trimethylsilanylethynylphenyl, 3-trimethylsilanylethynylphenyl, 4-trimethylsilanylethynylphenyl, 2-formylphenyl, 3-formylphenyl, 4-formylphenyl, 2-acetaminophenyl, 3-acetaminophenyl, 4-acetaminophenyl, 2-dimethylaminocarbonylphenyl, 3-dimethylaminocarbonylphenyl, 4-dimethylaminocarbonylphenyl, 2-methoxymethylphenyl, 3-methoxymethylphenyl, 4-methoxymethylphenyl, 2-ethoxymethylphenyl, 3-ethoxymethylphenyl, 4-ethoxymethylphenyl, 2-aminocarbonylphenyl, 3-aminocarbonylphenyl, 4-aminocarbonylphenyl, 2-methylaminocarbonylphenyl, 3-methylaminocarbonylphenyl, 4-methylaminocarbonylphenyl, 2-carboxymethylesterphenyl, 3-carboxymethylesterphenyl, 4-carboxymethylesterphenyl, 2-carboxyethylesterphenyl, 3-carboxyethylesterphenyl, 4-carboxyethylesterphenyl, 2-carboxy-tert-butylesterphenyl, 3-carboxy-tert-butylesterphenyl, 4-carboxy-tert-butylesterphenyl, 2-methylmercaptophenyl, 3-methylmercaptophenyl, 4-methylmercaptophenyl, 2-ethylmercaptophenyl, 3-ethylmercaptophenyl, 4-ethylmercaptophenyl, and 2-biphenyl, 3-biphenyl, 4-biphenyl, 2-bromophenyl, 3-bromophenyl, 4-bromophenyl, 2-iodophenyl, 3-iodophenyl, 4-iodophenyl, 2-trifluoromethoxyphenyl, 3-trifluoromethoxyphenyl, 4-trifluoromethoxyphenyl, 2-fluoro-3-trifluoromethylphenyl, 2-fluoro-4-methylphenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, 2-chloro-4-nitrophenyl, 2-chloro-4-methylphenyl, 2-chloro-5-trifluoromethylphenyl, 2-chloro-5-methoxyphenyl, 2-bromo-5-trifluoromethylphenyl, 2-bromo-5-methoxyphenyl, (2,4)-dibromophenyl, (2,4)-dimethylphenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-methoxy-5-nitrophenyl, 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, and (2,6)-dichlorophenyl, 3-chloro-2-fluorophenyl, 3-chloro-5-methylphenyl, (3,4)-dichlorophenyl, (3,4)-dimethylphenyl, 3-methyl-4-methoxyphenyl, 4-chloro-3-nitrophenyl, (3,4)-dimethoxyphenyl, 4-fluoro-3-trifluoromethylphenyl, 3-fluoro-4-trifluoromethylphenyl, (3,4)-difluorophenyl, 3-cyano-4-fluorophenyl, 3-cyano-4-methylphenyl, 3-cyano-4-methoxyphenyl, 3-bromo-4-fluorophenyl, 3-bromo-4-methylphenyl, 3-bromo-4-methoxyphenyl, 4-chloro-2-fluorophenyl, 4-chloro-3-trifluoromethyl, 4-bromo-3-methylphenyl, 4-bromo-5-methylphenyl, 3-chloro-4-fluorophenyl, 4-fluoro-3-nitrophenyl, 4-bromo-3-nitrophenyl, (3,4)-dibromophenyl, 4-chloro-3-methylphenyl, 4-bromo-3-methylphenyl, 4-fluoro-3-methylphenyl, 3-fluoro-4-methylphenyl, 3-fluoro-5-methylphenyl, 2-fluoro-3-methylphenyl, 4-methyl-3-nitrophenyl, (3,5)-dimethoxyphenyl, (3,5)-dimethylphenyl, (3,5)-bis-trifluoromethylphenyl, (3,5)-difluorophenyl, (3,5)-dinitrophenyl, (3,5)-dichlorophenyl, and 3-fluoro-5-trifluoromethylphenyl, 5-fluoro-3-trifluoromethylphenyl, (3,5)-dibromophenyl, 5-chloro-4-fluorophenyl, 5-chloro-4-methylphenyl, 5-bromo-4-methylphenyl, (3,3,4)-trifluorophenyl, (2,3,4)-trichlorophenyl, (2,3,6)-trifluorophenyl, 5-chloro-2-methoxyphenyl, (2,3)-difluoro-4-methyl, (2,4,5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (3,4,5)-trimethoxyphenyl, (2,3,4,5)-tetrafluorophenyl, 4-methoxy-(2,3,6)-trimethylphenyl, 4-methoxy-(2,3,6)-trimethylphenyl, 4-chloro-2,5-dimethylphenyl, 2-chloro-6-fluoro-3-methylphenyl, 6-chloro-2-fluoro-3-methyl, (2,4,6)-trimethylphenyl, (2,3,4,5,6)-pentafluorophenyl, 3-methylpyrid-2-yl, 4-methylpyrid-2-yl, 5-methylpyrid-2-yl, 6-methylpyrid-2-yl, 2-methylpyrid-3-yl, 4-methylpyrid-3-yl, 5-methylpyrid-3-yl, 6-methylpyrid-3-yl, 2-methylpyrid-4-yl, 3-methylpyrid-4-yl, 3-fluoropyrid-2-yl, 4-fluoropyrid-2-yl, 5-fluoropyrid-2-yl, 6-fluoropyrid-2-yl, 3-chloropyrid-2-yl, 4-chloropyrid-2-yl, 5-chloropyrid-2-yl, 6-chloropyrid-2-yl, 3-trifluoromethylpyrid-2-yl, 4-trifluoromethylpyrid-2-yl, 5-trifluoromethylpyrid-2-yl, 6-trifluoromethylpyrid-2-yl, 3-methoxypyrid-2-yl, 4-methoxypyrid-2-yl, 5-methoxypyrid-2-yl, 6-methoxypyrid-2-yl, 4-methylthiazol-2-yl, 5-methylthiazol-2-yl, 4-trifluoromethylthiazol-2-yl, 5-trifluoromethylthiazol-2-yl, 4-chlorothiazol-2-yl, 5-chlorothiazol-2-yl, 4-bromothiazol-2-yl, 5-bromothiazol-2-yl, 4-fluorothiazol-2-yl, 5-fluorothiazol-2-yl, 4-cyanothiazol-2-yl, 5-cyanothiazol-2-yl, 4-methoxythiazol-2-yl, 5-methoxythiazol-2-yl, 4-methyloxazol-2-yl, 5-methyloxazol-2-yl, 4-trifluoromethyloxazol-2-yl, 5-trifluoromethyloxazol-2-yl, 4-chloroxazol-2-yl, 5-chloroxazol-2-yl, 4-bromoxazol-2-yl, 5-bromoxazol-2-yl, 4-fluoroxazol-2-yl, and 5-fluoroxazol-2-yl, 4-cyano-oxazol-2-yl, 5-cyano-oxazol-2-yl, 4-methoxyoxazol-2-yl, 5-methoxyoxazol-2-yl, 2-methyl-(1,2,4)-thiadiazol-5-yl, 2-trifluoromethyl-(1,2,4)-thiadiazol-5-yl, 2-chloro-(1,2,4)-thiadiazol-5-yl, 2-fluoro-(1,2,4)-thiadiazol-5-yl, 2-methoxy-(1,2,4)-thiadiazol-5-yl, 2-cyano-(1,2,4)-thiadiazol-5-yl, 2-methyl-(1,2,4)-oxadiazol-5-yl, 2-trifluoromethyl-(1,2,4)-oxadiazol-5-yl, 2-chloro-(1,2,4)-oxadiazol-5-yl, 2-fluoro-(1,2,4)-oxadiazol-5-yl, 2-methoxy-(1,2,4)-oxadiazol-5-yl, and 2-cyano-(1,2,4)-oxadiazol-5-yl; and $R^{14}$, $R^{15}$, $R^{16}$, $R^{17}$, $R^{18}$, $R^{19}$ and $R^{20}$ each independently denote an alkyl radical selected from the group consisting of methyl, ethyl, n-propyl, isopropyl, n-butyl, sec-butyl, isobutyl, and tert-butyl;

in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

Most special preference is given to substituted 1-propiolylpiperazines corresponding to formula I, In which n is equal to 0, 1, or 2;

X denotes N or C—$R^2$;

$R^1$ denotes a hydrogen, or a halogen radical selected from the group consisting of F, Cl, and Br, or a $CF_3$ group, or a nitro group, a carboxyl group, a —C(=O)—O—$CH_3$ group, or a —C(=O)—O—$C_2H_5$ group, or a —C(=O)—NH—$R^{14}$ group, a —C(=O)—$NR^{15}R^{16}$ group, an —O—$R^{17}$ group, or an —S—$R^{18}$ group, or an —S(=O)$_2$—$R^{20}$ group, an alkyl radical selected from the group consisting of methyl, ethyl, n-propyl, isopropyl, n-butyl, sec-butyl, isobutyl, and tert-butyl, or denotes a radical selected from the group consisting of phenyl and oxadiazolyl, each of which is unsubstituted or substituted by optionally 1, 2, 3, 4, or 5 substituents independently selected from the group consisting of F, Cl, Br, I, —O—$CH_3$, —O—$C_2H_5$, and —O—$C_3H_7$;

$R^2$ denotes a hydrogen, or a halogen radical selected from the group consisting of F, Cl, and Br, or a $CF_3$ group, or a nitro group, a carboxyl group, a —C(=O)—O—$CH_3$ group, or a —C(=O)—O—$C_2H_5$ group, or a —C(=O)—NH—$R^{14}$ group, a —C(=O)—$NR^{15}R^{16}$ group, an —O—$R^{17}$ group, or an —S—$R^{18}$ group, or an —S(=O)$_2$—$R^{20}$ group, an alkyl radical selected from the group consisting of methyl, ethyl, n-propyl, isopropyl, n-butyl, sec-butyl, isobutyl, and tert-butyl, or denotes a radical selected from the group consisting of phenyl and oxadiazolyl, each of which is unsubstituted or substituted by optionally 1, 2, 3, 4, or 5 substituents independently selected from the group consisting of F, Cl, Br, I, —O—$CH_3$, —O—$C_2H_5$, and —O—$C_3H_7$;

$R^3$ denotes an oxo group, an alkyl radical selected from the group consisting of methyl, ethyl, n-propyl, isopropyl, n-butyl, sec-butyl, isobutyl, and tert-butyl or an unsubstituted phenyl radical;

R[4] denotes a hydrogen, or a —C(=O)—NH$_2$ group, a —C(=O)—NH—R[14] group, or a —C(=O)—NR[15]R[16] group, an alkyl radical selected from the group consisting of methyl, ethyl, n-propyl, isopropyl, n-butyl, sec-butyl, isobutyl, tert-butyl, n-pentyl, sec-pentyl, neopentyl, n-hexyl, n-heptyl, and n-octyl or a radical selected from the group consisting of cyclopropyl, cyclobutyl, cyclopentyl, cyclohexyl, cycloheptyl, cyclopentenyl, cyclohexenyl, phenyl, pyrid-2-yl, pyrid-3-yl, pyrid-4-yl, pyrrol-2-yl, pyrrol-3-yl, thiophen-2-yl, thiophen-3-yl, 4-methylthiophen-2-yl, 3-methylthiophen-2-yl, 5-methylthiophen-2-yl, furan-2-yl, furan-3-yl, imidazol-2-yl, imidazol-4-yl, thiazol-2-yl, thiazol-4-yl, thiazol-5-yl, oxazol-2-yl, oxazol-4-yl, oxazol-5-yl, (1,2,4)-thiadiazol-5-yl, (1,2,4)-oxadiazol-5-yl, naphth-1-yl, naphth-2-yl, indol-3-yl, indol-4-yl, indol-5-yl, indol-6-yl, indol-7-yl, 1-methylindol-2-yl, 1-methylindol-3-yl, 1-methylindol-4-yl, 1-methylindol-5-yl, and 1-methylindol-6-yl, 1-methylindol-7-yl, quinolin-3-yl, quinolin-4-yl, quinolin-2-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-hydroxyphenyl, 3-hydroxyphenyl, 4-hydroxyphenyl, 2-aminophenyl, 3-aminophenyl, 4-aminophenyl, 2-dimethylaminophenyl, 3-dimethylaminophenyl, 4-dimethylaminophenyl, 2-methylaminophenyl, 3-methylaminophenyl, 4-methylaminophenyl, 2-acetylphenyl, 3-acetylphenyl, 4-acetylphenyl, 2-methylsulfinylphenyl, and 3-methylsulfinylphenyl, 4-methylsulfinylphenyl, 2-methylsulfonylphenyl, 3-methylsulfonylphenyl, 4-methylsulfonylphenyl, 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-trifluoromethylphenyl, 3-trifluoromethylphenyl, 4-trifluoromethylphenyl, 2-difluoromethylphenyl, 3-difluoromethylphenyl, 4-difluoromethylphenyl, 2-fluoromethylphenyl, 3-fluoromethylphenyl, 4-fluoromethylphenyl, 2-nitrophenyl, 3-nitrophenyl, 4-nitrophenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-tert-butylphenyl, 3-tert-butylphenyl, 4-tert-butylphenyl, 2-carboxyphenyl, 3-carboxyphenyl, 4-carboxyphenyl, 2-vinylphenyl, 3-vinylphenyl, 4-vinylphenyl, 2-ethynylphenyl, 3-ethynylphenyl, 4-ethynylphenyl, 2-allylphenyl, 3-allylphenyl, 4-allylphenyl, 2-trimethylsilanylethynylphenyl, 3-trimethylsilanylethynylphenyl, 4-trimethylsilanylethynylphenyl, 2-formylphenyl, 3-formylphenyl, 4-formylphenyl, 2-acetaminophenyl, 3-acetaminophenyl, 4-acetaminophenyl, 2-dimethylaminocarbonylphenyl, 3-dimethylaminocarbonylphenyl, 4-dimethylaminocarbonylphenyl, 2-methoxymethylphenyl, 3-methoxymethylphenyl, 4-methoxymethylphenyl, 2-ethoxymethylphenyl, 3-ethoxymethylphenyl, 4-ethoxymethylphenyl, 2-aminocarbonylphenyl, 3-aminocarbonylphenyl, 4-aminocarbonylphenyl, 2-methylaminocarbonylphenyl, 3-methylaminocarbonylphenyl, 4-methylaminocarbonylphenyl, 2-carboxymethylesterphenyl, 3-carboxymethylesterphenyl, 4-carboxymethylesterphenyl, 2-carboxyethylesterphenyl, 3-carboxyethylesterphenyl, 4-carboxyethylesterphenyl, 2-carboxy-tert-butylesterphenyl, 3-carboxy-tert-butylesterphenyl, 4-carboxy-tert-butylesterphenyl, 2-methylmercaptophenyl, 3-methylmercaptophenyl, 4-methylmercaptophenyl, 2-ethylmercaptophenyl, and 3-ethylmercaptophenyl, 4-ethylmercaptophenyl, 2-biphenyl, 3-biphenyl, 4-biphenyl, 2-bromophenyl, 3-bromophenyl, 4-bromophenyl, 2-iodophenyl, 3-iodophenyl, 4-iodophenyl, 2-trifluoromethoxyphenyl, 3-trifluoromethoxyphenyl, 4-trifluoromethoxyphenyl, 2-fluoro4-methylphenyl, (2,3)-dimethylphenyl, (2,4)-dichlorophenyl, (2,4)-difluorophenyl, 2-chloro-4-methylphenyl, 2-chloro-5-trifluoromethylphenyl, 2-chloro-5-methoxyphenyl, 2-bromo-5-trifluoromethylphenyl, 2-bromo-5-methoxyphenyl, (2,4)-dimethylphenyl, (2,6)-dimethylphenyl, 3-chloro-5-methylphenyl, (3,4)-dimethylphenyl, 3-methyl-4-methoxyphenyl, (3,4)-difluorophenyl, 3-cyano-4-fluorophenyl, 3-cyano-4-methylphenyl, 3-cyano-4-methoxyphenyl, 3-bromo-4-fluorophenyl, 3-bromo-4-methylphenyl, 3-bromo-4-methoxyphenyl, 4-chloro-2-fluorophenyl, 4-fluoro-3-methylphenyl, 3-fluoro4-methylphenyl, 3-fluoro-5-methylphenyl, 2-fluoro-3-methylphenyl, (3,5)-dimethylphenyl, and (3,5)-dichlorophenyl; and R[14], R[15], R[16], R[17], R[18], and R[20] each independently denote an alkyl radical selected from the group consisting of methyl, ethyl, n-propyl, isopropyl, n-butyl, sec-butyl, isobutyl, and tert-butyl;

in each case optionally in the form of one of the pure stereoisomers thereof, particularly enantiomers or diastereoisomers thereof, the racemates thereof or in the form of a mixture of stereoisomers and particularly of the enantiomers and/or diastereoisomers in an arbitrary mixture ratio, or in each case in the form of appropriate salts, preferably in the form of appropriate hydrochlorides, or in each case in the form of appropriate solvates.

Preference is most particularly given to the compound of the invention 1-(3-phenylpropiolyl)-4-(thiazol-2-yl)piperazine of the following formula:

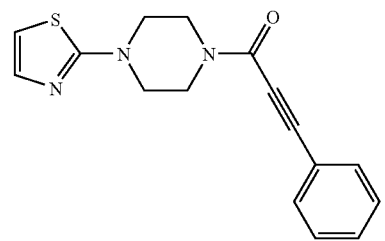

and its appropriate salts and also optionally in each case its appropriate solvates.

Even more preference is given to compounds corresponding to formula I selected from the group consisting of

[AAA00100] 4-(3-Methylmercapto-1,2,4-thiadiazol-5-yl)-1-(3-phenylpropiolyl)piperazine

[AAA00101] 4-(3-Methansulfonyl-1,2,4-thiadiazol-5-yl)-1-(3-phenylpropiolyl)piperazine

[AAA00102] 4-(3-Methoxy-1,2,4-thiadiazol-5-yl)-1-(3-phenylpropiolyl)piperazine

[AAA00103] 4-(1,2,4-Thiadiazol-5-yl)-1-(3-phenylpropiolyl)piperazine

[AAA00104] 4-(3-Methyl-1,2,4-thiadiazol-5-yl)-1-(3-phenylpropiolyl)piperazine

[AAA00105] 4-(3-Trifluoromethyl-1,2,4-thiadiazol-5-yl)-1-(3-phenylpropiolyl)piperazine

[AAA00106] 4-(5-(3-Methyl-1,2,4-oxadiazol-5-yl)thiazol-2-yl)-1-(3-phenylpropiolyl)piperazine

[AAA00107] 4-(4-tert-Butylthiazol-2-yl)-1-(3-(4-aminophenyl)propiolyl)piperazine
[AAA1] 4-(Thiazol-2-yl)-1-(3-(2-carboxyphenyl)propiolyl)piperazine methyl ester
[AAA10] 4-(Thiazol-2-yl)-1-(3-(2-thienyl)propiolyl)piperazine
[AAA11] 4-(Thiazol-2-yl)-1-(3-(3-thienyl)propiolyl)piperazine
[AAA12] 4-(Thiazol-2-yl)-1-(3-(2-methoxyphenyl)propiolyl)piperazine
[AAA13] 4-(Thiazol-2-yl)-1-(3-(3-methoxyphenyl)propiolyl)piperazine
[AAA14] 4-(Thiazol-2-yl)-1-(3-(4-methoxyphenyl)propiolyl)piperazine
[AAA15] 4-(Thiazol-2-yl)-1-(3-(2-cyanophenyl)propiolyl)piperazine
[AAA16] 4-(Thiazol-2-yl)-1-(3-(3-cyanophenyl)propiolyl)piperazine
[AAA17] 4-(Thiazol-2-yl)-1-(3-(4-cyanophenyl)propiolyl)piperazine
[AAA18] 4-(Thiazol-2-yl)-1-(3-(2,4-dimethylphenyl)propiolyl)piperazine
[AAA19] 4-(Thiazol-2-yl)-1-(3-(3,5-dimethylphenyl)propiolyl)piperazine
[AAA2] 4-(Thiazol-2-yl)-1-(3-(4-carboxyphenyl)propiolyl)piperazine methyl ester
[AAA20] 4-(Thiazol-2-yl)-1-(3-(2,6-dimethylphenyl)propiolyl)piperazine
[AAA21] 4-(Thiazol-2-yl)-1-(3-(2-fluorophenyl)propiolyl)piperazine
[AAA22] 4-(Thiazol-2-yl)-1-(3-(3-fluorophenyl)propiolyl)piperazine
[AAA23] 4-(Thiazol-2-yl)-1-(3-(2-chlorophenyl)propiolyl)piperazine
[AAA24] 4-(Thiazol-2-yl)-1-(3-(3-chlorophenyl)propiolyl)piperazine
[AAA25] 4-(Thiazol-2-yl)-1-(3-naphthylpropiolyl)piperazine
[AAA26] 4-(Thiazol-2-yl)-1-(3-(2,3-dimethylphenyl)propiolyl)piperazine
[AAA27] 4-(Thiazol-2-yl)-1-(3-(3,4-dimethylphenyl)propiolyl)piperazine
[AAA28] 4-(Thiazol-2-yl)-1-(3-(3-nitrophenyl)propiolyl)piperazine
[AAA29] 4-(Thiazol-2-yl)-1-(3-(2-nitrophenyl)propiolyl)piperazine
[AAA3] 4-(Thiazol-2-yl)-1-(3-(3-carboxyphenyl)propiolyl)piperazine ethyl ester
[AAA30] 4-(Thiazol-2-yl)-1-(3-(3-formylphenyl)propiolyl)piperazine
[AAA31] 4-(Thiazol-2-yl)-1-(3-(3-ethenylphenyl)propiolyl)piperazine
[AAA32] 4-(Thiazol-2-yl)-1-(3-pyrid-2-ylpropiolyl)piperazine
[AAA33] 4-(Thiazol-2-yl)-1-(3-pyrid-3-ylpropiolyl)piperazine
[AAA34] 4-(Thiazol-2-yl)-1-(3-pyrid-4-ylpropiolyl)piperazine
[AAA35] 4-(Thiazol-2-yl)-1-(3-(quinolin-6-yl)propiolyl)piperazine
[AAA36] 4-(Thiazol-2-yl)-1-(3-(3-isopropylphenyl)propiolyl)piperazine
[AAA37] 4-(Thiazol-2-yl)-1-(3-biphenyl-3-ylpropiolyl)piperazine
[AAA38] 4-(Thiazol-2-yl)-1-(3-naphth-2-ylpropiolyl)piperazine
[AAA39] 4-(Thiazol-2-yl)-1-(3-(1-methyl-indol-5-yl)propiolyl)piperazine
[AAA4] 4-(Thiazol-2-yl)-1-(3-(2-hydroxyphenyl)propiolyl)piperazine
[AAA40] 4-(Thiazol-2-yl)-1-(3-(3-methylmercaptophenyl)propiolyl)piperazine
[AAA41] 4-(Thiazol-2-yl)-1-(3-(3-cyano-4-fluorophenyl)propiolyl)piperazine
[AAA42] 4-(Thiazol-2-yl)-1-(3-(3-methoxymethylphenyl)propiolyl)piperazine
[AAA43] 4-(Thiazol-2-yl)-1-(3-(3-hydroxyphenyl)propiolyl)piperazine
[AAA44] 4-(Thiazol-2-yl)-1-(3-(3-acetaminophenyl)propiolyl)piperazine
[AAA45] 4-(Thiazol-2-yl)-1-(3-(4-acetaminophenyl)propiolyl)piperazine
[AAA46] 4-(Thiazol-2-yl)-1-(3-(2-carboxyphenyl)propiolyl)piperazine
[AAA47] 4-(Thiazol-2-yl)-1-(3-(3-carboxyphenyl)propiolyl)piperazine
[AAA48] 4-(Thiazol-2-yl)-1-(3-(4-carboxyphenyl)propiolyl)piperazine
[AAA49] 4-(Thiazol-2-yl)-1-(3-(3-carboxyphenyl)propiolyl)piperazine methyl ester
[AAA5] 4-(Thiazol-2-yl)-1-(3-(4-hydroxyphenyl)propiolyl)piperazine
[AAA50] 4-(Thiazol-2-yl)-1-(3-(3-aminocarbonylphenyl)propiolyl)piperazine
[AAA51] 4-(Thiazol-2-yl)-1-(3-(3-methylaminocarbonylphenyl)propiolyl)piperazine
[AAA52] 4-(Thiazol-2-yl)-1-(3-(3-dimethylaminocarbonylphenyl)propiolyl)piperazine
[AAA53] 4-(Thiazol-2-yl)-1-(3-(2-tolyl)propiolyl)piperazine
[AAA54] 4-(Thiazol-2-yl)-1-(3-(3-tolyl)propiolyl)piperazine hydrochloride
[AAA55] 4-(Thiazol-2-yl)-1-(3-(4-tolyl)propiolyl)piperazine hydrochloride
[AAA56] 4-(Thiazol-2-yl)-1-(3-phenylpropiolyl)piperazine hydrochloride
[AAA57] 4-(Thiazol-2-yl)-1-(3-(2-trifluoromethylphenyl)propiolyl)piperazine hydrochloride
[AAA58] 4-(Thiazol-2-yl)-1-(3-(3-trifluoromethylphenyl)propiolyl)piperazine hydrochloride
[AAA59] 4-(Thiazol-2-yl)-1-(3-(4-trifluoromethylphenyl)propiolyl)piperazine hydrochloride
[AAA6] 4-(Thiazol-2-yl)-1-(3-(2-aminophenyl)propiolyl)piperazine
[AAA60] 4-(Thiazol-2-yl)-1-(3-pentylpropiolyl)piperazine
[AAA61] 4-(Thiazol-2-yl)-1-(3-(4-fluorophenyl)propiolyl)piperazine
[AAA62] 4-(Thiazol-2-yl)-1-(3-(4-chlorophenyl)propiolyl)piperazine
[AAA63] 2-Methyl-4-(thiazol-2-yl)-1-(3-phenylpropiolyl)piperazine
[AAA64] (S)2-Methyl-4-(thiazol-2-yl)-1-(3-phenylpropiolyl)piperazine
[AAA65] (R)2-Methyl-4-(thiazol-2-yl)-1-(3-phenylpropiolyl)piperazine
[AAA66] 2-Methyl-4-(thiazol-2-yl)-1-(3-phenylpropiolyl)piperazine hydrochloride
[AAA67] 2-Methyl-4-(thiazol-2-yl)-1-(3-(3-tolyl)propiolyl)piperazine
[AAA68] 2-Methyl-4-(thiazol-2-yl)-1-(3-(3-tolyl)propiolyl)piperazine hydrochloride
[AAA69] 4-(Thiazol-2-yl)-1-(3-cyclohexylpropiolyl)piperazine

[AAA7] 4-(Thiazol-2-yl)-1-(3-(3-aminophenyl)propiolyl)piperazine
[AAA70] 4-(Thiazol-2-yl)-1-(3-methylpropiolyl)piperazine
[AAA71] 2-Ethyl-4-(thiazol-2-yl)-1-(3-phenylpropiolyl)piperazine
[AAA72] 2-Phenyl-4-(thiazol-2-yl)-1-(3-phenylpropiolyl)piperazine
[AAA73] 4-(Thiazol-2-yl)-1-(3-(2-furyl)propiolyl)piperazine
[AAA74] 4-(Thiazol-2-yl)-1-(3-(3-furyl)propiolyl)piperazine
[AAA75] cis-2,6-Dimethyl-4-(thiazol-2-yl)-1-(3-phenylpropiolyl)piperazine
[AAA76] 4-(5-Carboxy-thiazol-2-yl)-1-(3-phenylpropiolyl)piperazine ethyl ester
[AAA77] 4-(4-Carboxy-thiazol-2-yl)-1-(3-phenylpropiolyl)piperazine ethyl ester
[AAA78] 4-(5-Carboxy-thiazol-2-yl)-1-(3-phenylpropiolyl)piperazine
[AAA79] 4-(4-Carboxy-thiazol-2-yl)-1-(3-phenylpropiolyl)piperazine
[AAA8] 4-(Thiazol-2-yl)-1-(3-(4-aminophenyl)propiolyl)piperazine
[AAA80] 4-(5-Methylaminocarbonylthiazol-2-yl)-1-(3-phenylpropiolyl)piperazine
[AAA81] 4-(5-Dimethylaminocarbonylthiazol-2-yl)-1-(3-phenylpropiolyl)piperazine
[AAA82] 4-(3-Phenyl-1,2,4-thiadiazol-5-yl)-1-(3-phenylpropiolyl)piperazine
[AAA83] 4-(Thiazol-2-yl)-1-(3-(quinol-7-yl)propiolyl)piperazine
[AAA84] 4-(Thiazol-2-yl)-1-(3-phenylpropiolyl)piperazine-3-on
[AAA85] 4-(3-(4-Fluorobenzyl)-1,2,4-thiadiazol-5-yl)-1-(3-phenylpropiolyl)piperazine
[AAA86] 4-(5-Nitrothiazol-2-yl)-1-(3-phenylpropiolyl)piperazine
[AAA87] 4-(4-tert-Butylthiazol-2-yl)-1-(3-phenylpropiolyl)piperazine
[AAA88] 4-(5-Methylthiazol-2-yl)-1-(3-phenylpropiolyl)piperazine
[AAA89] 4-(4,5-Dimethylthiazol-2-yl)-1-(3-phenylpropiolyl)piperazine
[AAA9] 4-(Thiazol-2-yl)-1-(3-(indol-5-yl)propiolyl)piperazine
[AAA90] 4-(5-Bromo-4-phenylthiazol-2-yl)-1-(3-phenylpropiolyl)piperazine
[AAA91] 4-(5-Bromo-4-methylthiazol-2-yl)-1-(3-phenylpropiolyl)piperazine
[AAA92] 4-(4-Methylthiazol-2-yl)-1-(3-phenylpropiolyl)piperazine
[AAA93] 4-(4-Trifluoromethylthiazol-2-yl)-1-(3-phenylpropiolyl)piperazine
[AAA94] 4-(4-Chlorothiazol-2-yl)-1-(3-phenylpropiolyl)piperazine
[AAA95] 4-(5-Chlorothiazol-2-yl)-1-(3-phenylpropiolyl)piperazine
[AAA96] 4-(4-Bromothiazol-2-yl)-1-(3-phenylpropiolyl)piperazine
[AAA97] 4-(5-Bromothiazol-2-yl)-1-(3-phenylpropiolyl)piperazine
[AAA98] 4-(5-Phenylthiazol-2-yl)-1-(3-phenylpropiolyl)piperazine
[AAA99] 4-(4phenylthiazol-2-yl)-1-(3-phenylpropiolyl)piperazine
[BBB2] 4-(Thiazol-2-yl)-1-propiolylpiperazine;
[CCC1] 4-(3-Phenyl-1,2,4-thiadiazol-5-yl)-1-(3-(2-methoxyphenyl)propiolyl)piperazine
[CCC2] 4-(3-Phenyl-1,2,4-thiadiazol-5-yl)-1-(3-(4-methoxyphenyl)propiolyl)piperazine
[CCC3] 4-(3-Phenyl-1,2,4-thiadiazol-5-yl)-1-(3-(2-fluorophenyl)propiolyl)piperazine
[CCC4] 4-(3-Phenyl-1,2,4-thiadiazol-5-yl)-1-(3-(3-fluorophenyl)propiolyl)piperazine
[CCC5] 4-(3-Phenyl-1,2,4-thiadiazol-5-yl)-1-(3-(4-fluorophenyl)propiolyl)piperazine
[CCC6] 4-(3-Phenyl-1,2,4-thiadiazol-5-yl)-1-(3-(2,4-dichlorophenyl)propiolyl)piperazine
[CCC7] 4-(3-Phenyl-1,2,4-thiadiazol-5-yl)-1-(3-(3,5-dichlorophenyl)propiolyl)piperazine
[CCC8] 4-(3-(4-Fluorophenyl)-1,2,4-thiadiazol-5-yl)-1-(3-(tol-2-yl)propiolyl)piperazine
[CCC9] 4-(3-(4-Fluorophenyl)-1,2,4-thiadiazol-5-yl)-1-(3-(3-methoxyphenyl)propiolyl)piperazine
[CCC10] 4-(3-(4-Fluorophenyl)-1,2,4-thiadiazol-5-yl)-1-(3-(3-fluoro-4-methylphenyl)propiolyl)piperazine
[CCC11] 4-(3-(4-Fluorophenyl)-1,2,4-thiadiazol-5-yl)-1-(3-(2,4-difluorophenyl)propiolyl)piperazine
[CCC12] 4-(3-(4-Fluorophenyl)-1,2,4-thiadiazol-5-yl)-1-(3-(tol-3-yl)propiolyl)piperazine
[CCC13] 4-(3-(4-Fluorophenyl)-1,2,4-thiadiazol-5-yl)-1-(3-(4-trifluoromethylphenyl)propiolyl)piperazine
[CCC14] 4-(3-(4-Fluorophenyl)-1,2,4-thiadiazol-5-yl)-1-(3-(3-trifluoromethylphenyl)propiolyl)piperazine
[CCC15] 4-(3-(4-Fluorophenyl)-1,2,4-thiadiazol-5-yl)-1-(3-(2-chloro-5-trifluoromethylphenyl)propiolyl)piperazine
[CCC16] 4-(3-tert-Butyl-1,2,4-thiadiazol-5-yl)-1-(3-(thiophen-2-yl)propiolyl)piperazine
[CCC17] 4-(3-tert-Butyl-1,2,4-thiadiazol-5-yl)-1-(3-(3-trifluoromethylphenyl)propiolyl)piperazine
[CCC18] 4-(3-tert-Butyl-1,2,4-thiadiazol-5-yl)-1-(3-(2-methoxyphenyl)propiolyl)piperazine
[CCC19] 4-(3-tert-Butyl-1,2,4-thiadiazol-5-yl)-1-(3-(tol-2-yl)propiolyl)piperazine
[CCC20] 4-(3-tert-Butyl-1,2,4-thiadiazol-5-yl)-1-(3-(3-fluoro-4-methylphenyl)propiolyl)piperazine
[CCC21] 4-(3-tert-Butyl-1,2,4-thiadiazol-5-yl)-1-(3-(2-chloro-5-trifluoromethylphenyl)propiolyl)piperazine
[CCC22] 4-(Thiazol-2-yl)-1-(3-(2,4-difluorophenyl)propiolyl)piperazine
[CCC23] 4-(Thiazol-2-yl)-1-(3-(2-bromo-5-methoxyphenyl)propiolyl)piperazine
[CCC24] 4-(Thiazol-2-yl)-1-(3-(3-bromo-4-methoxyphenyl)propiolyl)piperazine
[CCC25] 4-(Thiazol-2-yl)-1-(3-(3,5-dichlorophenyl)propiolyl)piperazine
[CCC26] 4-(Thiazol-2-yl)-1-(3-(4-fluoro-3-methylphenyl)propiolyl)piperazine
[CCC27] 4-(4-tert-Butylthiazol-2-yl)-1-(3-(3-cyanophenyl)propiolyl)piperazine
[CCC28] 4-(4-tert-Butylthiazol-2-yl)-1-(3-(2-trifluoromethylphenyl)propiolyl)piperazine
[CCC29] 4-(4phenylthiazol-2-yl)-1-(3-(2,3-dimethylphenyl)propiolyl)piperazine
[CCC30] 4-(4phenylthiazol-2-yl)-1-(3-(4-fluorophenyl)propiolyl)piperazine
[CCC31] 4-(4-Methylthiazol-2-yl)-1-(3-(tol-3-yl)propiolyl)piperazine
[CCC32] 4-(4-Methylthiazol-2-yl)-1-(3-(thiophen-2-yl)propiolyl)piperazine
[CCC33] 4-(5-Methylthiazol-2-yl)-1-(3-(tol-4-yl)propiolyl)piperazine

[CCC34] 4-(5-Methylthiazol-2-yl)-1-(3-(2-cyanophenyl)propiolyl)piperazine

[CCC35] 4-(4,5-Dimethylthiazol-2-yl)-1-(3-(3-cyanophenyl)propiolyl)piperazine

[CCC36] 4-(4,5-Dimethylthiazol-2-yl)-1-(3-(3,4-dimethylphenyl)propiolyl)piperazine

[CCC37] 4-(4-(4-Methoxyphenyl)thiazol-2-yl)-1-(3-(2,4-dimethylphenyl)-propiolyl)piperazine

[CCC38] 4-(4-(4-Methoxyphenyl)thiazol-2-yl)-1-(3-(4-trifluoromethylphenyl)propiolyl)piperazine

[CCC39] 4-(4-(4-Fluorophenyl)thiazol-2-yl)-1-(3-(2-cyanophenyl)propiolyl)piperazine

[CCC40] 4-(4-(4-Chlorophenyl)thiazol-2-yl)-1-(3-(4-cyanophenyl)propiolyl)piperazine

[AAA00108] 4-(Thiazol-2-yl)-1-(3-(1-Methyl-indol-6-yl)propiolyl)piperazine

[AAA00109] 4-(Thiazol-2-yl)-1-(3-(3-acetylphenyl)propiolyl)piperazine

[AAA00110] 4-(Thiazol-2-yl)-1-(3-(3-fluoro-5-methylphenyl)propiolyl)piperazine

[AAA00111] 4-(Thiazol-2-yl)-1-(3-(2-fluoro-3-methylphenyl)propiolyl)piperazine

[AAA00112] 4-(Thiazol-2-yl)-1-(3-(3-methylaminophenyl)propiolyl)piperazine

[AAA00113] 4-(Thiazol-2-yl)-1-(3-(3-dimethylaminophenyl)propiolyl)piperazine

[AAA00114] 4-(Thiazol-2-yl)-1-(dimethylcarbamoylpropiolyl)piperazine

[AAA00115] 4-(Thiazol-2-yl)-1-(3-(3-methylsulfinylphenyl)propiolyl)piperazine

[AAA00116] 4-(Thiazol-2-yl)-1-(3-(3-methylsulfonylphenyl)propiolyl)piperazine

[AAA00117] 4-(Thiazol-2-yl)-1-(3-(3-ethynylphenyl)propiolyl)piperazine

[AAA00118] 4-(Thiazol-2-yl)-1-(3-(4-methylthiophen-2-yl)propiolyl)piperazine

[AAA00119] 2-Methyl-4-(thiazol-2-yl)-1-(3-(3-chlorophenyl)propiolyl)piperazine

[AAA00120] 4-(Thiazol-2-yl)-1-(3-(3-ethylphenyl)propiolyl)piperazine

[AAA00121] 2-tert-Butyl-4-(thiazol-2-yl)-1-(3-phenylpropiolyl)piperazine

[AAA00122] 4-(Thiazol-2-yl)-1-(3-(3-difluoromethylphenyl)propiolyl)piperazine

[AAA00123] 2-Methyl-4-(thiazol-2-yl)-1-(3-(3-cyanophenyl)propiolyl)piperazine

[AAA00124] 2-isopropyl-4-(thiazol-2-yl)-1-(3-phenylpropiolyl)piperazine

[AAA00125] 4-(Thiazol-2-yl)-1-(3-(3-trimethylsilanylethynylphenyl)propiolyl)piperazine;

in each case optionally in the form of pure stereoisomers thereof particularly enantiomers or diastereoisomers, the racemates thereof or in the form of a mixture of stereoisomers, particularly the enantiomers and/or diastereoisomers, in an arbitrary mixture ratio, or in each case in the form of appropriate salts thereof, or in each case in the form of appropriate solvates thereof.

Another object of the present invention is a process the production of compounds of the above general formula I according to which at least one compound corresponding to formula II,

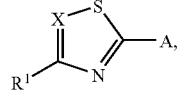

in which the radicals X and $R^1$ have the meanings stated above and A denotes a leaving group, preferably a halogen radical or a sulfonic acid ester, more preferably chlorine or bromine, is caused to react with at least one compound corresponding to formula III,

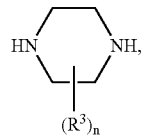

in which $R^3$ and n have the meanings stated above, optionally in a reaction medium, optionally in the presence of at least one base and/or at least one organometallic compound and/or at least one metallic hydride reagent, preferably at a temperature of from −70° C. to 300° C., preferably from −70° C. to 150° C., to produce at least one corresponding compound corresponding to formula IV, optionally in the form of an appropriate salt thereof,

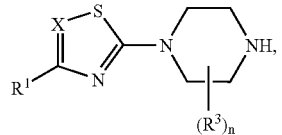

in which X, $R^1$, $R^3$, and n have the meanings stated above, and the said product is optionally purified and/or isolated;

or at least one compound corresponding to formula II is caused to react with at least one compound corresponding to formula V,

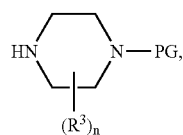

in which $R^3$ and n have the meanings stated above and PG denotes a protective group, preferably a protective group selected from the group consisting of tert-butyloxycarbonyl, benzyl, carbobenzoxy, and 9-fluorenylmethyloxycarbonyl optionally in a reaction medium, optionally in the presence of at least one base and/or at least one organometallic compound and/or at least one metallic hydride reagent, preferably at a temperature of from −70° C. to 300° C. to produce at least one corresponding compound corresponding to formula VI,

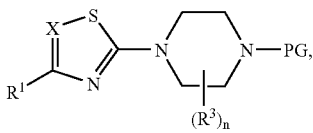

in which R$^1$, R$^3$, X, n and PG have the meanings stated above, and the resulting product is optionally purified and/or isolated;

or at least one compound corresponding to formula VII,

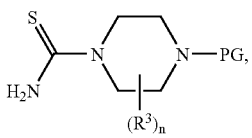

in which R$^3$ and n have the meanings stated above and PG denotes a protective group, preferably a protective group selected from the group consisting of tert-butyloxycarbonyl, benzyl, carbobenzoxy, and 9-fluorenylmethyloxycarbonyl, is caused to react with at least one compound corresponding to formula R$^1$—C(═O)—CH$_2$-A or (C$_{1-5}$ alkyl-O)$_2$—CH—CH$_2$-A, in which R$^1$ has the meaning stated above and A denotes a leaving group, preferably a halogen radical, more preferably a bromine atom, in a reaction medium, optionally in the presence of at least one organic base or in the presence of at least one acid, preferably in the presence of at least one base selected from the group consisting of triethylamine, diisopropylethylamine, N-methylmorpholine, dimethylaminopyridine, and pyridine or in the presence of at least one acid selected from the group consisting of acetic acid, trifluoroacetic acid, and hydrochloric acid, preferably at a temperature between −70° C. and 300° C. to produce at least one corresponding compound corresponding to formula VI, optionally in the form of an appropriate salt in which R$^1$, R$^3$, and n have the meanings stated above, PG has the meaning stated above and X denotes CH, and the said product is optionally purified and/or isolated;

and at least one compound corresponding to formula VI, when PG denotes a tert-butoxycarbonyl group or 9-fluorenylmethyloxycarbonyl group, in a reaction medium, in the presence of at least one acid, preferably in the presence of at least one acid selected from the group consisting of hydrochloric acid and trifluoroacetic acid, preferably at a temperature between −70° C. and 100° C. or, when PG denotes a benzyl group or benzyloxycarbonyl group, in a reaction medium, in the presence of hydrogen and in the presence of at least one catalyst, preferably in the presence of palladium on carbon, preferably at a temperature between −70° C. and 100° C., is converted to at least one corresponding compound corresponding to formula IV, optionally in the form of an appropriate salt thereof, in which X, R$^1$, R$^3$, and n have the meanings stated above, and the resulting product is optionally purified and/or isolated;

and at least one compound corresponding to formula IV is caused to react with at least one compound corresponding to formula R$^4$—C≡C—C(═O)—OH, in which R$^4$ has the meaning stated above, in a reaction medium, optionally in the presence of at least one suitable coupling agent, optionally in the presence of at least one base, preferably at a temperature of from −70° C. to 100° C., or is caused to react with at least one compound corresponding to formula R$^4$—C≡C—C(═O)-A, in which R$^4$ has the meaning stated above and A denotes a leaving group, preferably a halogen radical, more preferably or chlorine or bromine atom, in a reaction medium, optionally in the presence of at least one base, at a temperature of from −70° C. to 100° C., to form at least one corresponding compound corresponding to formula 1, optionally in the form of an appropriate salt thereof,

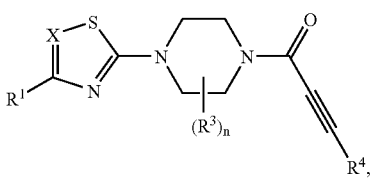

in which X and R$^1$, R$^3$, R$^4$, and n have the meanings stated above, and the resulting product is optionally purified and/or isolated;

or at least one compound corresponding to formula IV is caused to react with propynoic acid [HC≡C—C(═O)—OH] in a reaction medium, optionally in the presence of at least one suitable coupling agent, optionally in the presence of at least one base, preferably at a temperature of from −70° C. to 100° C., or is caused to react with at least one compound corresponding to formula HC≡C—C(═O)-A in which A denotes a leaving group, preferably a halogen radical, more preferably a chlorine radical or bromine radical, in a reaction medium, optionally in the presence of at least one base, preferably at a temperature of from −70° C. to 100° C., to form at least one corresponding compound corresponding to formula VIII, optionally in the form of an appropriate salt thereof,

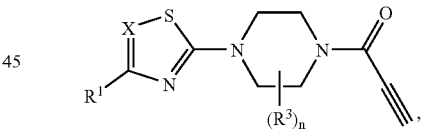

in which R$^1$, R$^3$, X, and n have the meanings stated above, and the resulting product is optionally purified and/or isolated;

and at least one compound corresponding to formula VIII is caused to react with at least one compound corresponding to formula R$^4$-A in which R$^4$ has the meaning stated above with the exception of hydrogen and A denotes a leaving group, preferably a halogen radical or a sulfonic acid ester, more preferably iodine, bromine, or triflate, in a reaction medium, optionally in the presence of at least one catalyst, preferably in the presence of a palladium catalyst selected from the group consisting of palladium chloride [PdCl$_2$], palladium acetate [Pd(OAc)$_2$], tetrakis(triphenylphosphine)palladium [Pd(PPh$_3$)$_4$], bis(triphenylphosphine)palladium dichloride [Pd(PPh$_3$)$_2$Cl$_2$] and bis(triphenylphosphine)palladium acetate [Pd(PPh$_3$)$_2$(OAc)$_2$], optionally in the presence of at least one ligand, preferably in the presence of at least one ligand selected from the group consisting of triphenylphosphine, triphenylarsine, and tri-2-furylphosphine, optionally in the presence of at least one inorganic salt, preferably in the presence of at least one inorganic salt selected from the group consisting of lithium chloride and zinc chloride, optionally in the presence of at least one copper salt, preferably in the presence of copper(I) iodide, optionally in the presence of at least one organic or inorganic base, preferably in the presence of at least one base selected from the group consisting of triethylamine, [1,4]-diazabicyclo-[2,2,2]-octane, diisopropylamine, diisopropylethylamine, potassium carbonate, and sodium hydrogencarbonate, preferably at a temperature between −70° C. and 300° C. to form at least one corresponding compound corresponding to formula I, optionally in the form of an appropriate salt thereof, and the resulting product is optionally purified and/or isolated.

Another object of the present invention is a process the production of compounds of the above general formula I according to which at least one compound corresponding to formula II,

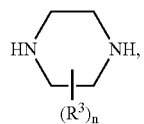

III in which $R^3$ and n have the meanings stated above, is caused to react with at least one compound corresponding to formula $R^4$—C≡C—C(=O)—OH, in which $R^4$ has the meaning stated above, in a reaction medium, optionally in the presence of at least one suitable coupling agent, optionally in the presence of at least one base, preferably at a temperature ranging from −70° C. to 100° C., or is caused to react with at least one compound corresponding to formula $R^4$—C≡C—C(=O)-A, in which $R^4$ has the meaning stated above and A denotes a leaving group, preferably a halogen radical, more preferably or a chlorine radical or bromine radical, in a reaction medium, optionally in the presence of at least one base, preferably at a temperature ranging from −70° C. to 100° C., to form at least one corresponding compound corresponding to formula IX, optionally in the form of an appropriate salt thereof,

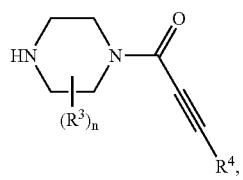

IX in which $R^3$, $R^4$, and n have the meanings stated above, and the resulting product is optionally purified and/or isolated;

or at least one compound corresponding to formula V,

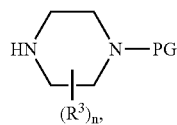

V in which $R^3$ and n have the meanings stated above and PG denotes a protective group, preferably a protective group selected from the group consisting of tert-butyloxycarbonyl, benzyl, carbobenzoxy, and 9-fluorenylmethyloxycarbonyl, is caused to react with at least one compound corresponding to formula $R^4$—C≡C—C(=O)—OH, in which $R^4$ has the meaning stated above, in a reaction medium, optionally in the presence of at least one suitable coupling agent, optionally in the presence of at least one base, preferably at a temperature ranging from −70° C. to 100° C., or is caused to react with at least one compound corresponding to formula $R^4$—C≡C—C(=O)-A, in which $R^4$ has the meaning stated above and A denotes a leaving group, preferably a halogen radical, more preferably or a chlorine radical or bromine radical, in a reaction medium, optionally in the presence of at least one base, preferably at a temperature ranging from −70° C. to 100° C., to form at least one corresponding compound corresponding to formula XI, optionally in the form of an appropriate salt thereof,

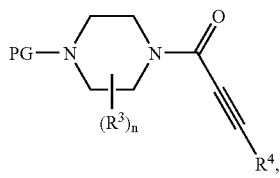

XI in which $R^3$, $R^4$, and n and PG have the meanings stated above, and the resulting product is optionally purified and/or isolated; and at least one compound corresponding to formula XI when PG denotes a tert-butoxycarbonyl group or 9-fluorenylmethyloxycarbonyl group, in a reaction medium, in the presence of at least one acid, preferably in the presence of at least one acid selected from the group consisting of hydrochloric acid and trifluoroacetic acid, preferably at a temperature ranging from −70° C. to 100° C. or, when PG denotes a benzyl group or a benzyloxycarbonyl group, in a reaction medium, in the presence of hydrogen and in the presence of at least one catalyst, preferably in the presence of palladium on carbon, preferably at a temperature ranging from −70° C. to 100° C., is converted to at least one corresponding compound corresponding to formula IX, optionally in the form of an appropriate salt thereof, in which $R^1$, $R^3$, and n have the meanings stated above, and the resulting product is optionally purified and/or isolated;

and at least one compound corresponding to formula IX is caused to react with at least one compound corresponding to formula II,

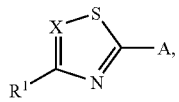

II in which the radicals X and $R^1$ have the meanings stated above and A denotes a leaving group, preferably a halogen radical or a sulfonic acid ester, more preferably a chlorine radical or bromine radical, in a reaction medium, optionally in the presence of at least one base and/or at least one organometallic compound and/or at least one metallic hydride reagent, preferably at a temperature ranging from −70° C. to 300° C. to form at least one corresponding compound corresponding to formula 1, optionally in the form of an appropriate salt thereof, and the resulting product is optionally purified and/or isolated.

A process of the invention the production of substituted 1-propiolylpiperazines of the aforementioned formula I is illustrated by the following scheme 1.

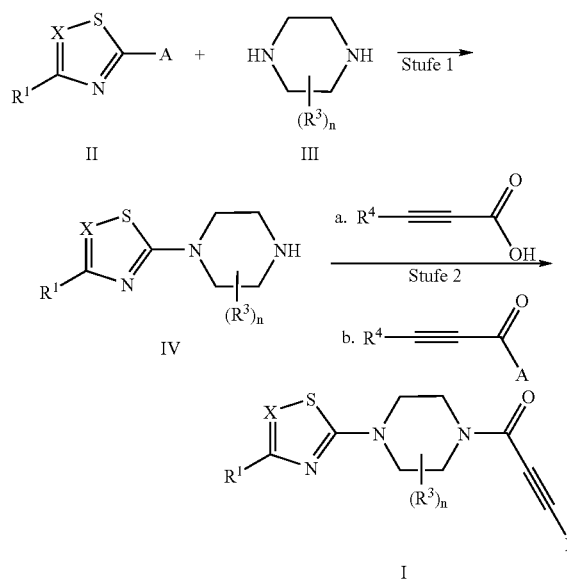

In stage 1 thiazoles or thiadiazoles of the above general formula II, in which A denotes a leaving group, preferably a halogen radical or a sulfonic acid ester selected from the group consisting of mesylate, triflate, and tosylate, more preferably a chlorine atom or bromine atom, are caused to react with piperazines of the above general formula III, optionally in a reaction medium, preferably a reaction medium selected from the group consisting of methanol, ethanol, isopropanol, n-butanol, diethyl ether, tetrahydrofuran, dichloromethane, chloroform, dimethylformamide, acetonitrile, pyridine, dioxane, ethyl acetate, dimethylsulfoxide, toluene and appropriate mixtures thereof, more preferably a reaction medium selected from the group consisting of methanol, ethanol, and n-butanol, optionally in the presence of an organic or inorganic base, preferably selected from the group consisting of triethylamine, sodium hydrogencarbonate, dimethylaminopyridine, potassium carbonate, and sodium hydroxide, and/or optionally in the presence of an organometallic compound or a metallic hydride reagent, preferably selected from the group consisting of n-butyllithium, phenyllithium, sodiumlithium, potassiumlithium, and sodium amide, preferably at temperatures ranging from −70° C. to 150° C., to form compounds corresponding to formula IV.

In stage 2 compounds of the above general formula IV are caused to react with carboxylic acids of the above general formula R⁴—C≡C—(C═O)—OH in a reaction medium preferably selected from the group consisting of diethyl ether, tetrahydrofuran, acetonitrile, methanol, ethanol, (1,2)-dichloroethane, dimethylformamide, dichloromethane, and appropriate mixtures thereof, optionally in the presence of at least one coupling agent preferably selected from the group consisting of 1-benzotriazolyloxy-tris(dimethylamino)phosphonium hexafluorophosphate (BOP), dicyclohexylcarbodiimide (DCC), N'-(3-dimethylaminopropyl)-N-ethylcarbodiimide (EDCI), diisoproylcarbodiimide, 1,1'-carbonyldiimidazole (CDI), N-[(dimethyamino)-1H-1,2,3-triazolo[4,5-b]pyridino-1-ylmethylene]-N-methylmethanaminium hexafluorophosphate N-oxide (HATU), O-(benzotriazol-1-yl)-N,N,N',N'-tetramethyluronium hexafluorophosphate (HBTU), O(benzotriazol-1-yl)-N,N,N',N'-tetramethyluronium tetrafluoroborate (TBTU) and 1-hydroxy-7-azabenzotriazole (HOAt), preferably in the presence of TBTU as coupling agent, optionally in the presence of at least one organic base, preferably selected from the group consisting of triethylamine, pyridine, dimethylaminopyridine, N-methylmorpholine, and diisopropylethylamine, preferably in the presence of diisopropylethylamine, preferably at temperatures ranging from −70° C. to 100° C. to form compounds corresponding to formula I.

Alternatively, compounds of the above general formula IV are caused to react with carboxylic derivatives of the above general formula R⁴C≡C—(C═O)-A in which A denotes a leaving group, preferably a halogen radical, more preferably chlorine or bromine, in a reaction medium preferably selected from the group consisting of diethyl ether, tetrahydrofuran, acetonitrile, methanol, ethanol, dimethylformamide, dichloromethane, and suitable mixtures thereof, optionally in the presence of an organic or inorganic base preferably selected from the group consisting of triethylamine, dimethylaminopyridine, pyridine, and diisopropylamine, at temperatures ranging from −70° C. to 100° C. to produce compounds corresponding to formula I.

Another process of the invention the production of substituted 1-propiolylpiperazines of the above general formula I is illustrated below under scheme 2.

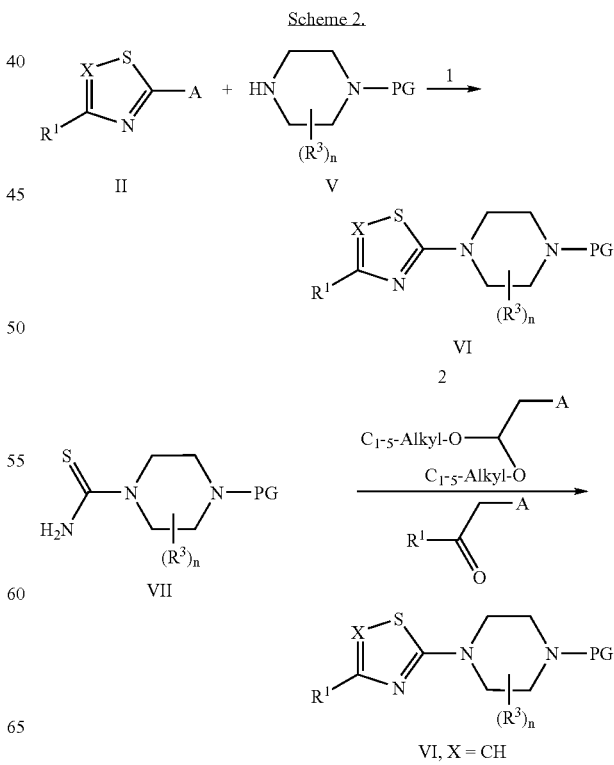

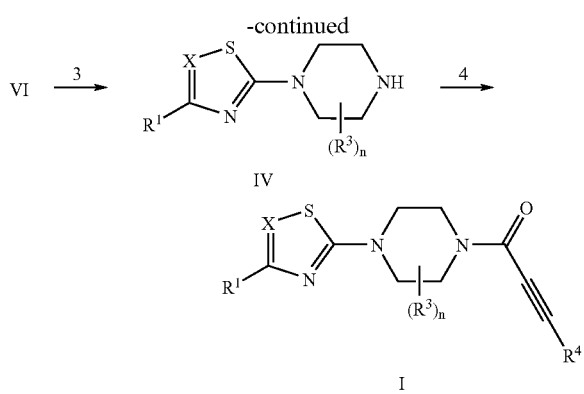

In stage 1 thiazoles or thiadiazoles of the above general formula II, in which A denotes a leaving group, preferably a halogen radical or a sulfonic acid ester selected from the group consisting of mesylate, triflate, and tosylate, more preferably a chlorine radical or bromine atom, are caused to react with piperazines of the above general formula V, in which PG denotes a protective group, preferably a protective group selected from the group consisting of tert-butyloxycarbonyl, carbobenzoxy, benzyl, and 9-fluorenylmethyloxycarbonyl to form compounds corresponding to formula VI. The precise conditions can be discerned from the publication Journal of Medicinal Chemistry 1972, 15(3), pages 295 to 301. The relevant parts of this publication are to be regarded as part of the disclosure of this application.

In stage 2 compounds of the above general formula VII, in which PG denotes a protective group, preferably a protective group selected from the group consisting of tert-butyloxycarbonyl, benzyl, carbobenzoxy, and 9-fluorenylmethyloxycarbonyl, are caused to react with at least one compound corresponding to formula $R^1$—C(=O)—$CH_2$-A or $(C_{1-5}$ alkyl-O$)_2$—CH—$CH_2$-A, preferably with at least one compound corresponding to formula $R^1$—C(=O)—$CH_2$-A or $(C_2H_5)_2$—CH—$CH_2$-A in which A denotes a leaving group, preferably a halogen radical, more preferably or a bromine atom, in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulfoxide, toluene and corresponding mixtures, more preferably in ethanol and/or dioxane, optionally in the presence of at least one organic base or in the presence of at least one acid, preferably in the presence of at least one base selected from the group consisting of triethylamine, diisopropylethylamine, N-methylmorpholine, dimethylaminopyridine and pyridine or in the presence of at least one acid selected from the group consisting of acetic acid, trifluoroacetic acid, and hydrochloric acid, preferably at a temperature ranging from —70° C. to 300° C. to produce a corresponding compound corresponding to formula VI. The precise conditions can be discerned from the publication Journal of Medicinal Chemistry 1998, 41(25), pages 5027 to 5054. The relevant parts of this publication are to be regarded as part of the disclosure.

In stage 3 compounds corresponding to formula VI, when PG denotes a tert-butoxycarbonyl group or 9-fluorenylmethyloxycarbonyl group, in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulfoxide, toluene and corresponding mixtures, in the presence of at least one acid, preferably in the presence of at least one acid selected from the group consisting of hydrochloric acid and trifluoroacetic acid, preferably at a temperature ranging from −70° C. to 100° C. or when PG denotes a benzyl group or benzyloxycarbonyl group, in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulfoxide, toluene and corresponding mixtures, in the presence of hydrogen and in the presence of at least one catalyst, preferably in the presence of palladium on carbon, preferably at a temperature ranging from −70° C. to 100° C. are converted to a corresponding compound corresponding to formula IV.

Suitable methods the removal of the aforementioned protective groups can be discerned from the books Protective Groups in Organic Synthesis, T. W. Greene et al., $3^{rd}$ Edition, 1999, Wiley, New York and Protecting Groups, P. J. Kocienski, $3^{rd}$ Edition, 2004, Georg Thieme Verlag, Stuttgart 2004. The relevant parts the references are to be regarded as part of the disclosure of this application.

In stage 4, compounds of the above general formula IV are caused to react with carboxylic acids of the above general formula $R^4$—C≡C—(C=O)—OH or with carboxylic derivatives of the above general formula $R^4$—C≡C—(C=O)-A as described in scheme 1, stage 2, to form compounds corresponding to formula I.

Another process of the invention the production of substituted 1-propiolylpiperazines of the above general formula I is illustrated below under scheme 3.

Scheme 3.

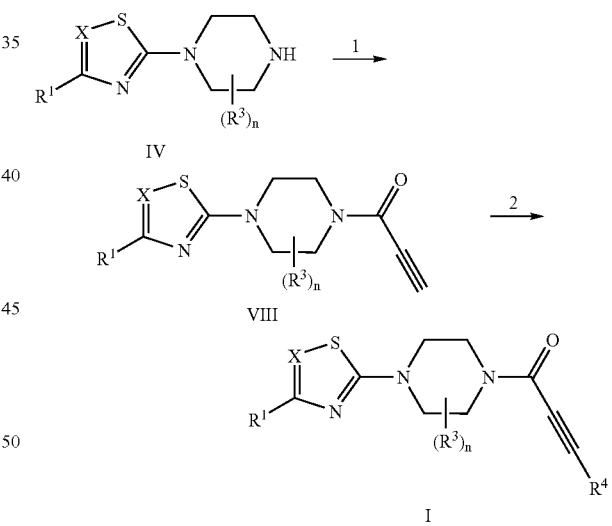

In stage 1 compounds of the above general formula IV are caused to react with propynoic acid H—C≡C—(C=O)—OH or with carboxylic derivatives corresponding to formula H—C≡C—(C=O)-A in which A denotes a leaving group, preferably a halogen radical, more preferably chlorine or bromine, as described in scheme 1, stage 2, to form compounds corresponding to formula VIII.

In stage 2 compounds of the above general formula VIII are caused to react with compounds corresponding to formula $R^4$-A, in which $R^4$ has the meaning stated above with the exception of hydrogen and A denotes a leaving group, preferably a halogen radical or a sulfonic acid ester, more preferably iodine, bromine, or triflate, in a reaction medium, preferably in a reaction medium selected from the group consisting of methanol, ethyl acetate, ethanol, isopropanol, n-butanol, diethyl ether, dioxane, tetrahydrofuran, chloroform, dichloromethane, dimethylformamide, acetonitrile, pyridine, dimethyl sulfoxide, water, toluene and appropriate mixtures thereof, preferably in dimethylformamide, water, ethyl acetate, tetrahydrofuran and appropriate mixtures thereof, optionally in the presence of at least one catalyst, preferably in the presence of a palladium catalyst selected from the group consisting of palladium chloride [PdCl$_2$], palladium acetate [Pd(OAc)$_2$], tetrakis(triphenylphosphine) palladium [Pd(PPh$_3$)$_4$], bis(triphenylphosphine)palladium dichloride [Pd(PPh$_3$)$_2$Cl$_2$] and bis(triphenylphosphine)palladium acetate [Pd(PPh$_3$)$_2$(OAc)$_2$], preferably in the presence of Pd(PPh$_3$)$_4$, Pd(PPh$_3$)$_2$Cl$_2$, or Pd(PPh$_3$)$_2$(OAc)$_2$, optionally in the presence of at least one ligand, preferably in the presence of at least one ligand selected from the group consisting of triphenylphosphine, triphenylarsine, and tri-2-furylphosphine, preferably in the presence of triphenylphosphine, optionally in the presence of at least one inorganic salt, preferably in the presence of at least one inorganic salt selected from the group consisting of lithium chloride and zinc chloride, optionally in the presence of at least one copper salt, preferably in the presence of copper(I) iodide, optionally in the presence of at least one organic or inorganic base, preferably in the presence of at least one base selected from the group consisting of triethylamine, [1,4]-diazabicyclo-[2,2,2]-octane, diisopropylamine, diisopropylethylamine, potassium carbonate, and sodium hydrogencarbonate, preferably at a temperature ranging from −70° C. to 300° C. to produce a compound of formula I.

Particular preference is given to the reaction of compounds corresponding to formula R$^4$—I or R$^4$—Br with compounds corresponding to formula VIII in dimethylformamide in the presence of Pd(PPh$_3$)$_2$Cl$_2$, copper(I) iodide, and diisopropylamine or triethylamine.

Another process of the invention the production of substituted 1-propiolylpiperazines of the above general formula I is illustrated below under scheme 4.

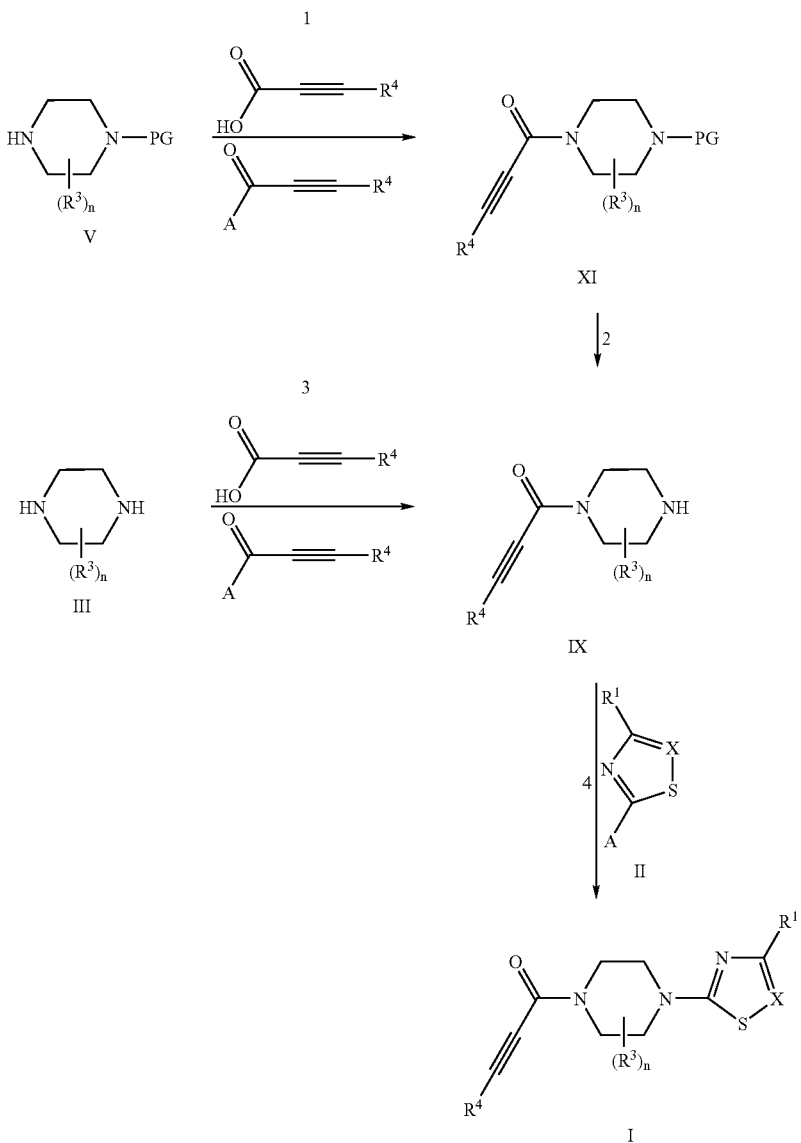

In stage 1 compounds corresponding to formula V, in which PG denotes a protective group, preferably a protective group selected from the group consisting of ?? or tert-butyloxycarbonyl, benzyl, carbobenzoxy, and 9-fluorenyl-methyloxycarbonyl, are caused to react with compounds corresponding to formula $R^4$—C≡C—(C=O)—OH or $R^4$—C≡C—(C=O)-A in which A denotes a leaving group, preferably a halogen radical, more preferably chlorine or bromine, as in scheme 1, stage 2, to produce compounds corresponding to formula XI.

In stage 2, compounds corresponding to formula XI, in which PG denotes a protective group, preferably a protective group selected from the group consisting of tert-butyloxy-carbonyl, benzyl, carbobenzoxy, and 9-fluorenylmethyloxy-carbonyl, as described in scheme 2, stage 3, are converted to compounds corresponding to formula IX.

In stage 3, compounds of the above general formula III are caused to react with propynoic acid H—C≡C—(C=O)—OH or with carboxylic derivatives of the above general formula HC—C≡C—(C=O)-A, in which A denotes a leaving group, preferably a halogen radical, more preferably chlorine or bromine, as described in scheme 1, stage 2, to form compounds corresponding to formula IX.

In stage 4, compounds corresponding to formula IX are caused to react with compounds corresponding to formula II, as in scheme 1, stage 1, to form compounds corresponding to formula I.

The compounds of the aforementioned formulas II, III, V, and VII and corresponding to formulas $R^4$—C≡C—(C=O)—OH and $R^4$—C≡C—(C=O)-A are all commercially available and/or can be prepared by conventional processes known to the person skilled in the art.

The reactions described above can in each case be carried out under conventional conditions familiar to the person skilled in the art, example in respect of pressure or order of addition of the components. The procedure giving optimum results under any specific conditions can be determined by the person skilled in the art if necessary by simple preliminary experiments.

If desired and/or necessary, the intermediates and end products obtained by the reactions described above can in each case be purified and/or isolated by conventional methods known to the person skilled in the art. Suitable purification processes are, example, extraction processes and chromatography processes, such as column chromatography or preparative chromatography.

All of the process steps described above and in each case also the purification and/or isolation of intermediates or end products can be carried out partly or entirely under an inert gas atmosphere, preferably under a blanket of nitrogen.

If the substituted 1-propiolylpiperazines according to the invention of the aforementioned general formulas I, Ib, Ic, Id, Ie, If, Ig, Ih, and Ii, referred to below simply as substituted 1-propiolylpiperazines according to the invention, are obtained in the form of a mixture of their stereoisomers, preferably in the form of their racemates or other mixtures of their various enantiomers and/or diastereomers, after their preparation, these can be separated and optionally isolated by conventional methods known to the person skilled in the art. There may be mentioned by way of example chromatography separation methods, in particular liquid chromatography processes carried out under standard pressure or under elevated pressure, preferably MPLC and HPLC processes, as well as methods of fractional crystallization. In these processes, in particular, it is possible to separate from one another individual enantiomers e.g. diastereomeric salts formed by means of HPLC on chiral phases or by means of crystallization with chiral acids, example (+)-tartaric acid, (−)-tartaric acid or (+)-10-camphorsulfonic acid.

The substituted 1-propiolylpiperazines according to the invention of the aforementioned general formula I and optionally any appropriate stereoisomers can be obtained in the form of corresponding salts, in particular obtained in the form of corresponding physiologically acceptable salts, by conventional processes known to the person skilled in the art, and the medicinal drug according to the invention may contain one or more salts of one or more of these compounds.

The respective salts of the substituted 1-propiolylpiperazines according to the invention of the aforementioned general formula I and of appropriate stereoisomers can be obtained, example, by reaction with one or more inorganic acids and/or one or more organic acids. Suitable acids can preferably be selected from the group consisting of perchloric acid, hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharic acid, cyclohexanesulfamic acid, aspartame, monomethylsebacic acid, 5-oxo-proline, hexane-1-sulfonic acid, nicotinic acid, 2-aminobenzoic acid, 3-aminobenzoic acid, 4-aminobenzoic acid, 2,4,6-trimethylbenzoic acid, α-liponic acid, acetylglycine, hippuric acid, phosphoric acid, maleic acid, malonic acid, and aspartic acid.

The 1-propiolylpiperazines according to the invention of the aforementioned general formula I and optionally appropriate stereoisomers and the respective physiologically acceptable salts thereof can also be obtained in the form of their solvates, in particular in the form of their hydrates, by conventional processes known to the person skilled in the art.

It has been found, surprisingly, that the substituted 1-propiolylpiperazines of the aforementioned general formula I according to the invention are suitable mGluR5 receptor regulation and therefore can be employed in particular as pharmaceutical active compounds in medicinal drugs the inhibition and/or treatment of disorders or diseases associated with these receptors or processes.

The substituted 1-propiolylpiperazines according to the invention of the aforementioned general formula I and optionally appropriate stereoisomers and the respective salts and solvates are toxicologically acceptable and are therefore suitable as pharmaceutically active compounds in medicinal drugs.

The present invention therefore also provides a medicinal drug comprising at least one 1-propiolylpiperazine of the invention of the aforementioned general formula I, in each case optionally in the form of one of its pure stereoisomers, in particular enantiomers or diastereomers, its racemates or in the form of a mixture of stereoisomers, in particular the enantiomers and/or diastereomers, in an arbitrary mixture ratio, or in each case in the form of an appropriate salt, or in each case in the form of an appropriate solvate, and optionally one or more pharmaceutically acceptable adjuvants.

The medicinal drug according to the invention is suitable mGluR5 receptor regulation, in particular inhibition of the mGluR5 receptor.

The medicinal drug according to the invention is preferably suitable the inhibition and/or treatment of disorders and/or diseases which are at least partly mediated by mGluR5 receptors.

More preferably, the medicinal drug according to the invention is therefore suitable the inhibition and/or treatment of pain, preferably selected from the group consisting of acute pain, chronic pain, neuropathic pain and visceral pain; migraine; depression; neurodegenerative diseases, preferably selected from the group consisting of Parkinson's disease, Alzheimer's disease, Huntington's disease and multiple sclerosis; cognitive diseases, preferably cognitive deficiency states, more preferably the attention deficit syndrome (ADS); panic attacks; epilepsy; coughing; urinary incontinence; diarrhea; pruritus; schizophrenia; cerebral ischemias; muscle spasms; cramps; disorders in food intake, preferably selected from the group consisting of bulimia, cachexia, anorexia and obesity; abuse of alcohol and/or drugs (in particular nicotine and/or cocaine) and/or of medicinal drugs; dependency on alcohol and/or drugs (in particular nicotine and/or cocaine) and/or on medicinal drugs, preferably the inhibition and/or reduction of withdrawal symptoms following dependency on alcohol and/or drugs (in particular nicotine and/or cocaine) and/or on medicinal drugs; development of immunity to medicinal drugs; in particular to opioids; gastro-esophageal reflux syndrome; diuresis; antinatriuresis; influencing the cardiovascular system; anxiolysis; increasing vigilance; increasing libido, modulation of movement activity, and local anesthesia.

Very preferably, the medicinal drug according to the invention is suitable the inhibition and/or treatment of pain, preferably of acute pain, chronic pain, neuropathic pain or visceral pain; panic attacks, anxiety, depression; epilepsy; Parkinson's disease; disorders in food intake, preferably selected from the group consisting of bulimia, cachexia, anorexia and obesity; abuse of alcohol and/or drugs (in particular nicotine and/or cocaine) and/or medicinal drugs; dependency on alcohol and/or drugs (in particular nicotine and/or cocaine) and/or on medicinal drugs; preferably the inhibition and/or reduction of withdrawal symptoms following dependency on alcohol and/or drugs (in particular nicotine and/or cocaine) and/or medicinal drugs; development of immunity to medicinal drugs, in particular to opioids, or anxiolysis.

More preferably, the medicinal drug according to the invention is suitable the inhibition and/or treatment of pain, preferably acute pain, chronic pain, neuropathic pain or visceral pain, disorders in food intake, preferably selected from the group consisting of bulimia, cachexia, anorexia, and obesity, panic attacks, anxiety, or anxiolysis.

Even more preferably, the medicinal drug according to the invention is suitable the inhibition and/or treatment of pain, preferably acute pain, chronic pain, neuropathic pain or visceral pain, panic attacks, anxiety, or anxiolysis.

Most preferably, the medicinal drug according to the invention is suitable the inhibition and/or treatment of pain, preferably acute pain, chronic pain, neuropathic pain or visceral pain.

The present invention also provides the use of at least one substituted 1-propiolylpiperazine of the invention of the aforementioned general formula I, in each case optionally in the form of one of its pure stereoisomers, in particular enantiomers or diastereomers, its racemates or in the form of a mixture of stereoisomers, in particular the enantiomers and/or diastereomers, in any desired mixture ratio, or in each case in the form of an appropriate salt, or in each case in the form of an appropriate solvate, and optionally one or more pharmaceutically acceptable adjuvants, the preparation of a medicinal drug mGluR5 receptor regulation, preferably inhibition of the mGluR5 receptor.

Preference is given to the use of at least one substituted 1-propiolylpiperazine according to the invention of the aforementioned general formula I, in each case optionally in the form of one of its pure stereoisomers, in particular enantiomers or diastereomers, its racemates or in the form of a mixture of stereoisomers, in particular the enantiomers and/or diastereomers, in any desired mixture ratio, or in each case in the form of an appropriate salt, or in each case in the form of an appropriate solvate, and optionally one or more pharmaceutically acceptable adjuvants the preparation of a medicinal drug the inhibition and/or treatment of disorders and/or diseases which are at least partly mediated by mGluR5 receptors.

Greater preference is given to the use of at least one substituted 1-propiolylpiperazine of the invention of the aforementioned general formula I, in each case optionally in the form of one of its pure stereoisomers, in particular enantiomers or diastereomers, its racemates or in the form of a mixture of stereoisomers, in particular the enantiomers and/or diastereomers, in any desired mixture ratio, or in each case in the form of an appropriate salt, or in each case in the form of an appropriate solvate, and optionally one or more pharmaceutically acceptable adjuvants the preparation of a medicinal drug the inhibition and/or treatment of pain, preferably selected from the group consisting of acute pain, chronic pain, neuropathic pain and visceral pain, migraine, depression, neurodegenerative diseases, preferably selected from the group consisting of Parkinson's disease, Alzheimer's disease, Huntington's disease and multiple sclerosis, cognitive diseases, preferably cognitive deficiency states, more preferably the attention deficit syndrome (ADS), panic attacks, epilepsy, coughing, urinary incontinence, diarrhea, pruritus, schizophrenia, cerebral ischemias, muscle spasms, cramps, disorders in food intake, preferably selected from the group consisting of bulimia, cachexia, anorexia, and obesity, abuse of alcohol and/or drugs (in particular nicotine and/or cocaine) and/or of medicinal drugs, dependency on alcohol and/or drugs (in particular nicotine and/or cocaine) and/or on medicinal drugs, preferably the inhibition and/or reduction of withdrawal symptoms following dependency on alcohol and/or drugs (in particular nicotine and/or cocaine) and/or on medicinal drugs, development of immunity to drugs and/or medicinal drugs, in particular to opioids, the gastro-esophageal reflux syndrome, diuresis, antinatriuresis, influencing the cardiovascular system, anxiolysis, increasing vigilance, increasing libido, modulating movement activity, and local anesthesia.

More preference is given to the use of at least one of the substituted 1-propiolylpiperazine of the invention of the above general formula I, in each case optionally in the form of a pure stereoisomer thereof, particularly enantiomers or diastereoisomers thereof, racemates thereof or in the form of a mixture of stereoisomers and particularly of the enantiomers and/or diastereoisomers in an arbitrary mixture ratio, or in each case in the form of an appropriate salt, or in each case in the form of an appropriate solvate, and also optionally one or more pharmaceutically compatible adjuvants the production of a medicinal drug the inhibition and/or treatment of pain, preferably acute pain, chronic pain, neuropathic pain or visceral pain, disturbances of food intake, preferably selected from the group consisting of bulimia, cachexia, anorexia, and obesity, panic attacks, anxiety, or anxiolysis.

Even more preference is given to the use at least one of the substituted 1-propiolylpiperazine of the invention of the above general formula I, in each case optionally in the form of a pure stereoisomer thereof, particularly an enantiomer or diastereoisomer thereof, a racemate thereof or in the form of a mixture of stereoisomers and particularly of the enantiomers and/or diastereoisomers in an arbitrary mixture ratio, or in each case in the form of an appropriate salt, or in each case in the form of an appropriate solvate, and also optionally one or more pharmaceutically compatible adjuvants the production of a medicinal drug the inhibition and/or treatment of pain, preferably acute pain, chronic pain, neuropathic pain or visceral pain, panic attacks, anxiety, or anxiolysis.

The greatest preference is given to the use at least one of the substituted 1-propiolylpiperazine of the invention of the above general formula I, in each case optionally in the form of a pure stereoisomer thereof, particularly an enantiomer or diastereoisomer thereof, a racemate thereof or in the form of a mixture of stereoisomers and particularly of enantiomers and/or diastereoisomers in an arbitrary mixture ratio, or in each case in the form of an appropriate salt, or in each case in the form of an appropriate solvate, and also optionally one or more pharmaceutically compatible adjuvants the production of a medicinal drug inhibition and/or treatment of pain, preferably acute pain, chronic pain, neuropathic pain, or visceral pain.

The medicinal drug according to the invention is suitable administration to adults and children, including infants and babies.

The medicinal drug according to the invention can be in a liquid, semi-solid or solid medicinal drug form, example in the form of injection solutions, drops, juices, syrups, sprays, suspensions, tablets, patches, capsules, plasters, suppositories, ointments, creams, lotions, gels, emulsions, aerosols or in multiparticulate form, example in the form of pellets or granules, optionally compressed to tablets, filled into capsules, or suspended in a liquid, and can also be administered as such.

In addition to at least one substituted 1-propiolylpiperazine according to the invention of the aforementioned general formula I, optionally in the form of its pure stereoisomers, in particular enantiomers or diastereomers, its racemates or in the form of mixtures of the stereoisomers, in particular the enantiomers or diastereomers, in any desired mixture ratio, or optionally in the form of an appropriate salt or in each case in the form of an appropriate solvate, the medicinal drug according to the invention conventionally comprises further physiologically acceptable pharmaceutical adjuvants, which can preferably be selected from the group consisting of vehicles, fillers, solvents, diluents, surface-active substances, dyestuffs, preservatives, disintegrating agents, slip agents, lubricants, flavorings and binders. The choice of the physiologically acceptable adjuvants and the amounts thereof to be employed depend on whether the medicinal drug is to be administered orally, subcutaneously, parenterally, intravenously, intraperitoneally, intradermally, intramuscularly, intranasally, buccally, rectally or locally, example to combat infections of the skin, the mucous membranes, or the eyes. Formulations in the form of tablets, coated tablets, capsules, granules, pellets, drops, juices and syrups are preferably suitable oral administration, and solutions, suspensions, readily reconstitutable dry formulations and sprays are suitable parenteral, topical, and inhalatory administration.

The substituted 1-propiolylpiperazines of the aforementioned general formula I employed in the medicinal drug according to the invention, in a depot in dissolved form or in a plaster, optionally with the addition of agents which promote penetration of the skin, are suitable formulations percutaneous administration.

Formulation forms which can be used orally or percutaneously can, if necessary, provide delayed release of the respective substituted 1-propiolylpiperazines of the aforementioned general formula I.

The preparation of the medicinal drugs according to the invention is carried out by means of conventional means, devices, methods and processes which are well-known from the prior art, such as are described, example, in "Remington's Pharmaceutical Sciences", editor A. R. Gennaro, 17th edition, Mack Publishing Company, Easton, Pa., 1985, in particular in Section 8, Chapters 76 to 93. The relevant description is included herein by reference and forms part of the disclosure.

The amount of the respective substituted 1-propiolylpiperazines of the aforementioned general formula I to be administered to the patient can vary and depends, example, on the weight or age of the patient and on the mode of administration, the indication and the severity of the disease. It is usual to administer from 0.005 to 5,000 mg/kg, preferably from 0.05 to 500 mg/kg, and more preferably from 0.05 to 100 mg/kg, and most preferably from 0.05 to 10 mg/kg of body weight of the patient of at least one such compound.

Pharmacological Methods:

I. Method the Determination of the Inhibition of the [$^3$H]-MPEP Binding in the mGluR5 Receptor Binding Assay Pig brain homogenate is prepared by homogenization (Polytron PT 3000, Kinematica AG, 10,000 revolutions per minute 90 seconds) of pig brain halves without medulla, cerebellum and pons in a buffer solution having a pH of 8.0 (30 mM of hepes, Sigma, order no. H3375+1 tablet of Complete to 100 ml, Roche Diagnostics, order no. 1836145) in a ratio of 1:20 (brain weight/volume) and differential centrifugation at 900×g and 40,000×g. In each case 450 µg of protein from brain homogenate are incubated with 5 nM [$^3$H]-MPEP (Tocris, order no. R1212) (MPEP=2-methyl-6-(3-methoxyphenyl)ethynylpyridine) and the compounds to be investigated (10 µM in the test) in a buffer solution (as above) in 250 µl incubation batches in 96-well microtiter plates at room temperature 60 min.

Thereafter, the batches are filtered with the aid of a Brandel cell harvester (Brandel, Robotic 9600 model) onto Unifilter plates with glass fiber filter mats (Perkin Elmer, order no. 6005177) and then rinsed with buffer solution (as above) 3 times with 250 µl per sample each time. The filter plates are then dried 60 min at 55° C. 30 µl Ultima Gold™ scintillator (Packard BioScience, order no. 6013159) are subsequently added per well and, after 3 hours, the samples are measured on a β-counter (Mikrobeta, Perkin Elmer). The non-specific binding is determined by addition of 10 µM of MPEP (Tocris, order no. 1212).

II. Method Determination of the $Ca^{2+}$ Influx in the mGluR5 Receptor Assay

An agonistic and/or antagonistic action of substances can be determined with the following assay on the mGluR5 receptor of the rat species. According to this assay, the intracellular release of $Ca^{2+}$ after activation of the mGluR5 receptor is quantified with the aid of a $Ca^{2+}$-sensitive dyestuff (Fluo-4 type, Molecular Probes Europe BV, Leiden, Holland) in a FlexStation (Molecular Devices, Sunnyvale, USA).

Preparation of Cortical Neurons:

Cortical neurons are prepared from postnatal rats (P2-6) under sterile conditions. this, the cortex is removed and transferred directly into collagenase solution (PAA Laboratories GmbH, Coelbe, Germany) and incubated 45 minutes in a heated shaking machine (37° C., 300 revolutions per minute). The collagenase solution is then removed and culture medium is added to the tissue.

Culture Medium (100 ml):
Neurobasal medium (Gibco Invitrogen GmbH, Karlsruhe, Germany)
2 mM of L-glutamine (Sigma, Taufkirchen, Germany)
1% by volume of antibiotics/antimycotics solution (PAA Laboratories GmbH, Coelbe, Germany)
15 ng/ml of NGF (Gibco Invitrogen GmbH, Karlsruhe, Germany)
1 ml of B27 Supplement (Gibco Invitrogen GmbH, Karlsruhe, Germany)
1 ml of ITS Supplement (Sigma, Taufkirchen, Germany)

The cells are thinned out by resuspension and, after the addition of 15 ml of Neurobasal medium, are centrifuged through a 70 μm filter insert (BD Biosciences, Heidelberg, Germany). The resulting cell pellet is taken up in culture medium. The cells are then plated out on black 96-well plates coated with poly-D-lysine and with a clear base (BD Biosciences, Heidelberg, Germany), which have additionally been coated beforehand with Laminin (2 μg/cm$^2$, Gibco Invitrogen GmbH, Karlsruhe, Germany). The cell density is 15,000 cells/well. The cells are incubated at 37° C. under 5% $CO_2$, and the medium is changed on the 2nd or 3rd day after preparation. The functional investigation is carried out on the 3rd -7th day after preparation, depending on the cell growth.

FlexStation Assay

For the functional investigation, the cells are loaded with 2 μM of Fluo-4 and 0.01 vol. % Pluronic F127 (Molecular Probes Europe BV, Leiden, Holland) in HBSS buffer solution (Hank's buffer saline solution, Gibco Invitrogen GmbH, Karlsruhe, Germany) 30 min at 37° C. The plates are then washed 2× with HBSS buffer solution and, after further incubation 15 minutes at room temperature, are used on a FlexStation $Ca^{2+}$ measurement. The $Ca^{2+}$-dependent fluorescence is measured before and after the addition of substances ($\lambda_{ex}$=485 nm, $\lambda_{em}$=525 nm). Quantification is effected by measurement of the highest fluorescence intensity over time. The FlexStation protocol consists of 2 additions of substance. Test substances are first pipetted onto the cells in various concentrations (0.024 μM-100 μM). After incubation 3 minutes, 10 μM of DHPG ((S)-3,5-dihydroxyphenylglycine, Tocris Biotrend Chemikalien GmbH, Cologne, Germany) are applied and the influx of $Ca^{2+}$ is determined simultaneously. mGluR5 antagonists led to a suppression of the $Ca^{2+}$ influx.

In order to determine the $IC_{50}$ value, the substances were added in various concentrations. Triplicate determinations (n=3) were carried out and these were repeated in at least 2 independent experiments (N=2).

III Formalin Test in Rats

The formalin test (D. Dubuisson, S. G. Dennis, Pain 4, 161-174 (1977) represents a model acute and chronic pain. By means of a single subcutaneous formalin injection into the dorsal side of a hind paw, a biphasic nociceptive reaction was induced in free-moving test animals, as discerned by observation of two distinct behavior patterns. The reaction is manifested in two phases, of which the first phase is an immediate reaction (paw licking and shaking) lasting up to 10 minutes, while the second phase emerges after a period of inactivity and likewise consists of paw licking and shaking and can last up to 60 minutes. The first phase reflects direct stimulation of the peripheral nocicensors with a high spinal nociceptive input, ie release of glutamate (acute pain phase). The second phase reflects a spinal and peripheral hypersensibilization (chronic pain phase). The current assays concentrated on the chronic pain components (Phase 2).

Formalin is injected subcutaneously into the dorsal side of the right hind paw of each animal in a volume of 50 μL and a concentration of 5%. The substances under test were applied intraperitoneally (i.p.) 15 minutes prior to the formalin injection. The specific behavior changes of the animal, such as lifting and shaking its paw and shifting its weight, and biting and licking reactions are observed in an observation room over a period lasting from the 21$^{st}$ to the 27$^{th}$ minute following the formalin injection. The summary of the various behavior patterns is based on the so-called pain rate (PR) based on said 3 minutes of observation representing the calculation of a mean nociceptive reaction. Calculation of the PR is effected on the basis of numerical weighting (factor 1, 2, or 3) of the observed behavior patterns (giving a behavior score of 1, 2, or 3) and is calculated using the following formula:

$$PR=[(T_0\times 0)+(T_1\times 1)+(T_2\times 2)+(T_3\times 3)]/180,$$

where $T_0$, $T_1$, $T_2$, and $T_3$ are indicative of the time in seconds during which the animal shows a behavior pattern 0, 1, 2, or 3. The size of the test group is 10 animals (n=10).

The invention is explained in further detail below with reference to some illustrative examples. These explanations are merely examples and do not restrict the general inventive idea.

EXAMPLES

The yields of the compounds prepared were not optimized. All the temperatures are uncorrected. The term "equivalent" denotes the equivalent weight of a substance, "RT" denotes room temperature, "conc." denotes concentrated, "min" denotes minutes, "h" denotes hours, "M" is the concentration stated in mol/l and "aq." denotes aqueous, "satd" denotes saturated, "soln" denotes solution, and CC denotes column chromatography. Further abbreviations include:

CDI 1,1'-carbonyldiimidazole
DCC dicyclohexylcarbodiimide
DIC N,N'-diisopropylcarbodiimide
DCE dichloroethane
DCM dichloromethane
DMF N,N-Dimethylformamide
DIPE diisopropyl ether
DIPEA diisopropylethylamine
EDCI   N-ethyl-N'-(3-dimethylaminopropyl)carbodiimide hydrochloride
EA ethyl acetate
$H_2O$ water
HOBt 1-hydroxybenzotriazole
MEAN acetonitrile
MeOH methanol
TEA triethylamine
TUTU   O-(benzotriazole-1-cl)-N,N,N',N'-tetramethyluronium tetrafluoroborate
TMSCl trimethylchlorsilane
THF tetrahydrofuran The chemicals and solvents used were obtained commercially from the conventional suppliers (Acros, Avocado, Aldrich, Bachem, Fluka, Lancaster, Maybridge, Merck, Sigma, TCI etc.) or synthesized by conventional methods known to the person skilled in the art.

Silica gel 60 (0.040-0.063 mm) supplied by E. Merck, Darmstadt was employed as the stationary phase the column chromatography. The thin layer chromatography analyses were carried out with HPTLC precoated plates, silica gel 60 F 254 supplied by E. Merck, Darmstadt. The mixture ratios of solvents and mobile phases chromatographic analyses are always stated in volume/volume. The analysis was carried out by mass spectroscopy and NMR.

Manual Synthesis

Example 1

1-(3-phenylpropiolyl)4-(thiazol-2-yl)piperazine a) Synthesis of 1-thiazol-2-ylpiperazine [Precursor BBB1]

3.61 g (22.0 mmol) of 2-bromothiazole were dissolved in n-butanol (20 ml) together with 1.90 g (22.0 mmol) piperazine. The reaction solution was heated at 120° C. 3 h and stirred at RT a further 16 h. The precipitate formed was then filtered off and the filtrate was concentrated in vacuo. The residue was taken up in DCM, and a 1 M aq. sodium carbonate soln was added. After separation of the phases, the organic phase was dried over magnesium sulfate, filtered and concentrated in vacuo. A column chromatography (MeOH:DIPE 1:1) was carried out on the residue to give 1.06 g (6.3 mmol, 28% of theory) of 1-thiazol-2-ylpiperazine.

b) Synthesis of 1-(3-phenylpropiolyl)-4-(thiazol-2-yl)piperazine 0.818 g (5.60 mmol) of phenylpropiolic acid were dissolved in DMF (5 ml) together with 0.947 g (5.60 mmol) of 1-thiazol-2-ylpiperazine. After addition of 0.756 g (5.69 mmol) of 1-hydroxybenzotriazole and 0.706 g (5.60 mmol) of DCC, the reaction solution was stirred at RT 16 h. It was then diluted with a 1 M aq. sodium carbonate soln and extracted with EA and THF in succession. The combined organic phases were dried over magnesium sulfate, filtered and concentrated in vacuo. A column chromatography (MeOH:DIPE 1:1) was carried out with the residue to give 1.32 g (4.44 mmol, 79% of theory) 1-(3-phenylpropiolyl)-4-(thiazol-2-yl)-piperazine.

The synthesis of the starting compounds which are not commercially available is described below in detail:

Precursor BBB2: Synthesis of 4-(thiazol-2-yl)-1-propiolylpiperazine 16.9 g (100 mmol) of 1-thiazol-2-ylpiperacine [Precursor BBB1], 6.2 ml (100 mmol) of propiolic acid, 17.5 ml (100 mmol) of DIPEA and 32.1 g (100 mmol) of TBTU were dissolved in MeCN (1000 ml) and the solution was stirred over a period of 3 h at RT. The reaction mixture was then conc. in vacuo. The residue was taken up in chloroform and successively washed with a 10% strength aq. NaOH solution, water and a satd aq. NaCl solution. The organic phase was dried over MgSO$_4$, filtered, and conc. in vacuo. Recrystallization from EA gave a yield of 7.5 g (34 mmol, 34%) of 4-(thiazol-2-yl)-1-propiolylpiperazine from the crude product.

Precursor BBB3: synthesis of 6-bromoquinoline

To a mixture of 24 g (140.0 mmol) of 4-bromoaniline, 8.2 ml (80.0 mmol) of nitrobenzene, 38.7 ml (530.0 mmol) of glycerol, 4.7 g (17 mmol) of iron sulfate heptahydrate, and 8.65 g (140 mmol) of boric acid there were added, at −10° C., 22.5 ml of conc. H$_2$SO$_4$. The reaction mixture was then heated under reflux over a period of 10 h. Following adjustment of the pH to pH>12 with a 50% strength aq. NaOH solution there were obtained from the residue 3.69 g (17.7 mmol, 13%) of 6-bromoquinoline by steam distillation.

Precursor BBB4: Synthesis of 5-bromo-1-methylindole 980 mg (5.0 mmol) of 5-bromoindole were added to a solution of 420 mg (7.5 mmol) of pulverized KOH in dimethyl sulfoxide (15 ml) following stirring 15 min at RT. After stirring at RT a further 5 min, 342 µl (5.5 mmol) of iodomethane were added and the mixture was then stirred at RT over a period of 1 h. Following neutralization with 5% strength aq. hydrochloric acid, the reaction mixture was extracted with EA. The organic phase was successively washed with water and a satd aq. NaCl soln and dried over MgSO$_4$. Following filtration and removal of the solvent in vacuo there were obtained 980 mg (4.7 mmol, 93%) of 5-bromo-1-methylindole.

Precursor BBB5: Synthesis of 3-methoxymethyliodobenzene

To a solution of 508 µl (4.0 mmol) of 3-iodobenzylalcohol and 1.25 ml (20.0 mmol) of iodomethane in MeCN (20 ml) there were added 829 mg (6.0 mmol) of potassium carbonate. After stirring 3 h at 30° C., 320 mg (8.00 mmol) of NaH were added and stirring was continued a further 3 h at RT. Water was then added to the reaction mixture, which was extracted with chloroform. The organic phase was successively washed with water and a satd aq. NaCl soln and dried over MgSO$_4$. Following filtration and removal of the solvent in vacuo there were obtained 863 mg (3.5 mmol, 87%) of 3-methoxymethyliodobenzene.

Precursor BBB6: Synthesis of (4-chlorophenyl)propiolic acid

Starting from 4-chlorobenzaldehyde, (4-chlorophenyl) propiolic acid was obtained according by the method described below Precursor BBB7.

Precursor BBB7: (4-fluorophenyl)propiolic acid a) synthesis of ethyl 3-(4-fluorophenyl)acrylate Sodium sand was produced from 11.67 g (507.6 mmol) of sodium in toluene (160 ml). Following decantation of the toluene, EA (185 ml) and ethanol (2 ml) were successively gently added. The mixture was then cooled to 0° C., and 43.2 ml (402.8 mmol) of 4-fluorobenzaldehyde were slowly added dropwise over a period of 90 min such that the temperature of the reaction mixture did not exceed 5° C. Stirring was then continued at RT over a period of 1 h. Following the addition of acetic acid (40 ml) and water (40 ml), the phases were separated. The aqueous phase was extracted with EA and the combined organic phases were washed with a 6N HCl soln and dried over MgSO$_4$. Following filtration and removal of the solvent in vacuo, the residue was subjected to a vacuum distillation. This yielded 37.0 g (190 mmol, 47%) of ethyl 3-(4-fluorophenyl)acrylate.

b) Synthesis of ethyl 2,3-dibromo-3-(4-fluorophenyl)propionate

To a solution of 37.0 g (0.19 mol) of ethyl 3-(4-fluorophenyl)acrylate in carbon tetrachloride (23 ml) there were added dropwise 9.72 ml (0.19 mol) of bromine at 0° C. Concentration in vacuo caused crystallization of 46.1 g (0.13 mol, 69%) of ethyl 2,3-dibromo-3-(4-fluorophenyl)propionate, which was filtered off in vacuo and washed with hexane.

c) Synthesis of (4-fluorophenyl)propiolic acid 21.9 g (390.7 mmol) of KOH were dissolved in ethanol (170 ml) with heating to 70° C. Following cooling of the mixture to 40° C., 46.1 g (0.13 mmol) of ethyl 2,3-dibromo-3-(4-fluorophenyl)propionate were added. The mixture was then heated under reflux over a period of 3 h. After cooling to RT, the resulting precipitate was isolated by filtration.

The reaction solution was neutralized with conc. HCl and concentrated in vacuo. The residue was dissolved in water (100 ml) together with the precipitate that was previously filtered off in vacuo. The solution was adjusted to pH 1 with 20% strength sulfuric acid with cooling in an ice bath. Following stirring 20 min at RT, the resulting precipitate was filtered off in vacuo and washed with 2% strength sulfuric acid. Following recrystallization from MeCN and recrystallization of the residue from ethanol there were obtained 1.37 g (8.4 mmol, 6%) of (4-fluorophenyl)propiolic acid.

Precursor BBB8: tol-2-ylpropiolic acid a) Synthesis of 2,3-dibromo-3-tol-2-ylpropionic acid To a solution of 30 g (185.2 mmol) of 3-tol-2-ylacrylic acid in carbon tetrachloride at 0° C., 15.2 ml (296.7 mmol) of bromine were slowly added dropwise such that the temperature of the reaction mixture did not exceed 5° C. The reaction solution was then heated under reflux over a period of 2 h and then allowed to stand over a period of 12 h at RT. The resulting precipitate was isolated by filtration and washed with carbon tetrachloride, to give 51.0 g (158.9 mmol, 86%) of 2,3-dibromo-3-tol-2-ylpropionic acid.

b) Synthesis of tol-2-ylpropiolic acid

To a suspension of 35.5 g of KOH in ethanol (250 ml) there were added 51.0 g (158.9 mmol) of 2,3-dibromo-3-tol-2-ylpropionic acid portionwise over a period of 30 min. The mixture was then heated under reflux over a period of 4 h. Following removal of the solvent in vacuo, the residue was taken up in 10% strength hydrochloric acid. The solution was washed with EA and then set to pH>10 with a 6N aq. NaOH solution. The mixture was then extracted with EA and the organic phase was dried over MgSO$_4$. Following filtration and the removal of solvent in vacuo, there were obtained 13.8 g (86.2 mmol, 54%) of tol-2-ylpropiolic acid.

Precursor BBB9: Synthesis of tol-3-ylpropiolic acid

Starting from 3-tol-3-ylacrylic acid, tol-3-ylpropiolic acid was obtained according to the process described above Precursor BBB8.

Precursor BBB10: Synthesis of tol-4-ylpropiolic acid

Starting from 3-tol-4-ylacrylic acid, tol-4-ylpropiolic acid was obtained according to the process described above Precursor BBB8.

Precursor BBB11: Synthesis of (2-trifluoromethylphenyl)propiolic acid

Starting from 3-(2-trifluoromethylphenyl)acrylic acid, (2-trifluoromethylphenyl)propiolic acid was obtained according to the process described above Precursor BBB8.

Precursor BBB12: Synthesis of (3-trifluoromethylphenyl)propiolic acid

Starting from 3-(3-trifluoromethylphenyl)acrylic acid, (3-trifluoromethylphenyl)propiolic acid was obtained according to the process described above Precursor BBB8.

Precursor BBB13: Synthesis of (4-trifluoromethylphenyl)propiolic acid

Starting from 3-(4-trifluoromethylphenyl)acrylic acid, (4-trifluoromethylphenyl)propiolic acid was obtained according to the process described above Precursor BBB8.

Precursor BBB14: Synthesis of 3-methyl-1-thiazol-2-ylpiperazine 30.06 g (300.0 mmol) of 2-methylpiperazine were combined with 4.51 ml (50.0 mmol) of 2-bromothiazole. This mixture was fused and refluxed 5 min. The reaction mixture was cooled and taken up in 10% strength hydrochloric acid and washed with EA. The aqueous phase was set to pH>12 with a 10% strength aq. NaOH solution and then extracted with EA. The organic phase was dried over MgSO$_4$ and conc. in vacuo. There were obtained 8.26 g (45.1 mmol, 90%) of 3-methyl-1-thiazol-2-ylpiperazine.

Precursor BBB15: Synthesis of (S)-3-methyl-1-thiazol-2-ylpiperazine (S)-3-methyl-1-thiazol-2-ylpiperazine was obtained by reaction of (S)-2-methylpiperazine with 2-bromothiazole under the conditions described above Precursor BBB14.

Precursor BBB16: Synthesis of (R)-3-methyl-1-thiazol-2-ylpiperazine (R)-3-methyl-1-thiazol-2-ylpiperazine was obtained by reaction of 2-methylpiperazine with 2-bromothiazole under the conditions described above Precursor BBB14.

Precursor BBB17: Cyclohexylpropiolic acid a) synthesis of ethyl 3-cyclohexyl-3-oxo-2-(triphenyl λ5-phosphanylidene)propionate To a solution of 4.74 g (13.6 mmol) of ethyl (triphenyl λ5-phosphanylidene)acetate and 1.9 ml (13.6 mmol) of TEA in toluene (75 ml) there were added 2.0 g (13.6 mmol) of cyclohexylcarboxylic acid chloride. Following stirring 2 h at RT, the reaction solution was successively washed with water and a satd aq. NaCl solution. The organic phase was dried over MgSO$_4$, filtered, and conc. in vacuo. From the residue 2.85 g (6.2 mmol, 46%) of ethyl 3-cyclohexyl-3-oxo-2-(triphenyl λ5-phosphanylidene)propionate were recrystallized from ethanol.

b) Synthesis of cyclohexylpropiolic acid 2.0 g (4.36 mmol) of ethyl 3-cyclohexyl-3-oxo-2-(triphenyl λ5-phosphanylidene)propionate were filled together with ca 15 g of glass splinters into a pyrex tube, which was then connected to a cold trap. The upper part of the pyrex tube was heated with an open gas flame until the entire starting material had distilled over into the cold trap. The resulting distilled mixture was taken up in ethanol (25 ml) and 2 ml of a 50% strength aq. KOH solution were added thereto. Stirring was then continued 16 h at RT. The solvent was then removed in vacuo and the residue taken up in water. The resulting precipitate was filtered off in vacuo and the filtrate was set to pH<2 with hydrochloric acid and the mixture extracted with chloroform. The organic phase was successively washed with water and a satd aq. NaCl solution and dried over MgSO$_4$. Following filtration and the removal of solvent in vacuo, from the residue, 500 mg (3.3 mmol, 75%) of cyclohexylpropiolic acid were recrystallized from diethyl ether.

Precursor BBB18: Synthesis of quinolin-7-yl trifluoromethanesulfonate

A solution of 2.9 g (20.0 mmol) of 7-hydroxyquinoline and 4.45 ml (32.0 mmol) of triethylamine in DCE (200 ml) was added dropwise to a solution of 4.71 ml (28.0 mmol) of trifluoromethanesulfonic anhydride in DCE (40 ml). Stirring was then continued overnight at RT. The solution was then washed successively with water and a satd aq. NaCl solution and dried over MgSO$_4$. Following filtration and concentration in vacuo, the residue was subjected to CC (DCE), to give 3.86 g (13.9 mmol, 70%) of quinolin-7-yl trifluoromethanesulfonate.

Precursor BBB19: Synthesis of 3-ethyl-1-thiazol-2-ylpiperazine 3-ethyl-1-thiazol-2-ylpiperazine was obtained by reaction of 2-ethylpiperazine with 2-bromothiazole under the conditions described above Precursor BBB14.

Precursor BBB20: Synthesis of 3-phenyl-1-thiazol-2-ylpiperazine 3-phenyl-1-thiazol-2-ylpiperazine was obtained by reaction of 2-phenylpiperazine with 2-bromothiazole under the conditions described above Precursor BBB1.

Precursor BBB21: synthesis of Furan-2-ylpropiolic acid

Starting from furan 2-carboxylic acid chloride, furan-2-ylpropiolic acid was obtained under the conditions described above Precursor BBB17.

Precursor BBB22: synthesis of Furan-3-ylpropiolic acid

Starting from furan 3-carboxylic acid chloride, furan-3-ylpropiolic acid was obtained under the conditions described above Precursor BBB17.

Precursor BBB23: Synthesis of cis-3,5-dimethyl-1-thiazol-2-ylpiperazine cis-3,5-Dimethyl-1-thiazol-2-ylpiperazine was obtained by reaction of cis-2,6-dimethylpiperazine with 2-bromothiazole under the conditions described above Precursor BBB14.

Precursor BBB24: Synthesis of ethyl 2-piperazin-1-ylthiazole-5-carboxylate 1.02 g (5.0 mmol) of ethyl 2-bromothiazole-5-carboxylate and 4.31 g (50 mmol) of piperazine were dissolved in ethanol (20 ml) and the mixture was heated under reflux over a period of 4 h. The solution was then concentrated in vacuo, taken up in EA and washed successively with water and a satd aq. NaCl solution. Following drying of the organic phase over MgSO$_4$, filtration and removal of solvent in vacuo there were obtained 1.12 g (4.6 mmol, 93%) of ethyl 2-piperazin-1-ylthiazole-5-carboxylate.

Precursor BBB25: Synthesis of 2-piperazin-1-ylthiazole-4-carboxylic acid ethyl ester Ethyl 2-piperazin-1-ylthiazole-4-carboxylate was obtained by reaction of ethyl 2-bromothiazole-4-carboxylate with piperazine under the conditions described above Precursor BBB24.

Precursor BBB27: Synthesis of 1-[3-(4-fluorobenzyl)-[1,2,4]-thiadiazol-5-yl]piperazine 1-[3-(4-Fluorobenzyl)-[1,2,4]-thiadiazol-5-yl]piperazine was obtained by reaction of piperazine with 5-chloro-3-(4-fluorobenzyl)-[1,2,4]-thiadiazole under the conditions described above Precursor BBB1.

Precursor BBB28: Synthesis of (2,4-difluorophenyl)propiolic Acid 4.95 ml (41.4 mmol) of 2,4-difluoroiodobenzene and 2.56 ml (41.4 mmol) of propiolic acid were dissolved in DMF (16 ml). Following cooling of the reaction medium to 0° C. (ice-water bath), 578 mg (0.83 mmol) of Pd(PPh$_3$)$_2$Cl$_2$ and 308 mg (1.66 mmol) of CuI were added. The reaction solution was then cooled to −10° C. (ice methanol bath) and 14.5 ml (103.4 mmol) of diisopropylamine were added dropwise at this temperature. The cooling bath was then removed and the reaction mixture was stirred a further 16 h after RT had been re-established. The reaction solution was then diluted with EA and washed successively with a 2N HCl solution and a satd aq. NaCl solution. Following drying over MgSO$_4$, filtration, and removal of solvent in vacuo, the residue was boiled with hexane and filtered after cooling to RT. The residue was dissolved in diethyl ether at 30° C. and filtered at this temperature. By removal of solvent in vacuo there were obtained from the filtrate 6.43 g (35.3 mmol, 85%) of (2,4-difluorophenyl)propiolic acid.

Precursor BBB29: Synthesis of 1-(5-nitrothiazol-2-yl)piperazine 1-(5-nitrothiazol-2-yl)piperazine was obtained by reaction of 2-bromo-5-nitrothiazole with piperazine under the conditions described above Precursor BBB24.

Precursor BBB30: Synthesis of 2-bromo-4-tert-butylthiazole

85% strength phosphoric acid (50 ml) and 65% strength nitric acid (20 ml) were combined at 0° C. 3.12 g (20.0 mmol) of 4-tert-butylthiazol-2-ylamine were added to this solution and a solution of 1.38 g (20 mmol) of $NaNO_2$ in water (10 ml) was subsequently added dropwise at 0° C. in the course of 30 min. The reaction solution was stirred at 0° C. 1 h and then added dropwise to a suspension of 20.0 g of NaBr and 5.8 g of CuBr in water (20 ml) cooled to 0° C. The mixture was stirred until evolution of gas could no longer be observed. Subsequently, the mixture was adjusted to a pH>10 using 50% strength aq. KOH solution and the product was separated off by steam distillation. The distillate was extracted with EE. The organic phase was dried over $MgSO_4$, filtered, and concentrated in vacuo. 3.03 g (13.8 mmol, 69%) of 2-bromo-4-tert-butylthiazole were obtained as a residue.

Precursor BBB31: Synthesis of 1-(4-tert-butylthiazol-2-yl)piperazine 1-(4-tert-Butylthiazol-2-yl)piperazine was obtained by means of the reaction of 2-bromo-4-tert-butylthiazole [Precursor BBB30] with piperazine according to the conditions described above Precursor BBB1.

Precursor BBB32: Synthesis of 2-bromo-5-methylthiazole

Starting from 5-methylthiazol-2-ylamine, 2-bromo-5-methylthiazole was obtained according to the process described above Precursor BBB30.

Precursor BBB33: Synthesis of 1-(5-methylthiazol-2-yl)piperazine 1-(5-Methylthiazol-2-yl)piperazine was obtained by the reaction of 2-bromo-5-methylthiazole [Precursor BBB32] with piperazine according to the conditions described above Precursor BBB1.

Precursor BBB34: Synthesis of 2-bromo-4,5-dimethylthiazole

Starting from 4,5-dimethylthiazol-2-ylamine, 2-bromo-4,5-dimethylthiazole was obtained according to the process described above Precursor BBB30.

Precursor BBB35: Synthesis of 1-(4,5-dimethylthiazol-2-yl)piperazine 1-(4,5-Dimethylthiazol-2-yl)piperazine was obtained by the reaction of 2-bromo-4,5-dimethylthiazole [Precursor BBB34] with piperazine according to the conditions described above Precursor BBB1.

Precursor BBB36: Synthesis of 2,5-dibromo-4-phenylthiazole

Starting from 4-phenylthiazol-2-ylamine, 2,5-dibromo-4-phenylthiazole was obtained according to the process described Precursor BBB30.

Precursor BBB37: Synthesis of 1-(5-bromo-4-phenylthiazol-2-yl)piperazine 1-(5-Bromo-4-phenylthiazol-2-yl)piperazine was obtained by the reaction of 2,5-dibromo-4-phenylthiazole [Precursor BBB36] with piperazine according to the conditions described above Precursor BBB1.

Precursor BBB38: Synthesis of 2,5-dibromo-4-methylthiazole

Starting from 4-methylthiazol-2-ylamine, 2,5-dibromo-4-methylthiazole was obtained according to the conditions described above Precursor BBB30.

Precursor BBB39: Synthesis of 1-(5-bromo-4-methylthiazol-2-yl)piperazine 1-(5-Bromo-4-methylthiazol-2-yl)piperazine was obtained by the reaction of 2,5-dibromo-4-methylthiazole [Precursor BBB38] with piperazine according to the conditions described above Precursor BBB1.

Precursor BBB40: Synthesis of 2-chloro-4-methylthiazole 4.02 ml (30.0 mmol) of isoamyl nitrite were added at 0° C. to a solution of 2.28 g (20.0 mmol) of 4-methylthiazol-2-ylamine and 2.68 g (20.0 mmol) of $CuCl_2$ in MeCN (200 ml). Subsequently, the reaction solution was stirred at RT 16 h and concentrated in vacuo. The residue was taken up using chloroform and filtered through kieselguhr. The filtrate was concentrated in vacuo. 1.27 g (9.6 mmol, 48%) of 2-chloro-4-methylthiazole were obtained by CC of the residue using a DCE-ethanol mixture.

Precursor BBB41: Synthesis of 1-(4-methylthiazol-2-yl)piperazine 1-(4-Methylthiazol-2-yl)piperazine was obtained by the reaction of 2-chloro-4-methylthiazole [Precursor BBB40] with piperazine according to the conditions described above Precursor BBB1.

Precursor BBB42: Synthesis of 2-chloro-4-trifluoromethylthiazole

Starting from 4-trifluoromethylthiazol-2-ylamine, 2-chloro-4-trifluoromethylthiazole was obtained according to the process described above Precursor BBB40.

Precursor BBB43: Synthesis of 1-(4-trifluoromethylthiazol-2-yl)piperazine 1-(4-Trifluoromethylthiazol-2-yl)piperazine was obtained by the reaction of 2-chloro-4-trifluoromethylthiazole [Precursor BBB42] with piperazine according to the conditions described above Precursor BBB1.

Precursor BBB44: Synthesis of 2,4-dichlorothiazole 1.67 ml (21.0 mmol) of pyridine were added with cooling (ice bath) to 13.3 ml (145.0 mmol) of $POCl_3$. Subsequently, 2.5 g (21.0 mmol) of thiazolidine-2,4-dione were added and the reaction solution was heated under reflux 5 h. After concentration in vacuo, the residue was taken up in DCE (20 ml) and subsequently concentrated again in vacuo. The residue was poured onto ice and extracted with ether. The organic phase was washed successively with a 5% strength aq. NaOH soln and a satd aq. NaCl soln and dried over $MgSO_4$. After filtration and concentration in vacuo, 1.41 g of 2,4-dichlorothiazole were obtained, which was employed further reaction without further purification.

Precursor BBB45: Synthesis of 1-(4-chlorothiazol-2-yl)piperazine 1-(4-Chlorothiazol-2-yl)piperazine was obtained by the reaction of 2,4-dichlorothiazole with piperazine according to the conditions described above Precursor BBB24.

Precursor BBB46: Synthesis of 2-bromo-5-chlorothiazole

Starting from 5-chlorothiazol-2-ylamine, 2-bromo-5-chlorothiazole was obtained according to the process described above Precursor BBB30.

Precursor BBB47: Synthesis of 1-(5-chlorothiazol-2-yl)piperazine 1-(5-Chlorothiazol-2-yl)piperazine was obtained by the reaction of 2-bromo-5-chlorothiazole with piperazine according to the conditions described above Precursor BBB1.

Precursor BBB48: Synthesis of 1-(5-bromothiazol-2-yl)piperazine 1-(5-Bromothiazol-2-yl)piperazine was obtained by the reaction of 2,5-dibromothiazole with piperazine according to the conditions described above Precursor BBB1.

Precursor BBB49: Synthesis of 1-(4-bromothiazol-2-yl)piperazine 1-(4-Bromothiazol-2-yl)piperazine was obtained by the reaction of 2,4-dibromothiazole with piperazine according to the conditions described above Precursor BBB1.

Precursor BBB50: Synthesis of 1-(3-methylsulfanyl-[1,2,4]-thiadiazol-5-yl)piperazine 1-(3-Methylsulfanyl-[1,2,4]-thiadiazol-5-yl)piperazine was obtained by the reaction of 5-chloro-3-methylsulfanyl-[1,2,4]-thiadiazole with piperazine according to the conditions described above Precursor BBB24.

Precursor BBB51: Synthesis of 1-(3-methanesulfonyl-[1,2,4]-thiadiazol-5-yl)piperazine 1-(3-Methanesulfonyl-[1,2,4]-thiadiazol-5-yl)piperazine was obtained by the reaction of 5-chloro-3-methanesulfonyl-[1,2,4]-thiadiazole with piperazine according to the conditions described above Precursor BBB24.

Precursor BBB52: Synthesis of 1-(3-methoxy-[1,2,4]-thiadiazol-5-yl)piperazine 100 mg (4.0 mmol) of sodium were added to ethanol (20 ml). After reaction of the sodium was complete, 500 mg (2.0 mmol) of 1-(3-methanesulfonyl-[1,2,4]-thiadiazol-5-yl)piperazine were added and the mixture was subsequently stirred at 50° C. 2 h. The cooled reaction solution was poured into a satd aq. NaCl soln cooled to 0° C. This mixture was extracted with EA. The organic phase was dried over MgSO$_4$, filtered and concentrated in vacuo. 310 mg (1.54 mmol, 77%) of 1-(3-methoxy-[1,2,4]-thiadiazol-5-yl)piperazine were obtained.

Precursor BBB53: Synthesis of 5-chloro-[1,2,4]-thiadiazole 41.8 g (0.225 mol) of perchloromethylchloromercaptan were added to a solution of 20.1 g (0.25 mol) of formamidine hydrochloride in DCM (250 ml). After cooling to −14° C., a solution of 50 g of NaOH in 75 ml of water was added such that the temperature of the reaction mixture did not exceed −5° C. The latter was stirred a further 1 h, the reaction solution warming to RT. The resulting precipitate was filtered out and washed with DCM. The aqueous phase was separated from the filtrate and the organic phase was dried over Na$_2$SO$_4$. After filtration and concentration in vacuo, a vacuum distillation (Vigreux column) was carried out on the residue. 1.7 g (15 mmol, 6%) of 5-chloro-[1,2,4]-thiadiazole were obtained.

Precursor BBB54: Synthesis of 5-chloro-3-methyl-[1,2,4]-thiadiazole

Starting from acetamidine hydrochloride, 5-chloro-3-methyl-[1,2,4]-thiadiazole was obtained according to the process described above Precursor BBB53.

Precursor BBB55: Synthesis of 5-chloro-3-trichloromethyl-[1,2,4]-thiadiazole Starting from trichloroacetamidine hydrochloride, 5-chloro-3-trichloromethyl-[1,2,4]-thiadiazole was obtained according to the process described above Precursor BBB53.

Precursor BBB56: Synthesis of 5-chloro-3-trifluoromethyl-[1,2,4]-thiadiazole Chlorine gas was passed into a mixture of 103.4 g of anhydrous SbF$_3$ and 18.2 g of SbCl$_5$ at 150° C. until the increase in weight was 2.4 g. Subsequently, 40.0 g (168.1 mmol) of 5-chloro-3-trichloromethyl-[1,2,4]-thiadiazole were added dropwise over a period of 30 min. After this, the mixture was heated under reflux a further 4 h. After concentration in vacuo, a vacuum distillation (Vigreux column) was carried out on the residue to give 22.4 g (118.8 mmol, 71%) of 5-chloro-3-trifluoromethyl-[1,2,4]-thiadiazole.

Precursor BBB57: Synthesis of 1-[1,2,4]-thiadiazol-5-ylpiperazine

1-[1,2,4]-Thiadiazol-5-ylpiperazine was obtained by the reaction of 5-chloro-[1,2,4]-thiadiazole [Precursor BBB53] with piperazine according to the conditions described above Precursor BBB24.

Precursor BBB58: Synthesis of 1-(3-methyl-[1,2,4]-thiadiazol-5-yl)piperazine 1-(3-Methyl-[1,2,4]-thiadiazol-5-yl)piperazine was obtained by the reaction of 5-chloro-3-methyl-[1,2,4]-thiadiazole [Precursor BBB54] with piperazine according to the conditions described above Precursor BBB24.

Precursor BBB59: Synthesis of 1-(3-trifluoromethyl-[1,2,4]-thiadiazol-5-yl)-piperazine 1-(3-Trifluoromethyl-[1,2,4]-thiadiazol-5-yl)piperazine was obtained by the reaction of 5-chloro-3-trifluoromethyl-

[1,2,4]-thiadiazole [Precursor BBB56] with piperazine according to the conditions described above Precursor BBB24.

Precursor BBB60: Synthesis of tert-butyl 4-(5-ethoxycarbonylthiazol-2-yl)-piperazine-1-carboxylate A solution of 3.65 g (16.7 mmol) of di-tert-butyl pyrocarbonate in MeOH (25 ml) was added at 10° C. to a solution of 3.69 g (16.0 mmol) of ethyl 2-piperazin-1-ylthiazole-5-carboxylate [Precursor BBB24] in MeOH (50 ml). Subsequently, the reaction solution was stirred at 40° C. 2 h. After removal of the solvent in vacuo, from the residue 5.33 g (15.6 mmol, 98%) of tert-butyl 4-(5-ethoxycarbonylthiazol-2-yl)piperazine-1-carboxylate were recrystallized from water.

Precursor BBB61: Synthesis of tert-butyl 4-(5-carboxythiazol-2-yl)piperazine-1-carboxylate 5.33 g (15.6 mmol) of tert-butyl 4-(5-ethoxycarbonylthiazol-2-yl)piperazine-1-carboxylate [Precursor BBB60] were dissolved in ethanol together with 0.96 g (17.1 mmol) of KOH (100 ml) and stirred at 40° C. 4 h. The resulting precipitate was filtered off and dissolved in water. After this, the solution was adjusted to a pH<2 with 10% strength hydrochloric acid and extracted with chloroform. The organic phase was washed with water and a satd aq. NaCl soln and dried over MgSO$_4$. After filtration and concentration in vacuo, 2.77 g (8.8 mmol, 56%) of tert-butyl 4-(5-carboxythiazol-2-yl)piperazine-1-carboxylate were obtained from the residue by recrystallization from diethyl ether.

Precursor BBB62: Synthesis of tert-butyl 4-[5-(3-methyl-[1,2,4]-oxadiazol-5-yl)-thiazol-2-yl]piperazine-1-carboxylate 939 mg (3.0 mmol) of tert-butyl 4-(5-carboxythiazol-2-yl)piperazine-1-carboxylate [Precursor BBB61] were dissolved in DMF (15 ml) together with 534 mg (3.3 mmol) of CDI and the solution was stirred at RT 4 h. Subsequently, 243 mg (3.3 mmol) of N-hydroxyacetamidine were added and the mixture was stirred at 120° C. a further 4 h. The reaction solution was then poured onto water and the resulting precipitate was filtered off and washed with water. By means of CC (DCE/ethanol mixture) of the residue, 220 mg (0.63 mmol, 21%) of tert-butyl 4-[5-(3-methyl-[1,2,4]-oxadiazol-5-yl)-thiazol-2-yl]piperazine-1-carboxylate were obtained.

Precursor BBB63: Synthesis of 1-[5-(3-methyl-[1,2,4]-oxadiazol-5-yl)thiazol-2-yl]piperazine A satd ethanolic HCl soln (4 ml) was added to a solution of 220 mg (0.63 mmol) of tert-butyl 4-[5-(3-methyl-[1,2,4]-oxadiazol-5-yl)thiazol-2-yl]-piperazine-1-carboxylate [Precursor BBB62] in DCE (10 ml). After stirring at RT 5 min, the reaction solution was concentrated in vacuo. The residue was taken up in DCM and washed successively with a 1% strength aq. NaOH soln and water. The organic phase was dried over MgSO$_4$, filtered and concentrated in vacuo. 152 mg (0.61 mmol, 96%) of 1-[5-(3-methyl-[1,2,4]-oxadiazol-5-yl)thiazol-2-yl]piperazine were obtained here.

Precursor BBB65: Synthesis of 4-(4-tert-butylthiazol-2-yl)-1-propiolylpiperazine 4-(4-tert-Butylthiazol-2-yl)-1-propiolylpiperazine was obtained by the reaction of 1-(4-tert-butylthiazol-2-yl)piperazine [Precursor BBB31] with propiolic acid according to the conditions described above Precursor BBB2.

Precursor BBB67: Synthesis of (4-methylthiophen-2-yl)propiolic acid

Starting from 4-methylthiophene-2-carbonyl chloride, (4-methylthiophen-2-yl)-propiolic acid was obtained according to the conditions described above Precursor BBB17.

Precursor BBB68: Synthesis of (3-chlorophenyl)propiolic acid

Starting from 3-chlorobenzaldehyde, (3-chlorophenyl) propiolic acid was obtained according to the process described Precursor BBB7.

Precursor BBB69: Synthesis of 3-tert-butyl-1-thiazol-2-ylpiperazine 3-tert-Butyl-1-thiazol-2-ylpiperazine was obtained by the reaction of 2-tert-butylpiperazine with 2-bromothiazole according to the conditions described Precursor BBB14.

Precursor BBB70: Synthesis of 3-isopropyl-1-thiazol-2-ylpiperazine

3-Isopropyl-1-thiazol-2-ylpiperazine was obtained by the reaction of 2-isopropylpiperazine with 2-bromothiazole according to the conditions described Precursor BBB14.

Example AAA1

Synthesis of 4-(thiazol-2-yl)-1-(3-(2-carboxyphenyl) propiolyl)-piperazine methyl ester 664 mg (3 mmol) of 4-(thiazol-2-yl)-1-propiolylpiperazine [Precursor BBB2], 786 mg (3 mmol) of methyl 2-iodobenzoate, 39 mg (0.054 mmol) of Pd(PPh$_3$)$_2$Cl$_2$ and 21 mg (0.111 mmol) of CuI were dissolved in DMF (15 ml) and treated with 1.05 ml (7.5 mmol) of diisopropylamine. Subsequently, the reaction solution was stirred at 60° C. 1 h. The cooled solution was poured into water and the mixture was subsequently extracted with DCM. The organic phase was washed successively with water and a satd aq. NaCl soln and dried over MgSO$_4$. After filtering off and removing the solvent in vacuo, CC using a mixture of chloroform and EA was carried out on the residue, and 621 mg (1.8 mmol, 58%) of 4-(thiazol-2-yl)-1-(3-(2-carboxyphenyl)-propiolyl)piperazine methyl ester were isolated.

Example AAA2

Synthesis of 4-(thiazol-2-yl)-1-(3-(4-carboxyphenyl) propiolyl)-piperazine methyl ester 4-(Thiazol-2-yl)-1-(3-(4-carboxyphenyl)propiolyl)piperazine methyl ester was obtained by the reaction of 4-(thiazol-2-yl)-1-propiolylpiperazine [Precursor BBB2] with methyl 4-iodobenzoate according to the conditions described in the case of Example AAA1.

Example AAA3

Synthesis of 4-(thiazol-2-yl)-1-(3-(3-carboxyphenyl) propiolyl)-piperazine ethyl ester 4-(Thiazol-2-yl)-1-(3-(3-carboxyphenyl)propiolyl)piperazine ethyl ester was obtained by the reaction of 4-(thiazol-2-yl)-1-propiolylpiperazine [Precursor BBB2] with ethyl 3-iodobenzoate according to the conditions described in the case of Example AAA1.

Example AAA4

Synthesis of 4-(thiazol-2-yl)-1-(3-(2-hydroxyphenyl)propiolyl)-piperazine 4-(Thiazol-2-yl)-1-(3-(2-hydroxyphenyl)propiolyl)piperazine was obtained by the reaction of 4-(thiazol-2-yl)-1-propiolylpiperazine [Precursor BBB2] with 2-iodophenol according to the conditions described in the case of Example AAA1.

Example AAA5

Synthesis of 4-(thiazol-2-yl)-1-(3-(4-hydroxyphenyl)propiolyl)-piperazine 4-(Thiazol-2-yl)-1-(3-(4-hydroxyphenyl)propiolyl)piperazine was obtained by the reaction of 4-(thiazol-2-yl)-1-propiolylpiperazine [Precursor BBB2] with 4-iodophenol according to the conditions described in the case of Example AAA1.

Example AAA6

Synthesis of 4-(thiazol-2-yl)-1-(3-(2-aminophenyl)propiolyl)-piperazine 4-(Thiazol-2-yl)-1-(3-(2-aminophenyl)propiolyl)piperazine was obtained by the reaction of 4-(thiazol-2-yl)-1-propiolylpiperazine [Precursor BBB2] with 2-iodoaniline according to the conditions described in the case of Example AAA1.

Example AAA7

Synthesis of 4-(thiazol-2-yl)-1-(3-(3-aminophenyl)propiolyl)-piperazine 4-(Thiazol-2-yl)-1-(3-(3-aminophenyl)propiolyl)piperazine was obtained by the reaction of 4-(thiazol-2-yl)-1-propiolylpiperazine [Precursor BBB2] with 3-iodoaniline according to the conditions described in the case of Example AAA1.

Example AAA8

Synthesis of 4-(thiazol-2-yl)-1-(3-(4-aminophenyl)propiolyl)-piperazine 4-(Thiazol-2-yl)-1-(3-(4-aminophenyl)propiolyl)piperazine was obtained by the reaction of 4-(thiazol-2-yl)-1-propiolylpiperazine [Precursor BBB2] with 4-iodoaniline according to the conditions described in the case of Example AAA1.

Example AAA9

Synthesis of 4-(thiazol-2-yl)-1-(3-(indol-5-yl)propiolyl)piperazine 4-(Thiazol-2-yl)-1-(3-(indol-5-yl)propiolyl)piperazine was obtained by the reaction of 4-(thiazol-2-yl)-1-propiolylpiperazine [Precursor BBB2] with 5-iodoindole according to the conditions described in the case of Example AAA1.

Example AAA10

Synthesis of 4-(thiazol-2-yl)-1-(3-(2-thienyl)propiolyl)-piperazine 4-(Thiazol-2-yl)-1-(3-(2-thienyl)propiolyl)piperazine was obtained by the reaction of 4-(thiazol-2-yl)-1-propiolylpiperazine [Precursor BBB2] with 2-iodothiophene according to the conditions described in the case of Example AAA1.

Example AAA11

Synthesis of 4-(thiazol-2-yl)-1-(3-(3-thienyl)propiolyl)-piperazine 4-(Thiazol-2-yl)-1-(3-(3-thienyl)propiolyl)piperazine was obtained by the reaction of 4-(thiazol-2-yl)-1-propiolylpiperazine [Precursor BBB2] with 3-iodothiophene according to the conditions described in the case of Example AAA1.

Example AAA12

Synthesis of 4-(thiazol-2-yl)-1-(3-(2-methoxyphenyl)propiolyl)-piperazine 4-(Thiazol-2-yl)-1-(3-(2-methoxyphenyl)propiolyl)piperazine was obtained by the reaction of 4-(thiazol-2-yl)-1-propiolylpiperazine [Precursor BBB2] with 2-iodoanisole according to the conditions described in the case of Example AAA1.

Example AAA13

Synthesis of 4-(thiazol-2-yl)-1-(3-(3-methoxyphenyl)propiolyl)-piperazine 4-(Thiazol-2-yl)-1-(3-(3-methoxyphenyl)propiolyl)piperazine was obtained by the reaction of 4-(thiazol-2-yl)-1-propiolylpiperazine [Precursor BBB2] with 3-iodoanisole according to the conditions described in the case of Example AAA1.

Example AAA14

Synthesis of 4-(thiazol-2-yl)-1-(3-(4-methoxyphenyl)propiolyl)-piperazine 4-(Thiazol-2-yl)-1-(3-(4-methoxyphenyl)propiolyl)piperazine was obtained by the reaction of 4-(thiazol-2-yl)-1-propiolylpiperazine [Precursor BBB2] with 4-iodoanisole according to the conditions described in the case of Example AAA1.

Example AAA15

Synthesis of 4-(thiazol-2-yl)-1-(3-(2-cyanophenyl)propiolyl)-piperazine 4-(Thiazol-2-yl)-1-(3-(2-cyanophenyl)propiolyl)piperazine was obtained by the reaction of 4-(thiazol-2-yl)-1- propiolylpiperazine [Precursor BBB2] with 2-iodo-benzonitrile according to the conditions described in the case of Example AAA1.

Example AAA16

Synthesis of 4-(thiazol-2-yl)-1-(3-(3-cyanophenyl)propiolyl)-piperazine 4-(Thiazol-2-yl)-1-(3-(2-cyanophenyl)propiolyl)piperazine was obtained by the reaction of 4-(thiazol-2-yl)-1-propiolylpiperazine [Precursor BBB2] with 3-iodo-benzonitrile according to the conditions described in the case of Example AAA1.

Example AAA17

Synthesis of 4-(thiazol-2-yl)-1-(3-(4-cyanophenyl)propiolyl)-piperazine 4-(Thiazol-2-yl)-1-(3-(2-cyanophenyl)propiolyl)piperazine was obtained by the reaction of 4-(thiazol-2-yl)-1-propiolylpiperazine [Precursor BBB2] with 4-iodo-benzonitrile according to the conditions described in the case of Example AAA1.

Example AAA18

Synthesis of 4-(thiazol-2-yl)-1-(3-(2,4-dimethylphenyl)-propiolyl)piperazine 4-(Thiazol-2-yl)-1-(3-(2,4-dimethylphenyl)propiolyl)piperazine was obtained by the reaction of 4-(thiazol-2-yl)-1-propiolylpiperazine [Precursor BBB2] with 2,4-dimethyl-iodobenzene according to the conditions described in the case of Example AAA1.

Example AAA19

Synthesis of 4-(thiazol-2-yl)-1-(3-(3,5-dimethylphenyl)-propiolyl)piperazine 4-(Thiazol-2-yl)-1-(3-(3,5-dimethylphenyl)propiolyl)piperazine was obtained by the reaction of 4-(thiazol-2-yl)-1-propiolylpiperazine [Precursor BBB2] with 3,5-dimethyl-iodobenzene according to the conditions described in the case of Example AAA1.

Example AAA20

Synthesis of 4-(thiazol-2-yl)-1-(3-(2,6-dimethylphenyl)propiolyl)piperazine 4-(Thiazol-2-yl)-1-(3-(2,6-dimethylphenyl)propiolyl)piperazine was obtained by the reaction of 4-(thiazol-2-yl)-1-propiolylpiperazine [Precursor BBB2] with 2,6-dimethyl-iodobenzene according to the conditions described in the case of Example AAA1.

Example AAA21

Synthesis of 4-(thiazol-2-yl)-1-(3-(2-fluorophenyl)propiolyl)-piperazine 4-(Thiazol-2-yl)-1-(3-(2-fluorophenyl)propiolyl)piperazine was obtained by the reaction of 4-(thiazol-2-yl)-1-propiolylpiperazine [Precursor BBB2] with 2-iodo-fluorobenzene according to the conditions described in the case of Example AAA1.

Example AAA22

Synthesis of 4-(thiazol-2-yl)-1-(3-(3-fluorophenyl)propiolyl)-piperazine 4-(Thiazol-2-yl)-1-(3-(3-fluorophenyl)propiolyl)piperazine was obtained by the reaction of 4-(thiazol-2-yl)-1-propiolylpiperazine [Precursor BBB2] with 3-iodo-fluorobenzene according to the conditions described in the case of Example AAA1.

Example AAA23

Synthesis of 4-(thiazol-2-yl-1-(3-(2-chlorophenyl)propiolyl)-piperazine 4-(Thiazol-2-yl)-1-(3-(2-chlorophenyl)propiolyl)piperazine was obtained by the reaction of 4-(thiazol-2-yl)-1-propiolylpiperazine [Precursor BBB2] with 2-iodo-chlorobenzene according to the conditions described in the case of Example AAA1.

Example AAA24

Synthesis of 4-(thiazol-2-yl)-1-(3-(3-chlorophenyl)propiolyl)-piperazine 4-(Thiazol-2-yl)-1-(3-(3-chlorophenyl)propiolyl)piperazine was obtained by the reaction of 4-(thiazol-2-yl)-1-propiolylpiperazine [Precursor BBB2] with 3-iodo-chlorobenzene according to the conditions described in the case of Example AAA1.

Example AAA25

Synthesis of 4-(thiazol-2-yl)-1-(3-naphthylpropiolyl)piperazine 4-(Thiazol-2-yl)-1-(3-naphthylpropiolyl)piperazine was obtained by the reaction of 4-(thiazol-2-yl)-1-propiolylpiperazine [Precursor BBB2] with 1-iodonaphthalene-chlorobenzene according to the conditions described in the case of Example AAA1.

Example AAA26

Synthesis of 4-(thiazol-2-yl)-1-(3-(2,3-dimethylphenyl)-propiolyl)piperazine 4-(Thiazol-2-yl)-1-(3-(2,3-dimethylphenyl)propiolyl)piperazine was obtained by the reaction of 4-(thiazol-2-yl)-1-propiolylpiperazine [Precursor BBB2] with 2,3-dimethyl-iodobenzene according to the conditions described in the case of Example AAA1.

Example AAA27

Synthesis of 4-(thiazol-2-yl)-1-(3-(3,4-dimethylphenyl)-propiolyl)piperazine 4-(Thiazol-2-yl)-1-(3-(3,4-dimethylphenyl)propiolyl)piperazine was obtained by the reaction of 4-(thiazol-2-yl)-1- propiolylpiperazine [Precursor BBB2] with 3,4-dimethyl-iodobenzene according to the conditions described in the case of Example AAA1.

Example AAA28

Synthesis of 4-(thiazol-2-yl)-1-(3-(3-nitrophenyl) propiolyl)-piperazine 4-(Thiazol-2-yl)-1-(3-(3-nitrophenyl)propiolyl)piperazine was obtained by the reaction of 4-(thiazol-2-yl)-1-propiolylpiperazine [Precursor BBB2] with 3-nitroiodobenzene according to the conditions described in the case of Example AAA1.

Example AAA29

Synthesis of 4-(thiazol-2-yl)-1-(3-(2-nitrophenyl) propiolyl)-piperazine 4-(Thiazol-2-yl)-1-(3-(2-nitrophenyl)propiolyl)piperazine was obtained by the reaction of 4-(thiazol-2-yl)-1-propiolylpiperazine [Precursor BBB2] with 2-nitroiodobenzene according to the conditions described in the case of Example AAA1.

Example AAA30

Synthesis of 4-(thiazol-2-yl)-1-(3-(3-formylphenyl) propiolyl)-piperazine 4-(Thiazol-2-yl)-1-(3-(3-formylphenyl)propiolyl)piperazine was obtained by the reaction of 4-(thiazol-2-yl)-1-propiolylpiperazine [Precursor BBB2] with 3-iodo-benzaldehyde according to the conditions described in the case of Example AAA1.

Example AAA31

Synthesis of 4-(thiazol-2-yl)-1-(3-(3-vinylphenyl) propiolyl)-piperazine 4-(Thiazol-2-yl)-1-(3-(3-vinylphenyl)propiolyl)piperazine was obtained by the reaction of 4-(thiazol-2-yl)-1-propiolylpiperazine [Precursor BBB2] with 3-iodostyrene according to the conditions described in the case of Example AAA1.

Example AAA32

Synthesis of 4-(thiazol-2-yl)-1-(3-pyrid-2-ylpropiolyl)piperazine 4-(Thiazol-2-yl)-1-(3-pyrid-2-ylpropiolyl)piperazine was obtained by the reaction of 4-(thiazol-2-yl)-1-propiolylpiperazine [Precursor BBB2] with 2-iodopyridine according to the conditions described in the case of Example AAA1.

Example AAA33

Synthesis of 4-(thiazol-2-yl)-1-(3-pyrid-3-ylpropiolyl)piperazine 4-(Thiazol-2-yl)-1-(3-pyrid-3-ylpropiolyl)piperazine was obtained by the reaction of 4-(thiazol-2-yl)-1-propiolylpiperazine [Precursor BBB2] with 3-iodopyridine according to the conditions described in the case of Example AAA1.

Example AAA34

Synthesis of 4-(thiazol-2-yl)-1-(3-pyrid-4-ylpropiolyl)piperazine 4-(Thiazol-2-yl)-1-(3-pyrid-4-ylpropiolyl)piperazine was obtained by the reaction of 4-(thiazol-2-yl)-1-propiolylpiperazine [Precursor BBB2] with 4-iodopyridine according to the conditions described in the case of Example AAA1.

Example AAA35

Synthesis of 4-(thiazol-2-yl)-1-(3-(quinolin-6-yl) propiolyl)-piperazine 442 mg (2.0 mmol) of 4-(thiazol-2-yl)-1-propiolylpiperazine [Precursor BBB2], 416 mg (2.0 mmol) of 6-bromoquinoline [Precursor BBB3], 25 mg (0.035 mmol) of $Pd(PPh_3)_2Cl_2$ and 14 mg (0.074 mmol) of CuI were dissolved in DMF (10 ml) and treated with 0.7 ml (5.0 mmol) of TEA. Subsequently, the reaction solution was heated at 110° C. 20 min in a microwave (CEM Discover LabMate, Intellivent Pressure, monomode cavity, 50 W). The cooled solution was poured into water and was subsequently extracted with chloroform. The organic phase was washed successively with water and a satd aq. NaCl soln and dried over $MgSO_4$. After filtering off and removing the solvents in vacuo, 103 mg (1.8 mmol, 15%) of 4-(thiazol-2-yl)-1-(3-(quinolin-6-yl)propiolyl)piperazine were obtained from the residue by CC using a mixture of hexane and EA.

Example AAA36

Synthesis of 4-(thiazol-2-yl)-1-(3-(3-isopropylphenyl)-propiolyl)piperazine 4-(Thiazol-2-yl)-1-(3-(3-isopropylphenyl)propiolyl)piperazine was obtained by the reaction of 4-(thiazol-2-yl)-1-propiolylpiperazine [Precursor BBB2] with 3-bromo-isopropylbenzene according to the conditions described in the case of Example AAA35.

Example AAA37

Synthesis of 4-(thiazol-2-yl)-1-(3-biphenyl-3-ylpropiolyl)-piperazine 4-(Thiazol-2-yl)-1-(3-biphenyl-3-ylpropiolyl)piperazine was obtained by the reaction of 4-(thiazol-2-yl)-1-propiolylpiperazine [Precursor BBB2] with 3-bromobiphenyl according to the conditions described in the case of Example AAA35.

Example AAA38

Synthesis of 4-(thiazol-2-yl)-1-(3-naphth-2-ylpropiolyl)-piperazine 4-(Thiazol-2-yl)-1-(3-naphth-2-ylpropiolyl)piperazine was obtained by the reaction of 4-(thiazol-2-yl)-1-propiolylpiperazine [Precursor BBB2] with 2-bromonaphthalene according to the conditions described in the case of Example AAA35.

Example AAA39

Synthesis of 4-(thiazol-2-yl)-1-(3-(1-methylindol-5-yl)-propiolyl)piperazine 4-(Thiazol-2-yl)-1-(3-(1-methyl-indol-5-yl)propiolyl) piperazine was obtained by the reaction of 4-(thiazol-2-yl)-1-propiolylpiperazine [Precursor BBB2] with 5-bromo-1-

Example AAA40

Synthesis of 4-(thiazol-2-yl)-1-(3-(3-methylmercaptophenyl)-propiolyl)piperazine 4-(Thiazol-2-yl)-1-(3-(3-methylmercapto-phenyl)propiolyl)piperazine was obtained by the reaction of 4-(thiazol-2-yl)-1-propiolylpiperazine [Precursor BBB2] with 3-bromothioanisole according to the conditions described in the case of Example AAA35.

Example AAA41

Synthesis of 4-(thiazol-2-yl)-1-(3-(3-cyano-4-fluorophenyl)-propiolyl)piperazine 4-(Thiazol-2-yl)-1-(3-(3-cyano-4-fluorophenyl)propiolyl)piperazine was obtained by the reaction of 4-(thiazol-2-yl)-1-propiolylpiperazine [Precursor BBB2] with 5-bromo-2-fluorobenzonitrile according to the conditions described in the case of Example AAA35.

Example AAA42

Synthesis of 4-(thiazol-2-yl)-1-(3-(3-methoxymethylphenyl)-propiolyl)piperazine 4-(Thiazol-2-yl)-1-(3-(3-methoxymethylphenyl)propiolyl)piperazine was obtained by the reaction of 4-(thiazol-2-yl)-1-propiolylpiperazine [Precursor BBB2] with 3-methoxymethyl-iodobenzene [Precursor BBB5] according to the conditions described in the case of Example AAA1.

Example AAA43

Synthesis of 4-(thiazol-2-yl)-1-(3-(3-hydroxyphenyl)propiolyl)-piperazine

A solution of 57 mg (0.83 mmol) of sodium nitrite in water (10 ml) was added dropwise at 40° C. to a solution of 224 mg (0.72 mmol) of 4-(thiazol-2-yl)-1-(3-(3-aminophenyl)propiolyl)piperazine [Example AAA7] in 5% strength sulfuric acid (100 ml). On completion of the addition, the mixture was stirred at 80° C. a further 2 h. Subsequently, the reaction solution was neutralized with a satd aq. NaHCO₃ soln and extracted with chloroform. The organic phase was washed successively with water and a satd aq. NaCl soln and dried over MgSO₄. After filtration and removal of the solvent in vacuo, from the residue 120 mg (0.38 mmol, 53%) of 4-(thiazol-2-yl)-1-(3-(3-hydroxy-phenyl)propiolyl)piperazine were recrystallized from diethyl ether.

Example AAA44

Synthesis of 4-(thiazol-2-yl)-1-(3-(3-acetaminophenyl)-propiolyl)piperazine 209 mg (0.67 mmol) of 4-(thiazol-2-yl)-1-(3-(3-aminophenyl)propiolyl)piperazine [Example AAA7] and 193 µl (1.1 mmol) of DIPEA were dissolved in dichloroethane (5 ml), and 65 µl (1.0 mmol) of acetyl chloride were added. After stirring at RT 1 h, the reaction solution was washed successively with a 3% strength aq. Na₂CO₃ soln and a satd aq. NaCl soln and dried over MgSO₄. After filtration and removal of the solvent in vacuo, from the residue 161 mg (0.45 mmol, 68%) of 4-(thiazol-2-yl)-1-(3-(3-acetaminophenyl)propiolyl)piperazine were recrystallized from diethyl ether.

Example AAA45

Synthesis of 4-(thiazol-2-yl)-1-(3-(4-acetaminophenyl)-propiolyl)piperazine 4-(Thiazol-2-yl)-1-(3-(4-acetaminophenyl)propiolyl)piperazine was obtained by the reaction of 4-(thiazol-2-yl)-1-(3-(4-aminophenyl)propiolyl)piperazine [Example AAA8] with acetyl chloride according to the conditions described in the case of Example AAA44.

Example AAA46

Synthesis of 4-(thiazol-2-yl)-1-(3-(2-carboxyphenyl) propiolyl)-piperazine 257 mg (0.72 mmol) of 4-(thiazol-2-yl)-1-(3-(2-carboxyphenyl)propiolyl)piperazine methyl ester [Example AAA1] were dissolved in ethanol (10 ml), and 0.32 ml of a 10% strength aq. NaOH soln were added. The reaction solution was stirred at 70° C. 30 min. Subsequently, the ethanol was distilled off and the residue was taken up in water. The solution obtained was washed with EA and subsequently adjusted to a pH<3 using a 3% strength HCl soln. After this, the mixture was extracted with chloroform and the organic phase was dried over MgSO₄, filtered and concentrated in vacuo. 72 mg (21 mmol, 29%) of 4-(thiazol-2-yl)-1-(3-(2-carboxyphenyl)propiolyl)-piperazine were obtained by recrystallization of the residue from diethyl ether, followed by a second recrystallization from ethanol.

Example AAA47

Synthesis of 4-(thiazol-2-yl)-1-(3-(3-carboxyphenyl) propiolyl)-piperazine 4-(Thiazol-2-yl)-1-(3-(3-carboxyphenyl)propiolyl)piperazine was obtained by the reaction of 4-(thiazol-2-yl)-1-(3-(3-carboxyphenyl)propiolyl)piperazine ethyl ester [Example AAA3] with NaOH according to the conditions described in the case of Example AAA46.

Example AAA48

Synthesis of 4-(thiazol-2-yl)-1-(3-(4-carboxyphenyl) propiolyl)-piperazine 4-(Thiazol-2-yl)-1-(3-(4-carboxyphenyl)propiolyl)piperazine was obtained by the reaction of 4-(thiazol-2-yl)-1-(3-(4-carboxyphenyl)propiolyl)piperazine methyl ester [Example AAA2] with NaOH according to the conditions described in the case of Example AAA46.

Example AAA49

Synthesis of 4-(thiazol-2-yl)-1-(3-(3-carboxyphenyl) propiolyl)-piperazine methyl ester 347 mg (1.00 mmol) of 4-(thiazol-2-yl)-1-(3-(3-carboxyphenyl)propiolyl)piperazine [Example AAA47] were dissolved in DCE (20 ml), and 170 mg (1.05 mmol) of CDI were added. After stirring at RT 45 min, MeOH (80 ml) was added and the mixture was stirred at 50° C. 16 h. Subsequently, it was concentrated in vacuo and the residue was taken up in chloroform. The solution obtained was washed successively with a 3% strength Na₂CO₃ soln, water and a satd aq. NaCl soln, dried over MgSO₄, filtered and concentrated in vacuo. 127 mg (0.36 mmol, 36%) of 4-(thiazol-2-yl)-1-(3-(3-carboxyphenyl)propiolyl)piperazine methyl ester were obtained by recrystallization of the residue from ether.

Example AAA50

Synthesis of 4-(thiazol-2-yl)-1-(3-(3-aminocarbonylphenyl)-propiolyl)piperazine 172 mg (0.50 mmol) of 4-(thiazol-2-yl)-1-(3-(3-carboxyphenyl)propiolyl)piperazine [Example AAA47] were dissolved in THF (5 ml) and treated with 86 mg (0.53 mmol) of CDI. After stirring at RT 60 min, NH₃ was passed through the solution over a period of 5 min. Subsequently, the mixture was stirred at RT a further 16 h and concentrated in vacuo. The residue was suspended in MeCN, filtered off and washed with ether. 107 mg (0.32 mmol, 63%) of 4-(thiazol-2-yl)-1-(3-(3-amino-carbonylphenyl)propiolyl)piperazine were obtained.

Example AAA51

Synthesis of 4-(thiazol-2-yl)-1-(3-(3-methylaminocarbonylphenyl)propiolyl)piperazine 480 mg (1.40 mmol) of 4-(thiazol-2-yl)-1-(3-(3-carboxyphenyl)propiolyl)piperazine [Example AAA47] were dissolved in DCE (10 ml), and 239 mg (1.47 mmol) of CDI were added. After stirring at RT 45 min, 4 ml of an approximately 15% strength solution of methylamine in dioxane were added. Subsequently, the mixture was stirred at RT a further 2 h. The resulting precipitate was filtered off and washed with DCE. 337 mg (0.95 mmol, 68%) of 4-(thiazol-2-yl)-1-(3-(3-methylamino-carbonylphenyl)propiolyl)piperazine were obtained by recrystallization of the residue from ethanol.

Example AAA52

Synthesis of 4-(thiazol-2-yl)-1-(3-(3-dimethylaminocarbonylphenyl)propiolyl)piperazine 480 mg (1.40 mmol) of 4-(thiazol-2-yl)-1-(3-(3-carboxyphenyl)propiolyl)piperazine [Example AAA47] were dissolved in DCE (10 ml), and 239 mg (1.47 mmol) of CDI were added. After stirring at RT 45 min, 5 ml of an approximately 8% strength solution of dimethylamine in dioxane were added. Subsequently, the mixture was stirred at RT a further 2 h. After this, the reaction solution was washed successively with a 5% strength aq. Na₂CO₃ soln, water and a satd aq. NaCl soln and dried over MgSO₄. After filtration and removal of the solvent in vacuo, 283 mg (0.77 mmol, 55%) of 4-(thiazol-2-yl)-1-(3-(3-dimethylaminocarbonylphenyl)propiolyl)-piperazine were obtained by recrystallization of the residue from diethyl ether.

Example AAA53

Synthesis of 4-(thiazol-2-yl)-1-(3-(2-tolyl)propiolyl) piperazine hydrochloride

A solution of 338 mg (2.0 mmol) of 1-thiazol-2-ylpiperazine [Precursor BBB1] in DMF (1.5 ml) was added to 320 mg (2.0 mmol) of tol-2-ylpropiolic acid [Precursor BBB8]. To the reaction solution there were then added 0.31 ml (2.0 mmol) of DIC and 270 mg (2.0 mmol) of HOBt and the mixture was stirred at RT 16 h. After this, it was diluted with a 1 M aq. Na₂CO₃ soln and extracted successively with EA and THF. The combined organic phases were dried over MgSO₄, filtered and concentrated in vacuo. The residue was taken up using acetone (20 ml) and treated successively with 40 μl of water and 280 μl of TMSCI and stirred at RT 30 min. The resulting precipitate was filtered off to give 453 mg (1.3 mmol, 65%) of 4-(thiazol-2-yl)-1-(3-(2-tolyl)propiolyl)-piperazine hydrochloride.

Example AAA54

Synthesis of 4-(thiazol-2-yl)-1-(3-(3-tolyl)propiolyl) piperazine hydrochloride 4-(Thiazol-2-yl)-1-(3-(3-tolyl)propiolyl)piperazine hydrochloride was obtained by the reaction of tol-3-ylpropiolic acid [Precursor BBB9] with 1-thiazol-2-ylpiperazine [Precursor BBB1] according to the conditions described in the case of Example AAA53.

Example AAA55

Synthesis of 4-(thiazol-2-yl)-1-(3-(4-tolyl)propiolyl) piperazine hydrochloride 4-(Thiazol-2-yl)-1-(3-(4-tolyl)propiolyl)piperazine hydrochloride was obtained by the reaction of tol-4-ylpropiolic acid [Precursor BBB10] with 1-thiazol-2-ylpiperazine [Precursor BBB1] according to the conditions described in the case of Example AAA53.

Example AAA56

Synthesis of 4-(thiazol-2-yl)-1-(3-phenylpropiolyl)piperazine hydrochloride 4-(Thiazol-2-yl)-1-(3-phenylpropiolyl)piperazine hydrochloride was obtained by the reaction of phenylpropiolic acid with 1-thiazol-2-ylpiperazine [Precursor BBB1] according to the conditions described in the case of Example AAA53.

Example AAA57

Synthesis of 4-(thiazol-2-yl)-1-(3-(2-trifluoromethylphenyl)propiolyl)piperazine hydrochloride 4-(Thiazol-2-yl)-1-(3-(2-trifluoromethylphenyl)propiolyl)piperazine hydrochloride was obtained by the reaction of (2-trifluoromethylphenyl)propiolic acid [Precursor BBB11] with 1-thiazol-2-ylpiperazine [Precursor BBB1] according to the conditions described in the case of Example AAA53.

Example AAA58

Synthesis of 4-(thiazol-2-yl)-1-(3-(3-trifluoromethylphenyl)propiolyl)piperazine hydrochloride 4-(Thiazol-2-yl)-1-(3-(3-trifluoromethylphenyl)propiolyl)piperazine hydrochloride was obtained by the reaction of (3-trifluoromethylphenyl)propiolic acid [Precursor BBB12] with 1-thiazol-2-ylpiperazine [Precursor BBB1] according to the conditions described in the case of Example AAA53.

Example AAA59

Synthesis of 4-(thiazol-2-yl)-1-(3-(4-trifluoromethylphenyl)propiolyl)piperazine hydrochloride 4-(Thiazol-2-yl)-1-(3-(4-trifluoromethylphenyl)propiolyl)piperazine hydrochloride was obtained by the reaction of (4-trifluoromethylphenyl)propiolic acid [Precursor BBB13] with 1-thiazol-2-ylpiperazine [Precursor BBB1] according to the conditions described in the case of Example AAA53.

Example AAA60

Synthesis of 4-(thiazol-2-yl)-1-(3-pentylpropiolyl)piperazine 4-(Thiazol-2-yl)-1-(3-pentylpropiolyl)piperazine was obtained by the reaction of 2-octynoic acid with 1-thiazol-2-ylpiperazine [Precursor BBB1] according to the conditions described in the case of Example 1.

Example AAA61

Synthesis of 4-(thiazol-2-yl)-1-(3-(4-fluorophenyl)propiolyl)-piperazine

To a solution of 1.0 g (6.1 mmol) of (4-fluorophenyl)propiolic acid [Precursor BBB7] in DCE (70 ml) there were added 1.0 g (6.4 mmol) of CDI, and the mixture was stirred at RT 100 min. After cooling to 10° C., 1.0 g (6.0 mmol) of 1-thiazol-2-ylpiperazine [Precursor BBB1] was added and the mixture was stirred at RT a further 2 h. Subsequently, the reaction solution was washed successively with water, a 3% strength HCl soln and a satd aq. NaCl soln and dried over MgSO$_4$. After filtration and removal of the solvent in vacuo, 785 mg (2.5 mmol, 42%) of 4-(thiazol-2-yl)-1-(3-(4-fluorophenyl)propiolyl)-piperazine were obtained from the residue by recrystallization from diethyl ether.

Example AAA62

Synthesis of 4-(thiazol-2-yl)-1-(3-(4-chlorophenyl)propiolyl)-piperazine

To a solution of 722 mg (4.0 mmol) of (4-chlorophenyl)propiolic acid [Precursor BBB6] in DCE (25 ml) there were added 681 mg (4.2 mmol) of CDI, and the mixture was stirred at RT 60 min. After cooling to 10° C., 677 mg (4.0 mmol) of 1-thiazol-2-ylpiperazine [Precursor BBB1] were added and the mixture was stirred at RT 1 h. After removal of the solvent in vacuo, 607 mg (1.8 mmol, 46%) of 4-(thiazol-2-yl)-1-(3-(4-chlorophenyl)-propiolyl)piperazine were obtained from the residue by recrystallization from ethanol.

Example AAA63

Synthesis of 2-methyl-4-(thiazol-2-yl)-1-(3-phenyl-propiolyl)-piperazine 1.42 ml (8.6 mmol) of DIPEA, 1.58 g (8.6 mmol) of 3-methyl-1-thiazol-2-ylpiperazine [Precursor BBB14] and 2.76 g (8.6 mmol) of TBTU were added to a solution of 1.40 g (8.6 mmol) of phenylpropiolic acid in MeCN (90 ml). After stirring at RT 2 h, the mixture was concentrated in vacuo. The residue was taken up in chloroform, washed successively with 10% strength aq. NaOH soln, water and with satd aq. NaCl soln and dried over MgSO$_4$. After filtration and concentration in vacuo, CC of the residue was carried out using a mixture of hexane and EA. 1.67 g (5.4 mmol, 62%) of 2-methyl-4-(thiazol-2-yl)-1-(3-phenylpropiolyl)piperazine were obtained by recrystallization of the crude product obtained from DIPE.

Example AAA64

Synthesis of (S)-2-methyl-4-(thiazol-2-yl)-1-(3-phenylpropiolyl)piperazine (S)-2-Methyl-4-(thiazol-2-yl)-1-(3-phenylpropiolyl)piperazine was obtained by the reaction of (S)-3-methyl-1-thiazol-2-ylpiperazine [Precursor BBB15] with phenylpropiolic acid according to the conditions described in the case of Example AAA63.

Example AAA65

Synthesis of (R)-2-methyl-4-(thiazol-2-yl)-1-(3-phenylpropiolyl)piperazine (R)-2-Methyl-4-(thiazol-2-yl)-1-(3-phenylpropiolyl)piperazine was obtained by the reaction of (R)-3-methyl-1-thiazol-2-ylpiperazine [Precursor BBB16] with phenylpropiolic acid according to the conditions described in the case of Example AAA63.

Example AAA66

Synthesis of 2-methyl-4-(thiazol-2-yl)-1-(3-phenyl-propiolyl)-piperazine hydrochloride 1.67 g (5.4 mmol) of 2-methyl-4-(thiazol-2-yl)-1-(3-phenylpropiolyl)piperazine (AAA63) were dissolved in diethyl ether, and a solution of HCl in diethyl ether was added. The resulting precipitate was filtered off with suction and washed with diethyl ether. 1.75 g (5.0 mmol, 93%) of 2-methyl-4-(thiazol-2-yl)-1-(3-phenylpropiolyl)-piperazine hydrochloride were obtained.

Example AAA67

Synthesis of 2-methyl-4-(thiazol-2-yl)-1-(3-(3-tolyl)propiolyl)-piperazine hydrochloride 2-Methyl-4-(thiazol-2-yl)-1-(3-(3-tolyl)propiolyl)piperazine hydrochloride was obtained by the reaction of tol-3-ylpropiolic acid [Precursor BBB9] with 3-methyl-1-thiazol-2-ylpiperazine [Precursor BBB14] according to the conditions described in the case of Example AAA53.

Example AAA68

Synthesis of 2-methyl-4-(thiazol-2-yl)-1-(3-(3-tolyl)propiolyl)-piperazine

2-Methyl-4-(thiazol-2-yl)-1-(3-(3-tolyl)propiolyl)piperazine was obtained by the reaction of tol-3-ylpropiolic acid [Precursor BBB9] with 3-methyl-i-thiazol-2-ylpiperazine [Precursor BBB14] according to the conditions described in the case of Example 1.

Example AAA69

Synthesis of 4-(thiazol-2-yl)-1-(3-cyclohexylpropiolyl)-piperazine 4-(Thiazol-2-yl)-1-(3-cyclohexylpropiolyl)piperazine was obtained by the reaction of cyclohexylpropiolic acid

[Precursor BBB17] with 1-thiazol-2-ylpiperazine [Precursor BBB1] according to the conditions described in the case of Example AAA62.

Example AAA70

Synthesis of 4-(thiazol-2-yl)-1-(3-methylpropiolyl)piperazine 4-(Thiazol-2-yl)-1-(3-methylpropiolyl)piperazine was obtained by the reaction of 2-butynoic acid with 1-thiazol-2-ylpiperazine [Precursor BBB1] according to the conditions described in the case of Example 1.

Example AAA71

Synthesis of 2-ethyl-4-(thiazol-2-yl)-1-(3-phenyl-propiolyl)-piperazine

2-Ethyl-4-(thiazol-2-yl)-1-(3-phenylpropiolyl)piperazine was obtained by the reaction of 3-ethyl-1-thiazol-2-ylpiperazine [Precursor BBB19] with phenylpropiolic acid according to the conditions described in the case of Example AAA63.

Example AAA72

Synthesis of 2-phenyl-4-(thiazol-2-yl)-1-(3-phenyl-propiolyl)-piperazine

2-Phenyl-4-(thiazol-2-yl)-1-(3-phenylpropiolyl)piperazine was obtained by the reaction of 3-phenyl-1-thiazol-2-ylpiperazine [Precursor BBB20] with phenylpropiolic acid according to the conditions described in the case of Example AAA63.

Example AAA73

Synthesis of 4-(thiazol-2-yl)-1-(3-(2-furyl)propiolyl)piperazine 4-(Thiazol-2-yl)-1-(3-(2-furyl)propiolyl)piperazine was obtained by the reaction of furan-2-ylpropiolic acid [Precursor BBB21] with phenylpropiolic acid according to the conditions described in the case of Example AAA62.

Example AAA74

Synthesis of 4-(thiazol-2-yl)-1-(3-(3-furyl)propiolyl)piperazine 4-(Thiazol-2-yl)-1-(3-(3-furyl)propiolyl)piperazine was obtained by the reaction of furan-3-ylpropiolic acid [Precursor BBB22] with phenylpropiolic acid according to the conditions described in the case of Example AAA62.

Example AAA75

Synthesis of cis-2,6-dimethyl-4-(thiazol-2-yl)-1-(3-phenylpropiolyl)piperazine cis-2,6-Dimethyl-4-(thiazol-2-yl)-1-(3-phenylpropiolyl)piperazine was obtained by the reaction of cis-3,5-dimethyl-1-thiazol-2-ylpiperazine [Precursor BBB23] with phenyl-propiolic acid according to the conditions described in the case of Example AAA63.

Example AAA76

Synthesis of 4-(5-carboxythiazol-2-yl)-1-(3-phenyl-propiolyl)-piperazine ethyl ester To a solution of 678 mg (4.64 mmol) of phenylpropiolic acid in DCE (20 ml) there were added 790 mg (4.87 mmol) of CDI, and the mixture was stirred at RT 50 min. After cooling to 10° C., 1.12 g (4.64 mmol) of ethyl 2-piperazin-1-ylthiazole-5-carboxylate [Precursor BBB24] were added and the mixture was stirred at RT 2 h. The reaction solution was washed with water and a satd aq. NaCl soln and dried over $MgSO_4$. After filtration and concentration in vacuo, 890 mg (2.41 mmol, 52%) of 4-(5-carboxythiazol-2-yl)-1-(3-phenylpropiolyl)piperazine ethyl ester were obtained from the residue by recrystallization from ethanol.

Example AAA77

Synthesis of 4-(4-carboxythiazol-2-yl)-1-(3-phenyl-propiolyl)-piperazine ethyl ester 4-(4-Carboxythiazol-2-yl)-1-(3-phenylpropiolyl)piperazine ethyl ester was obtained by the reaction of ethyl 2-piperazin-1-ylthiazole-4-carboxylate [Precursor BBB25] with phenylpropiolic acid according to the conditions described in the case of Example AAA76.

Example AAA78

Synthesis of 4-(5-carboxythiazol-2-yl)-1-(3-phenyl-propiolyl)-piperazine 4-(5-Carboxythiazol-2-yl)-1-(3-phenylpropiolyl)piperazine was obtained by the reaction of 4-(5-carboxythiazol-2-yl)-1-(3-phenylpropiolyl)piperazine ethyl ester [Example AAA76] with NaOH according to the conditions described in the case of Example AAA46.

Example AAA79

Synthesis of 4-(4-carboxythiazol-2-yl)-1-(3-phenyl-propiolyl)-piperazine 4-(4-Carboxythiazol-2-yl)-1-(3-phenylpropiolyl)piperazine was obtained by the reaction of 4-(4-carboxythiazol-2-yl)-1-(3-phenylpropiolyl)piperazine ethyl ester [Example AAA77] with NaOH according to the conditions described in the case of Example AAA46.

Example AAA80

Synthesis of 4-(5-methylaminocarbonylthiazol-2-yl)-1-(3-phenylpropiolyl)piperazine Starting from 4-(5-carboxythiazol-2-yl)-1-(3-phenylpropiolyl)piperazine [Example AAA78], 4-(5-methylaminocarbonylthiazol-2-yl)-1-(3-phenylpropiolyl)piperazine was obtained according to the process described under AAA51.

Example AAA81

Synthesis of 4-(5-dimethylaminocarbonylthiazol-2-yl)-1-(3-phenylpropiolyl)piperazine Starting from 4-(5-carboxythiazol-2-yl)-1-(3-phenylpropiolyl)piperazine [Example AAA78], 4-(5-dimethylaminocarbonylthiazol-2-yl)-1-(3-phenylpropiolyl)piperazine was obtained according to the process described under AAA52.

Example AAA82

Synthesis of 4-(3-phenyl-1,2,4-thiadiazol-5-yl)-1-(3-phenylpropiolyl)piperazine 4-(3-Phenyl-1,2,4-thiadiazol-5-yl)-1-(3-phenylpropiolyl)piperazine was obtained by the reaction of 1-(3-phenyl-[1,2,4]-thiadiazol-5-yl)piperazine with phenylpropiolic acid according to the conditions described in the case of Example AAA76.

Example AAA83

Synthesis of 4-(thiazol-2-yl)-1-(3-(quinol-7-yl)propiolyl)-piperazine 4-(Thiazol-2-yl)-1-(3-(quinol-7-yl)propiolyl)piperazine was obtained by the reaction of 4-(thiazol-2-yl)-1-propiolylpiperazine [Precursor BBB2] with quinolin-7-yl trifluoromethanesulfonate [Precursor BBB19] according to the conditions described in the case of Example AAA1.

Example AAA85

Synthesis of 4-(3-(4-fluorobenzyl)-1,2,4-thiadiazol-5-yl)-1-(3-phenylpropiolyl)piperazine 4-(3-(4-Fluorobenzyl)-1,2,4-thiadiazol-5-yl)-1-(3-phenylpropiolyl)piperazine was obtained by the reaction of 1-[3-(4-fluorobenzyl)-[1,2,4]-thiadiazol-5-yl]piperazine [Precursor BBB27] with phenylpropiolic acid according to the conditions described in the case of Example AAA76.

Example AAA86

Synthesis of 4-(5-nitrothiazol-2-yl)-1-(3-phenylpropiolyl)-piperazine 4-(5-Nitrothiazol-2-yl)-1-(3-phenylpropiolyl)piperazine was obtained by the reaction of 1-(5-nitrothiazol-2-yl)piperazine [Precursor BBB29] with phenylpropiolic acid according to the conditions described in the case of Example AAA76.

Example AAA87

Synthesis of 4-(4-tert-butylthiazol-2-yl)-1-(3-phenylpropiolyl)-piperazine 4-(4-tert-Butylthiazol-2-yl)-1-(3-phenylpropiolyl)piperazine was obtained by the reaction of 1-(4-tert-butylthiazol-2-yl)piperazine [Precursor BBB31] with phenylpropiolic acid according to the conditions described in the case of Example AAA76.

Example AAA88

Synthesis of 4-(5-methylthiazol-2-yl)-1-(3-phenylpropiolyl)-piperazine 4-(5-Methylthiazol-2-yl)-1-(3-phenylpropiolyl)piperazine was obtained by the reaction of 1-(5-methylthiazol-2-yl)piperazine [Precursor BBB33] with phenylpropiolic acid according to the conditions described in the case of Example AAA76.

Example AAA89

Synthesis of 4-(4,5-dimethylthiazol-2-yl)-1-(3-phenylpropiolyl)piperazine 4-(4,5-Dimethylthiazol-2-yl)-1-(3-phenylpropiolyl)piperazine was obtained by the reaction of 1-(4,5-dimethylthiazol-2-yl)piperazine [Precursor BBB35] with phenylpropiolic acid according to the conditions described in the case of Example AAA76.

Example AAA90

Synthesis of 4-(5-bromo-4-phenylthiazol-2-yl)-1-(3-phenylpropiolyl)piperazine 4-(5-Bromo-4-phenylthiazol-2-yl)-1-(3-phenylpropiolyl)piperazine was obtained by the reaction of 1-(5-bromo-4-phenylthiazol-2-yl)piperazine [Precursor BBB37] with phenylpropiolic acid according to the conditions described in the case of Example AAA76.

Example AAA91

Synthesis of 4-(5-bromo-4-methylthiazol-2-yl)-1-(3-phenylpropiolyl)piperazine 4-(5-Bromo-4-methylthiazol-2-yl)-1-(3-phenylpropiolyl)piperazine was obtained by the reaction of 1-(5-bromo-4-methylthiazol-2-yl)piperazine [Precursor BBB39] with phenylpropiolic acid according to the conditions described in the case of Example AAA76.

Example AAA92

Synthesis of 4-(4-methylthiazol-2-yl)-1-(3-phenylpropiolyl)-piperazine 4-(4-Methylthiazol-2-yl)-1-(3-phenylpropiolyl)piperazine was obtained by the reaction of 1-(4-methylthiazol-2-yl)piperazine [Precursor BBB41] with phenylpropiolic acid according to the conditions described in the case of Example AAA76.

Example AAA93

Synthesis of 4-(4-trifluoromethylthiazol-2-yl)-1-(3-phenylpropiolyl)piperazine 4-(4-Trifluoromethylthiazol-2-yl)-1-(3-phenylpropiolyl)piperazine was obtained by the reaction of 1-(4-trifluoromethylthiazol-2-yl)piperazine [Precursor BBB43] with phenylpropiolic acid according to the conditions described in the case of Example AAA76.

Example AAA94

Synthesis of 4-(4-chlorothiazol-2-yl)-1-(3-phenylpropiolyl)-piperazine 4-(4-Chlorothiazol-2-yl)-1-(3-phenylpropiolyl)piperazine was obtained by the reaction of 1-(4-chlorothiazol-2-yl)

Example AAA95

Synthesis of 4-(5-chlorothiazol-2-yl)-1-(3-phenyl-propiolyl)-piperazine 4-(5-Chlorothiazol-2-yl)-1-(3-phenylpropiolyl)piperazine was obtained by the reaction of 1-(5-chlorothiazol-2-yl)piperazine [Precursor BBB47] with phenylpropiolic acid according to the conditions described in the case of Example AAA76.

Example AAA96

Synthesis of 4-(5-bromothiazol-2-yl)-1-(3-phenyl-propiolyl)-piperazine 4-(5-Bromothiazol-2-yl)-1-(3-phenylpropiolyl)piperazine was obtained by the reaction of 1-(5-bromothiazol-2-yl)piperazine [Precursor BBB48] with phenylpropiolic acid according to the conditions described in the case of Example AAA76.

Example AAA97

Synthesis of 4-(4-bromothiazol-2-yl)-1-(3-phenyl-propiolyl)-piperazine 4-(4-Bromothiazol-2-yl)-1-(3-phenylpropiolyl)piperazine was obtained by the reaction of 1-(4-bromothiazol-2-yl)piperazine [Precursor BBB49] with phenylpropiolic acid according to the conditions described in the case of Example AAA76.

Example AAA98

Synthesis of 4-(5-phenylthiazol-2-yl)-1-(3-phenyl-propiolyl)-piperazine

A solution of 265 mg (2.5 mmol) of $Na_2CO_3$ in water (1.6 ml) was added to a solution of 376 mg (1.0 mmol) of 4-(5-bromothiazol-2-yl)-1-(3-phenylpropiolyl)piperazine [Example AAA96], 171 mg (1.4 mmol) of phenylboronic acid and 30 mg of $Pd(PPh_3)_2Cl_2$ in DCE (4 ml). Subsequently, the mixture was heated under reflux 3 h. Water was added to the cooled reaction solution and the mixture was extracted with EA. The organic phase was washed with water and a satd aq. NaCl soln, dried over $MgSO_4$, filtered and concentrated in vacuo. The residue was recrystallized from diethyl ether. 160 mg (0.43 mmol, 43%) of 4-(5-phenylthiazol-2-yl)-1-(3-phenylpropiolyl)piperazine were obtained by CC (chloroform) of the recrystallization product.

Example AAA99

Synthesis of 4-(4-phenylthiazol-2-yl)-1-(3-phenyl-propiolyl)-piperazine

Starting from 4-(4-bromothiazol-2-yl)-1-(3-phenylpropiolyl)piperazine [Example AAA97], 4-(4-phenylthiazol-2-yl)-1-(3-phenylpropiolyl)piperazine was obtained according to the process described under AAA98.

piperazine [Precursor BBB45] with phenylpropiolic acid according to the conditions described in the case of Example AAA76.

Example AAA00100

Synthesis of 4-(3-methylmercapto-1,2,4-thiadiazol-5-yl)-1-(3-phenylpropiolyl)piperazine 4-(3-Methylmercapto-1,2,4-thiadiazol-5-yl)-1-(3-phenylpropiolyl)piperazine was obtained by the reaction of 1-(3-methylsulfanyl-[1,2,4]-thiadiazol-5-yl)piperazine [Precursor BBB50] with phenylpropiolic acid according to the conditions described in the case of Example AAA76.

Example AAA00101

Synthesis of 4-(3-methanesulfonyl-1,2,4-thiadiazol-5-yl)-1-(3-phenylpropiolyl)piperazine 4-(3-Methanesulfonyl-1,2,4-thiadiazol-5-yl)-1-(3-phenylpropiolyl)piperazine was obtained by the reaction of 1-(3-methanesulfonyl-[1,2,4]-thiadiazol-5-yl)piperazine [Precursor BBB51] with phenylpropiolic acid according to the conditions described in the case of Example AAA76.

Example AAA00102

Synthesis of 4-(3-methoxy-1,2,4-thiadiazol-5-yl)-1-(3-phenylpropiolyl)piperazine 4-(3-Methoxy-1,2,4-thiadiazol-5-yl)-1-(3-phenylpropiolyl)piperazine was obtained by the reaction of 1-(3-methoxy-[1,2,4]-thiadiazol-5-yl)piperazine [Precursor BBB52] with phenylpropiolic acid according to the conditions described in the case of Example AAA76.

Example AAA00103

Synthesis of 4-(1,2,4-thiadiazol-5-yl)-1-(3-phenyl-propiolyl)piperazine 4-(1,2,4-Thiadiazol-5-yl)-1-(3-phenylpropiolyl)piperazine was obtained by the reaction of 1-[1,2,4]-thiadiazol-5-ylpiperazine [Precursor BBB57] with phenylpropiolic acid according to the conditions described in the case of Example AAA76.

Example AAA00104

Synthesis of 4-(3-methyl-1,2,4-thiadiazol-5-yl)-1-(3-phenylpropiolyl)piperazine 4-(3-Methyl-1,2,4-thiadiazol-5-yl)-1-(3-phenylpropiolyl)piperazine was obtained by the reaction of 1-(3-methyl-[1,2,4]-thiadiazol-5-yl)piperazine [Precursor BBB58] with phenylpropiolic acid according to the conditions described in the case of Example AAA76.

Example AAA00105

Synthesis of 4-(3-trifluoromethyl-1,2,4-thiadiazol-5-yl)-1-(3-phenylpropiolyl)piperazine 4-(3-Trifluoromethyl-1,2,4-thiadiazol-5-yl)-1-(3-phenylpropiolyl)piperazine was obtained by the reaction of 1-(3-trifluoromethyl-[1,2,4]-thiadiazol-5-yl)piperazine [Precursor BBB59] with phenylpropiolic acid according to the conditions described in the case of Example AAA76.

Example AAA00106

Synthesis of 4-(5-(3-methyl-1,2,4-oxadiazol-5-yl)thiazol-2-yl)-1-(3-phenylpropiolyl)piperazine 4-(5-(3-Methyl-1,2,4-oxadiazol-5-yl)thiazol-2-yl)-1-(3-phenylpropiolyl)piperazine was obtained by the reaction of 1-[5-(3-methyl-[1,2,4]-oxadiazol-5-yl)thiazol-2-yl]-piperazine [Precursor BBB63] with phenylpropiolic acid according to the conditions described in the case of Example AAA76.

Example AAA00107

Synthesis of 4-(4-tert-butylthiazol-2-yl)-1-(3-(4-amino-phenyl)propiolyl)piperazine 4-(4-tert-Butylthiazol-2-yl)-1-(3-(4-aminophenyl)propiolyl)piperazine was obtained by the reaction of 4-(4-tert-butylthiazol-2-yl)-1-propiolylpiperazine [Precursor BBB65] with 4-iodoaniline according to the conditions described in the case of Example AAA1.

Example AAA00108

Synthesis of 4-(thiazol-2-yl)-1-(3-(1-methylindol-6-yl)-propiolyl)piperazine 4-(Thiazol-2-yl)-1-(3-(1-methylindol-6-yl)propiolyl)piperazine was obtained by the reaction of 4-(thiazol-2-yl)-1-propiolylpiperazine [Precursor BBB2] with 6-bromo-1-methylindole under the conditions described in the case of Example AAA35.

Example AAA00109

Synthesis of 4-(thiazol-2-yl)-1-(3-(3-acetylphenyl)-propiolyl)piperazine 4-(Thiazol-2-yl)-1-(3-(3-acetylphenyl)propiolyl)piperazine was obtained by the reaction of 4-(thiazol-2-yl)-1-propiolylpiperazine [Precursor BBB2] with 3-acetyl-iodobenzene under the conditions described in the case of Example AAA1.

Example AAA00110

Synthesis of 4-(thiazol-2-yl)-1-(3-(3-fluoro-5-methylphenyl)-propiolyl)piperazine 4-(Thiazol-2-yl)-1-(3-(3-fluoro-5-methylphenyl)propiolyl)piperazine was obtained by the reaction of 4-(thiazol-2-yl)-1-propiolylpiperazine [Precursor BBB2] with 3-bromo-5-fluorotoluene under the conditions described in the case of Example AAA35.

Example AAA00111

Synthesis of 4-(thiazol-2-yl)-1-(3-(2-fluoro-3-methylphenyl)-propiolyl)piperazine 4-(Thiazol-2-yl)-1-(3-(2-fluoro-3-methylphenyl)propiolyl)piperazine was obtained by the reaction of 4-(thiazol-2-yl)-1-propiolylpiperazine [Precursor BBB2] with 3-bromo-2-fluorotoluene under the conditions described in the case of Example AAA35.

Example AAA00112

Synthesis of 4-(thiazol-2-yl)-1-(3-(3-methylaminophenyl)-propiolyl)piperazine 4-(Thiazol-2-yl)-1-(3-(3-methylaminophenyl)propiolyl)piperazine was obtained by the reaction of 4-(thiazol-2-yl)-1-propiolylpiperazine [Precursor BBB2] with 3-iodo-N-methylaniline under the conditions described in the case of Example AAA1.

Example AAA00113

Synthesis of 4-(thiazol-2-yl)-1-(3-(3-dimethylaminophenyl)-propiolyl)piperazine 4-(Thiazol-2-yl)-1-(3-(3-dimethylaminophenyl)propiolyl)piperazine was obtained by the reaction of 4-(thiazol-2-yl)-1-propiolylpiperazine [Precursor BBB2] with 3-iodo-N,N-dimethylaniline under the conditions described in the case of Example AAA1.

Example AAA00114

Synthesis of 4-(thiazol-2-yl)-1-(3-(3-dimethylaminophenyl)-propiolyl)piperazine 240 mg (6.0 mmol) of sodium hydride were added with cooling (ice bath) to a solution of 885 mg (4.0 mmol) of 4-(thiazol-2-yl)-1-propiolylpiperazine [Precursor BBB2] in MeCN (10 ml). After stirring at RT 15 min, 479 µl (5.2 mmol) of dimethylcarbamoyl chloride were added to the mixture, which was then stirred at RT a further 16 h. Subsequently, it was diluted with water and toluene and the phases were separated. The aqueous phase was extracted with toluene and the combined organic phases were dried over $MgSO_4$, filtered and concentrated in vacuo. CC of the residue was carried out using a mixture of chloroform and EA, and 137 mg (0.5 mmol, 12%) of 4-(thiazol-2-yl)-1-(3-(3-dimethylaminophenyl)propiolyl)piperazine were isolated.

Example AAA00115

Synthesis of 4-(thiazol-2-yl)-1-(3-(3-methylsulfinylphenyl)-propiolyl)piperazine 4-(Thiazol-2-yl)-1-(3-(3-methylsulfinylphenyl)propiolyl)piperazine was obtained by the reaction of 4-(thiazol-2-yl)-1-propiolylpiperazine [Precursor BBB2] with 3-methylsulfinylbromobenzene under the conditions described in the case of Example AAA35.

Example AAA00116

Synthesis of 4-(thiazol-2-yl)-1-(3-(3-methylsulfonylphenyl)propiolyl)piperazine 4-(Thiazol-2-yl)-1-(3-(3-methylsulfonylphenyl)propiolyl)piperazine was obtained by the reaction of 4-(thiazol-2-yl)-1-propiolylpiperazine [Precursor BBB2] with 3-methyl-sulfonylbrombenzene under the conditions described in the case of Example AAA35.

Example AAA00117

Synthesis of 4-(thiazol-2-yl)-1-(3-(3-ethynylphenyl)-propiolyl)piperazine

A mixture of 387 mg (0.98 mmol) of 4-(thiazol-2-yl)-1-(3-(3-trimethylsilanylethynylphenyl)propiolyl)piperazine

[Example AAA00125] and 39 mg of tetrabutylammonium fluoride trihydrate in MeCN (20 ml) was stirred at RT 120 min. Subsequently, it was concentrated in vacuo. The residue was taken up using DCM and washed with water. The organic phase was dried over MgSO$_4$, filtered and concentrated in vacuo. CC of the residue was carried out using DCE, 214 mg (0.67 mmol, 68%) of 4-(thiazol-2-yl)-1-(3-(3-ethynylphenyl)propiolyl)piperazine being obtained.

Example AAA118

Synthesis of 4-(thiazol-2-yl)-1-(3-(4-methylthiophen-2-yl)-propiolyl)piperazine 4-(Thiazol-2-yl)-1-(3-(4-methylthiophen-2-yl)propiolyl)piperazine was obtained by the reaction of 1-thiazol-2-ylpiperazine [Precursor BBB1] with (4-methylthiophen-2-yl)-propiolic acid [Precursor BBB67] under the conditions described in the case of Example AAA63.

Example AAA119

Synthesis of 2-methyl-4-(thiazol-2-yl)-1-(3-(3-chlorophenyl)-propiolyl)piperazine 2-Methyl-4-(thiazol-2-yl)-1-(3-(3-chlorophenyl)propiolyl)piperazine was obtained by the reaction of 3-methyl-i-thiazol-2-ylpiperazine [Precursor BBB14] with (3-chlorophenyl)propiolic acid [Precursor BBB68] under the conditions described in the case of Example AAA63.

Example AAA00120

Synthesis of 4-(thiazol-2-yl)-1-(3-(3-ethylphenyl)propiolyl)piperazine 4-(Thiazol-2-yl)-1-(3-(3-ethylphenyl)propiolyl)piperazine was obtained by the reaction of 4-(thiazol-2-yl)-1-propiolylpiperazine [Precursor BBB2] with 3-iodoethylbenzene under the conditions described in the case of Example AAA1.

Example AAA121

Synthesis of 2-tert-butyl-4-(thiazol-2-yl)-1-(3-phenylpropiolyl)piperazine 2-tert-Butyl-4-(thiazol-2-yl)-1-(3-phenylpropiolyl)piperazine was obtained by the reaction of 3-tert-butyl-1-thiazol-2-ylpiperazine [Precursor BBB69] with phenylpropiolic acid under the conditions described in the case of Example AAA63.

Example AAA00122

Synthesis of 4-(thiazol-2-yl)-1-(3-(3-difluoromethylphenyl)-propiolyl)piperazine 4-(Thiazol-2-yl)-1-(3-(3-difluoromethylphenyl)propiolyl)piperazine was obtained by the reaction of 4-(thiazol-2-yl)-1-propiolylpiperazine [Precursor BBB2] with 3-difluoro-methyliodobenzene under the conditions described in the case of Example AAA1.

Example AAA123

Synthesis of 2-methyl-4-(thiazol-2-yl)-1-(3-(3-cyanophenyl)-propiolyl)piperazine 2-Methyl-4-(thiazol-2-yl)-1-(3-(3-cyanophenyl)propiolyl)piperazine was obtained by the reaction of 3-methyl-1-thiazol-2-ylpiperazine [Precursor BBB14] with (3-cyanophenyl)propiolic acid under the conditions described in the case of Example AAA63.

Example AAA124

Synthesis of 2-isopropyl-4-(thiazol-2-yl)-1-(3-phenylpropiolyl)piperazine

2-Isopropyl-4-(thiazol-2-yl)-1-(3-phenylpropiolyl)piperazine was obtained by the reaction of 3-isopropyl-1-thiazol-2-ylpiperazine [Precursor BBB70] with phenylpropiolic acid under the conditions described in the case of Example AAA63.

Example AAA00125

Synthesis of 4-(thiazol-2-yl)-1-(3-(3-trimethylsilanylethynylphenyl)propiolyl)piperazine 4-(Thiazol-2-yl)-1-(3-(3-trimethylsilanylethynylphenyl)propiolyl)piperazine was obtained by the reaction of 4-(thiazol-2-yl)-1-propiolylpiperazine [Precursor BBB2] with 3-trimethylsilanylethynyliodobenzene under the conditions described in the case of Example AAA1.

The examples of the invention are summarized in the following overview:

| | |
|---|---|
| AAA00100 | 4-(3-Methylmercapto1,2,4-thiadiazol-5-yl)1-(3-phenylpropiolyl)piperazine |
| AAA00101 | 4-(3-Methanesulfonyl1,2,4-thiadiazol-5-yl)1-(3-phenylpropiolyl)piperazine |
| AAA00102 | 4-(3-Methoxy-1,2,4-thiadiazol-5-yl)1-(3-phenylpropiolyl)piperazine |
| AAA00103 | 4-(1,2,4-Thiadiazol-5-yl)1-(3-phenylpropiolyl)piperazine |
| AAA00104 | 4-(3-Methyl1,2,4-thiadiazol-5-yl)1-(3-phenylpropiolyl)piperazine |
| AAA00105 | 4-(3-Trifluoromethyl1,2,4-thiadiazol-5-yl)1-(3-phenylpropiolyl)piperazine |
| AAA00106 | 4-(5-(3-Methyl-1,2,4-oxadiazol-5-yl)thiazol-2-yl)1-(3-phenylpropiolyl)piperazine |
| AAA00107 | 4-(4-tert-Butylthiazol-2-yl)1-(3-(4-aminophenyl)propiolyl)piperazine |
| AAA1 | 4-(Thiazol-2-yl)1-(3-(2-carboxyphenyl)propiolyl)piperazine methyl ester |
| AAA10 | 4-(Thiazol-2-yl)1-(3-(2-thienyl)propiolyl)piperazine |
| AAA11 | 4-(Thiazol-2-yl)1-(3-(3-thienyl)propiolyl)piperazine |
| AAA12 | 4-(Thiazol-2-yl)1-(3-(2-methoxyphenyl)propiolyl)piperazine |
| AAA13 | 4-(Thiazol-2-yl)1-(3-(3-methoxyphenyl)propiolyl)piperazine |
| AAA14 | 4-(Thiazol-2-yl)1-(3-(4-methoxyphenyl)propiolyl)piperazine |
| AAA15 | 4-(Thiazol-2-yl)1-(3-(2-cyanophenyl)propiolyl)piperazine |
| AAA16 | 4-(Thiazol-2-yl)1-(3-(3-cyanophenyl)propiolyl)piperazine |
| AAA17 | 4-(Thiazol-2-yl)1-(3-(4-cyanophenyl)propiolyl)piperazine |

-continued

| | |
|---|---|
| AAA18 | 4-(Thiazol-2-yl)1-(3-(2,4-dimethylphenyl)propiolyl)piperazine |
| AAA19 | 4-(Thiazol-2-yl)1-(3-(3,5-dimethylphenyl)propiolyl)piperazine |
| AAA2 | 4-(Thiazol-2-yl)1-(3-(4-carboxyphenyl)propiolyl)piperazine methyl ester |
| AAA20 | 4-(Thiazol-2-yl)1-(3-(2,6-dimethylphenyl)propiolyl)piperazine |
| AAA21 | 4-(Thiazol-2-yl)1-(3-(2-fluorophenyl)propiolyl)piperazine |
| AAA22 | 4-(Thiazol-2-yl)1-(3-(3-fluorophenyl)propiolyl)piperazine |
| AAA23 | 4-(Thiazol-2-yl)1-(3-(2-chlorophenyl)propiolyl)piperazine |
| AAA24 | 4-(Thiazol-2-yl)1-(3-(3-chlorophenyl)propiolyl)piperazine |
| AAA25 | 4-(Thiazol-2-yl)1-(3-naphthylpropiolyl)piperazine |
| AAA26 | 4-(Thiazol-2-yl)1-(3-(2,3-dimethylphenyl)propiolyl)piperazine |
| AAA27 | 4-(Thiazol-2-yl)1-(3-(3,4-dimethylphenyl)propiolyl)piperazine |
| AAA28 | 4-(Thiazol-2-yl)1-(3-(3-nitrophenyl)propiolyl)piperazine |
| AAA29 | 4-(Thiazol-2-yl)1-(3-(2-nitrophenyl)propiolyl)piperazine |
| AAA3 | 4-(Thiazol-2-yl)1-(3-(3-carboxyphenyl)propiolyl)piperazine ethyl ester |
| AAA30 | 4-(Thiazol-2-yl)1-(3-(3-formylphenyl)propiolyl)piperazine |
| AAA31 | 4-(Thiazol-2-yl)1-(3-(3-ethenylphenyl)propiolyl)piperazine |
| AAA32 | 4-(Thiazol-2-yl)1-(3-pyrid-2-ylpropiolyl)piperazine |
| AAA33 | 4-(Thiazol-2-yl)1-(3-pyrid-3-ylpropiolyl)piperazine |
| AAA24 | 4-(Thiazol-2-yl)1-(3-pyrid-4-ylpropiolyl)piperazine |
| AAA35 | 4-(Thiazol-2-yl)1-(3-(quinolin-6-yl)propiolyl)piperazine |
| AAA36 | 4-(Thiazol-2-yl)1-(3-(3-isopropylphenyl)propiolyl)piperazine |
| AAA37 | 4-(Thiazol-2-yl)1-(3-biphenyl3-ylpropiolyl)piperazine |
| AAA38 | 4-(Thiazol-2-yl)1-(3-naphth-2-ylpropiolyl)piperazine |
| AAA39 | 4-(Thiazol-2-yl)1-(3-(1-methylindol-5-yl)propiolyl)piperazine |
| AAA4 | 4-(Thiazol-2-yl)1-(3-(2-hydroxyphenyl)propiolyl)piperazine |
| AAA40 | 4-(Thiazol-2-yl)1-(3-(3-methylmercaptophenyl)propiolyl)piperazine |
| AAA41 | 4-(Thiazol-2-yl)1-(3-(3-cyano-4-fluor-phenyl)propiolyl)piperazine |
| AAA42 | 4-(Thiazol-2-yl)1-(3-(3-methoxymethylphenyl)propiolyl)piperazine |
| AAA43 | 4-(Thiazol-2-yl)1-(3-(3-hydroxyphenyl)propiolyl)piperazine |
| AAA44 | 4-(Thiazol-2-yl)1-(3-(3-acetaminophenyl)propiolyl)piperazine |
| AAA45 | 4-(Thiazol-2-yl)1-(3-(4-acetaminophenyl)propiolyl)piperazine |
| AAA46 | 4-(Thiazol-2-yl)1-(3-(2-carboxyphenyl)propiolyl)piperazine |
| AAA47 | 4-(Thiazol-2-yl)1-(3-(3-carboxyphenyl)propiolyl)piperazine |
| AAA48 | 4-(Thiazol-2-yl)1-(3-(4-carboxyphenyl)propiolyl)piperazine |
| AAA49 | 4-(Thiazol-2-yl)1-(3-(3-carboxyphenyl)propiolyl)piperazine methyl ester |
| AAA5 | 4-(Thiazol-2-yl)1-(3-(4-hydroxyphenyl)propiolyl)piperazine |
| AAA50 | 4-(Thiazol-2-yl)1-(3-(3-aminocarbonylphenyl)propiolyl)piperazine |
| AAA51 | 4-(Thiazol-2-yl)1-(3-(3-methylaminocarbonylphenyl)propiolyl)piperazine |
| AAA52 | 4-(Thiazol-2-yl)-1-(3-(3-dimethylaminocarbonylphenyl)propiolyl)piperazine |
| AAA53 | 4-(Thiazol-2-yl)-1-(3-(2-tolyl)propiolyl)piperazine hydrochloride |
| AAA54 | 4-(Thiazol-2-yl)-1-(3-(3-tolyl)propiolyl)piperazine hydrochloride |
| AAA55 | 4-(Thiazol-2-yl)-1-(3-(4-tolyl)propiolyl)piperazine hydrochloride |
| AAA56 | 4-(Thiazol-2-yl)-1-(3-phenylpropiolyl)piperazine hydrochloride |
| AAA57 | 4-(Thiazol-2-yl)-1-(3-(2-trifluoromethylphenyl)propiolyl)piperazine hydrochloride |
| AAA58 | 4-(Thiazol-2-yl)-1-(3-(3-trifluoromethylphenyl)propiolyl)piperazine hydrochloride |
| AAA59 | 4-(Thiazol-2-yl)-1-(3-(4-trifluormethylphenyl)propiolyl)piperazine hydrochloride |
| AAA6 | 4-(Thiazol-2-yl)-1-(3-(2-aminophenyl)propiolyl)piperazine |
| AAA60 | 4-(Thiazol-2-yl)-1-(3-pentylpropiolyl)piperazine |
| AAA61 | 4-(Thiazol-2-yl)-1-(3-(4-fluorophenyl)propiolyl)piperazine |
| AAA62 | 4-(Thiazol-2-yl)-1-(3-(4-chlorophenyl)propiolyl)piperazine |
| AAA63 | 2-Methyl-4-(thiazol-2-yl)-1-(3-phenylpropiolyl)piperazine |
| AAA64 | (S)-2-Methyl-4-(thiazol-2-yl)-1-(3-phenylpropiolyl)piperazine |
| AAA65 | (R)-2-Methyl-4-(thiazol-2-yl)-1-(3-phenylpropiolyl)piperazine |
| AAA66 | 2-Methyl-4-(thiazol-2-yl)-1-(3-phenylpropiolyl)piperazine hydrochloride |
| AAA67 | 2-Methyl-4-(thiazol-2-yl)-1-(3-(3-tolyl)propiolyl)piperazine |
| AAA68 | 2-Methyl-4-(thiazol-2-yl)-1-(3-(3-tolyl)propiolyl)piperazine hydrochloride |
| AAA69 | 4-(Thiazol-2-yl)-1-(3-cyclohexylpropiolyl)piperazine |
| AAA7 | 4-(Thiazol-2-yl)-1-(3-(3-aminophenyl)propiolyl)piperazine |
| AAA70 | 4-(Thiazol-2-yl)-1-(3-methylpropiolyl)piperazine |
| AAA71 | 2-Ethyl-4-(thiazol-2-yl)-1-(3-phenylpropiolyl)piperazine |
| AAA72 | 2-Phenyl-4-(thiazol-2-yl)-1-(3-phenylpropiolyl)piperazine |
| AAA73 | 4-(Thiazol-2-yl)-1-(3-(2-furyl)propiolyl)piperazine |
| AAA74 | 4-(Thiazol-2-yl)-1-(3-(3-furyl)propiolyl)piperazine |
| AAA75 | cis-2,6-Dimethyl-4-(thiazol-2-yl)-1-(3-phenylpropiolyl)piperazine |
| AAA76 | 4-(5-Carboxy-thiazol-2-yl)-1-(3-phenylpropiolyl)piperazine ethyl ester |
| AAA77 | 4-(4-Carboxy-thiazol-2-yl)-1-(3-phenylpropiolyl)piperazine ethyl ester |
| AAA78 | 4-(5-Carboxy-thiazol-2-yl)-1-(3-phenylpropiolyl)piperazine |
| AAA79 | 4-(4-Carboxy-thiazol-2-yl)-1-(3-phenylpropiolyl)piperazine |
| AAA8 | 4-(Thiazol-2-yl)-1-(3-(4-amino-phenyl)propiolyl)piperazine |
| AAA80 | 4-(5-Methylaminocarbonylthiazol-2-yl)-1-(3-phenylpropiolyl)piperazine |
| AAA81 | 4-(5-Dimethylaminocarbonylthiazol-2-yl)-1-(3-phenylpropiolyl)piperazine |
| AAA82 | 4-(3-Phenyl-1,2,4-thiadiazol-5-yl)-1-(3-phenylpropiolyl)piperazine |
| AAA83 | 4-(Thiazol-2-yl)-1-(3-(quinol-7-yl)propiolyl)piperazine |
| AAA84 | 4-(Thiazol-2-yl)-1-(3-phenylpropiolyl)piperazine-3-on |
| AAA85 | 4-(3-(4-Fluorbenzyl)-1,2,4-thiadiazol-5-yl)-1-(3-phenylpropiolyl)piperazine |
| AAA86 | 4-(5-Nitrothiazol-2-yl)-1-(3-phenylpropiolyl)piperazine |
| AAA87 | 4-(4-tert-Butylthiazol-2-yl)-1-(3-phenylpropiolyl)piperazine |
| AAA88 | 4-(5-Methylthiazol-2-yl)-1-(3-phenylpropiolyl)piperazine |
| AAA89 | 4-(4,5-Dimethylthiazol-2-yl)-1-(3-phenylpropiolyl)piperazine |

-continued

| | |
|---|---|
| AAA9 | 4-(Thiazol-2-yl)-1-(3-(indol-5-yl)propiolyl)piperazine |
| AAA90 | 4-(5-Bromo-4-phenylthiazol-2-yl)-1-(3-phenylpropiolyl)piperazine |
| AAA91 | 4-(5-Bromo-4-methylthiazol-2-yl)-1-(3-phenylpropiolyl)piperazine |
| AAA92 | 4-(4-Methylthiazol-2-yl)-1-(3-phenylpropiolyl)piperazine |
| AAA93 | 4-(4-Trifluormethylthiazol-2-yl)-1-(3-phenylpropiolyl)piperazine |
| AAA94 | 4-(4-Chlor-thiazol-2-yl)-1-(3-phenylpropiolyl)piperazine |
| AAA95 | 4-(5-Chlor-thiazol-2-yl)-1-(3-phenylpropiolyl)piperazine |
| AAA96 | 4-(4-Bromothiazol-2-yl)-1-(3-phenylpropiolyl)piperazine |
| AAA97 | 4-(5-Bromothiazol-2-yl)-1-(3-phenylpropiolyl)piperazine |
| AAA98 | 4-(5-Phenylthiazol-2-yl)-1-(3-phenylpropiolyl)piperazine |
| AAA99 | 4-(4-Phenylthiazol-2-yl)-1-(3-phenylpropiolyl)piperazine |
| AAA00108 | 4-(Thiazol-2-yl)-1-(3-(1-methylindol-6-yl)propiolyl)piperazine |
| AAA00109 | 4-(Thiazol-2-yl)-1-(3-(3-acetylphenyl)propiolyl)piperazine |
| AAA00110 | 4-(Thiazol-2-yl)-1-(3-(3-fluoro-5-methylphenyl)propiolyl)piperazine |
| AAA00111 | 4-(Thiazol-2-yl)-1-(3-(2-fluoro-3-methylphenyl)propiolyl)piperazine |
| AAA00112 | 4-(Thiazol-2-yl)-1-(3-(3-methylaminophenyl)propiolyl)piperazine |
| AAA00113 | 4-(Thiazol-2-yl)-1-(3-(3-dimethylaminophenyl)propiolyl)piperazine |
| AAA00114 | 4-(Thiazol-2-yl)-1-(dimethylcarbamoylpropiolyl)piperazine |
| AAA00115 | 4-(Thiazol-2-yl)-1-(3-(3-methylsulfinylphenyl)propiolyl)piperazine |
| AAA00116 | 4-(Thiazol-2-yl)-1-(3-(3-methylsulfonylphenyl)propiolyl)piperazine |
| AAA00117 | 4-(Thiazol-2-yl)-1-(3-(3-ethynylphenyl)propiolyl)piperazine |
| AAA00118 | 4-(Thiazol-2-yl)-1-(3-(4-methylthiophen-2-yl)propiolyl)piperazine |
| AAA00119 | 2-Methyl-4-(thiazol-2-yl)-1-(3-(3-chlor-phenyl)propiolyl)piperazine |
| AAA00120 | 4-(Thiazol-2-yl)-1-(3-(3-ethylphenyl)propiolyl)piperazine |
| AAA00121 | 2-tert-Butyl-4-(thiazol-2-yl)-1-(3-phenylpropiolyl)piperazine |
| AAA00122 | 4-(Thiazol-2-yl)-1-(3-(3-difluormethylphenyl)propiolyl)piperazine |
| AAA00123 | 2-Methyl-4-(thiazol-2-yl)-1-(3-(3-cyano-phenyl)propiolyl)piperazine |
| AAA00124 | 2-Isopropyl-4-(thiazol-2-yl)-1-(3-phenylpropiolyl)piperazine |
| AAA00125 | 4-(Thiazol-2-yl)-1-(3-(3-trimethylsilanylethynylphenyl)propiolyl)piperazine |

Combined Synthesis:

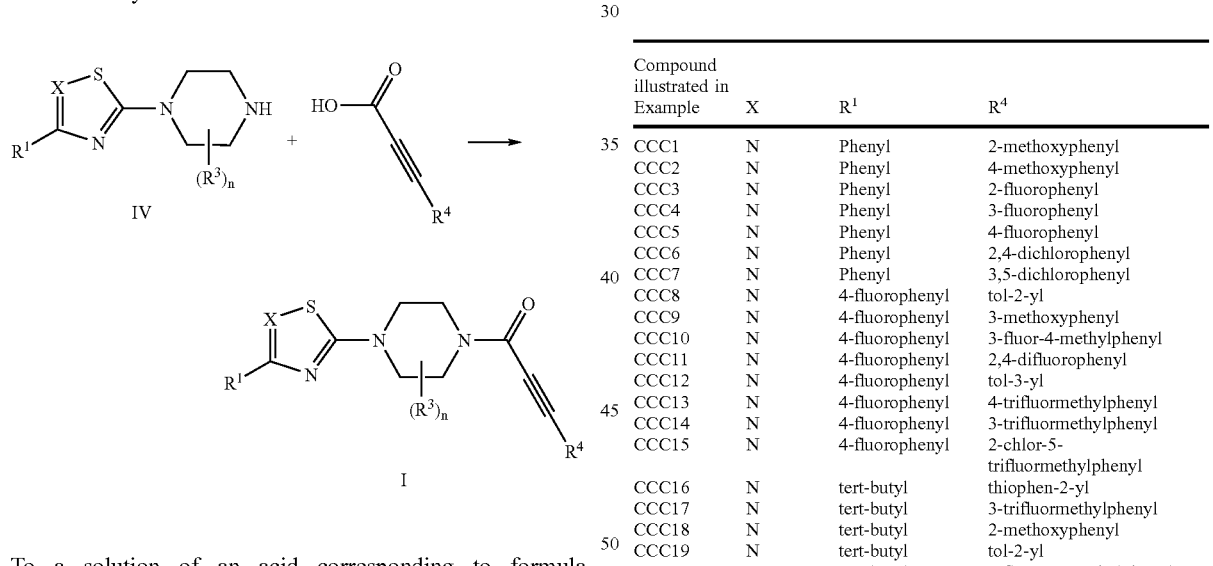

To a solution of an acid corresponding to formula $R^4$—C≡C—(C=O)—OH (100 μmol) in DCM (2 ml) there was added a solution of carbonyldiimidazole (105 μmol) in DCM (1.05 ml), and the reaction mixture was stirred one hour at 20° C. Water (3 ml) was added to the reaction solution, and the mixture was extracted. After separating the aqueous phase, the organic phase was extracted with water (3 ml) and with sat. aq. NaCl soln (3 ml). The separated organic phase was dried over $MgSO_4$, isolated by filtration and the solvent removed by distillation. The substances were purified by means of preparative HPLC.

The following compounds were produced starting from acids $R^4$—C≡C—(C=O)—OH and amines corresponding to formula IV, in which n is in each case equal to 0, which compounds are either commercially available or obtainable by methods known to those skilled in the art:

| Compound illustrated in Example | X | $R^1$ | $R^4$ |
|---|---|---|---|
| CCC1 | N | Phenyl | 2-methoxyphenyl |
| CCC2 | N | Phenyl | 4-methoxyphenyl |
| CCC3 | N | Phenyl | 2-fluorophenyl |
| CCC4 | N | Phenyl | 3-fluorophenyl |
| CCC5 | N | Phenyl | 4-fluorophenyl |
| CCC6 | N | Phenyl | 2,4-dichlorophenyl |
| CCC7 | N | Phenyl | 3,5-dichlorophenyl |
| CCC8 | N | 4-fluorophenyl | tol-2-yl |
| CCC9 | N | 4-fluorophenyl | 3-methoxyphenyl |
| CCC10 | N | 4-fluorophenyl | 3-fluor-4-methylphenyl |
| CCC11 | N | 4-fluorophenyl | 2,4-difluorophenyl |
| CCC12 | N | 4-fluorophenyl | tol-3-yl |
| CCC13 | N | 4-fluorophenyl | 4-trifluormethylphenyl |
| CCC14 | N | 4-fluorophenyl | 3-trifluormethylphenyl |
| CCC15 | N | 4-fluorophenyl | 2-chlor-5-trifluormethylphenyl |
| CCC16 | N | tert-butyl | thiophen-2-yl |
| CCC17 | N | tert-butyl | 3-trifluormethylphenyl |
| CCC18 | N | tert-butyl | 2-methoxyphenyl |
| CCC19 | N | tert-butyl | tol-2-yl |
| CCC20 | N | tert-butyl | 3-fluoro-4-methylphenyl |
| CCC21 | N | tert-butyl | 2-chloro-5-trifluormethylphenyl |
| CCC22 | CH | H | 2,4-difluorophenyl |
| CCC23 | CH | H | 2-bromo-5-methoxyphenyl |
| CCC24 | CH | H | 3-bromo-4-methoxyphenyl |
| CCC25 | CH | H | 3,5-dichlorophenyl |
| CCC26 | CH | H | 4-fluoro-3-methylphenyl |
| CCC27 | CH | tert-butyl | 3-cyanophenyl |
| CCC28 | CH | tert-butyl | 2-trifluoromethylphenyl |
| CCC29 | CH | Phenyl | 2,3-dimethylphenyl |
| CCC30 | CH | Phenyl | 4-fluorophenyl |
| CCC31 | CH | Methyl | tol-3-yl |
| CCC32 | CH | Methyl | thiophen-2-yl |
| CCC33 | C-methyl | H | tol-4-yl |
| CCC34 | C-methyl | H | 2-cyanophenyl |
| CCC35 | C-methyl | Methyl | 3-cyanophenyl |
| CCC36 | C-methyl | Methyl | 3,4-dimethylphenyl |
| CCC37 | CH | 4-methoxyphenyl | 2,4-dimethylphenyl |

-continued

| Compound illustrated in Example | X | R¹ | R⁴ |
|---|---|---|---|
| CCC38 | CH | 4-methoxyphenyl | 4-trifluoromethylphenyl |
| CCC39 | CH | 4-fluorophenyl | 2-cyanophenyl |
| CCC40 | CH | 4-chlorophenyl | 4-cyanophenyl |

Pharmacological Data:

The affinity of the substituted 1-propiolylpiperazines according to the invention the mGluR5 receptor was determined as described above. The substituted 1-propiolylpiperazines according to the invention show excellent affinity to the mGluR5 receptor. The pharmacological data the substituted 1-propiolylpiperazine compound according to Example 1 are shown in the following Table I:

TABLE I

| Compound according to Example | IC$_{50}$ mGluR5 receptor [³H]-MPEP binding | IC$_{50}$ mGluR5 receptor Ca$^{2+}$ influx |
|---|---|---|
| 1 | 100 nM | 190 nM |

The pharmacological data further substituted 1-propiolylpiperazine compounds according to Examples AAA1 to AAA0025 and CCC1 to CCC40 are shown in the following Table II:

TABLE II

| Compound according to Example | mGluR5-receptor (% inhibition 10 μM) in pigs | IC$_{50}$ mGluR5-receptor [³H]-MPEP binding |
|---|---|---|
| AAA00101 | 30 | |
| AAA00102 | 61 | |
| AAA00103 | 83 | |
| AAA00104 | 91 | |
| AAA00105 | 65 | |
| AAA00106 | 68 | |
| AAA00107 | 30 | |
| AAA10 | | 0.98 |
| AAA11 | 52 | |
| AAA12 | 34 | |
| AAA13 | 87 | |
| AAA14 | 34 | |
| AAA15 | 54 | |
| AAA16 | 93 | |
| AAA21 | | 0.83 |
| AAA22 | 86 | |
| AAA23 | 70 | |
| AAA24 | 88 | |
| AAA28 | 82 | |
| AAA3 | 40 | |
| AAA30 | 91 | |
| AAA31 | | 0.038 |
| AAA32 | 57 | |
| AAA33 | 50 | |
| AAA34 | 71 | |
| AAA36 | 40 | |
| AAA37 | 45 | |
| AAA38 | 82 | |
| AAA39 | 74 | |
| AAA4 | | 0.45 |
| AAA40 | 80 | |
| AAA41 | 78 | |
| AAA42 | 88 | |
| AAA43 | 83 | |
| AAA44 | 30 | |
| AAA49 | 43 | |
| AAA5 | 35 | |
| AAA53 | 33 | |
| AAA54 | 97 | |
| AAA55 | 41 | |
| AAA56 | | 0.15 |
| AAA57 | 81 | |
| AAA58 | | 0.24 |
| AAA6 | 54 | |
| AAA60 | | 1.85 |
| AAA61 | 76 | |
| AAA63 | 89 | |
| AAA64 | 72 | |
| AAA65 | 93 | |
| AAA66 | 93 | |
| AAA67 | 94 | |
| AAA68 | | 0.013 |
| AAA69 | 72 | |
| AAA7 | 91 | |
| AAA71 | | 0.038 |
| AAA72 | 81 | |
| AAA73 | 74 | |
| AAA74 | | 3.19 |
| AAA75 | 97 | |
| AAA76 | | 0.17 |
| AAA77 | 89 | |
| AAA8 | 65 | |
| AAA80 | 76 | |
| AAA81 | 72 | |
| AAA82 | 37 | |
| AAA85 | 93 | |
| AAA86 | 31 | |
| AAA88 | 94 | |
| AAA89 | 86 | |
| AAA9 | | 0.7 |
| AAA92 | 87 | |
| AAA93 | 52 | |
| AAA94 | 91 | |
| AAA95 | 58 | |
| AAA96 | | 0.36 |
| AAA97 | | 0.72 |
| AAA99 | 87 | |
| AAA00108 | | 1.24 |
| AAA00110 | | 1.39 |
| AAA00111 | 31 | |
| AAA00112 | | 0.56 |
| AAA00113 | 27 | |
| AAA00114 | 14 | |
| AAA00115 | 17 | |
| AAA00116 | 31 | |
| AAA00117 | | 0.026 |
| AAA00118 | | 0.093 |
| AAA00119 | | 0.009 |
| AAA00120 | | 0.26 |
| AAA00121 | | 0.11 |
| AAA00122 | | 0.062 |
| AAA00123 | | 0.019 |
| CCC3 | 28 | |
| CCC4 | 59 | |
| CCC5 | 25 | |
| CCC8 | 25 | |
| CCC16 | 33 | |
| CCC22 | | 10.50 |
| CCC23 | 30 | |
| CCC31 | 93 | |
| CCC33 | 43 | |

The 1-propiolylpiperazine compounds according to the invention of the above formula I also show excellent reduction of the nociceptive behavior of rats in the formalin test, as illustrated in the following Table III:

TABLE III

| Compound according to Example | Dose [mg/kg] | Reduction of nociceptive behavior of rats compared with control rats [%] |
|---|---|---|
| AAA24 | 46.4 (i.p.) | 43 |
| AAA54 | 10.0 (i.v.) | 72 |
| AAA56 | 46.4 (i.p.) | 85 |
| AAA68 | 46.4 (p.o.) | 66 |

The foregoing description and examples have been set forth merely to illustrate the invention and are not intended to be limiting. Since modifications of the described embodiments incorporating the spirit and substance of the invention may occur to persons skillin in the art, the invention should be construed broadly to include all variations within the scope of the appended aims and equivalents thereof.

What is claimed is:

1. A substituted 1-propiolylpiperazine compound corresponding to formula I:

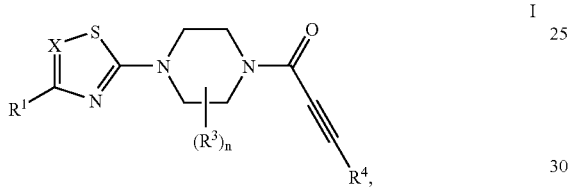

wherein

X denotes N or C—$R^2$;

$R^1$ and $R^2$ each independently denote a hydrogen, a halogen, or a nitro group, a cyano group, or an amino group, a hydroxyl group, a thiol group, or a carboxyl group, or a formyl group, an —NH—C(=O)—H group, an —NH—$R^5$ group, an —N$R^6R^7$ group, or a —C(=O)—$R^8$ group, or a —C(=O)—O—$R^9$ group, an —O—C(=O)—$R^{10}$ group, an —NH—C(=O)—$R^{11}$ group, or an —N$R^{12}$—C(=O)—$R^{13}$ group, or a —C(=O)—$NH_2$ group, a —C(=O)—NH—$R^{14}$ group, a —C(O)—N$R^{15}R^{16}$ group, or an —O—$R^{17}$ group, or an —S—$R^{18}$ group, or an —S(=O)—$R^{19}$ group, an —S(=O)$_2$—$R^{20}$ group, or an —NH—C(=O)—NH—$R^{21}$ group, or an —NH—C(=S)—NH—$R^{22}$ group, an —NH—S(=O)$_2$—$R^{23}$ group, an —N$R^{24}$—S(=O)$_2$—$R^{25}$ group, or a linear or branched, saturated or unsaturated, unsubstituted or at least monosubstituted aliphatic radical which optionally contains at least one hetero atom as link, or an unsubstituted or at least monosubstituted, unsaturated or saturated cycloaliphatic radical which optionally contains at least one hetero atom as ring member, and which can be bonded via a linear or branched, unsubstituted or at least monosubstituted alkylene group, alkenylene group or alkynylene group optionally containing at least one hetero atom as link and/or optionally condensed with an unsubstituted or at least monosubstituted monocyclic or polycyclic ring system, or an unsubstituted or at least monosubstituted aryl radical or an unsubstituted or at least monosubstituted heteroaryl radical, and which can be bonded via a linear or branched, unsubstituted or at least monosubstituted alkylene group, alkenylene group or alkynylene group optionally containing at least one hetero atom as link and/or optionally condensed with an unsubstituted or at least monosubstituted monocyclic or polycyclic ring system;

$R^3$ denotes a halogen, or a nitro group, a cyano group, or an amino group, a hydroxyl group, a thiol group, or a carboxyl group, or a formyl group, an —NH—C(=O)—H group, an oxo group (=O), an —NH—$R^5$ group, an —N$R^6R^7$ group, or a —C(=O)—$R^8$ group, or a —C(=O)—O—$R^9$ group, an —O—C(=O)—$R^{10}$ group, an —NH—C(=O)—$R^{11}$ group, or an —N$R^{12}$—C(=O)—$R^{13}$ group, or a —C(=O)—$NH_2$ group, a —C(=O)—NH—$R^{14}$ group, a —C(=O)—N$R^{15}R^{16}$ group, or an —O—$R^{17}$ group, or an —S—$R^{18}$ group, an —S(=O)—$R^{19}$ group, an —S(=O)$_2$—$R^{20}$ group, or an —NH—C(=O)—NH—$R^{21}$ group, or an —NH—C(=S)—NH—$R^{22}$ group, an —NH—S(=O)$_2$—$R^{23}$ group, an —N$R^{24}$—S(=O)$_2$—$R^{25}$ group, a linear or branched, saturated or unsaturated, unsubstituted or at least monosubstituted aliphatic radical which optionally contains at least one hetero atom as link, an unsubstituted or at least monosubstituted, unsaturated or saturated cycloaliphatic radical which optionally contains at least one hetero atom as ring member, and which can be bonded via a linear or branched, unsubstituted or at least monosubstituted alkylene group, alkenylene group or alkynylene group optionally containing at least one hetero atom as link and/or optionally condensed with an unsubstituted or at least monosubstituted monocyclic or polycyclic ring system, or an unsubstituted or at least monosubstituted aryl radical or an unsubstituted or at least monosubstituted heteroaryl radical, and which can be bonded via a linear or branched, unsubstituted or at least monosubstituted alkylene group, alkenylene group or alkynylene group optionally containing at least one hetero atom as link and/or optionally condensed with an unsubstituted or at least monosubstituted monocyclic or polycyclic ring system;

$R^4$ denotes a hydrogen, a fluorine atom, a chlorine atom, a bromine atom, a nitro group, a cyano group, or an amino group, or a hydroxyl group, a thiol group, a carboxyl group, or a formyl group, or an —NH—C(=O)—H group, an —NH—$R^5$ group, an —N$R^6R^7$ group, or a —C(=O)—$R^8$ group, or a —C(=O)—O—$R^9$ group, an —O—C(=O)—$R^{10}$ group, an —NH—C(=O)—$R^{13}$ group, or an —N$R^{12}$—C(=O)—$R^{13}$ group, or a —C(=O)—$NH_2$ group, a —C(=O)—NH—$R^{14}$ group, a —C(=O)—N$R^{15}R^{16}$ group, or an —O—$R^{17}$ group, or an —S—$R^{18}$ group, an —S(=O)—$R^{19}$ group, an —S(=O)$_2$—$R^{20}$ group, or an —NH—C(=O)—NH—$R^{21}$ group, or an —NH—C(=S)—NH—$R^{22}$ group, an —NH—S(=O)$_2$—$R^{23}$ group, an —N$R^{24}$—S(=O)$_2$—$R^{25}$ group, a linear or branched, saturated or unsaturated, unsubstituted or at least monosubstituted aliphatic radical which optionally contains at least one hetero atom as link, an unsubstituted or at least monosubstituted, unsaturated or saturated cycloaliphatic radical which optionally contains at least one hetero atom as ring member, and which can be bonded via a linear or branched, unsubstituted or at least monosubstituted alkylene group, alkenylene group or alkynylene group optionally containing at least one hetero atom as link and/or optionally condensed with an unsubstituted or at least monosubstituted monocyclic or polycyclic ring system, or an unsubstituted or at least monosubstituted aryl radical or an unsubstituted or at least monosubstituted heteroaryl radical, and which can be bonded via a linear or branched, unsubstituted or at least monosubstituted alkylene group, alkenylene group or alkynylene group optionally containing at least one hetero atom as link and/or optionally condensed with an unsubstituted or at least monosubstituted monocyclic or polycyclic ring system;

$R^5$ to $R^{25}$ each independently denote a linear or branched, saturated or unsaturated, unsubstituted or at least monosubstituted aliphatic radical which optionally contains at least one hetero atom as link, an unsubstituted or at least monosubstituted, unsaturated or saturated cycloaliphatic radical which optionally contains at least one hetero atom as ring member, and which can be bonded via a linear or branched, unsubstituted or at least monosubstituted alkylene group, alkenylene group or alkynylene group optionally containing at least one hetero atom as link and/or optionally condensed with an unsubstituted or at least monosubstituted monocyclic or polycyclic ring system, or an unsubstituted or at least monosubstituted aryl radical or an unsubstituted or at least monosubstituted heteroaryl radical, and which can be bonded via a linear or branched, unsubstituted or at least monosubstituted alkylene group, alkenylene group or alkynylene group optionally containing at least one hetero atom as link, and n is 0, 1, 2, 3, 4, 5, 6, 7 or 8;

in the form of a pure stereoisomer or a mixture of stereoisomers in any mixing ratio;

or a salt or solvate thereof.

2. A compound according to claim 1, wherein said compound is in the form of a pure enantiomer or diastereoisomer.

3. A compound according to claim 1, wherein said compound is in the form of a racemic mixture.

4. A compound according to claim 1, wherein said compound is in the form of a hydrate.

5. A compound according to claim 1, wherein said compound is in the form of a hydrochloride salt.

6. A compound according to claim 1 wherein: $R^1$ and $R^2$ each independently denote a hydrogen, a halogen, or a nitro group, a cyano group, or an amino group, a hydroxyl group, a thiol group, or a carboxyl group, or a formyl group, an —NH—C(=O)—H group, an —NH—$R^5$ group, an —NR$^6$R$^7$ group, or a —C(=O)—R$^8$ group, or a —C(=O)—O—R$^9$ group, an —O—C(=O)—R$^{10}$ group, an —NH—C(=O)—R$^{11}$ group, or an —NR$^{12}$—C(=O)—R$^{13}$ group, or a —C(=O)—NH$_2$ group, a —C(=O)—NH—R$^{14}$ group, a —C(=O)—NR$^{15}$R$^{16}$ group, or an —O—R$^{17}$ group, or an —S—R$^{18}$ group, an —S(=O)—R$^{19}$ group, an —S(=O)$_2$—R$^{20}$ group, or an —NH—C(=O)—NH—R$^{21}$ group, or an —NH—C(=S)—NH—R$^{22}$ group, an —NH—S(=O)$_2$—R$^{23}$ group, an —NR$^{24}$—S(=O)$_2$—R$^{25}$ group, a linear or branched, saturated or unsaturated, unsubstituted or at least monosubstituted aliphatic $C_{1-8}$ radical which optionally contains 1, 2, or 3 hetero atoms independently selected from the group consisting of oxygen, sulfur, and nitrogen, as link(s), an unsubstituted or at least monosubstituted, unsaturated or saturated three-membered, four-membered, five-membered, six-membered, seven-membered, eight-membered, or nine-membered cycloaliphatic radical optionally containing at least one hetero atom as ring member, and which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl radical or heteroaryl radical, which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or can be condensed with an unsubstituted or at least monosubstituted monocyclic or polycyclic ring system;

$R^3$ denotes a halogen, or a nitro group, a cyano group, or an amino group, a hydroxyl group, a thiol group, or a carboxyl group, or a formyl group, an —NH—C(=O)—H group, an oxo group (=O), an —NH—R$^5$ group, an —NR$^6$R$^7$ group, or a —C(=O)—R$^8$ group, or a —C(=O)—O—R$^9$ group, an —O—C(=O)—R$^{10}$ group, an —NH—C(=O)—R$^{11}$ group, or —NR$^{12}$—C(=O)—R$^{13}$ group, a —C(=O)—NH$_2$ group, a —C(=O)—NH—R$^{14}$ group, or a —C(=O)—NR$^{15}$R$^{16}$ group, or an —O—R$^{17}$ group, an —S—R$^{18}$ group, an —S(=O)—R$^{19}$ group, or an —S(=O)$_2$—R$^{20}$ group, or an —NH—C(=O)—NH—R$^{21}$ group, an —NH—C(=S)—NH—R$^{22}$ group, an —NH—S(=O)$_2$—R$^{23}$ group, or an —NR$^{24}$—S(=O)$_2$—R$^{25}$ group, a linear or branched, saturated or unsaturated, unsubstituted or at least monosubstituted aliphatic $C_{1-8}$ radical which optionally contains 1, 2, or 3 hetero atoms independently selected from the group consisting of oxygen, sulfur, and nitrogen, as link(s), an unsubstituted or at least monosubstituted, unsaturated or saturated three-membered, four-membered, five-membered, six-membered, seven-membered, eight-membered, or nine-membered cycloaliphatic radical optionally containing at least one hetero atom as ring member, and which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl radical or heteroaryl radical, which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or can be condensed with an unsubstituted or at least monosubstituted monocyclic or polycyclic ring system;

$R^4$ denotes a hydrogen, or a —C(=O)—NH$_2$ group, a —C(=O)—NH—R$^{14}$ group, or a —C(=O)—NR$^{15}$R$^{16}$ group, a linear or branched, saturated or unsaturated, unsubstituted or at least monosubstituted aliphatic $C_{1-8}$ radical, an unsubstituted or at least monosubstituted, unsaturated or saturated three-membered, four-membered, five-membered, six-membered, seven-membered, eight-membered, or nine-membered cycloaliphatic radical which optionally contains at least one hetero atom as ring member, and which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl radical or heteroaryl radical, which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or can be condensed with an unsubstituted or at least monosubstituted monocyclic or polycyclic ring system, and $R^5$ to $R^{25}$ independently each denote a linear or branched, saturated or unsaturated, unsubstituted or at least monosubstituted aliphatic $C_{1-8}$ radical, an unsubstituted or at least monosubstituted, unsaturated or saturated three-membered, four-membered, five-membered, six-membered, seven-membered, eight-membered, or nine-membered cycloaliphatic radical which optionally contains at least one hetero atom as ring member, and which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl radical or heteroaryl radical, which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or can be condensed with an unsubstituted or at least monosubstituted monocyclic or polycyclic ring system; wherein the aforementioned cycloaliphatic radicals optionally 1, 2, 3, 4, or 5 hetero atom(s) as ring member(s) exhibit can, which can be independently selected from the group consisting of nitrogen, oxygen, and sulfur, the rings of the aforementioned monocyclic or bicyclic ring systems are each four-membered, five-membered, or six-membered and each has optionally 0, 1, 2, 3, 4, or 5 hetero atom(s) as ring member(s), which are independently selected from the group consisting of oxygen, nitrogen, and sulfur; and the aforementioned heteroaryl radicals can optionally have 1, 2, 3, 4, or 5 hetero atom(s) as ring member(s), which can be independently selected from the group consisting of oxygen, sulfur, and nitrogen.

7. A compound according to claim 1, wherein $R^1$ denotes a hydrogen, or a halogen, or a nitro group, or a cyano group, an amino group, a hydroxyl group, or a thiol group, or a carboxyl group, a formyl group, an —NH—C(=O)—H group, an —NH—$R^5$ group, an —$NR^6R^7$ group, or a —C(=O)—$R^8$ group, or a —C(=O)—O—$R^9$ group, an —O—C(=)—$R^{10}$ group, an —NH—C(=O)—$R^{11}$ group, or an —$NR^{12}$—C(=O)—$R^{13}$ group, or a —C(=O)—$NH_2$ group, a —C(=O)—NH—$R^{14}$ group, a —C(=O)—$NR^{15}R^{16}$ group, or an —O—$R^{17}$ group, or an —S—$R^{18}$ group, an —S(=O)—$R^{19}$ group, an —S(=O)$_2$—$R^{20}$ group, or an —NH—C(=O)—NH—$R^{21}$ group, or an —NH—C(=S)—NH—$R^{22}$ group, an —NH—S(=O)$_2$—$R^{23}$ group, an —$NR^{24}$—S(=O)$_2$—$R^{25}$ group, a linear or branched, saturated or unsaturated, unsubstituted or at least monosubstituted aliphatic $C_{1-8}$ radical which optionally contains 1, 2, or 3 hetero atoms independently selected from the group consisting of oxygen, sulfur, and nitrogen, as link(s), an unsubstituted or at least monosubstituted, unsaturated or saturated three-membered, four-membered, five-membered, six-membered, seven-membered, eight-membered, or nine-membered cycloaliphatic radical optionally containing at least one hetero atom as ring member, and which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), anchor optionally condensed with an unsubstituted or at least monosubstituted monocyclic or polycyclic ring system, or an unsubstituted or at least monosubstituted five-membered to fourteen-membered aryl radical or heteroaryl radical, which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or can be condensed with an unsubstituted or at least monosubstituted monocyclic or polycyclic ring system.

8. A compound according to claim 7, wherein $R^1$ denotes a hydrogen, or a halogen selected from the group consisting of F, Cl, Br, and I, or a nitro group, or a $CF_3$ group, a cyano group, an amino group, or a hydroxyl group, or a thiol group, a carboxyl group, an —NH—$R^5$ group, or an —$NR^6R^7$ group, or a —C(=O)—$R^8$ group, a —C(=O)—O—$R^9$ group, an —O—C(=O)—$R^{10}$ group, or a —C(=O)—$NH_2$ group, or a —C(=O)—NH—$R^{14}$ group, a —C(=O)—$NR^{15}R^{16}$ group, an —O—$R^{17}$ group, or an —S—$R^{18}$ group, or an —S(=O)—$R^{19}$ group, an —S(=O)$_2$—$R^{20}$ group, a linear or branched $C_{1-8}$ alkyl radical, or a linear or branched $C_{2-8}$ alkenyl radical, a linear or branched $C_{2-8}$ alkynyl radical, denotes an unsubstituted or at least monosubstituted unsaturated or three-membered, four-membered, five-membered, six-membered, or seven-membered saturated cycloaliphatic radical which optionally contains 1, 2, or 3 hetero atoms independently selected from the group consisting of oxygen, sulfur, and nitrogen, as link(s), and which can be bonded via a linear or branched, unsubstituted or at least monosubstituted $C_{1-5}$ alkylene group, $C_{2-5}$ alkenylene group or $C_{2-5}$ alkynylene group or an unsubstituted or at least monosubstituted five-membered to fourteen-membered aryl radical or heteroaryl radical, which can be bonded via a linear or branched, unsubstituted or at least monosubstituted $C_{1-5}$ alkylene group, $C_{2-5}$ alkenylene group or $C_{2-5}$ alkynylene group.

9. A compound according to claim 8, wherein $R^1$ denotes a hydrogen, or a halogen selected from the group consisting of F, Cl, and Br, or a $CF_3$ group, a nitro group, a cyano group, an amino group, or a hydroxyl group, or a thiol group, a carboxyl group, an —NH—$R^5$ group, or an —$NR^6R^7$ group, or a —C(=O)—$R^8$ group, a —C(=O)—O—$R^9$ group, an —O—C(=O)—$R^{10}$ group, or a —C(=O)—NH—$R^{14}$ group, or a —C(=O)—$NR^{15}R^{16}$ group, an —O—$R^{17}$ group, an —S—$R^{18}$ group, or an —S(=O)—$R^{19}$ group, or an —S(=O)$_2$—$R^{20}$ group, a linear or branched $C_{1-4}$ alkyl radical, or a linear or branched $C_{2-4}$ alkenyl radical, or a linear or branched $C_{2-4}$ alkynyl radical, or a radical selected from the group consisting of cyclopropyl group, cyclobutyl group, cyclopentyl group, cyclohexyl group, pyrrolidinyl group, tetrahydrofuranyl group, tetrahydrothiophenyl group piperidinyl group, tetrahydropyranyl group, piperazinyl group, morpholinyl group, thiomorpholinyl group, dioxolanyl group, azepanyl group, diazepanyl group, imidazolidinyl group, phenyl, naphthyl group, anthracenyl group, pyrrolyl group, indolyl group, furanyl group, benzo [b]furanyl group, thiophenyl group, benzo [b]thiophenyl group, pyrazolyl group, imidazolyl group, thiazolyl group, dithiazolyl group, thiadiazolyl group, triazolyl group, oxazolyl group, oxadiazolyl group, isoxazolyl group, pyridinyl group, pyridazinyl group, pyrimidinyl group, pyrazinyl group, pyranyl group, indazolyl group, purinyl group, indolizinyl group, quinolinyl radical, isoquinolinyl radical, and quinazolinyl radical, each of which can be bonded via a $C_{1-3}$ alkylene group, $C_{2-3}$ alkenylene group or $C_{2-3}$ alkynylene group and/or is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH$_3$, —O—C$_2$H5, —O—C$_3$H$_7$, —NH$_2$, —N(CH$_3$)$_2$, —N(C$_2$H$_5$)$_2$, —NH—CH$_3$, —NH—C$_2$H$_5$, —N$_2$, —CF$_3$, —O—CF$_3$, —S—CF$_3$, —SH, —NH—S(=O)$_2$—CH$_3$, —C(=O)—OH, —C(=O)—CH$_3$, —C(=O)—C$_2$H$_5$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, and —C(=O)—O—C$_2$H$_5$.

10. A compound according to claim 9, wherein $R^1$ denotes a hydrogen, or a halogen selected from the group consisting of F, Cl, and Br, or a CF$_3$ group, or a nitro group, a cyano group, an amino group, or a dimethylamino group, or a diethylamino group, a monomethylamino group, a monoethylamino group, or a hydroxyl group, or a thiol group, a carboxyl group, a —C(=O)—O—CH$_3$ group, or a —C(=O)—O—C$_2$H$_5$ group, or a —C(=O)—NH—R$^{14}$ group, a —C(=O)—NR$^{15}$R$^{16}$ group, an —O—R$^{17}$ group, or an —S—R$^{18}$ group, or an —S(=O)—R$^{19}$ group, an —S(=O)$_2$—R$^{20}$ group, an alkyl radical selected from the group consisting of methyl, ethyl, n-propyl, isopropyl, n-butyl, sec-butyl, isobutyl, and tert-butyl, or an alkenyl radical selected from the group consisting of vinyl, 1-propenyl, 2-propenyl, 1-butenyl, 2-butenyl, and 3-butenyl, or an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH$_3$, —O—C$_2$H$_5$, and —O—C$_3$H$_7$.

11. A compound according to claim 1, wherein $R^2$ denotes a hydrogen, or a halogen, or a nitro group, or a cyano group, an amino group, a hydroxyl group, or a thiol group, or a carboxyl group, a formyl group, an —NH—C(=O)—H group, an —NH—R$^5$ group, an —NR$^6$R$^7$ group, or a —C(=O)—R$^8$ group, or a —C(=O)—O—R$^9$ group, an —O—C(=O)—R$^{10}$ group, an —NH—C(=O)—R$^{11}$ group, or an —NR$^{12}$—C(=O)—R$^{18}$ group, or a —C(=O)—NH$_2$ group, a —C(=O)—NH—R$^{14}$ group, a —C(=O)—NR$^{15}$R$^{16}$ group, or an —O—R$^{17}$ group, or an —S—R$^{18}$ group, an —S(=O)—R$^{19}$ group, an —S(=O)$_2$—R$^{20}$ group, or an —NH—C(=O)—NH—R$^{21}$ group, or an —NH—C(=S)—NH—R$^{22}$ group, an —NH—S(=O)$_2$—R$^{23}$ group, an —NR$^{24}$—S(=O)$_2$—R$^{25}$ group, a linear or branched, saturated or unsaturated, unsubstituted or at least monosubstituted aliphatic $C_{1-8}$ radical which optionally contains 1, 2, or 3 hetero atoms independently selected from the group consisting of oxygen, sulfur, and nitrogen, as link(s), an unsubstituted or at least monosubstituted, unsaturated or saturated three-membered, four-membered, five-membered, six-membered, seven-membered, eight-membered, or nine-membered cycloaliphatic radical optionally containing at least one hetero atom as ring member, and which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl radical or heteroaryl radical, which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or can be condensed with an unsubstituted or at least monosubstituted monocyclic or polycyclic ring system.

12. A compound according to claim 11, wherein $R^2$ denotes a hydrogen, or a halogen selected from the group consisting of F, Cl, Br, and I, or a nitro group, or a CF$_3$ group, a cyano group, an amino group, or a hydroxyl group, or a thiol group, a carboxyl group, an —NH—R$^5$ group, or an —NR$^6$R$^7$ group, or a —C(=O)—R$^8$ group, a —C(=O)—O—R$^9$ group, an —O—C(=O)—R$^{10}$ group, or a —C(=O)—NH$_2$ group, or a —C(=O)—NH—R$^{14}$ group, a —C(=O)—NR$^{15}$R$^{16}$ group, an —O—R$^{17}$ group, or an —S—R$^{18}$ group, or an —S(=O)—R$^{19}$ group, an —S(=O)$_2$—R$^{20}$ group, a linear or branched $C_{1-8}$ alkyl radical, or a linear or branched $C_{2-8}$ alkenyl radical or a linear or branched $C_{2-8}$ alkynyl radical, an unsubstituted or at least monosubstituted unsaturated or saturated three-membered, four-membered, five-membered, six-membered, or seven-membered cycloaliphatic radical which optionally contains 1, 2, or 3 hetero atoms independently selected from the group consisting of oxygen, sulfur, and nitrogen, as ring member(s), and which can be bonded via a linear or branched, unsubstituted or at least monosubstituted $C_{1-5}$ alkylene group, $C_{2-5}$ alkenylene group or $C_{2-5}$ alkynylene group or an unsubstituted or at least monosubstituted five-membered to fourteen-membered aryl radical or heteroaryl radical, which can be bonded via a linear or branched, unsubstituted or at least monosubstituted $C_{1-5}$ alkylene group, $C_{2-5}$ alkenylene group or $C_{2-5}$ alkynylene group.

13. A compound according to claim 12, wherein $R^2$ denotes a hydrogen, or a halogen selected from the group consisting of F, Cl, and Br, or a CF$_3$ group, a nitro group, a cyano group, an amino group, or a hydroxyl group, or a thiol group, a carboxyl group, an —NH—R$^5$ group, or an —NR$^6$R$^7$ group, or a —C(=O)—R$^8$ group, a —C(=O)—O—R$^9$ group, an —O—C(=O)—R$^{10}$ group, or a —C(=O)—NH—R$^{14}$ group, or a —C(=O)—NR$^{15}$R$^{16}$ group, an —S(=O)—R$^{19}$ group, an —S(=O)$_2$—R$^{20}$ group, or an —O—R$^{17}$ group, or an —S—R$^{18}$ group, a linear or branched $C_{1-4}$ alkyl radical, or a linear or branched $C_{2-4}$ alkenyl radical, or a linear or branched $C_{2-4}$ alkynyl radical, or a radical selected from the group consisting of cyclopropyl group, cyclobutyl group, cyclopentyl group, cyclohexyl group, pyrrolidinyl group, tetrahydrofuranyl group, tetrahydrothiophenyl group piperidinyl group, tetrahydropyranyl group, piperazinyl group, morpholinyl group, thiomorpholinyl group, dioxolanyl group, azepanyl group, diazepanyl group, imidazolidinyl group, phenyl, naphthyl group, anthracenyl group, pyrrolyl group, indolyl group, furanyl group, benzo[b]furanyl group, thiophenyl group, benzo[b]thiophenyl group, pyrazolyl group, imidazolyl group, thiazolyl group, dithiazolyl group, thiadiazolyl group, triazolyl group, oxazolyl group, oxadiazolyl group, isoxazolyl group, pyridinyl group, pyridazinyl group, pyrimidinyl group, pyrazinyl group, pyranyl group, indazolyl group, purinyl group, indolizinyl group, quinolinyl radical, isoquinolinyl radical, and quinazolinyl radical, each of which can be bonded via a $C_{1-3}$ alkylene group, $C_{2-3}$ alkenylene group or $C_{2-3}$ alkynylene group and/or is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, —O—$C_3H_7$, —$NH_2$, —$N(CH_3)_2$, —$N(C_2H_5)_2$, —NH—$CH_3$, —NH—$C_2H_5$, —$NO_2$, —$CF_3$, —O—$CF_3$, —S—$CF_3$, —SH, —NH—S(=O)$_2$—$CH_3$, —C(=O)—OH, —C(=O)—$CH_3$, —C(=O)—$C_2H_6$, —C(=O)—$N(CH_3)_2$, —C(=O)—NH—$CH_3$, —NH—C(=O)—$CH_3$, —NH—C(=O)—$C_2H_5$, —C(=O)—O—$CH_3$, and —C(=O)—O—$C_2H_5$.

14. A compound according to claim 13, wherein $R^2$ denotes a hydrogen, or a halogen selected from the group consisting of F, Cl, and Br, or a $CF_3$ group, or a nitro group, a cyano group, an amino group, or a dimethylamino group, or a diethylamino group, a monomethylamino group, a monoethylamino group, or a hydroxyl group, or a thiol group, a carboxyl group, a —C(=O)—O—$CH_3$ group, or a —C(=O)—O—$C_2H_5$ group, or a —C(=O)—NH—$R^{14}$ group, a —C(=O)—$NR^{15}R^{16}$ group, an —O—$R^{17}$ group, or an —S—$R^{18}$ group, or an —S(=O)—$R^{19}$ group, an —S(=O)$_2$—$R^{20}$ group, an alkyl radical selected from the group consisting of methyl, ethyl, n-propyl, isopropyl, n-butyl, sec-butyl, isobutyl, and tert-butyl, or an alkenyl radical selected from the group consisting of vinyl, 1-propenyl, 2-propenyl, 1-butenyl, 2-butenyl, and 3-butenyl, or an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, and —O—$C_3H_7$.

15. A compound according to claim 1, wherein $R^3$ denotes a halogen, or a nitro group, a cyano group, or an amino group, a hydroxyl group, a thiol group, or a carboxyl group, or a formyl group, an —NH—C(=O)—H group, an oxo group (=O), an —NH—$R^5$ group, an —$NR^6R^7$ group, or a —C(=O)—$R^8$ group, or a —C(=O)—O—$R^9$ group, an —O—C(=O)—$R^{10}$ group, an —NH—C(=O)—$R^{11}$ group, or —$NR^{12}$—C(=O)—$R^{13}$ group, a —C(=O)—$NH_2$ group, a —C(=O)—NH—$R^{14}$ group, or a —C(=O)—$NR^{15}R^{16}$ group, or an —O—$R^{17}$ group, an —S—$R^{18}$ group, an —S(=O)—$R^{19}$ group, or an —S(=O)$_2$—$R^{20}$ group, or an —NH—C(=O)—NH—$R^{21}$ group, an —NH—C(=S)—NH—$R^{22}$ group, an —NH—S(=O)$_2$—$R^{23}$ group, or an —$NR^{24}$—S(=O)$_2$—$R^{25}$ group, a linear or branched, saturated or unsaturated, unsubstituted or at least monosubstituted aliphatic $C_{1-8}$ radical which optionally contains 1, 2, or 3 hetero atoms independently selected from the group consisting of oxygen, sulfur, and nitrogen, as link(s), an unsubstituted or at least monosubstituted, unsaturated or saturated three-membered, four-membered, five-membered, six-membered, seven-membered, eight-membered, or nine-membered cycloaliphatic radical optionally containing at least one hetero atom as ring member, and which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl radical or heteroaryl radical, which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or can be condensed with an unsubstituted or at least monosubstituted monocyclic or polycyclic ring system.

16. A compound according to claim 15, wherein $R^3$ denotes a halogen selected from the group consisting of F, Cl, and Br, a nitro group, a cyano group, an amino group, a hydroxyl group, a thiol group, a carboxyl group, an oxo group (=O) or a linear or branched $C_{1-4}$ alkyl radical, or a radical selected from the group consisting of cyclopropyl group, cyclobutyl group, cyclopentyl group, cyclohexyl group, pyrrolidinyl group, tetrahydrofuranyl group, tetrahydrothiophenyl group piperidinyl group, tetrahydropyranyl group, piperazinyl group, morpholinyl group, thiomorpholinyl group, dioxolanyl group, azepanyl group, diazepanyl group, imidazolidinyl group, phenyl, naphthyl group, anthracenyl group, pyrrolyl group, indolyl group, furanyl group, benzo[b]furanyl group, thiophenyl group, benzo[b]thiophenyl group, pyrazolyl group, imidazolyl group, thiazolyl group, dithiazolyl group, thiadiazolyl group, triazolyl group, oxazolyl group, oxadiazolyl group, isoxazolyl group, pyridinyl group, pyridazinyl group, pyrimidinyl group, pyrazinyl group, pyranyl group, indazolyl group, purinyl group, indolizinyl group, quinolinyl radical, isoquinolinyl radical, and quinazolinyl radical, which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, and —O—$C_3H_7$.

17. A compound according to claim 16, wherein $R^3$ denotes an oxo group (=O), denotes an alkyl radical selected from the group consisting of methyl, ethyl, n-propyl, isopropyl, n-butyl, sec-butyl, isobutyl, and tert-butyl or a phenyl radical, which is unsubstituted or substituted by 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—$CH_3$, —O—$C_2H_5$, and —O—$C_3H_7$.

18. A compound according to claim 1, wherein $R^4$ denotes a hydrogen, or a —C(=O)—$NH_2$ group, a —C(=O)—NH—$R^{14}$ group, or a —C(=O)—$NR^{15}R^{16}$ group, a linear or branched, saturated or unsaturated, unsubstituted or at least monosubstituted aliphatic $C_{1-8}$ radical, an unsubstituted or at least monosubstituted, unsaturated or saturated three-membered, four-membered, five-membered, six-membered, seven-membered, eight-membered, or nine-membered cycloaliphatic radical which optionally contains at least one hetero atom as ring member, and which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from said group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl radical or heteroaryl radical, which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or can be condensed with an unsubstituted or at least monosubstituted monocyclic or polycyclic ring system.

19. A compound according to claim 18, wherein $R^4$ denotes a hydrogen, or a —C(=O)—NH$_2$ group, a —C(=O)—NH—$R^{14}$ group, or a —C(=O)—NR$^{15}$R$^{16}$ group, a linear or branched, unsubstituted or at least monosubstituted $C_{1-8}$ alkyl radical, or a linear or branched, unsubstituted or at least monosubstituted $C_{2-8}$ alkenyl radical, or a linear or branched, unsubstituted or at least monosubstituted $C_{2-8}$ alkynyl radical, or an unsubstituted or at least monosubstituted unsaturated or saturated four-membered, five-membered, six-membered, or seven-membered cycloaliphatic radical, which can be condensed with an unsaturated, saturated or aromatic, unsubstituted or at least monosubstituted monocyclic or bicyclic ring system, and each of the rings can contain 1, 2, or 3 hetero atoms, which can be independently selected from the group consisting of oxygen, nitrogen, and sulfur and each of the rings of the monocyclic or bicyclic ring system is four-membered, five-membered, or six-membered, or an unsubstituted or at least monosubstituted five-membered, or six-membered aryl radical or heteroaryl radical, which can be condensed with a saturated, unsaturated or aromatic, unsubstituted or at least monosubstituted monocyclic or bicyclic ring system, and the heteroaryl radical and optionally one or both rings of the monocyclic or bicyclic ring system each have 1, 2, or 3 hetero atoms, which can be independently selected from the group consisting of oxygen, nitrogen, and sulfur and each of the rings of the monocyclic or bicyclic ring system is four-membered, five-membered, or six-membered.

20. A compound according to claim 19, wherein $R^4$ denotes a hydrogen, or a —C(=O)—NH$_2$ group, a —C(=O)—NH—$R^{14}$ group, or a —C(=O)—NR$^{15}$R$^{16}$ group, an alkyl radical selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, n-heptyl, and n-octyl, or a radical selected from the group consisting of cyclopropyl, cyclobutyl, cyclopentyl, cyclohexyl, cycloheptyl, cyclopentenyl, cyclohexenyl, pyrrolidinyl, tetrahydrofuranyl, tetrahydrothiophenyl, piperidinyl, tetrahydropyranyl, piperazinyl, morpholinyl, thiomorpholinyl, dioxolanyl, azepanyl, diazepanyl, imidazolidinyl, phenyl, naphthyl, anthracenyl, furanyl, thiophenyl, pyrazolyl, pyrazinyl, pyrimidinyl, pyridinyl, pyrrolyl, oxazolyl, isoxazolyl, thiazolyl, dithiazolyl, oxadiazolyl, triazolyl, imidazolyl, indolyl, benzo[b]thiophenyl, benzo[b]furanyl, quinolinyl, isoquinolinyl and or quinazolyl, each of which can be optionally substituted by 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, vinyl, allyl, ethynyl, propinyl, —C≡C—Si(CH$_3$)$_3$, —C≡C—Si(C$_2$H$_5$)$_3$, —CH$_2$—O—CH$_3$, —CH$_2$—O—C$_2$H$_5$, —OH, —O—CH$_3$, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CH$_2$F, —CHF$_2$, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$, and phenyl.

21. A compound according to claim 20, wherein $R^4$ denotes a hydrogen, or a —C(=O)—NH$_2$ group, a —C(=O)—NH—$R^{14}$ group, or a —C(=O)—NR$^{15}$R$^{16}$ group, an alkyl radical selected from the group consisting of methyl, ethyl, n-propyl, isopropyl, n-butyl, sec-butyl, isobutyl, tert-butyl, n-pentyl, sec-pentyl, neopentyl, n-hexyl, n-heptyl, and n-octyl, or a radical selected from the group consisting of cyclopropyl, cyclobutyl, cyclopentyl, cyclohexyl, cycloheptyl, cyclopentenyl, cyclohexenyl, phenyl, pyrid-2-yl, pyrid-3-yl, pyrid-4-yl, pyrrol-2-yl, pyrrol-3-yl, thiophen-2-yl, thiophen-3-yl, 4-methylthiophen-2-yl, 3-methylthiophen-2-yl, 5-methylthiophen-2-yl, furan-2-yl, furan-3-yl, imidazol-2-yl, imidazol-4-yl, thiazol-2-yl, thiazol-4-yl, thiazol-5-yl, oxazol-2-yl, oxazol-4-yl, oxazol-5-yl, (1,2,4)-thiadiazol-5-yl, (1,2,4)-oxadiazol-5-yl, and naphth-1-yl, naphth-2-yl, anthracen-1-yl, anthracen-2-yl, anthracen-9-yl, indol-2-yl, indol-3-yl, indol-4-yl, indol-5-yl, indol-6-yl, indol-7-yl, 1-methylindol-2-yl, 1-methylindol-3-yl, 1-methylindol-4-yl, 1-methylindol-5-yl, 1-methylindol-6-yl, 1-methylindol-7-yl, quinolin-3-yl, quinolin-4-yl, quinolin-2-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, and isoquinolin-8-yl, 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-hydroxyphenyl, 3-hydroxyphenyl, 4-hydroxyphenyl, 2-aminophenyl, 3-aminophenyl, 4-aminophenyl, 2-dimethylaminophenyl, 3-dimethylaminophenyl, 4-dimethylaminophenyl, 2-methylaminophenyl, 3-methylaminophenyl, 4-methylaminophenyl, 2-acetylphenyl, 3-acetylphenyl, 4-acetylphenyl, 2-methylsulfinylphenyl, 3-methylsulfinylphenyl, 4-methylsulfinylphenyl, 2-methylsulfonylphenyl, 3-methylsulfonylphenyl, 4-methylsulfonylphenyl, 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-trifluoromethylphenyl, and 3-trifluoromethylphenyl, 4-trifluoromethylphenyl, 2-difluoromethylphenyl, 3-difluoromethylphenyl, 4-difluoromethylphenyl, 2-fluoromethylphenyl, 3-fluoromethylphenyl, 4-fluoromethylphenyl, 2-nitrophenyl, 3-nitrophenyl, 4-nitrophenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-tert-butylphenyl, 3-tert-butylphenyl, 4-tert-butylphenyl, 2-carboxyphenyl, 3-carboxyphenyl, 4-carboxyphenyl, 2-vinylphenyl, 3-vinylphenyl, 4-vinylphenyl, 2-ethynylphenyl, 3-ethynylphenyl, 4-ethynylphenyl, 2-allylphenyl, 3-allylphenyl, 4-allylphenyl, 2-trimethylsilanylethynylphenyl, 3-trimethylsilanylethynylphenyl, 4-trimethylsilanylethynylphenyl, 2-formylphenyl, 3-formylphenyl, 4-formylphenyl, 2-acetaminophenyl, 3-acetaminophenyl, 4-acetaminophenyl, 2-dimethylaminocarbonylphenyl, 3-dimethylaminocarbonylphenyl, 4-dimethylaminocarbonylphenyl, 2-methoxymethylphenyl, 3-methoxymethylphenyl, 4-methoxymethylphenyl, 2-ethoxymethylphenyl, and 3-ethoxymethylphenyl, 4-ethoxymethylphenyl, 2-aminocarbonylphenyl, 3-aminocarbonylphenyl, 4-aminocarbonylphenyl, 2-methylaminocarbonylphenyl, 3-methylaminocarbonylphenyl, 4-methylaminocarbonylphenyl, 2-carboxymethylesterphenyl, 3-carboxymethylesterphenyl, 4-carboxymethylesterphenyl, 2-carboxyethylesterphenyl, 3-carboxyethylesterphenyl, 4-carboxyethylesterphenyl, 2-carboxy-tert-butylesterphenyl, 3-carboxy-tert-butylesterphenyl, 4-carboxy-tert-butylesterphenyl, 2-methylmercaptophenyl, 3-methylmercaptophenyl, 4-methylmercaptophenyl, 2-ethylmercaptophenyl, 3-ethylmercaptophenyl, 4-ethylmercaptophenyl, 2-biphenyl, 3-biphenyl, 4-biphenyl, 2-bromophenyl, 3-bromophenyl, 4-bromophenyl, 2-iodophenyl, 3-iodophenyl, 4-iodophenyl, 2-trifluoromethoxyphenyl, 3-trifluoromethoxyphenyl, and 4-trifluoromethoxyphenyl, 2-fluoro-3-trifluoromethylphenyl, 2-fluoro-4-methylphenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, 2-chloro-4-nitrophenyl, 2-chloro-4-methylphenyl, 2-chloro-5-trifluoromethylphenyl, 2-chloro-5-methoxyphenyl, 2-bromo-5-trifluoromethylphenyl, 2-bromo-5-methoxyphenyl, (2,4)-dibromophenyl, (2,4)-dimethylphenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-methoxy-5-nitrophenyl, 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl, (2,6)-dibromophenyl, (2,6)-dichlorophenyl, 3-chloro-2-fluorophenyl, 3-chloro-5-methylphenyl, (3,4)-dichlorophenyl, (3,4)-dimethylphenyl, 3-methyl-4-methoxyphenyl, 4-chloro-3-nitrophenyl, (3,4)-dimethoxyphenyl, 4-fluoro-3-trifluoromethylphenyl, 3-fluoro-4-trifluoromethylphenyl, (3,4)-difluorophenyl, 3-cyano-4-fluorophenyl, 3-cyano-4-methylphenyl, 3-cyano-4-methoxyphenyl, 3-bromo-4-fluorophenyl, 3-bromo-4-methylphenyl, 3-bromo-4-methoxyphenyl, 4-chloro-2-fluorophenyl, 4-chloro-3-trifluoromethyl, 4-bromo-3-methylphenyl, 4-bromo-5-methylphenyl, 3-chloro-4-fluorophenyl, 4-fluoro-3-nitrophenyl, 4-bromo-3-nitrophenyl, (3,4)-dibromophenyl, 4-chloro-3-methylphenyl, 4-bromo-3-methylphenyl, 4-fluoro-3-methylphenyl, 3-fluoro-4-methylphenyl, 3-fluoro-5-methylphenyl, 2-fluoro-3-methylphenyl, 4-methyl-3-nitrophenyl, (3,5)-dimethoxyphenyl, (3,5)-dimethylphenyl, (3,5)-bis-trifluoromethylphenyl, (3,5)-difluorophenyl, (3,5)-dinitrophenyl, (3,5)-dichlorophenyl, 3-fluoro-5-trifluoromethylphenyl, 5-fluoro-3-trifluoromethylphenyl, (3,5)-dibromophenyl, 5-chloro-4-fluorophenyl, 5-chloro-4-fluorophenyl, 5-bromo-4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methyl, (2,4,5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (3,4, 5)-trimethoxyphenyl, (2,3,4,5)-tetrafluorophenyl, 4-methoxy-(2,3,6)-trimethylphenyl, 4-methoxy-(2,3,6)-trimethylphenyl, 4-chloro-2, 5-dimethylphenyl, 2-chloro-6-fluoro-3-methylphenyl, 6-chloro-2-fluoro-3-methyl, (2,4,6)-trimethylphenyl, (2,3,4,5,6)-pentafluorophenyl, 3-methylpyrid-2-yl, 4-methylpyrid-2-yl, 5-methylpyrid-2-yl, 6-methylpyrid-2-yl, 2-methylpyrid-3-yl, 4-methylpyrid-3-yl, 5-methylpyrid-3-yl, 6-methylpyrid-3-yl, 2-methylpyrid-4-yl, 3-methylpyrid-4-yl, 3-fluoropyrid-2-yl, 4-fluoropyrid-2-yl, 5-fluoropyrid-2-yl, 6-fluoropyrid-2-yl, 3-chloropyrid-2-yl, 4-chloropyrid-2-yl, 5-chloropyrid-2-yl, 6-chloropyrid-2-yl, 3-trifluoromethylpyrid-2-yl, 4-trifluoromethylpyrid-2-yl, 5-trifluoromethylpyrid-2-yl, 6-trifluoromethylpyrid-2-yl, 3-methoxypyrid-2-yl, 4-methoxypyrid-2-yl, 5-methoxypyrid-2-yl, 6-methoxypyrid-2-yl, 4-methylthiazol-2-yl, 5-methylthiazol-2-yl, 4-trifluoromethylthiazol-2-yl, 5-trifluoromethylthiazol-2-yl, 4-chlorothiazol-2-yl, 5-chlorothiazol-2-yl, 4-bromothiazol-2-yl, 5-bromothiazol-2-yl, 4-fluorothiazol-2-yl, 5-fluorothiazol-2-yl, 4-cyanothiazol-2-yl, 5-cyanothiazol-2-yl, 4-methoxythiazol-2-yl, 5-methoxythiazol-2-yl, and 4-methyloxazol-2-yl, 5-methyloxazol-2-yl, 4-trifluoromethyloxazol-2-yl, 5-trifluoromethyloxazol-2-yl, 4-chloroxazol-2-yl, 5-chloroxazol-2-yl, 4-bromoxazol-2-yl, 5-bromoxazol-2-yl, 4-fluoroxazol-2-yl, 5-fluoroxazol-2-yl, 4-cyano-oxazol-2-yl, 5-cyano-oxazol-2-yl, 4-methoxyoxazol-2-yl, 5-methoxyoxazol-2-yl, 2-methyl-(1,2,4)-thiadiazol-5-yl, 2-trifluoromethyl-(1,2,4)-thiadiazol-5-yl, 2-chloro-(1,2,4)-thiadiazol-5-yl, 2-fluoro-(1,2,4)-thiadiazol-5-yl, 2-methoxy-(1,2,4)-thiadiazol-5-yl, 2-cyano-(1,2,4)-thiadiazol-5-yl, 2-methyl-(1,2,4)-oxadiazol-5-yl, 2-trifluoromethyl-(1,2,4)-oxadiazol-5-yl, 2-chloro-(1,2,4)-oxadiazol-5-yl, 2-fluoro-(1,2,4)-oxadiazol-5-yl, 2-methoxy-(1,2,4)-oxadiazol-5-yl, and 2-cyano-(1,2,4)-oxadiazol-5-yl.

22. A compound according to claim 1, wherein n is 0, 1, 2, 3 or 4.

23. A compound according to claim 22, wherein n is 0, 1 or 2.

24. A compound according to claim 1, wherein $R^5$ to $R^{25}$ each independently denote a linear or branched, saturated or unsaturated, unsubstituted or at least monosubstituted aliphatic $C_{1-8}$ radical, an unsubstituted or at least monosubstituted, unsaturated or saturated three-membered, four-membered, five-membered, six-membered, seven-membered, eight-membered, or nine-membered cycloaliphatic radical which optionally contains at least one hetero atom as ring member, and which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from said group consisting of oxygen, sulfur, and nitrogen, as link(s), and/or optionally condensed with an unsubstituted or at least monosubstituted monocyclic or polycyclic ring system, or an unsubstituted or at least monosubstituted five-membered to fourteen-membered aryl radical or heteroaryl radical, which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s), and/or can be condensed with an unsubstituted or at least monosubstituted monocyclic or polycyclic ring system.

25. A compound according to claim 24, wherein $R^5$ to $R^{25}$ each independently denote a linear or branched, unsubstituted or at least monosubstituted $C_{1-8}$ alkyl radical, a linear or branched, unsubstituted or at least monosubstituted $C_{2-8}$ alkenyl radical, a linear or branched, unsubstituted or at least monosubstituted $C_{2-8}$ alkynyl radical, an unsubstituted or at least monosubstituted, unsaturated or saturated three-membered, four-membered, five-membered, six-membered, seven-membered, eight-membered, or nine-membered cycloaliphatic radical which optionally contains at least one hetero atom as ring member, and which can be bonded via a linear or branched, unsubstituted or at least monosubstituted $C_{1-5}$ alkylene group, $C_{2-5}$ alkenylene group or $C_{2-5}$ alkynylene group which optionally contains 1, 2, or 3 hetero atoms independently selected from the group consisting of oxygen, sulfur, and nitrogen, as link(s), or an unsubstituted or at least monosubstituted five-membered to fourteen-membered aryl radical or heteroaryl radical, and which can be bonded via a linear or branched, unsubstituted or at least monosubstituted $C_{1-5}$ alkylene group, $C_{2-5}$ alkenylene group or $C_{2-5}$ alkynylene group optionally containing 1, 2, or 3 hetero atoms independently selected from the group consisting of oxygen, sulfur, and nitrogen, as link(s).

26. A compound according to claim 1, wherein $R^5$ to $R^{25}$ each independently denote an alkyl radical selected from the group consisting of methyl, ethyl, n-propyl, isopropyl, n-butyl, sec-butyl, isobutyl, and tert-butyl, or an alkenyl radical selected from the group consisting of vinyl, 1-propenyl, 2-propenyl, 1-butenyl, 2-butenyl, and 3-butenyl, or an alkynyl radical selected from the group consisting of ethynyl, 1-propynyl, 2-propynyl, 1-butynyl, 2-butynyl, and 3-butynyl, or a radical selected from the group consisting of cyclopropyl group, cyclobutyl group, cyclopentyl group, cyclohexyl group, pyrrolidinyl group, tetrahydrofuranyl group, tetrahydrothiophenyl group piperidinyl group, tetrahydropyranyl group, piperazinyl group, morpholinyl group, thiomorpholinyl group, dioxolanyl group, azepanyl group, diazepanyl group, imidazolidinyl group, phenyl, naphthyl group, anthracenyl group, pyrrolyl group, indolyl group, furanyl group, benzo[b]furanyl group, thiophenyl group, benzo[b]thiophenyl group, pyrazolyl group, imidazolyl group, thiazolyl group, dithiazolyl group, thiadiazolyl group, triazolyl group, oxazolyl group, oxadiazolyl group, isoxazolyl group, pyridinyl group, pyridazinyl group, pyrimidinyl group, pyrazinyl group, pyranyl group, indazolyl group, purinyl group, indolizinyl group, quinolinyl group, isoquinolinyl group, and quinazolinyl group, while the respective cyclic radical can be bonded via a $C_{1-3}$ alkylene group, $C_{2-5}$ alkenylene group or $C_{2-3}$ alkynylene group optionally containing 1 or 2 hetero atoms selected from the group consisting of oxygen, sulfur, and nitrogen, as link(s), and/or is unsubstituted or substituted by 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH₃, —O—C₂H₅, —O—C₃H₇, —NH₂, —N(CH₃)₂, —N(C₂H₅)₂, —NH—CH₃, —NH—C₂H₅, —NO₂, —CF₃, —O—CF₃, —S—CF₃, —SH, —NH—S(=O)₂—CH₃, —C(=O)—OH, —C(=O)—CH₃, —C(=O)—C₂H₅, —C(=O)—N(CH₃)₂, —C(=O)—NH—CH₃, —NH—C(=O)—CH₃, —NH—C(=O)—C₂H₅, —C(=O)—O—CH₃, and —C(=O)—O—C₂H₅.

27. A compound according to claim 1, wherein:
n is 0, 1, 2, 3 or 4;
$R^1$ denotes a hydrogen, or a halogen selected from the group consisting of F, Cl, and Br, or a CF₃ group, or a nitro group, a cyano group, an amino group, or a dimethylamino group, or a diethylamino group, a hydroxyl group, a thiol group, or a carboxyl group, or a —C(=O)—O—CH₃ group, a —C(=O)—O—C₂H₅ group, a —C(=O)—NH—$R^{14}$ group, or a —C(=O)—NR¹⁵R¹⁶ group, or an —O—$R^{17}$ group, an —S—$R^{18}$ group, an —S*(=O)—$R^{19}$ group, or an —S(=O)₂—$R^{20}$ group, an alkyl radical selected from the group consisting of methyl, ethyl, n-propyl, isopropyl, n-butyl, sec-butyl, isobutyl, and tert-butyl, an alkenyl radical selected from the group consisting of vinyl, 1-propenyl, 2-propenyl, 1-butenyl, 2-butenyl, and 3-butenyl, an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH₃, —O—C₂H₅, and —O—C₃H₇;

$R^2$ denotes a hydrogen, or a halogen selected from the group consisting of F, Cl, and Br, or a CF₃ group, or a nitro group, a cyano group, an amino group, or a dimethylamino group, or a diethylamino group, a hydroxyl group, a thiol group, or a carboxyl group, or a —C(=O)—O—CH₃ group, a —C(=O)—O—C₂H₅ group, a —C(=O)—NH—$R^{14}$ group, or a —C(=O)—NR¹⁵R¹⁶ group, or an —O—$R^{17}$ group, an —S—$R^{18}$ group, an —S(=O)—$R^{19}$ group, or an —S(=O)₂—$R^{20}$ group, an alkyl radical selected from the group consisting of alkenyl radical selected from the group consisting of vinyl, 1-propenyl, 2-propenyl, 1-butenyl, 2-butenyl, and 3-butenyl, an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH₃, —O—C₂H₅, and —O—C₃H₇;

$R^3$ denotes an oxo group, an alkyl radical selected from the group consisting of methyl, ethyl, n-propyl, isopropyl, n-butyl, sec-butyl, isobutyl, and tert-butyl or a phenyl radical, which is unsubstituted or substituted by 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH₃, —O—C₂H₅, and —O—C₃H₇;

$R^4$ denotes a hydrogen, or a —C(=O)—NH₂ group, a —C(=O)—NH—$R^{14}$ group, or a —C(=O)—NR¹⁵R¹⁶ group, an alkyl radical selected from the group consisting of methyl, ethyl, n-propyl, isopropyl, n-butyl, sec-butyl, isobutyl, tert-butyl, n-pentyl, 2-pentyl, 3-pentyl, neopentyl, n-hexyl, n-heptyl, and n-octyl, or a radical selected from the group consisting of cyclopropyl, cyclobutyl, cyclopentyl, cyclohexyl, cycloheptyl, cyclopentenyl, cyclohexenyl, pyrrolidinyl, tetrahydrofuranyl, tetrahydrothiophenyl, piperidinyl, tetrahydropyranyl, piperazinyl, morpholinyl, thiomorpholinyl, dioxolanyl, azepanyl, diazepanyl, imidazolidinyl, phenyl, naphthyl, anthracenyl, furanyl, thiophenyl, pyrazolyl, pyrazinyl, pyrimidinyl, pyridinyl, pyrrolyl, oxazolyl, isoxazolyl, thiazolyl, dithiazolyl, oxadiazolyl, triazolyl, imidazolyl, indolyl, benzo[b]thiophenyl, benzo[b]furanyl, quinolinyl, isoquinolinyl, and quinazolyl, the in each case can be optionally substituted by 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, vinyl, allyl, ethynyl, propynyl, —C≡C—Si(CH₃)₃, —C≡C—Si(C₂H₅)₃, —CH₂—O—CH₃, —CH₂—O—C₂H₅, —OH, —O—CH₃, —O—C$_2$H$_5$, —O—C$_3$H$_7$, —S—CH$_3$, —S—C$_2$H$_5$, —S(=O)—CH$_3$, —S(=O)$_2$—CH$_3$, —S(=O)—C$_2$H$_5$, —S(=O)$_2$—C$_2$H$_5$, —NH$_2$, —N(CH$_3$)$_2$, —N(C$_2$H$_5$)$_2$, —NH—CH$_3$, —NH—C$_2$H$_5$, —NO$_2$, —CF$_3$, —CHF$_2$, —CH$_2$F, —O—CF$_3$, —S—CF$_3$, —SH, —NH—S(=O)$_2$—CH$_3$, —C(=O)—OH, —C(=O)—H; —C(=O)—CH$_3$, —C(=O)—C$_2$H$_5$, —C(=O)—NH$_2$, —C(=O)—N(CH$_3$)$_2$, —C(=O)—NH—CH$_3$, —NH—C(=O)—CH$_3$, —NH—C(=O)—C$_2$H$_5$, —C(=O)—O—CH$_3$, —C(=O)—O—C$_2$H$_5$, —C(=O)—O—C(CH$_3$)$_3$, and phenyl; and R$^{14}$, R$^{15}$, R$^{16}$, R$^{17}$, R$^{18}$, R$^{19}$ and R$^{20}$ each independently denote an alkyl radical selected from the group consisting of methyl, ethyl, n-propyl, isopropyl, n-butyl, sec-butyl, isobutyl, and tert-butyl.

28. A compound according to claim 1, wherein:

n is 0, 1, 2, 3 or 4;

R$^1$ denotes a hydrogen, or a halogen selected from the group consisting of F, Cl, and Br, or a CF$_3$ group, or a nitro group, a cyano group, an amino group, or a dimethylamino group, or a diethylamino group, a hydroxyl group, a thiol group, or a carboxyl group, or a —C(=O)—O—CH$_3$ group, a —C(=O)—O—C$_2$H$_5$ group, a —C(=O)—NH—R$^{14}$ group, or a —C(=O)—NR$^{15}$R$^{16}$ group, or an —O—R$^{17}$ group, an —S—R$^{18}$ group, an —S(=O)—R$^{19}$ group, or an —S(=O)$_2$—R$^{20}$ group, an alkyl radical selected from the group consisting of methyl, ethyl, n-propyl, isopropyl, n-butyl, sec-butyl, isobutyl, and tert-butyl, an alkenyl radical selected from the group consisting of vinyl, 1-propenyl, 2-propenyl, 1-butenyl, 2-butenyl, and 3-butenyl, an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH$_3$, —O—C$_2$H$_5$, and —O—C$_3$H$_7$;

R$^2$ denotes a hydrogen, or a halogen selected from the group consisting of F, Cl, and Br, or a CF$_3$ group, or a nitro group, a cyano group, an amino group, or a dimethylamino group, or a diethylamino group, a hydroxyl group, a thiol group, or a carboxyl group, or a —C(=O)—O—CH$_3$ group, a —C(=O)—O—C$_2$H$_5$ group, a —C(=O)—NH—R$^{14}$ group, or a —C(=O)—NR$^{15}$R$^{16}$ group, or an —O—R$^{17}$ group, an —S—R$^{18}$ group, an —S(=O)—R$^{19}$ group, or an —S(=O)$_2$—R$^{20}$ group, an alkyl radical selected from the group consisting of methyl, ethyl, n-propyl, isopropyl, n-butyl, sec-butyl, isobutyl, and tert-butyl, an alkenyl radical selected from the group consisting of vinyl, 1-propenyl, 2-propenyl, 1-butenyl, 2-butenyl, and 3-butenyl, denotes an alkynyl radical selected from the group consisting of ethynyl, 1-propynyl, 2-propynyl, 1-butynyl, 2-butynyl, and 3-butynyl or a radical selected from the group consisting of (1,3)-dioxolan-2-yl, phenyl, benzyl, phenethyl, oxadiazolyl, 2-pyridyl, 3-pyridyl, 4-pyridyl, 2-thienyl, 3-thienyl, 2-furyl, and 3-furyl, each of which is unsubstituted or substituted by optionally 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH$_3$, —O—C$_2$H$_5$, and —O—C$_3$H$_7$;

R$^3$ denotes an oxo group, an alkyl radical selected from the group consisting of methyl, ethyl, n-propyl, isopropyl, n-butyl, sec-butyl, isobutyl, and tert-butyl or a phenyl radical, which is unsubstituted or substituted by 1, 2, 3, 4, or 5 substituents independently selected from the group consisting of F, Cl, Br, I, —CN, methyl, ethyl, n-propyl, isopropyl, n-butyl, sec-butyl, isobutyl, tert-butyl, —OH, —O—CH$_3$, —O—C$_2$H$_5$, and —O—C$_3$H$_7$;

R$^4$ denotes a hydrogen, or a —C(=O)—NH$_2$ group, a —C(=O)—NH—R$^{14}$ group, or a —C(=O)—NR$^{15}$R$^{16}$ group, an alkyl radical selected from the group consisting of methyl, ethyl, n-propyl, isopropyl, n-butyl, sec-butyl, isobutyl, tert-butyl, n-pentyl, sec-pentyl, neopentyl, n-hexyl, n-heptyl, and n-octyl, or a radical selected from the group consisting of cyclopropyl, cyclobutyl, cyclopentyl, cyclohexyl, cycloheptyl, cyclopentenyl, cyclohexenyl, phenyl, pyrid-2-yl, pyrid-3-yl, pyrid-4-yl, pyrrol-2-yl, pyrrol-3-yl, thiophen-2-yl, thiophen-3-yl, 4-methylthiophen-2-yl, 3-methylthiophen-2-yl, 5-methylthiophen-2-yl, furan-2-yl, furan-3-yl, imidazol-2-yl, imidazol-4-yl, thiazol-2-yl, thiazol-4-yl, thiazol-5-yl, oxazol-2-yl, oxazol-4-yl, oxazol-5-yl, (1,2,4)-thiadiazol-5-yl, (1,2,4)-oxadiazol-5-yl, naphth-1-yl, naphth-2-yl, anthracen-1-yl, anthracen-2-yl, anthracen-9-yl, indol-2-yl, indol-3-yl, indol-4-yl, indol-5-yl, indol-6-yl, indol-7-yl, 1-methylindol-2-yl, 1-methylindol-3-yl, 1-methylindol-4-yl, 1-methylindol-5-yl, 1-methylindol-6-yl, 1-methylindol-7-yl, quinolin-3-yl, and quinolin-4-yl, quinolin-2-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-hydroxyphenyl, 3-hydroxyphenyl, 4-hydroxyphenyl, 2-aminophenyl, 3-aminophenyl, 4-aminophenyl, 2-dimethylaminophenyl, 3-dimethylaminophenyl, 4-dimethylaminophenyl, 2-methylaminophenyl, 3-methylaminophenyl, 4-methylaminophenyl, 2-acetylphenyl, 3-acetylphenyl, 4-acetylphenyl, 2-methylsulfinylphenyl, 3-methylsulfinylphenyl, 4-methylsulfinylphenyl, 2-methylsulfonylphenyl, 3-methylsulfonylphenyl, 4-methylsulfonylphenyl, and 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-trifluoromethylphenyl, 3-trifluoromethylphenyl, 4-trifluoromethylphenyl, 2-difluoromethylphenyl, 3-difluoromethylphenyl, 4-difluoromethylphenyl, 2-fluoromethylphenyl, 3-fluoromethylphenyl, 4-fluoromethylphenyl, 2-nitrophenyl, 3-nitrophenyl, 4-nitrophenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-tert-butylphenyl, 3-tert-butylphenyl, 4-tert-butylphenyl, 2-carboxyphenyl, 3-carboxyphenyl, 4-carboxyphenyl, 2-vinylphenyl, 3-vinylphenyl, 4-vinylphenyl, 2-ethynylphenyl, 3-ethynylphenyl, 4-ethynylphenyl, 2-allylphenyl, 3-allylphenyl, 4-allylphenyl, 2-trimethylsilanylethynylphenyl, 3-trimethylsilanylethynylphenyl, 4-trimethylsilanylethynylphenyl, 2-formylphenyl, 3-formylphenyl, 4-formylphenyl, 2-acetaminophenyl, 3-acetaminophenyl, 4-acetaminophenyl, 2-dimethylaminocarbonylphenyl, 3-dimethylaminocarbonylphenyl, 4-dimethylaminocarbonylphenyl, 2-methoxymethylphenyl, 3-methoxymethylphenyl, 4-methoxymethylphenyl, 2-ethoxymethylphenyl, 3-ethoxymethylphenyl, 4-ethoxymethylphenyl, 2-aminocarbonylphenyl, 3-aminocarbonylphenyl, 4-aminocarbonylphenyl, 2-methylaminocarbonylphenyl, 3-methylaminocarbonylphenyl, 4-methylaminocarbonylphenyl, 2-carboxymethylesterphenyl, 3-carboxymethylesterphenyl, 4-carboxymethylesterphenyl, 2-carboxyethylesterphenyl, 3-carboxyethylesterphenyl, 4-carboxyethylesterphenyl, 2-carboxy-tert-butylesterphenyl, 3-carboxy-tert-butylesterphenyl, 4-carboxy-tert-butylesterphenyl, 2-methylmercaptophenyl, 3-methylmercaptophenyl, 4-methylmercaptophenyl, 2-ethylmercaptophenyl, 3-ethylmercaptophenyl, 4-ethylmercaptophenyl, 2-biphenyl, 3-biphenyl, 4-biphenyl, 2-bromophenyl, 3-bromophenyl, 4-bromophenyl, 2-iodophenyl, 3-iodophenyl, and 4-iodophenyl, 2-trifluoromethoxyphenyl, 3-trifluoromethoxyphenyl, 4-trifluoromethoxyphenyl, 2-fluoro-3-trifluoromethylphenyl, 2-fluoro-4-methylphenyl, (2,3)-difluorophenyl, (2,3)-dimethylphenyl, (2,3)-dichlorophenyl, 3-fluoro-2-trifluoromethylphenyl, (2,4)-dichlorophenyl, (2,4)-difluorophenyl, 4-fluoro-2-trifluoromethylphenyl, (2,4)-dimethoxyphenyl, 2-chloro-4-fluorophenyl, 2-chloro-4-nitrophenyl, 2-chloro-4-methylphenyl, 2-chloro-5-trifluoromethylphenyl, 2-chloro-5-methoxyphenyl, 2-bromo-5-trifluoromethylphenyl, 2-bromo-5-methoxyphenyl, (2,4)-dibromophenyl, (2,4)-dimethylphenyl, 2-fluoro-4-trifluoromethylphenyl, (2,5)-difluorophenyl, 2-fluoro-5-trifluoromethylphenyl, 5-fluoro-2-trifluoromethylphenyl, 5-chloro-2-trifluoromethylphenyl, 5-bromo-2-trifluoromethylphenyl, (2,5)-dimethoxyphenyl, (2,5)-bis-trifluoromethylphenyl, (2,5)-dichlorophenyl, (2,5)-dibromophenyl, 2-methoxy-5-nitrophenyl, 2-fluoro-6-trifluoromethylphenyl, (2,6)-dimethoxyphenyl, (2,6)-dimethylphenyl, (2,6)-dichlorophenyl, 2-chloro-6-fluorophenyl, 2-bromo-6-chlorophenyl, 2-bromo-6-fluorophenyl, (2,6)-difluorophenyl, (2,6)-difluoro-3-methylphenyl (2,6)-dibromophenyl, (2,6)-dichlorophenyl, 3-chloro-2-fluorophenyl, 3-chloro-5-methylphenyl, (3,4)-dichlorophenyl, (3,4)-dimethylphenyl, 3-methyl-4-methoxyphenyl, 4-chloro-3-nitrophenyl, (3,4)-dimethoxyphenyl, 4-fluoro-3-trifluoromethylphenyl, 3-fluoro-4-trifluoromethylphenyl, (3,4)-difluorophenyl, 3-cyano-4-fluorophenyl, 3-cyano-4-methylphenyl, 3-cyano-4-methoxyphenyl, 3-bromo-4-fluorophenyl, 3-bromo-4-methylphenyl, 3-bromo-4-methoxyphenyl, 4-chloro-2-fluorophenyl, 4-chloro-3-trifluoromethyl, 4-bromo-3-methylphenyl, 4-bromo-5-methylphenyl, 3-chloro-4-fluorophenyl, 4-fluoro-3-nitrophenyl, 4-bromo-3-nitrophenyl, (3,4)-dibromophenyl, 4-chloro-3-methylphenyl, 4-bromo-3-methylphenyl, 4-fluoro-3-methylphenyl, 3-fluoro-4-methylphenyl, and 3-fluoro-5-methylphenyl, 2-fluoro-3-methylphenyl, 4-methyl-3-nitrophenyl, (3,5)-dimethoxyphenyl, (3,5)-dimethylphenyl, (3,5)-bis-trifluoromethylphenyl, (3,5)-difluorophenyl, (3,5)-dinitrophenyl, (3,5)-dichlorophenyl, 3-fluoro-5-trifluoromethylphenyl, 5-fluoro-3-trifluoromethylphenyl, (3,5)-dibromophenyl, 5-chloro-4-fluorophenyl, 5-chloro-4-fluorophenyl, 5-bromo-4-methylphenyl, (2,3,4)-trifluorophenyl, (2,3,4)-trichlorophenyl, (2,3,6)-trifluorophenyl, 5-chloro-2-methoxyphenyl, (2,3)-difluoro-4-methyl, (2,4, 5)-trifluorophenyl, (2,4,5)-trichlorophenyl, (2,4)-dichloro-5-fluorophenyl, (2,4,6)-trichlorophenyl, (2,4,6)-trimethylphenyl, (2,4,6)-trifluorophenyl, (2,4,6)-trimethoxyphenyl, (3,4,5)-trimethoxyphenyl, (2,3,4,5)-tetrafluorophenyl, 4-methoxy-(2,3,6)-trimethylphenyl, 4-methoxy-(2,3,6)-trimethylphenyl, and 4-chloro-2,5-dimethylphenyl, 2-chloro-6-fluoro-3-methylphenyl, 6-chloro-2-fluoro-3-methyl, (2,4,6)-trimethylphenyl, (2,3,4,5,6)-pentafluorophenyl, 3-methylpyrid-2-yl, 4-methylpyrid-2-yl, 5-methylpyrid-2-yl, 6-methylpyrid-2-yl, 2-methylpyrid-3-yl, 4-methylpyrid-3-yl, 5-methylpyrid-3-yl, 6-methylpyrid-3-yl, 2-methylpyrid-4-yl, 3-methylpyrid-4-yl, 3-fluoropyrid-2-yl, 4-fluoropyrid-2-yl, 5-fluoropyrid-2-yl, 6-fluoropyrid-2-yl, 3-chloropyrid-2-yl, 4-chloropyrid-2-yl, 5-chloropyrid-2-yl, 6-chloropyrid-2-yl, 3-trifluoromethylpyrid-2-yl, 4-trifluoromethylpyrid-2-yl, 5-trifluoromethylpyrid-2-yl, 6-trifluoromethylpyrid-2-yl, 3-methoxypyrid-2-yl, 4-methoxypyrid-2-yl, 5-methoxypyrid-2-yl, 6-methoxypyrid-2-yl, 4-methylthiazol-2-yl, 5-methylthiazol-2-yl, 4-trifluoromethylthiazol-2-yl, 5-trifluoromethylthiazol-2-yl, 4-chlorothiazol-2-yl, 5-chlorothiazol-2-yl, 4-bromothiazol-2-yl, 5-bromothiazol-2-yl, 4-fluorothiazol-2-yl, 5-fluorothiazol-2-yl, and 4-cyanothiazol-2-yl, 5-cyanothiazol-2-yl, 4-methoxythiazol-2-yl, 5-methoxythiazol-2-yl, 4-methyloxazol-2-yl, 5-methyloxazol-2-yl, 4-trifluoromethyloxazol-2-yl, 5-trifluoromethyloxazol-2-yl, 4-chloroxazol-2-yl, 5-chloroxazol-2-yl, 4-bromoxazol-2-yl, 5-bromoxazol-2-yl, 4-fluoroxazol-2-yl, 5-fluoroxazol-2-yl, 4-cyano-oxazol-2-yl, 5-cyano-oxazol-2-yl, 4-methoxyoxazol-2-yl, 5-methoxyoxazol-2-yl, 2-methyl-(1,2,4)-thiadiazol-5-yl, 2-trifluoromethyl-(1,2,4)-thiadiazol-5-yl, 2-chloro-(1,2,4)-thiadiazol-5-yl, 2-fluoro-(1,2,4)-thiadiazol-5-yl, 2-methoxy-(1,2,4)-thiadiazol-5-yl, 2-cyano-(1,2,4)-thiadiazol-5-yl, 2-methyl-(1,2,4)-oxadiazol-5-yl, 2-trifluoromethyl-(1,2,4)-oxadiazol-5-yl, 2-chloro-(1,2,4)-oxadiazol-5-yl, 2-fluoro-(1,2,4)-oxadiazol-5-yl, 2-methoxy-(1,2,4)-oxadiazol-5-yl, and 2-cyano-(1, 2,4)-oxadiazol-5-yl; and $R^{14}$, $R^{15}$, $R^{16}$, $R^{17}$, $R^{18}$, $R^{19}$ and $R^{20}$ each independently denote an alkyl radical selected from the group consisting of methyl, ethyl, n-propyl, isopropyl, n-butyl, sec-butyl, isobutyl, and tert-butyl.

29. A compound according to claim 1, wherein:

n is 0, 1 or 2;

$R^1$ denotes a hydrogen, or a halogen selected from the group consisting of F, Cl, and Br, or a $CF_3$ group, or a nitro group, a carboxyl group, a —C(=O)—O—CH$_3$ group, or a —C(=O)—O—C$_2$H$_5$ group, or a —C(=O)—NH—$R^{14}$ group, a —C(=O)—NR$^{15}$R$^{16}$ group, an —O—$R^{17}$ group, or an —S—$R^{18}$ group, or an —S(=O)$_2$—$R^{20}$ group, an alkyl radical selected from the group consisting of methyl, ethyl, n-propyl, isopropyl, n-butyl, sec-butyl, isobutyl, and tert-butyl, or denotes a radical selected from the group consisting of phenyl and oxadiazolyl, each of which is unsubstituted or substituted by optionally 1, 2, 3, 4, or 5 substituents independently selected from the group consisting of F, Cl, Br, I, —O—CH$_3$, —O—C$_2$H$_5$, and —O—C$_3$H$_7$;

$R^2$ denotes a hydrogen, or a halogen selected from the group consisting of F, Cl, and Br, or a $CF_3$ group, or a nitro group, a carboxyl group, a —C(=O)—O—CH$_3$ group, or a —C(=O)—O—C$_2$H$_5$ group, or a —C(=O)—NH—R$^{14}$ group, a —C(=O)—NR$^{15}$R$^{16}$ group, an —O—R$^{17}$ group, or an —S—R$^{18}$ group, or an —S(=O)$_2$—R$^{20}$ group, an alkyl radical selected from the group consisting of methyl, ethyl, n-propyl, isopropyl, n-butyl, sec-butyl, isobutyl, and tert-butyl, or denotes a radical selected from the group consisting of phenyl and oxadiazolyl, each of which is unsubstituted or substituted by optionally 1, 2, 3, 4, or 5 substituents independently selected from the group consisting of F, Cl, Br, I, —O—CH$_3$, —O—C$_2$H$_5$, and —O—C$_3$H$_7$;

R$^3$ denotes an oxo group, an alkyl radical selected from the group consisting of methyl, ethyl, n-propyl, isopropyl, n-butyl, sec-butyl, isobutyl, and tert-butyl or an unsubstituted phenyl radical;

R$^4$ denotes a hydrogen, or a —C(=O)—NH$_2$ group, a —C(=O)—NH—R$^{14}$ group, or a NR$^{15}$R$^{16}$ group, an alkyl radical selected from the group consisting of methyl, ethyl, n-propyl, isopropyl, n-butyl, sec-butyl, isobutyl, tert-butyl, n-pentyl, sec-pentyl, neopentyl, n-hexyl, n-heptyl, and n-octyl or a radical selected from the group consisting of cyclopropyl, cyclobutyl, cyclopentyl, cyclohexyl, cycloheptyl, cyclopentenyl, cyclohexenyl, phenyl, pyrid-2-yl, pyrid-3-yl, pyrid-4-yl, pyrrol-2-yl, pyrrol-3-yl, thiophen-2-yl, thiophen-3-yl, 4-methylthiophen-2-yl, 3-methylthiophen-2-yl, 5-methylthiophen-2-yl, furan-2-yl, furan-3-yl, imidazol-2-yl, imidazol-4-yl, thiazol-2-yl, thiazol-4-yl, thiazol-5-yl, oxazol-2-yl, oxazol-4-yl, oxazol-5-yl, (1,2,4)-thiadiazol-5-yl, (1,2,4)-oxadiazol-5-yl, naphth-1-yl, naphth-2-yl, indol-3-yl, indol-4-yl, indol-5-yl, indol-6-yl, indol-7-yl, 1-methylindol-2-yl, 1-methylindol-3-yl, 1-methylindol-4-yl, 1-methylindol-5-yl, 1-methylindol-6-yl, 1-methylindol-7-yl, quinolin-3-yl, quinolin-4-yl, quinolin-2-yl, quinolin-5-yl, quinolin-6-yl, and quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl, isoquinolin-8-yl, 2-methylphenyl, 3-methylphenyl, 4-methylphenyl, 2-fluorophenyl, 3-fluorophenyl, 4-fluorophenyl, 2-cyanophenyl, 3-cyanophenyl, 4-cyanophenyl, 2-hydroxyphenyl, 3-hydroxyphenyl, 4-hydroxyphenyl, 2-aminophenyl, 3-aminophenyl, 4-aminophenyl, 2-dimethylaminophenyl, 3-dimethylaminophenyl, 4-dimethylaminophenyl, 2-methylaminophenyl, 3-methylaminophenyl, 4-methylaminophenyl, 2-acetylphenyl, 3-acetylphenyl, 4-acetylphenyl, 2-methylsulfinylphenyl, 3-methylsulfinylphenyl, 4-methylsulfinylphenyl, 2-methylsulfonylphenyl, 3-methylsulfonylphenyl, 4-methylsulfonylphenyl, 2-methoxyphenyl, 3-methoxyphenyl, 4-methoxyphenyl, 2-chlorophenyl, 3-chlorophenyl, 4-chlorophenyl, 2-ethoxyphenyl, 3-ethoxyphenyl, 4-ethoxyphenyl, 2-trifluoromethylphenyl, 3-trifluoromethylphenyl, 4-trifluoromethylphenyl, and 2-difluoromethylphenyl, 3-difluoromethylphenyl, 4-difluoromethylphenyl, 2-fluoromethylphenyl, 3-fluoromethylphenyl, 4-fluoromethylphenyl, 2-nitrophenyl, 3-nitrophenyl, 4-nitrophenyl, 2-ethylphenyl, 3-ethylphenyl, 4-ethylphenyl, 2-propylphenyl, 3-propylphenyl, 4-propylphenyl, 2-isopropylphenyl, 3-isopropylphenyl, 4-isopropylphenyl, 2-tert-butylphenyl, 3-tert-butylphenyl, 4-tert-butylphenyl, 2-carboxyphenyl, 3-carboxyphenyl, 4-carboxyphenyl, 2-vinylphenyl, 3-vinylphenyl, 4-vinylphenyl, 2-ethynylphenyl, 3-ethynylphenyl, 4-ethynylphenyl, 2-allylphenyl, 3-allylphenyl, 4-allylphenyl, 2-trimethylsilanylethynylphenyl, 3-trimethylsilanylethynylphenyl, 4-trimethylsilanylethynylphenyl, 2-formylphenyl, 3-formylphenyl, 4-formylphenyl, 2-acetaminophenyl, 3-acetaminophenyl, 4-acetaminophenyl, 2-dimethylaminocarbonylphenyl, 3-dimethylaminocarbonylphenyl, 4-dimethylaminocarbonylphenyl, 2-methoxymethylphenyl, 3-methoxymethylphenyl, 4-methoxymethylphenyl, 2-ethoxymethylphenyl, 3-ethoxymethylphenyl, and 4-ethoxymethylphenyl, 2-aminocarbonylphenyl, 3-aminocarbonylphenyl, 4-aminocarbonylphenyl, 2-methylaminocarbonylphenyl, 3-methylaminocarbonylphenyl, 4-methylaminocarbonylphenyl, 2-carboxymethylesterphenyl, 3-carboxymethylesterphenyl, 4-carboxymethylesterphenyl, 2-carboxyethylesterphenyl, 3-carboxyethylesterphenyl, 4-carboxyethylesterphenyl, 2-carboxy-tert-butylesterphenyl, 3-carboxy-tert-butylesterphenyl, 4-carboxy-tert-butylesterphenyl, 2-methylmercaptophenyl, 3-methylmercaptophenyl, 4-methylmercaptophenyl, 2-ethylmercaptophenyl, 3-ethylmercaptophenyl, 4-ethylmercaptophenyl, 2-biphenyl, 3-biphenyl, 4-biphenyl, 2-bromophenyl, 3-bromophenyl, 4-bromophenyl, 2-iodophenyl, 3-iodophenyl, 4-iodophenyl, 2-trifluoromethoxyphenyl, 3-trifluoromethoxyphenyl, 4-trifluoromethoxyphenyl, 2-fluoro-4-methylphenyl, (2,3)-dimethylphenyl, (2,4)-dichlorophenyl, (2,4)-difluorophenyl, 2-chloro-4-methylphenyl, 2-chloro-5-trifluoromethylphenyl, 2-chloro-5-methoxyphenyl, 2-bromo-5-trifluoromethylphenyl, 2-bromo-5-methoxyphenyl, (2,4)-dimethylphenyl, (2,6)-dimethylphenyl, 3-chloro-5-methylphenyl, (3,4)-dimethylphenyl, 3-methyl-4-methoxyphenyl, (3,4)-difluorophenyl, 3-cyano-4-fluorophenyl, 3-cyano-4-methylphenyl, 3-cyano-4-methoxyphenyl, 3-bromo-4-fluorophenyl, 3-bromo-4-methylphenyl, 3-bromo-4-methoxyphenyl, 4-chloro-2-fluorophenyl, 4-fluoro-3-methylphenyl, 3-fluoro-4-methylphenyl, 3-fluoro-5-methylphenyl, 2-fluoro-3-methylphenyl, (3,5)-dimethylphenyl, and (3,5)-dichlorophenyl; and R$^{14}$, R$^{15}$, R$^{16}$, R$^{17}$, R$^{18}$, and R$^{20}$ each independently denote an alkyl radical selected from the group consisting of methyl, ethyl, n-propyl, isopropyl, n-butyl, sec-butyl, isobutyl, and tert-butyl.

30. A compound according to claim 1, selected from the group consisting of:

[AAA00100] 4-(3-Methylmercapto-1,2,4-thiadiazol-5-yl)-1-(3-phenylpropiolyl)piperazine

[AAA00101] 4-(3-Methansulfonyl-1,2,4-thiadiazol-5-yl)-1-(3-phenylpropiolyl)piperazine

[AAA00102] 4-(3-Methoxy-1,2,4-thiadiazol-5-yl)-1-(3-phenylpropiolyl)piperazine

[AAA00103] 4-(1,2,4-Thiadiazol-5-yl)-1-(3-phenylpropiolyl)piperazine

[AAA00104] 4-(3-Methyl-1,2,4-thiadiazol-5-yl)-1-(3-phenylpropiolyl)piperazine

[AAA00105] 4-(3-Trifluoromethyl-1,2,4-thiadiazol-5-yl)-1-(3-phenylpropiolyl)piperazine

[AAA00106] 4-(5-(3-Methyl-1,2,4-oxadiazol-5-yl)thiazol-2-yl)-1-(3-phenylpropiolyl)-piperazine

[AAA00107] 4-(4-tert-Butylthiazol-2-yl)-1-(3-(4-aminophenyl)propiolyl)piperazine

[AAA1] 4-(Thiazol-2-yl)-1-(3-(2-carboxyphenyl)propiolyl)piperazine methyl ester

[AAA10] 4-(Thiazol-2-yl)-1-(3-(2-thienyl)propiolyl)piperazine

[AAA11] 4-(Thiazol-2-yl)-1-(3-(3-thienyl)propiolyl)piperazine

[AAA12] 4-(Thiazol-2-yl)-1-(3-(2-methoxyphenyl)propiolyl)piperazine

[AAA13] 4-(Thiazol-2-yl)-1-(3-(3-methoxyphenyl)propiolyl)piperazine
[AAA14] 4-(Thiazol-2-yl)-1-(3-(4-methoxyphenyl)propiolyl)piperazine
[AAA15] 4-(Thiazol-2-yl)-1-(3-(2-cyanophenyl)propiolyl)piperazine
[AAA16] 4-(Thiazol-2-yl)-1-(3-(3-cyanophenyl)propiolyl)piperazine
[AAA17] 4-(Thiazol-2-yl)-1-(3-(4-cyanophenyl)propiolyl)piperazine
[AAA18] 4-(Thiazol-2-yl)-1-(3-(2,4-dimethylphenyl)propiolyl)piperazine
[AAA19] 4-(Thiazol-2-yl)-1-(3-(3,5-dimethylphenyl)propiolyl)piperazine
[AAA2] 4-(Thiazol-2-yl)-1-(3-(4-carboxyphenyl)propiolyl)piperazine methyl ester
[AAA20] 4-(Thiazol-2-yl)-1-(3-(2,6-dimethylphenyl)propiolyl)piperazine
[AAA21] 4-(Thiazol-2-yl)-1-(3-(2-fluorophenyl)propiolyl)piperazine
[AAA22] 4-(Thiazol-2-yl)-1-(3-(3-fluorophenyl)propiolyl)piperazine
[AAA23] 4-(Thiazol-2-yl)-1-(3-(2-chlorophenyl)propiolyl)piperazine
[AAA24] 4-(Thiazol-2-yl)-1-(3-(3-chlorophenyl)propiolyl)piperazine
[AAA25] 4-(Thiazol-2-yl)-1-(3-naphthylpropiolyl)piperazine
[AAA26] 4-(Thiazol-2-yl)-1-(3-(2,3-dimethylphenyl)propiolyl)piperazine
[AAA27] 4-(Thiazol-2-yl)-1-(3-(3,4-dimethylphenyl)propiolyl)piperazine
[AAA28] 4-(Thiazol-2-yl)-1-(3-(3-nitrophenyl)propiolyl)piperazine
[AAA29] 4-(Thiazol-2-yl)-1-(3-(2-nitrophenyl)propiolyl)piperazine
[AAA3] 4-(Thiazol-2-yl)-1-(3-(3-carboxyphenyl)propiolyl)piperazine ethyl ester
[AAA30] 4-(Thiazol-2-yl)-1-(3-(3-formylphenyl)propiolyl)piperazine
[AAA31] 4-(Thiazol-2-yl)-1-(3-(3-vinylphenyl)propiolyl)piperazine
[AAA32] 4-(Thiazol-2-yl)-1-(3-pyrid-2-ylpropiolyl)piperazine
[AAA33] 4-(Thiazol-2-yl)-1-(3-pyrid-3-ylpropiolyl)piperazine
[AAA34] 4-(Thiazol-2-yl)-1-(3-pyrid-4-ylpropiolyl)piperazine
[AAA35] 4-(Thiazol-2-yl)-1-(3-(quinolin-6-yl)propiolyl)piperazine
[AAA36] 4-(Thiazol-2-yl)-1-(3-(3-isopropylphenyl)propiolyl)piperazine
[AAA37] 4-(Thiazol-2-yl)-1-(3-biphenyl-3-ylpropiolyl)piperazine
[AAA38] 4-(Thiazol-2-yl)-1-(3-naphth-2-ylpropiolyl)piperazine
[AAA39] 4-(Thiazol-2-yl)-1-(3-(1-methylindol-5-yl)propiolyl)piperazine
[AAA4] 4-(Thiazol-2-yl)-1-(3-(2-hydroxyphenyl)propiolyl)piperazine
[AAA40] 4-(Thiazol-2-yl)-1-(3-(3-methylmercaptophenyl)propiolyl)piperazine
[AAA41] 4-(Thiazol-2-yl)-1-(3-(3-cyano-4-fluorophenyl)propiolyl)piperazine
[AAA42] 4-(Thiazol-2-yl)-1-(3-(3-methoxymethylphenyl)propiolyl)piperazine
[AAA43] 4-(Thiazol-2-yl)-1-(3-(3-hydroxyphenyl)propiolyl)piperazine
[AAA44] 4-(Thiazol-2-yl)-1-(3-(3-acetaminophenyl)propiolyl)piperazine
[AAA45] 4-(Thiazol-2-yl)-1-(3-(4-acetaminophenyl)propiolyl)piperazine
[AAA46] 4-(Thiazol-2-yl)-1-(3-(2-carboxyphenyl)propiolyl)piperazine
[AAA47] 4-(Thiazol-2-yl)-1-(3-(3-carboxyphenyl)propiolyl)piperazine
[AAA48] 4-(Thiazol-2-yl)-1-(3-(4-carboxyphenyl)propiolyl)piperazine
[AAA49] 4-(Thiazol-2-yl)-1-(3-(3-carboxyphenyl)propiolyl)piperazine methyl ester
[AAA5] 4-(Thiazol-2-yl)-1-(3-(4-hydroxyphenyl)propiolyl)piperazine
[AAA50] 4-(Thiazol-2-yl)-1-(3-(3-aminocarbonylphenyl)propiolyl)piperazine
[AAA51] 4-(Thiazol-2-yl)-1-(3-(3-methylaminocarbonylphenyl)propiolyl)piperazine
[AAA52] 4-(Thiazol-2-yl)-1-(3-(3-dimethylaminocarbonylphenyl)propiolyl)piperazine
[AAA53] 4-(Thiazol-2-yl)-1-(3-(2-tolyl)propiolyl)piperazine
[AAA54] 4-(Thiazol-2-yl)-1-(3-(3-tolyl)propiolyl)piperazine hydrochloride
[AAA55] 4-(Thiazol-2-yl)-1-(3-(4-tolyl)propiolyl)piperazine hydrochloride
[AAA56] 4-(Thiazol-2-yl)-1-(3-phenylpropiolyl)piperazine hydrochloride
[AAA57] 4-(Thiazol-2-yl)-1-(3-(2-trifluoromethylphenyl)propiolyl)piperazine hydrochloride
[AAA58] 4-(Thiazol-2-yl)-1-(3-(3-trifluoromethylphenyl)propiolyl)piperazine hydrochloride
[AAA59] 4-(Thiazol-2-yl)-1-(3-(4-trifluoromethylphenyl)propiolyl)piperazine hydrochloride
[AAA6] 4-(Thiazol-2-yl)-1-(3-(2-aminophenyl)propiolyl)piperazine
[AAA60] 4-(Thiazol-2-yl)-1-(3-pentylpropiolyl)piperazine
[AAA61] 4-(Thiazol-2-yl)-1-(3-(4-fluorophenyl)propiolyl)piperazine
[AAA62] 4-(Thiazol-2-yl)-1-(3-(4-chlorophenyl)propiolyl)piperazine
[AAA63] 2-Methyl-4-(thiazol-2-yl)-1-(3-phenylpropiolyl)piperazine
[AAA64] (S)$_2$-Methyl-4-(thiazol-2-yl)-1-(3-phenylpropiolyl)piperazine
[AAA65] (R)$_2$-Methyl-4-(thiazol-2-yl)-1-(3-phenylpropiolyl)piperazine
[AAA66] 2-Methyl-4-(thiazol-2-yl)-1-(3-phenylpropiolyl)piperazine hydrochloride
[AAA67] 2-Methyl-4-(thiazol-2-yl)-1-(3-(3-tolyl)propiolyl)piperazine
[AAA68] 2-Methyl-4-(thiazol-2-yl)-1-(3-(3-tolyl)propiolyl)piperazine hydrochloride
[AAA69] 4-(Thiazol-2-yl)-1-(3-cyclohexylpropiolyl)piperazine
[AAA7] 4-(Thiazol-2-yl)-1-(3-(3-aminophenyl)propiolyl)piperazine
[AAA70] 4-(Thiazol-2-yl)-1-(3-methylpropiolyl)piperazine
[AAA71] 2-Ethyl-4-(thiazol-2-yl)-1-(3-phenylpropiolyl)piperazine
[AAA72] 2-Phenyl-4-(thiazol-2-yl)-1-(3-phenylpropiolyl)piperazine

[AAA73] 4-(Thiazol-2-yl)-1-(3-(2-furyl)propiolyl)piperazine
[AAA74] 4-(Thiazol-2-yl)-1-(3-(3-furyl)propiolyl)piperazine
[AAA75] cis-2,6-Dimethyl-4-(thiazol-2-yl)-1-(3-phenylpropiolyl)piperazine
[AAA76] 4-(5-Carboxy-thiazol-2-yl)-1-(3-phenylpropiolyl)piperazine ethyl ester
[AAA77] 4-(4-Carboxy-thiazol-2-yl)-1-(3-phenylpropiolyl)piperazine ethyl ester
[AAA78] 4-(5-Carboxy-thiazol-2-yl)-1-(3-phenylpropiolyl)piperazine
[AAA79] 4-(4-Carboxy-thiazol-2-yl)-1-(3-phenylpropiolyl)piperazine
[AAA8] 4-(Thiazol-2-yl)-1-(3-(4-aminophenyl)propiolyl)piperazine
[AAA80] 4-(5-Methylaminocarbonylthiazol-2-yl)-1-(3-phenylpropiolyl)piperazine
[AAA81] 4-(5-Dimethylaminocarbonylthiazol-2-yl)-1-(3-phenylpropiolyl)piperazine
[AAA82] 4-(3-Phenyl-1,2,4-thiadiazol-5-yl)-1-(3-phenylpropiolyl)piperazine
[AAA83] 4-(Thiazol-2-yl)-1-(3-(quinol-7-yl)propiolyl)piperazine
[AAA84] 4-(Thiazol-2-yl)-1-(3-phenylpropiolyl)piperazine-3-on
[AAA85] 4-(3-(4-Fluorobenzyl)-1,2,4-thiadiazol-5-yl)-1-(3-phenylpropiolyl)piperazine
[AAA86] 4-(5-Nitro-thiazol-2-yl)-1-(3-phenylpropiolyl)piperazine
[AAA87] 4-(4-tert-Butylthiazol-2-yl)-1-(3-phenylpropiolyl)piperazine
[AAA88] 4-(5-Methylthiazol-2-yl)-1-(3-phenylpropiolyl)piperazine
[AAA89] 4-(4,5-Dimethylthiazol-2-yl)-1-(3-phenylpropiolyl)piperazine
[AAA9] 4-(Thiazol-2-yl)-1-(3-(indol-5-yl)propiolyl)piperazine
[AAA90] 4-(5-Bromo-4-phenylthiazol-2-yl)-1-(3-phenylpropiolyl)piperazine
[AAA91] 4-(5-Bromo-4-methylthiazol-2-yl)-1-(3-phenylpropiolyl)piperazine
[AAA92] 4-(4-Methylthiazol-2-yl)-1-(3-phenylpropiolyl)piperazine
[AAA93] 4-(4-Trifluoromethylthiazol-2-yl)-1-(3-phenylpropiolyl)piperazine
[AAA94] 4-(4-Chloro-thiazol-2-yl)-1-(3-phenylpropiolyl)piperazine
[AAA95] 4-(5-Chloro-thiazol-2-yl)-1-(3-phenylpropiolyl)piperazine
[AAA96] 4-(4-Bromo-thiazol-2-yl)-1-(3-phenylpropiolyl)piperazine
[AAA97] 4-(5-Bromo-thiazol-2-yl)-1-(3-phenylpropiolyl)piperazine
[AAA98] 4-(5-Phenylthiazol-2-yl)-1-(3-phenylpropiolyl)piperazine
[AAA99] 4-(4phenylthiazol-2-yl)-1-(3-phenylpropiolyl)piperazine
[BBB2] 4-(Thiazol-2-yl)-1-propiolylpiperazine
[CCC1] 4-(3-Phenyl-1,2,4-thiadiazol-5-yl)-1-(3-(2-methoxyphenyl)propiolyl)-piperazine
[CCC2] 4-(3-Phenyl-1,2,4-thiadiazol-5-yl)-1-(3-(4-methoxyphenyl)propiolyl)-piperazine
[CCC3] 4-(3-Phenyl-1,2,4-thiadiazol-5-yl)-1-(3-(2-fluorophenyl)propiolyl)piperazine
[CCC4] 4-(3-Phenyl-1,2,4-thiadiazol-5-yl)-1-(3-(3-fluorophenyl)propiolyl)piperazine
[CCC5] 4-(3-Phenyl-1,2,4-thiadiazol-5-yl)-1-(3-(4-fluorophenyl)propiolyl)piperazine
[CCC6] 4-(3-Phenyl-1,2,4-thiadiazol-5-yl)-1-(3-(2,4-dichlorophenyl)propiolyl)-piperazine
[CCC7] 4-(3-Phenyl-1,2,4-thiadiazol-5-yl)-1-(3-(3,5-dichlorophenyl)propiolyl)-piperazine
[CCC8] 4-(3-(4-Fluorophenyl)-1,2,4-thiadiazol-5-yl)-1-(3-(tol-2-yl)propiolyl)-piperazine
[CCC9] 4-(3-(4-Fluorophenyl)-1,2,4-thiadiazol-5-yl)-1-(3-(3-methoxyphenyl)-propiolyl)piperazine
[CCC10] 4-(3-(4-Fluorophenyl)-1,2,4-thiadiazol-5-yl)-1-(3-(3-fluoro-4-methylphenyl)-propiolyl)piperazine
[CCC11] 4-(3-(4-Fluorophenyl)-1,2,4-thiadiazol-5-yl)-1-(3-(2,4-difluorophenyl)-propiolyl)piperazine
[CCC12] 4-(3-(4-Fluorophenyl)-1,2,4-thiadiazol-5-yl)-1-(3-(tol-3-yl)propiolyl)-piperazine
[CCC13] 4-(3-(4-Fluorophenyl)-1,2,4-thiadiazol-5-yl)-1-(3-(4-trifluoromethylphenyl)-propiolyl)piperazine
[CCC14] 4-(3-(4-Fluorophenyl)-1,2,4-thiadiazol-5-yl)-1-(3-(3-trifluoromethylphenyl)-propiolyl)piperazine
[CCC15] 4-(3-(4-Fluorophenyl)-1,2,4-thiadiazol-5-yl)-1-(3-(2-chloro-5-trifluoromethylphenyl)propiolyl)piperazine
[CCC16] 4-(3-tert-Butyl-1,2,4-thiadiazol-5-yl)-1-(3-(thiophen-2-yl)propiolyl)-piperazine
[CCC17] 4-(3-tert-Butyl-1,2,4-thiadiazol-5-yl)-1-(3-(3-trifluoromethylphenyl)-propiolyl)piperazine
[CCC18] 4-(3-tert-Butyl-1,2,4-thiadiazol-5-yl)-1-(3-(2-methoxyphenyl)propiolyl)-piperazine
[CCC19] 4-(3-tert-Butyl-1,2,4-thiadiazol-5-yl)-1-(3-(tol-2-yl)propiolyl)piperazine
[CCC20] 4-(3-tert-Butyl-1,2,4-thiadiazol-5-yl)-1-(3-(3-fluoro-4-methylphenyl)-propiolyl)piperazine
[CCC2 1] 4-(3-tert-Butyl-1,2,4-thiadiazol-5-yl)-1-(3-(2-chloro-5-trifluoromethylphenyl)propiolyl)piperazine
[CCC22] 4-(Thiazol-2-yl)-1-(3-(2,4-difluorophenyl)propiolyl)piperazine
[CCC23] 4-(Thiazol-2-yl)-1-(3-(2-bromo-5-methoxyphenyl)propiolyl)piperazine
[CCC24] 4-(Thiazol-2-yl)-1-(3-(3-bromo-4-methoxyphenyl)propiolyl)piperazine
[CCC25] 4-(Thiazol-2-yl)-1-(3-(3,5-dichlorophenyl)propiolyl)piperazine
[CCC26] 4-(Thiazol-2-yl)-1-(3-(4-fluoro-3-methylphenyl)propiolyl)piperazine
[CCC27] 4-(4-tert-Butylthiazol-2-yl)-1-(3-(3-cyanophenyl)propiolyl)piperazine
[CCC28] 4-(4-tert-Butylthiazol-2-yl)-1-(3-(2-trifluoromethylphenyl)propiolyl)-piperazine
[CCC29] 4-(4phenylthiazol-2-yl)-1-(3-(2,3-dimethylphenyl)propiolyl)piperazine
[CCC30] 4-(4phenylthiazol-2-yl)-1-(3-(4-fluorophenyl)propiolyl)piperazine
[CCC31] 4-(4-Methylthiazol-2-yl)-1-(3-(tol-3-yl)propiolyl)piperazine
[CCC32] 4-(4-Methylthiazol-2-yl)-1-(3-(thiophen-2-yl)propiolyl)piperazine
[CCC33] 4-(5-Methylthiazol-2-yl)-1-(3-(tol-4-yl)propiolyl)piperazine
[CCC34] 4-(5-Methylthiazol-2-yl)-1-(3-(2-cyanophenyl)propiolyl)piperazine
[CCC35] 4-(4,5-Dimethylthiazol-2-yl)-1-(3-(3-cyanophenyl)propiolyl)piperazine
[CCC36] 4-(4,5-Dimethylthiazol-2-yl)-1-(3-(3,4-dimethylphenyl)propiolyl)piperazine
[CCC37] 4-(4-(4-Methoxyphenyl)thiazol-2-yl)-1-(3-(2,4-dimethylphenyl)-propiolyl)-piperazine

[CCC38] 4-(4-(4-Methoxyphenyl)thiazol-2-yl)-1-(3-(4-trifluoromethylphenyl)-propiolyl)piperazine
[CCC39] 4-(4-(4-Fluorophenyl)thiazol-2-yl)-1-(3-(2-cyanophenyl)propiolyl)piperazine
[CCC40] 4-(4-(4-Chlorophenyl)thiazol-2-yl)-1-(3-(4-cyanophenyl)propiolyl)piperazine
[AAA00108] 4-(Thiazol-2-yl)-1-(3-(1-Methylindol-6-yl)propiolyl)piperazine
[AAA00109] 4-(Thiazol-2-yl)-1-(3-(3-acetylphenyl)propiolyl)piperazine
[AAA00110] 4-(Thiazol-2-yl)-1-(3-(3-fluoro-5-methylphenyl)propiolyl)piperazine
[AAA00111] 4-(Thiazol-2-yl)-1-(3-(2-fluoro-3-methylphenyl)propiolyl)piperazine
[AAA00112] 4-(Thiazol-2-yl)-1-(3-(3-methylaminophenyl)propiolyl)piperazine
[AAA00113] 4-(Thiazol-2-yl)-1-(3-(3-dimethylaminophenyl)propiolyl)piperazine
[AAA00114] 4-(Thiazol-2-yl)-1-(dimethylcarbamoylpropiolyl)piperazine
[AAA00115] 4-(Thiazol-2-yl)-1-(3-(3-methylsulfinylphenyl)propiolyl)piperazine
[AAA00116] 4-(Thiazol-2-yl)-1-(3-(3-methylsulfonylphenyl)propiolyl)piperazine
[AAA00117] 4-(Thiazol-2-yl)-1-(3-(3-ethynylphenyl)propiolyl)piperazine
[AAA00118] 4-(Thiazol-2-yl)-1-(3-(4-methylthiophen-2-yl)propiolyl)piperazine
[AAA00119] 2-Methyl-4-(thiazol-2-yl)-1-(3-(3-chlorophenyl)propiolyl)piperazine
[AAA00120] 4-(Thiazol-2-yl)-1-(3-(3-ethylphenyl)propiolyl)piperazine
[AAA00121] 2-tert-Butyl-4-(thiazol-2-yl)-1-(3-phenylpropiolyl)piperazine
[AAA00122] 4-(Thiazol-2-yl)-1-(3-(3-difluoromethylphenyl)propiolyl)piperazine
[AAA00123] 2-Methyl-4-(thiazol-2-yl)-1-(3-(3-cyanophenyl)propiolyl)piperazine
[AAA00124] 2-Isopropyl-4-(thiazol-2-yl)-1-(3-phenylpropiolyl)piperazine, and
[AAA00125] 4-(Thiazol-2-yl)-1-(3-(3-trimethylsilanylethynylphenyl)propiolyl)piperazine.

31. A process for preparing a compound according to claim 1, said process comprising reacting a compound corresponding to formula II:

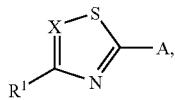

II wherein X and $R^1$ have the meanings given in claim 1, and A denotes a leaving group,
with a compound corresponding to formula III:

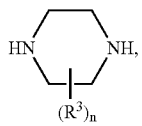

III wherein $R^3$ and n have the meanings given in claim 1,
to produce a compound corresponding to formula IV or a salt thereof,

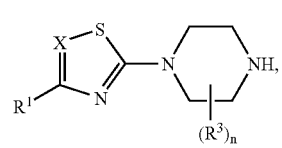

IV wherein X, $R^1$, $R^3$ and n have the meanings stated above, and optionally purifying or isolating the produced compound; or
reacting a compound corresponding to formula II with a compound corresponding to
formula V:

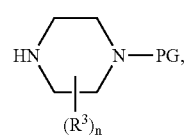

V wherein $R^3$ and n have the meanings stated above and PG denotes a protective group, to produce a compound corresponding to formula VI:

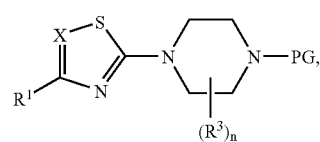

VI wherein $R^1$, $R^3$, X, n and PG have the meanings stated above, and
optionally purifying or isolating the produced compound; or
reacting a compound corresponding to formula VII,

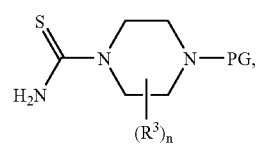

VII wherein $R^3$ and n have the meanings stated above and PG denotes a protective group, with a compound corresponding to the formula:

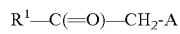

or

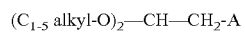

wherein $R^1$ has the meaning stated above and A denotes a leaving group, to produce a compound corresponding to formula VI or salt thereof, wherein $R^1$, $R^3$, n and PG have the meanings stated above, and X denotes CH, and optionally isolating or purifying the produced compound; and if PG denotes a tert-butoxycarbonyl group, 9-fluorenylmethyloxycarbonyl group, benzyl group or benzyloxycarbonyl group, converting the compound of formula VI to a compound of formula IV or salt thereof in which X, $R^1$, $R^3$, and n have the meanings stated above, and optionally purifying or isolating the resulting compound; and reacting the compound of formula IV in a reaction medium with a compound corresponding to the formula:

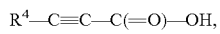

wherein $R^4$ has the meaning stated above, or a compound corresponding to the formula:

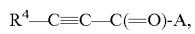

wherein $R^4$ has the meaning stated above, and A denotes a leaving group, to form a corresponding compound of formula I or salt thereof,

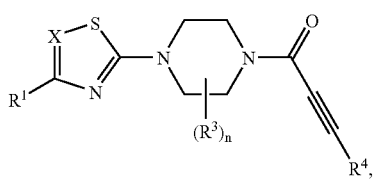

wherein X and $R^1$, $R^3$, $R^4$, and n have the meanings stated above, and optionally purifying or isolating the resulting product; or reacting the compound of formula IV with propynoic acid:

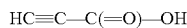

or with a compound corresponding to the formula:

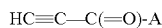

wherein A denotes a leaving group, to form a compound corresponding to formula VIII or salt thereof:

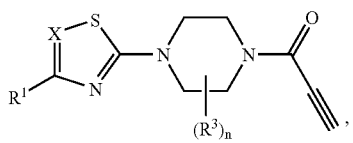

wherein $R^1$, $R^3$, X, and n have the meanings stated above, and reacting the compound of formula VIII with a compound corresponding to the formula:

wherein $R^4$ has the meaning stated above with the exception of hydrogen and A denotes a leaving group;

to form the corresponding compound of formula I or salt thereof, and optionally purifying or isolating the resulting product.

32. A process according to claim 31, wherein A denotes a halogen or a sulfonic acid ester.

33. A process according to claim 31, wherein the reaction is carried out in a reaction medium in the presence of at least one base or at least one organometallic compound or at least one metallic hydride reagent at a temperature of from −70° C. to 300° C.

34. A process according to claim 31, wherein PG denotes a protective group selected from the group consisting of tert-butyloxycarbonyl, benzyl, carbobenzoxy, and 9-fluorenylmethyloxycarbonyl.

35. A process according to claim 31, wherein the reaction is carried out in the presence of at least one organic base selected from the group consisting of triethylamine, diisopropylethylamine, N-methylmorpholine, dimethylaminopyridine and pyridine, or in the presence of at least one acid selected from the group consisting of acetic acid, trifluoroacetic acid and hydrochloric acid, at a temperature between −70° C. and 300° C.

36. A process according to claim 31, wherein a compound corresponding to formula VI in which PG denotes a tert-butoxycarbonyl group or 9-fluorenylmethyloxycarbonyl group is converted to a compound of formula IV or salt thereof in a reaction medium in the presence of hydrochloric acid or trifluoroacetic acid at a temperature between −70° C. and 100° C., or a compound of formula VI in which PG denotes a benzyl group or benzyloxycarbonyl group is converted to a compound of formula IV or salt thereof in a reaction medium in the presence of hydrogen and in the presence of a palladium on carbon catalyst at a temperature between −70° C. and 100° C.

37. A process according to claim 31, wherein a compound of formula IV is reacted with a compound of formula $R^4$—C≡C—C(=O)—OH, or a compound of formula $R^4$—C≡C—C(=O)-A in which A denotes chlorine or bromine atom, in the presence of a coupling agent anchor in the presence a base, at a temperature of from −70° C. to 100° C., or with propynoic acid or a compound of formula HC≡C—C(=O)-A, wherein A denotes a chlorine or bromine atom, in a reaction medium, in the presence of a coupling agent and/or in the presence of a base, at a temperature of from −70° C. to 100° C.

38. A process according to claim 31, wherein the compound of formula VIII is reacted with a compound of the formula $R^4$-A, wherein A denotes a sulfonic acid ester, iodine, bromine or triflate, in a reaction medium, in the presence of a palladium catalyst selected from the group consisting of palladium chloride [$PdCl_2$], palladium acetate [$Pd(OAc)_2$], tetrakis(triphenylphosphine)palladium [$Pd(PPh_3)_4$], bis(triphenylphosphine)palladium dichloride [$Pd(PPh_3)_2Cl_2$] and bis(triphenylphosphine)palladium acetate [$Pd(PPh_3)_2(OAc)_2$], and/or in the presence of a ligand selected from the group consisting of triphenylphosphine, triphenylarsine and tri-2-furylphosphine, anchor in the presence of an inorganic salt selected from the group consisting of lithium chloride and zinc chloride, and/or in the presence of copper(I) iodide, and/or in the presence of an organic or inorganic base selected from the group consisting of triethylamine, [1,4]-diazabicyclo-[2,2,2]-octane, diisopropylamine, diisopropylethylamine, potassium carbonate, and sodium hydrogencarbonate, at a temperature between −70° C. and 300° C.

39. A process for preparing a compound of formula I according to claim 1, said process comprising: reacting a compound corresponding to formula III:

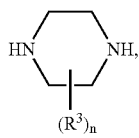

wherein $R^3$ and n have the meanings given in claim 1, with a compound corresponding to the formula:

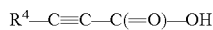

wherein $R^4$ has the meaning given in claim 1, or with a compound corresponding to the formula:

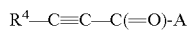

wherein $R^4$ has the meaning stated above and A denotes a leaving group, to form a corresponding compound of formula IX or salt thereof,

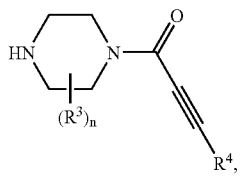

wherein $R^3$, $R^4$, and n have the meanings given above, and optionally purifying or isolating the resulting product; or reacting a compound corresponding to formula V,

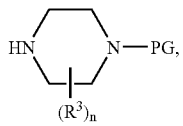

wherein $R^3$ and n have the meanings stated above, and PG denotes a protective group, with a compound corresponding to the formula:

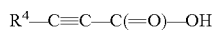

wherein $R^4$ has the meaning stated above, or with a compound corresponding to the formula:

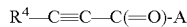

wherein $R^4$ has the meaning stated above and A denotes a leaving group, to form a corresponding compound of formula XI or salt thereof,

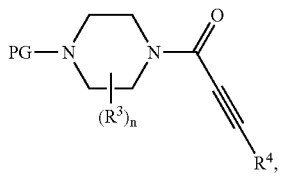

wherein $R^3$, $R^4$, and n and PG have the meanings stated above, and optionally purifying or isolating the resulting product; and if PG denotes a tert-butoxycarbonyl group or 9-fluorenylmethyloxycarbonyl group, converting the compound of formula XI to a corresponding compound of formula IX or salt thereof in a reaction medium, in the presence of at least one acid, or if PG denotes a benzyl group or a benzyloxycarbonyl group, converting the compound of formula XI to a corresponding compound of formula IX or salt thereof in a reaction medium in the presence of hydrogen and a catalyst, wherein $R^1$, $R^3$, and n have the meanings stated above, and optionally purifying or isolating the resulting product; and reacting the compound corresponding to formula IX with a compound corresponding to formula II:

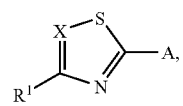

wherein X and $R^1$ have the meanings given in claim 1 and A denotes a leaving group, to form the corresponding compound of formula I or salt thereof, and optionally purifying or isolating the resulting product.

40. A process according to claim 39, wherein the compound of formula V is reacted with the compound of formula in a reaction medium, in the presence of a coupling agent and/or in the presence of a base, at a temperature ranging from −70° C. to 100° C.

41. A process according to claim 39, wherein the compound of formula IX is reacted with a compound of formula II in which A denotes a leaving group selected from the group consisting of halogens and sulfonic acid esters, in a reaction medium, in the presence of at least one base and/or at least one organometallic compound and/or at least one metallic hydride reagent, at a temperature ranging from −70° C. to 300° C.

42. A process according to claim 39, wherein PG denotes a protective group silected from the group consisting of tert-butyloxycarbonyl, benzyl, carbobenzoxy, and 9-fluorenylmethyloxycarbonyl, or wherein PG denotes a protective group selected from the group consisting of a benzyl group or a benzyloxycarbonyl group, and wherein said catalyst is a palladium on carbon catalyst and said conversion is carried out at a temperature ranging from −70° C. to 100° C.

43. A process according to claim 39, wherein the compound of formula XI is converted to a corresponding compound of formula IX said acid is selected from the group consisting of hydrochloric acid and trifluoroacetic acid and said conversion is carried out at a temperature ranging from −70° C. to 100° C.

44. A process according to claim 39, wherein the reaction is carried out in a reaction medium in the presence of a coupling agent, and/or in the presence of a base, at a temperature ranging from −70° C. to 100° C.

45. A pharmaceutical composition comprising a compound according to claim 1 and at least one physiologically acceptable adjuvant.

46. A method for the treatment of pain in a patient, wherein said pain is selected from the group consisting of acute pain, chronic pain, neuropathic pain and visceral pain, said method comprising administering to said patient a pharmaceutically effective amount of a compound according to claim 1.

* * * * *